(12) United States Patent
Freeman et al.

(10) Patent No.: US 11,529,338 B2
(45) Date of Patent: *Dec. 20, 2022

(54) COMPOSITIONS AND METHODS FOR TREATING CANCER

(71) Applicant: Cedars-Sinai Medical Center, Los Angeles, CA (US)

(72) Inventors: Michael Freeman, West Hollywood, CA (US); Mirja Rotinen, Beverly Hills, CA (US); Ramachandran Murali, Beverly Hills, CA (US); Sungyong You, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 16/640,902

(22) PCT Filed: Aug. 22, 2018

(86) PCT No.: PCT/US2018/047569
§ 371 (c)(1),
(2) Date: Feb. 21, 2020

(87) PCT Pub. No.: WO2019/040647
PCT Pub. Date: Feb. 28, 2019

(65) Prior Publication Data
US 2020/0188373 A1 Jun. 18, 2020

Related U.S. Application Data

(60) Provisional application No. 62/548,879, filed on Aug. 22, 2017.

(51) Int. Cl.
| | | |
|---|---|---|
| *A61K 31/445* | (2006.01) | |
| *A61K 31/165* | (2006.01) | |
| *A61K 31/343* | (2006.01) | |
| *A61K 31/381* | (2006.01) | |
| *A61K 31/397* | (2006.01) | |
| *A61K 31/416* | (2006.01) | |
| *A61K 31/4164* | (2006.01) | |
| *A61K 45/06* | (2006.01) | |

(52) U.S. Cl.
CPC .......... *A61K 31/445* (2013.01); *A61K 31/165* (2013.01); *A61K 31/343* (2013.01); *A61K 31/381* (2013.01); *A61K 31/397* (2013.01); *A61K 31/416* (2013.01); *A61K 31/4164* (2013.01); *A61K 45/06* (2013.01)

(58) Field of Classification Search
CPC .. A61K 31/165; A61K 31/397; A61K 31/416; A61K 31/4164; A61K 31/445
See application file for complete search history.

(56) References Cited

U.S. PATENT DOCUMENTS

| | | |
|---|---|---|
| 6,048,877 A | 4/2000 | Ahmad et al. |
| 10,927,070 B2 * | 2/2021 | Freeman ............... A61K 31/40 |
| 2006/0019256 A1 | 1/2006 | Clarke et al. |
| 2011/0053157 A1 | 3/2011 | Skog et al. |
| 2013/0150258 A1 | 6/2013 | Weichselbaum et al. |
| 2014/0056807 A1 | 2/2014 | Vizio et al. |
| 2016/0038444 A1 | 2/2016 | Alli et al. |
| 2016/0061842 A1 | 3/2016 | Vizio et al. |
| 2018/0282817 A1 | 10/2018 | You et al. |
| 2019/0194124 A1 | 6/2019 | Freeman et al. |

FOREIGN PATENT DOCUMENTS

| | | |
|---|---|---|
| WO | 2015166295 A1 | 11/2015 |
| WO | 2015188130 A1 | 12/2015 |
| WO | 2015197909 A1 | 12/2015 |
| WO | 2017213897 A1 | 12/2017 |

OTHER PUBLICATIONS

Carvalho et al., "Genomewide DNA Methylation Analysis Identifies Novel Methylated Genes in Non-Small-Cell Lung Carcinomas," J Thorac Oncol., 8(5):562-573, May 2013.
Extended Search Report of the European Patent Office dated Apr. 6, 2021 in EP Application No. 18848878.7; 14pgs.
Rybka et al., "Predictive QSAR Study of Chaicone Derivatives Cytotoxicity Activity Against HT-29 Hrnnan Colon Adenocarcinoma Cell Lines," Chemom Intell Lab. Syst., 132_18-29, Mar. 2014.
International Search Report and Written Opinion of the ISA/US in PCT/US2018/047569, dated Nov. 26, 2018; 14pgs.
Zhang et al., "Comprehensive Profiling of Novel microRNA-9 Targets and a Tumor Suppressor Role of microRNA-9 via Targeting IGF2BP1 in Hepatocellular Carcinoma," Oncotarget, 6(39):42040-42052, Dec. 2015.
Rotinen, et al., "ONECUT2 is a targetable master regulator of lethal prostate cancerthat suppresses the androgen axis," Nature Medicine, vol. 24, pp. 1887-1898, Dec. 2018.
Rotinen, et al., "ONECUT2 is a targetable master regulator of lethal prostate cancerthat suppresses the androgen axis," Supplementary Information, 25 pages, 2018.

* cited by examiner

*Primary Examiner* — James D. Anderson
(74) *Attorney, Agent, or Firm* — Haukaas Fortius PLLC; Michael Haukaas

(57) ABSTRACT

Provided herein are compositions and methods for treating, inhibiting and/or reducing the severity of neuroblastoma, small cell lung cancer (SCLC), large cell neuroendocrine cancer (LCNEC), large-cell carcinoma (LCC), squamous cell carcinoma (SqCC), and/or adenocarcinoma (AC) in subjects in need thereof. The methods include providing an agent that inhibits expression or activity of ONECUT2 and administering a therapeutically effective amount of the agent so as to treat, inhibit and/or reduce the severity of neuroblastoma, small cell lung cancer (SCLC), large cell neuroendocrine cancer (LCNEC), large-cell carcinoma (LCC), squamous cell carcinoma (SqCC), and/or adenocarcinoma (AC) in the subject.

14 Claims, 12 Drawing Sheets

| OC2-ASCL1 correlation in clinical samples | Correlation | P value |
|---|---|---|
| SCLC (Sato et al.) | 0.6669 | 0.0005 |
| SCLC (Bhattacharjee et al.) | 0.6212 | 0.0026 |
| Carcinoid Lung cancer | -0.1163 | 0.5884 |
| Lung cancer Adenocarinoma | 0.089 | 0.4182 |
| Lung Squamous Cell Carcinoma | 0.1654 | 0.2028 |
| Normal Lung | 0.5941 | -0.1561 |
| Basaloid Carcinoma of the lung | 0.1107 | 0.5022 |

FIG. 3

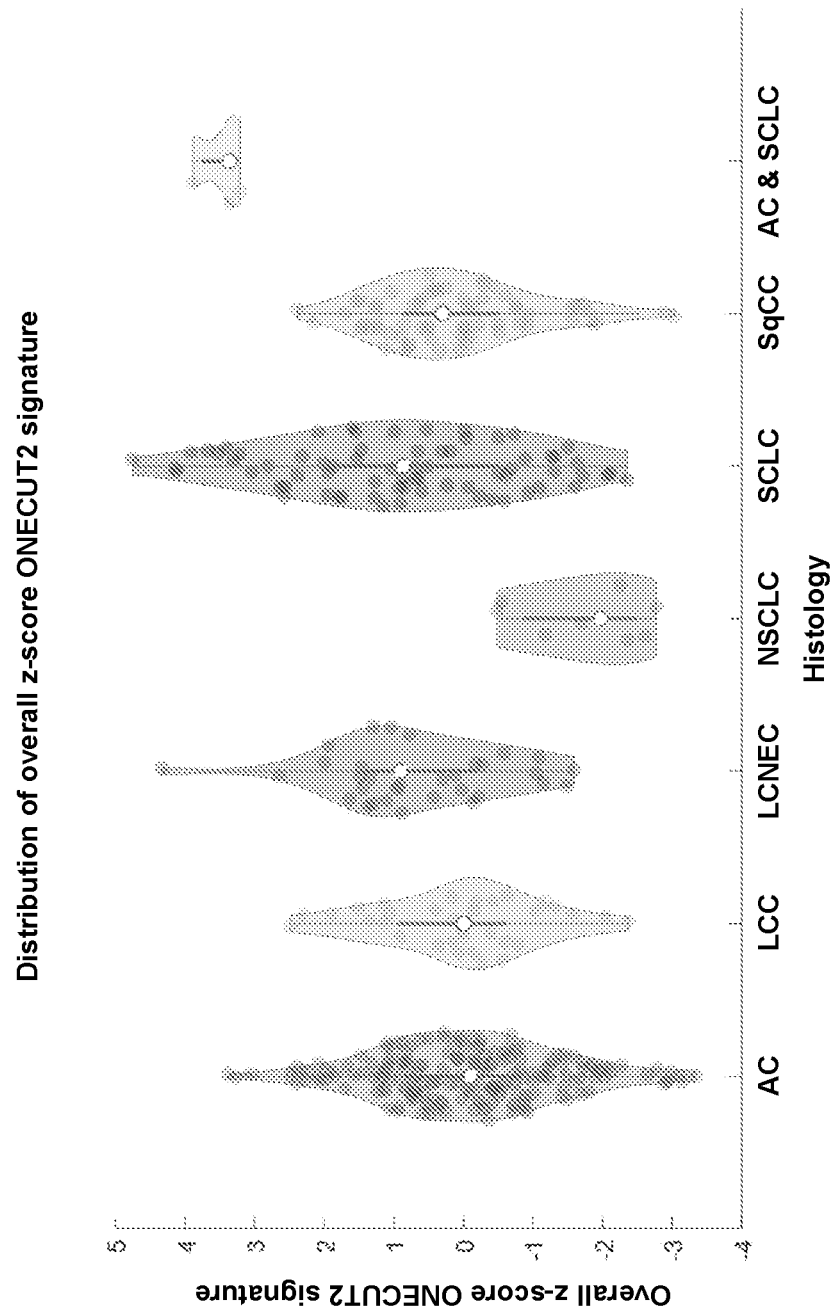

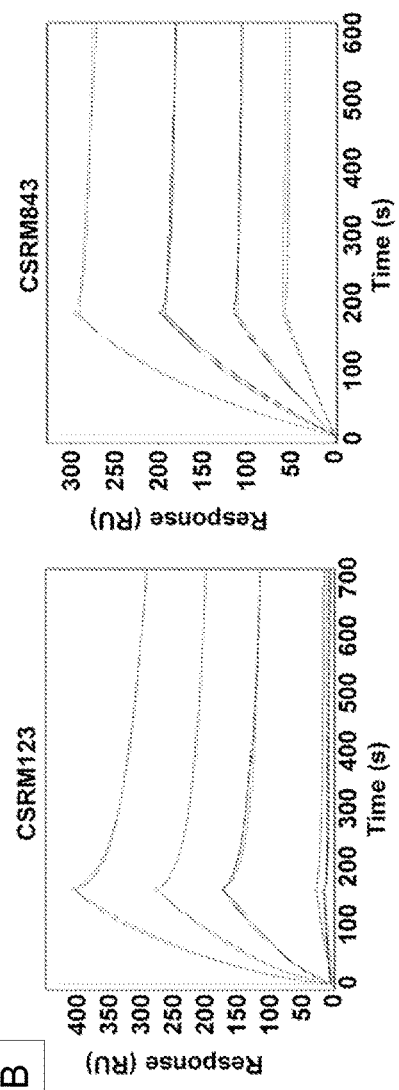
FIG. 12A
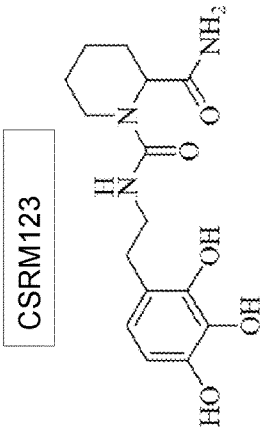
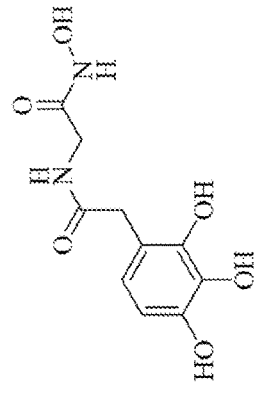
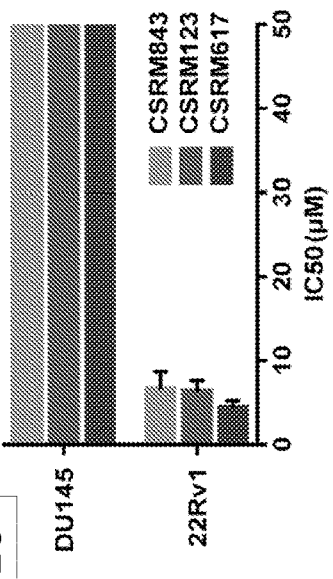
FIG. 12B
FIG. 12C

COMPOSITIONS AND METHODS FOR TREATING CANCER

CROSS-REFERENCE TO RELATED APPLICATIONS

This application is a National Stage filing under 35 U.S.C. § 371 of International Application No. PCT/US2018/047569, filed Aug. 22, 2018, which claims the benefit under 35 U.S.C § 119(e) of U.S. Provisional Patent Application No. 62/548,879 filed on Aug. 22, 2017, which applications are incorporated herein by reference in their entirety.

STATEMENT REGARDING FEDERALLY SPONSORED RESEARCH OR DEVELOPMENT

This invention was made with government support under Grant Nos. DK087806 and CA143777 awarded by National Institutes of Health and Grant Nos. W81XWH-14-1-0152 and W81XWH-16-1-0567 awarded by Department of Defense. The government has certain rights in the invention

TECHNICAL FIELD

The present disclosure relates generally to methods for treating small-cell lung cancer (SCLC) and neuroblastoma using inhibitors of ONECUT2. The present disclosure also relates generally to methods for treating cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

BACKGROUND

Patients diagnosed with small cell lung cancer generally have a poor prognosis. As such, there remains a need for compositions and methods for treating small cell lung cancer. There is also a need in the art for compositions and methods for treating neuroblastoma.

Patients diagnosed with large cell neuroendocrine cancer (LCNEC), large-cell carcinoma (LCC), squamous cell carcinoma (SqCC), and/or adenocarcinoma (AC) generally have a poor prognosis. As such, there remains a need for compositions and methods for treating large cell neuroendocrine cancer (LCNEC), large-cell carcinoma (LCC), squamous cell carcinoma (SqCC), and/or adenocarcinoma (AC).

SUMMARY OF THE INVENTION

The following embodiments and aspects thereof are described and illustrated in conjunction with systems, compositions and methods which are meant to be exemplary and illustrative, not limiting in scope.

In various embodiments, the present invention provides a method for treating cancer in a subject, comprising: administering to the subject a therapeutically effective amount of at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the cancer overexpresses ONECUT2.

In some embodiments, the neuroblastoma, small cell lung cancer (SCLC), large cell neuroendocrine cancer (LCNEC), large-cell carcinoma (LCC), squamous cell carcinoma (SqCC), adenocarcinoma (AC) each individually overexpress ONECUT2.

In some embodiments, the agent is Compound CSRM617 of structure:

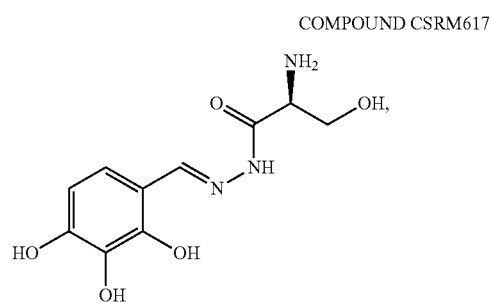 [SMILES: N[C@@H](CO)C(=O)N/N=C/c1ccc(O)c(O)c1O]

COMPOUND CSRM617 or a pharmacetucially acceptable salt thereof.

In some embodiments, the agent is a compound selected from:

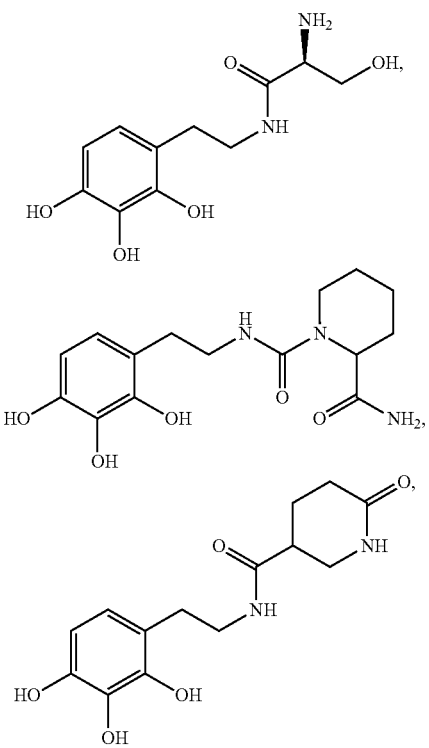

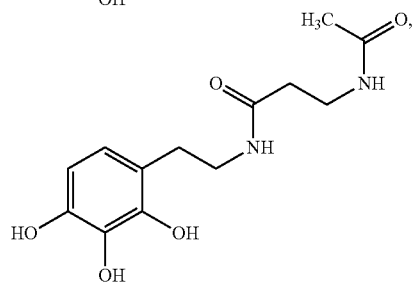

-continued

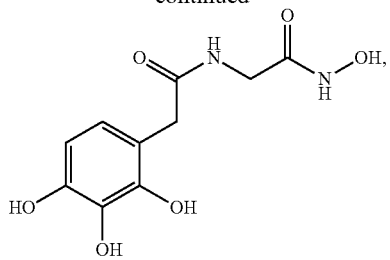

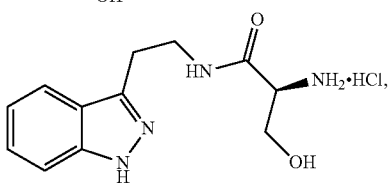

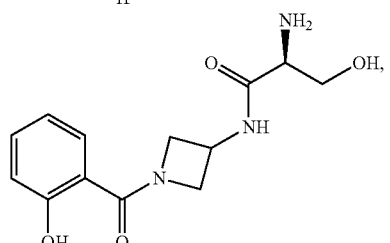

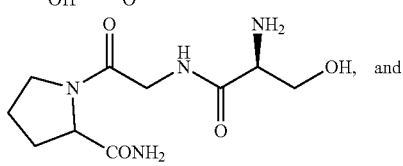

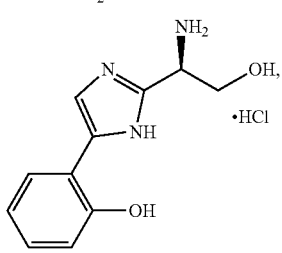

or a prodrug, isomer, dimer, enantiomer, derivative, or pharmaceutically acceptable salt thereof.

In some embodiments, the agent is a compound having the structure:

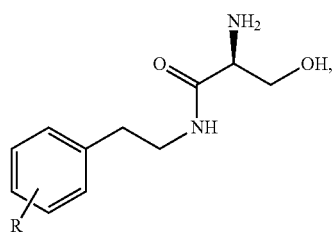

or a prodrug, isomer, dimer, enantiomer, derivative, or pharmaceutically acceptable salt thereof, wherein:

R is independently one or more of hydrogen or optionally substituted substituent.

In some embodiments, the agent is a compound having the structure:

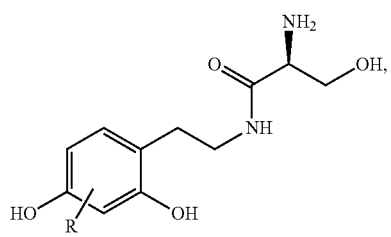

or a prodrug, isomer, dimer, enantiomer, derivative, or pharmaceutically acceptable salt thereof, wherein:

R is independently one or more of hydrogen or optionally substituted substituent.

In some embodiments, the agent is a compound having the structure:

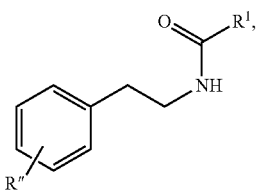

or a prodrug, isomer, dimer, enantiomer, derivative, or pharmaceutically acceptable salt thereof wherein:

R" is independently one or more of hydrogen or optionally substituted substituent; and $R^1$ is hydrogen or optionally substituted substituent.

In some embodiments, the agent is a compound having the structure:

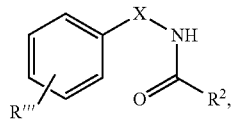

or a prodrug, isomer, dimer, enantiomer, derivative, or pharmaceutically acceptable salt thereof, wherein:

R''' is independently one or more of hydrogen or optionally substituted substituent;

$R^2$ is hydrogen or optionally substituted substituent; and

X is NHC(O), C(O)NH, OC(O), C(O)O, C(O), or CH=N.

In some embodiments, the agent is a compound having the structure:

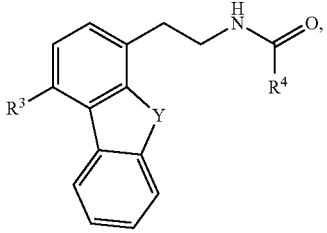

or a prodrug, isomer, dimer, enantiomer, derivative, or pharmaceutically acceptable salt thereof, wherein:

$R^3$ is hydrogen or optionally substituted substituent;

$R^4$ is hydrogen or optionally substituted substituent; and

Y is O or S.

In some embodiments, the agent is a compound having the structure:

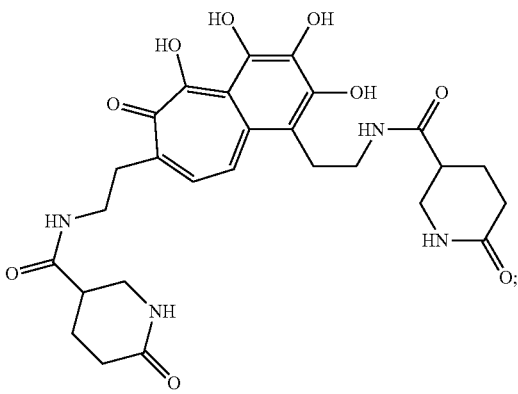 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

In some embodiments, the agent is a compound having the structure:

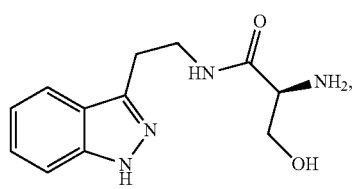 [SMILES: N[C@@H](CO)C(=O)NCCc1n[nH]c2ccccc12]

or a prodrug, isomer, dimer, enantiomer, derivative, or pharmaceutically acceptable salt thereof.

In some embodiments, the agent is a compound having the structure:

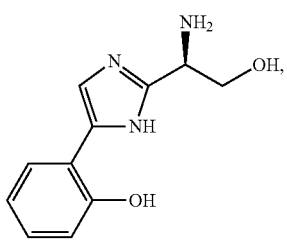 [SMILES: N[C@@H](CO)c1ncc(-c2ccccc2O)[nH]1]

or a prodrug, isomer, dimer, enantiomer, derivative, or pharmaceutically acceptable salt thereof.

In some embodiments, the agent is a compound selected from the group consisting of a compound of Formula I, a compound of Formula II, a compound of Formula III, a compound of Formula IV, and a compound of Formula V, or a prodrug, isomer, dimer, enantiomer, derivative, or pharmaceutically acceptable salt thereof.

In some embodiments, the ONECUT2 is selected from the group consisting of ONECUT2 gene, ONECUT2 protein, and combinations thereof.

In various embodiments, the present invention provides a method for treating small cell lung cancer (SCLC) or neuroblastoma in a subject in need thereof, comprising providing an agent that inhibits expression or activity of ONECUT2; and administering a therapeutically effective amount of the agent so as to treat SCLC or neuroblastoma in the subject.

In various embodiments, the present invention provides a method for treating, inhibiting, reducing the severity of and/or promoting prophylaxis of small cell lung cancer (SCLC) or neuroblastoma in a subject in need thereof, comprising providing an agent that inhibits expression or activity of ONECUT2; and administering a therapeutically effective amount of the agent so as to treat, inhibit, reduce the severity of and/or promoting prophylaxis of small cell lung cancer (SCLC) or neuroblastoma in the subject.

In various embodiments, the present invention provides a method of treating, inhibiting, reducing the severity of, delaying progression of and/or preventing metastases of small cell lung cancer (SCLC) or neuroblastoma in a subject, comprising: providing at least one agent that inhibits expression or activity of ONECUT2; administering to the subject a therapeutically effective amount of the at least one agent, thereby treating, inhibiting, reducing the severity of, delaying progression of and/or preventing metastases of small cell lung cancer (SCLC) or neuroblastoma in the subject.

In some embodiments, the method further comprising administering at least one additional anti-SCLC therapy or at least one additional anti-neuroblastoma therapy to the subject.

In some embodiments, the additional anti-SCLC therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

In some embodiments, the additional anti-neuroblastoma therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

In some embodiments, the subject is human.

In some embodiments, the agent is administered to the subject 1-3 times per day or 1-7 times per week.

In some embodiments, the agent is administrated to the subject for 1-5 days, 1-5 weeks, 1-5 months, or 1-5 years.

In some embodiments, the agent and the additional anti-SCLC therapy or the anti-neuroblastoma therapy are administered sequentially or simultaneously.

In some embodiments, the small cell lung cancer (SCLC) overexpresses ONECUT2.

In some embodiments, the neuroblastoma overexpresses ONECUT2.

In some embodiments, the agent is Compound CSRM617 of structure:

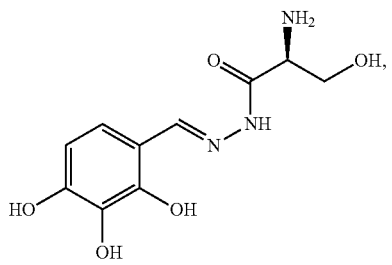

COMPOUOND CSRM617 or a pharmacetucially acceptable salt thereof.

In some embodiments, the agent is a compound selected from:

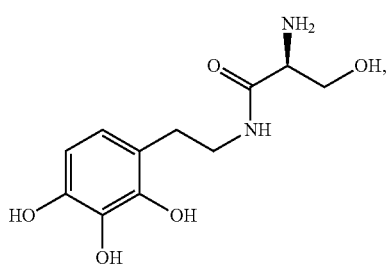

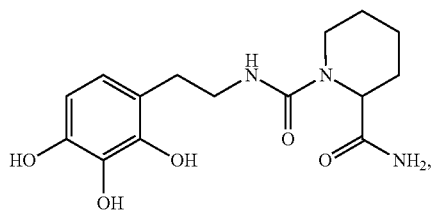

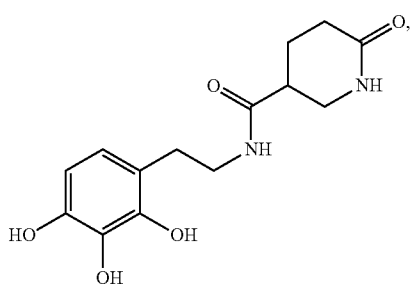

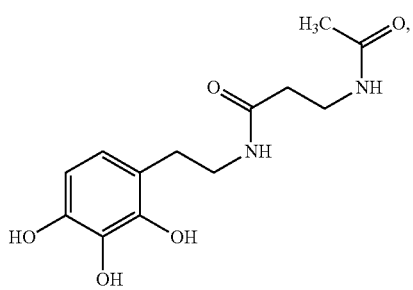

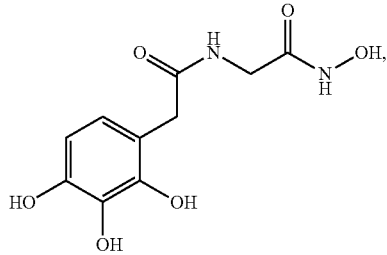

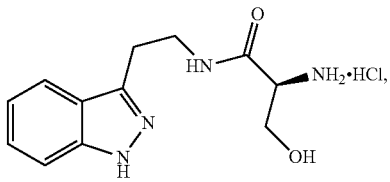

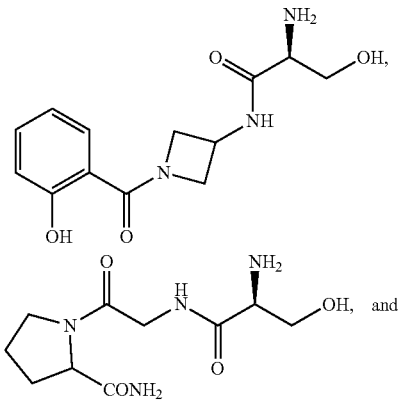

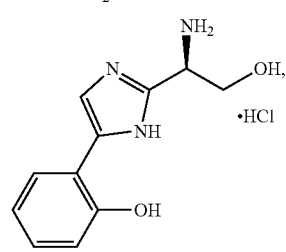

or a prodrug, isomer, dimer, enantiomer, derivative, or pharmaceutically acceptable salt thereof.

In some embodiments, the agent is a compound having the structure:

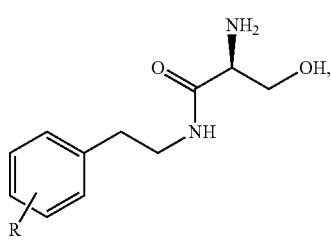

or a prodrug, isomer, dimer, enantiomer, derivative, or pharmaceutically acceptable salt thereof, wherein:

R is independently one or more of hydrogen or optionally substituted substituent.

In some embodiments, the agent is a compound having the structure:

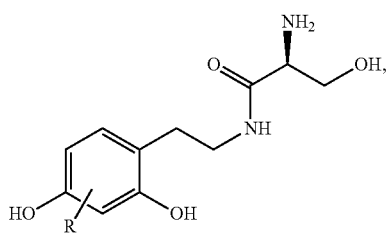

or a prodrug, isomer, dimer, enantiomer, derivative, or pharmaceutically acceptable salt thereof, wherein:
R is independently one or more of hydrogen or optionally substituted substituent.

In some embodiments, the agent is a compound having the structure:

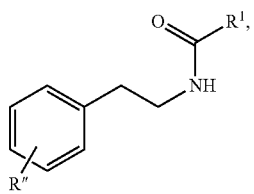

or a prodrug, isomer, dimer, enantiomer, derivative, or pharmaceutically acceptable salt thereof wherein:
R" is independently one or more of hydrogen or optionally substituted substituent; and
$R^1$ is hydrogen or optionally substituted substituent.

In some embodiments, the agent is a compound having the structure:

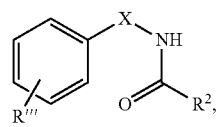

or a prodrug, isomer, dimer, enantiomer, derivative, or pharmaceutically acceptable salt thereof, wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N.

In some embodiments, the agent is a compound having the structure:

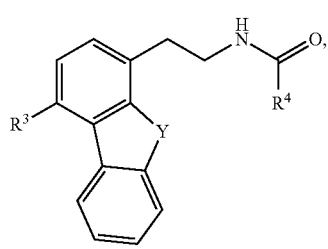

or a prodrug, isomer, dimer, enantiomer, derivative, or pharmaceutically acceptable salt thereof, wherein:
$R^3$ is hydrogen or optionally substituted substituent;
$R^4$ is hydrogen or optionally substituted substituent; and
Y is O or S.

In some embodiments, the agent is a compound having the structure:

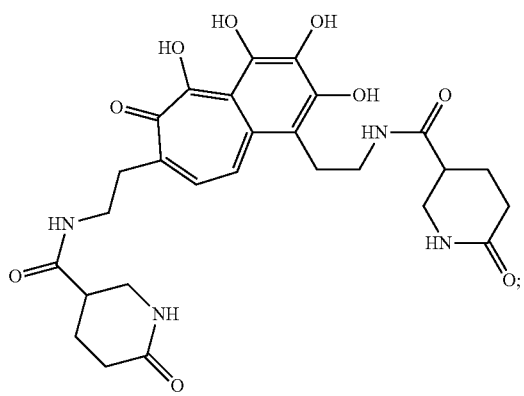 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

In some embodiments, the agent is a compound having the structure:

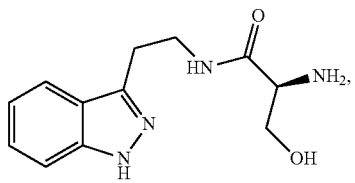 [SMILES: N[C@@H](CO)C(=O)NCCc1n[nH]c2ccccc12]

or a prodrug, isomer, dimer, enantiomer, derivative, or pharmaceutically acceptable salt thereof.

In some embodiments, the agent is a compound having the structure:

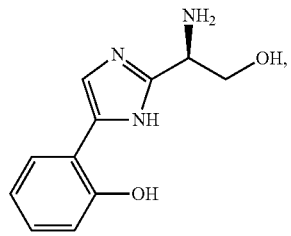 [SMILES: N[C@@H](CO)c1ncc(-c2ccccc2O)[nH]1]

or a prodrug, isomer, dimer, enantiomer, derivative, or pharmaceutically acceptable salt thereof.

In some embodiments, the agent is a compound selected from the group consisting of a compound of Formula I, a compound of Formula II, a compound of Formula III, a compound of Formula IV, and a compound of Formula V, or a prodrug, isomer, dimer, enantiomer, derivative, or pharmaceutically acceptable salt thereof.

In some embodiments, the ONECUT2 is selected from the group consisting of ONECUT2 gene, ONECUT2 protein, and combinations thereof.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 3 depicts in accordance with various embodiments of the invention, ONECUT2 and ASCL1 mRNA expression is positively correlated in SCLC cohorts.

FIG. 11 depicts in accordance with various embodiments of the invention, distribution of overall z-score ONECUT2 signature. ONECUT2 activity is significantly higher in large cell neuroendocrine cancer (LCNEC) and small cell lung cancer (SCLC). Small cell lung cancer (SCLC), large cell neuroendocrine cancer (LCNEC), large-cell carcinoma (LCC), squamous cell carcinoma (SqCC), adenocarcinoma (AC), Non-Small Cell Lung Cancer (NSCLC).

FIG. 12A-FIG. 12C depicts in accordance with various embodiments of the invention, CSRM617 derivatives. FIG. 12A depicts chemical structures of CSRM617 derivatives CSRM123 and CSRM843. FIG. 12B depicts dose-dependent binding of CSRM123 and CSRM843 to OC2-HOX, measured by surface plasmon resonance, is shown. The binding affinities for CSRM123 and CSRM843 are $K_D$=1.15 µM and KD=118 nM, respectively, based on 2:2 Langmuir model simulation (orange) of the bimolecular interactions. FIG. 12C depicts $IC_{50}$ values for compounds CSRM617, CSRM123 and CSRM843 in 22Rv1 and DU145 cell lines.

DETAILED DESCRIPTION OF THE INVENTION

Figure 1:
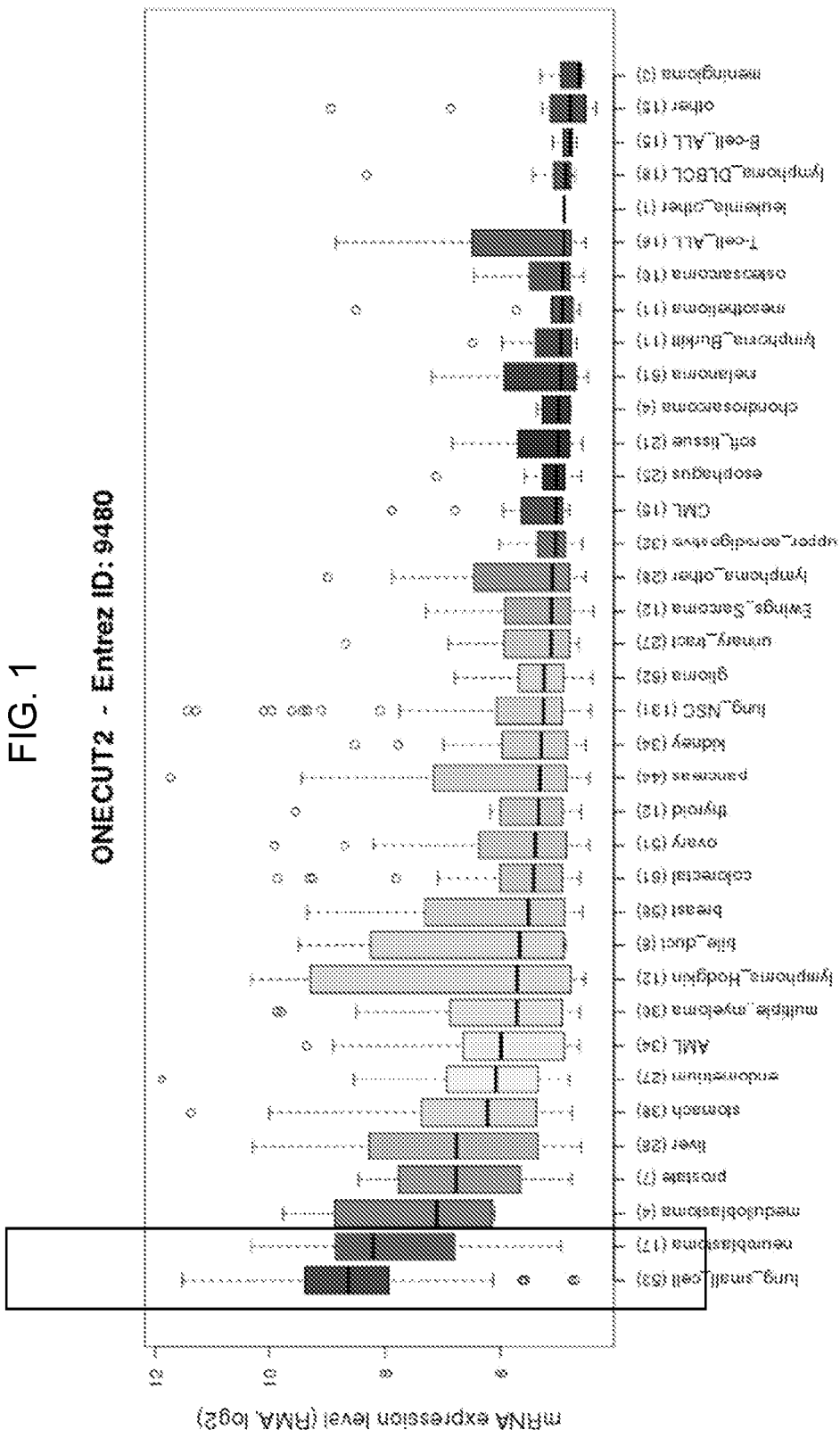
FIG. 1 depicts in accordance with various embodiments of the invention, ONECUT2 RNA expression is highest in small cell lung cancer (SCLC) and neuroblastoma cell lines. The box highlights data from 53 SCLC and 17 neuroblastoma cell lines. Y-axis is log 2 mRNA expression level. From the Cancer Cell Line Encyclopedia (www.broadinstitute.org).

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul, 6(7):511-9; Queen and Selick, *Humanized immunoglobulins*, U.S. Pat. No. 5,585,089 (1996 Dec); and Riechmann et al., *Reshaping human antibodies for therapy*, Nature 1988 Mar. 24, 332(6162):323-7.

For references on pediatrics, see Schwartz et al., *The 5-Minute Pediatric Consult* $4^{th}$ ed., Lippincott Williams & Wilkins, (Jun. 16, 2005); Robertson et al., *The Harriet Lane Handbook: A Manual for Pediatric House Officers* $17^{th}$ ed., Mosby (Jun. 24, 2005); and Hay et al., *Current Diagnosis and Treatment in Pediatrics* (*Current Pediatrics Diagnosis & Treatment*) $18^{th}$ed., McGraw-Hill Medical (Sep. 25, 2006).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

"Optional" or "optionally" means that the subsequently described circumstance may or may not occur, so that the description includes instances where the circumstance occurs and instances where it does not.

As used herein, the terms "treat," "treatment," "treating," or "amelioration" when used in reference to a disease, disorder, condition, medical condition, or disease condition, refer to both therapeutic treatment and prophylactic or preventative measures, wherein the object is to prevent, reverse, alleviate, ameliorate, inhibit, lessen, slow down or stop the progression or severity of a symptom of a disease, disorder, condition, medical condition, or disease condition. The term "treating" includes reducing or alleviating at least one adverse effect or symptom of a disease, disorder, condition, medical condition, or disease condition. Treatment is generally "effective" if one or more symptoms or clinical markers are reduced. Alternatively, treatment is "effective" if the progression of a disease, disorder, condition, medical condition, or disease condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the disease, disorder, condition, medical condition, or disease condition even if the treatment is ultimately unsuccessful. Those in need of treatment include those already with the disease, disorder, condition, medical condition, or disease condition as well as those prone to have the disease, disorder, condition, medical condition, or disease condition or those in whom the disease, disorder, condition, medical condition, disease condition is to be prevented.

The term "effective amount" as used herein refers to the amount of an agent, composition, or pharmaceutical composition as disclosed herein to decrease at least one or more symptom of the disease, disorder, condition, medical condition, or disease condition and relates to a sufficient amount of agent, composition, or pharmacological composition to provide the desired effect. The phrase "therapeutically effective amount" as used herein means a sufficient amount of the agent or composition to treat a disease, disorder, condition, medical condition, or disease condition at a reasonable benefit/risk ratio applicable to any medical treatment.

In addition, "therapeutically effective amount" as used herein refers to that amount which is capable of achieving beneficial results in a subject. A therapeutically effective amount can be determined on an individual basis and will be based, at least in part, on consideration of the physiological characteristics of the subject, the type of delivery system or therapeutic technique used and the time of administration relative to the progression of the disease, disorder, condition, medical condition, or disease condition.

"Beneficial results" or "desired results" may include, but are in no way limited to, lessening or alleviating the severity of the disease, disorder, condition, medical condition, or disease condition, preventing the disease, disorder, condition, medical condition, or disease condition from worsening, curing the disease, disorder, condition, medical condition, or disease condition, preventing the disease, disorder, condition, medical condition, or disease condition from developing, lowering the chances of a patient developing the disease, disorder, condition, medical condition, or disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of SCLC or neuroblastoma, delay or slowing of SCLC or neuroblastoma, and amelioration or palliation of symptoms associated with SCLC or neuroblastoma. As non-limiting examples, "beneficial results" or "desired results" may be alleviation of one or more symptom(s), diminishment of extent of the deficit, stabilized (i.e., not worsening) state of neuroblastoma, small cell lung cancer (SCLC), large cell neuroendocrine cancer (LCNEC), large-cell carcinoma (LCC), squamous cell carcinoma (SqCC), or adenocarcinoma (AC), delay or slowing of neuroblastoma, small cell lung cancer (SCLC), large cell neuroendocrine cancer (LCNEC), large-cell carcinoma (LCC), squamous cell carcinoma (SqCC), or adenocarcinoma (AC), and amelioration or palliation of symptoms associated with neuroblastoma, small cell lung cancer (SCLC), large cell neuroendocrine cancer (LCNEC), large-cell carcinoma (LCC), squamous cell carcinoma (SqCC), or adenocarcinoma (AC).

The term "disease" refers to an abnormal condition affecting the body of an organism. The term "disorder" refers to a functional abnormality or disturbance. The term "condition" as used herein refers generally to a disease, disorder, event, or change in health status. The term "medical condition" includes, but is not limited to, any condition, disease, or disorder manifested as one or more physical and/or psychological symptoms for which treatment and/or prevention is desirable, and includes previously and newly identified condition, disease, or disorder. The term "disease condition" refers to an abnormal condition affecting the body of an organism that may be caused by a disease.

"Diseases", "conditions", "disease conditions,", "disorders", and "medical conditions" as used herein may include, but are in no way limited to SCLC or neuroblastoma.

In various embodiments, the disease is small cell lung cancer (SCLC). In various embodiments, the disorder is small cell lung cancer (SCLC). In various embodiments, the condition is small cell lung cancer (SCLC). In various embodiments, the medical condition is small cell lung cancer (SCLC). In various embodiments, the disease condition is small cell lung cancer (SCLC).

In various embodiments, the disease is neuroblastoma. In various embodiments, the disorder is neuroblastoma. In various embodiments, the condition is neuroblastoma. In various embodiments, the medical condition is neuroblastoma. In various embodiments, the disease condition is neuroblastoma.

In various embodiments, the disease is selected from the group consisting of small cell lung cancer (SCLC), neuroblastoma, and combinations thereof. In various embodiments, the disorder is selected from the group consisting of small cell lung cancer (SCLC), neuroblastoma, and combinations thereof. In various embodiments, the condition is selected from the group consisting of small cell lung cancer (SCLC), neuroblastoma, and combinations thereof. In various embodiments, the medical condition is selected from the group consisting of small cell lung cancer (SCLC), neuroblastoma, and combinations thereof. In various embodiments, the disease condition is selected from the group consisting of small cell lung cancer (SCLC), neuroblastoma, and combinations thereof.

In various embodiments, the disease is lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disorder is lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the condition is lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the medical condition is lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disease condition is lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the disease is cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disorder is cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the condition is cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the medical condition is cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disease condition is cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the disease is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disorder is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the condition is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the medical condition is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disease condition is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the disease is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disorder is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the condition is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the medical condition is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In various embodiments, the disease condition is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the disease is not Non-Small Cell Lung Cancer (NSCLC). In some embodiments, the disorder is not Non-Small Cell Lung Cancer (NSCLC). In some embodiments, the conditions is not Non-Small Cell Lung Cancer (NSCLC). In some embodiments, the medical condition is not Non-Small Cell Lung Cancer (NSCLC). In some embodiments, the disease condition is not Non-Small Cell Lung Cancer (NSCLC).

In some embodiments, the disease condition is not adenocarcinoma (AC). In some embodiments, the disorder is not adenocarcinoma (AC). In some embodiments, the condition is not adenocarcinoma (AC). In some embodiments, the medical condition is not adenocarcinoma (AC). In some embodiments, the disease condition is not adenocarcinoma (AC).

In various embodiments, the disease is large cell neuroendocrine cancer (LCNEC). In various embodiments, the disorder is large cell neuroendocrine cancer (LCNEC). In various embodiments, the condition is large cell neuroendocrine cancer (LCNEC). In various embodiments, the medical condition is large cell neuroendocrine cancer (LCNEC). In various embodiments, the disease condition is large cell neuroendocrine cancer (LCNEC).

In various embodiments, the disease is large-cell carcinoma (LCC). In various embodiments, the disorder is large-cell carcinoma (LCC). In various embodiments, the condition is large-cell carcinoma (LCC). In various embodiments, the medical condition is large-cell carcinoma (LCC). In various embodiments, the disease condition is large-cell carcinoma (LCC).

In various embodiments, the disease is squamous cell carcinoma (SqCC). In various embodiments, the disorder is squamous cell carcinoma (SqCC). In various embodiments, the condition is squamous cell carcinoma (SqCC). In various embodiments, the medical condition is squamous cell carcinoma (SqCC). In various embodiments, the disease condition is squamous cell carcinoma (SqCC).

In various embodiments, the disease is adenocarcinoma (AC). In various embodiments, the disorder is adenocarcinoma (AC). In various embodiments, the condition is adenocarcinoma (AC). In various embodiments, the medical condition is adenocarcinoma (AC). In various embodiments, the disease condition is adenocarcinoma (AC).

A "healthy subject" or "normal subject" is a subject that does not have a disease, disorder, condition, medical condition, or disease condition.

The term "unhealthy subject" or "abnormal subject" is a subject that does have a disease, disorder, condition, medical condition, or disease condition.

As used herein, the term "one cut homeobox 2 (ONECUT2)" or "ONECUT2" refers to the onecut-2 transcription factor. ONECUT2 is also known as OC2 or OC-2. In some embodiments, ONECUT2 is also known as HNF6β.

"Overexpress" or "overexpression as used herein refers to excessive expression of a gene and/or protein, for example ONECUT2 (e.g., ONECUT2 protein and/or ONECUT2 gene), as that caused by, for example, increasing the frequency or level of transcription. In some embodiments, overexpression of ONECUT2 is determined relative to the level of ONECUT2 (e.g., ONECUT2 expression) in control (healthy) subjects and/or subjects whose SCLC or neuroblastoma is under remission and/or subjects with SCLC or neuroblastoma not associated with overexpression of ONECUT2. In exemplary embodiments, cancers that may overexpress ONECUT2 include but are not limited to SCLC or neuroblastoma. Methods for determining overexpression of ONECUT2 will be apparent to a person of skill in the art.

"Overexpress" or "overexpression as used herein refers to excessive expression of a gene and/or protein, for example ONECUT2 (e.g., ONECUT2 protein and/or ONECUT2 gene), as that caused by, for example, increasing the frequency or level of transcription. In some embodiments, overexpression of ONECUT2 is determined relative to the level of ONECUT2 (e.g., ONECUT2 expression) in control (healthy) subjects and/or subjects whose neuroblastoma, small cell lung cancer (SCLC), large cell neuroendocrine cancer (LCNEC), large-cell carcinoma (LCC), squamous cell carcinoma (SqCC), or adenocarcinoma (AC), is under remission and/or subjects with neuroblastoma, small cell lung cancer (SCLC), large cell neuroendocrine cancer (LCNEC), large-cell carcinoma (LCC), squamous cell carcinoma (SqCC), adenocarcinoma (AC), not associated with overexpression of ONECUT2. In exemplary embodiments, cancers that may overexpress ONECUT2 include but are not limited to neuroblastoma, small cell lung cancer (SCLC), large cell neuroendocrine cancer (LCNEC), large-cell carcinoma (LCC), squamous cell carcinoma (SqCC), adenocarcinoma (AC). Methods for determining overexpression of ONECUT2 will be apparent to a person of skill in the art.

ONECUT2 can be ONECUT2 gene, ONECUT2 protein, or both. In some embodiments, ONECUT2 is selected from the group consisting of ONECUT2 gene, ONECUT2 protein, and combinations thereof. In some embodiments, ONECUT2 is ONECUT2 gene. In some embodiments, ONECUT2 is ONECUT2 protein.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres, nanoparticles comprised of proteineous or non-proteineous components or nanospheres or lipid vesicles or polymer vesicles allowing controlled release. Via the topical route, the agent or composition can be in the form of aerosol, lotion, cream, gel, ointment, suspensions, solutions or emulsions. In an embodiment, an agent or composition may be provided in a powder form and mixed with a liquid, such as water, to form a beverage. In accordance with the present invention, "administering" can be self-administering. For example, it is considered as "administering" that a subject consumes an agent or composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In some embodiments, the subject is a human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age. Thus, adult and newborn subjects, as well as fetuses, are intended to be included within the scope of this term.

A subject can be one who has been previously diagnosed with or identified as suffering from or having a disease, disorder, condition, medical condition, or disease condition in need of treatment (e.g., SCLC or neuroblastoma; or SCLC or neuroblastoma that overexpresses ONECUT2) or one or more complications related to the disease, disorder, condition, medical condition, or disease condition, and optionally, have already undergone treatment for the disease, disorder, condition, medical condition, or disease condition or the one or more complications related to the disease, disorder, condition, medical condition, or disease condition. Alternatively, a subject can also be one who has not been previously diagnosed as having a disease, disorder, condition, medical condition, or disease condition or one or more complications related to the disease, disorder, condition, medical condition, or disease condition. For example, a subject can be one who exhibits one or more risk factors for a disease, disorder, condition, medical condition, or disease condition or one or more complications related to the disease, disorder, condition, medical condition, or disease condition or a subject who does not exhibit risk factors. For example, a subject can be one who exhibits one or more symptoms for a disease, disorder, condition, medical condition, or disease condition or one or more complications related to the disease, disorder, condition, medical condition, or disease condition, or a subject who does not exhibit symptoms. A "subject in need" of diagnosis or treatment for a particular disease, disorder, condition, medical condition, or disease condition, can be a subject suspected of having that disease, disorder, condition, medical condition, or disease condition diagnosed as having that disease, disorder, condition, medical condition, or disease condition, already treated or being treated for that disease, disorder, condition, medical condition, or disease condition, not treated for that disease, disorder, condition, medical condition, or disease condition, or at risk of developing that disease, disorder, condition, medical condition, or disease condition. A subject can be one who has been previously diagnosed with or identified as suffering from or having a disease, disorder, condition, medical condition, or disease condition in need of treatment (e.g., neuroblastoma, small cell lung cancer (SCLC), large cell neuroendocrine cancer (LCNEC), large-cell carcinoma (LCC), squamous cell carcinoma (SqCC), or adenocarcinoma (AC); or neuroblastoma, small cell lung cancer (SCLC), large cell neuroendocrine cancer (LCNEC), large-cell carcinoma (LCC), squamous cell carcinoma (SqCC), or adenocarcinoma (AC) that overexpresses ONECUT2) or one or more complications related to the disease, discorder, condition, medical condition, or disease condition, and optionally, have already undergone treatment for the disease, disorder, condition, medical condition, or disease condition or the one or more complications related to the disease, disorder, condition, medical condition, or disease condition.

In some embodiments, the subject is selected from the group consisting of a subject suspected of having small cell lung cancer, a subject that has small cell lung cancer, a subject diagnosed with small cell lung cancer, a subject that is at risk of developing small cell lung cancer, a subject that has been treated for small cell lung cancer, and a subject that is being treated for small cell lung cancer.

In some embodiments, the subject is selected from the group consisting of a subject suspected of having neuroblastoma, a subject that has neuroblastoma, a subject diagnosed with neuroblastoma, a subject that is at risk of developing neuroblastoma, a subject that has been treated for neuroblastoma, and a subject that is being treated for neuroblastoma.

In some embodiments, the subject is selected from the group consisting of a subject suspected of having neuroblastoma, small cell lung cancer (SCLC), large cell neuroendocrine cancer (LCNEC), large-cell carcinoma (LCC), squamous cell carcinoma (SqCC), or adenocarcinoma (AC); a subject that has neuroblastoma, small cell lung cancer (SCLC), large cell neuroendocrine cancer (LCNEC), large-cell carcinoma (LCC), squamous cell carcinoma (SqCC), or adenocarcinoma (AC); a subject diagnosed with neuroblastoma, small cell lung cancer (SCLC), large cell neuroendocrine cancer (LCNEC), large-cell carcinoma (LCC), squamous cell carcinoma (SqCC), or adenocarcinoma (AC); a subject that is at risk of developing neuroblastoma, small cell lung cancer (SCLC), large cell neuroendocrine cancer (LCNEC), large-cell carcinoma (LCC), squamous cell carcinoma (SqCC), or adenocarcinoma (AC); a subject that has been treated for neuroblastoma, small cell lung cancer (SCLC), large cell neuroendocrine cancer (LCNEC), large-cell carcinoma (LCC), squamous cell carcinoma (SqCC), or adenocarcinoma (AC); and a subject that is being treated for neuroblastoma, small cell lung cancer (SCLC), large cell neuroendocrine cancer (LCNEC), large-cell carcinoma (LCC), squamous cell carcinoma (SqCC), or adenocarcinoma (AC).

As used herein, the term "protein-drug conjugate," refers to complex molecules comprising proteins linked to a biologically active cytotoxic (anti-cancer) payload, drug, or drug-like small molecule. In some embodiments, a protein-drug conjugate, may be a complex molecule comprising a protein linked to a compound described herein, such as compound CSRM617, a compound of Formula I-V, or any pharmaceutically acceptable salt thereof. In some embodiments, the proteins are antibodies. Non-limiting examples of antibodies suitable for use in antibody-drug conjugates include a monoclonal antibody or fragment thereof, a polyclonal antibody or a fragment thereof, chimeric antibodies, humanized antibodies, human antibodies, or a single chain antibody that target small cell lung cancer cells or neuroblastoma cells, including but not limited to commercially available therapeutic antibodies.

As used herein, the term "photodynamic therapy", refers to a treatment that uses a drug, called a photosensitizer or photosensitizing agent, and light to kill cancer (for example, SCLC or neuroblastoma) cells. The photosensitizers only work after they have been activated by certain wavelengths of light. Photodynamic therapy (PDT) may also be called photoradiation therapy, phototherapy, photochemotherapy.

"Diagnostic" means identifying the presence or nature of a pathologic condition and includes identifying patients who are at risk of developing a specific disease, disorder, condition, medical condition, or disease condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a disease, disorder, condition, medical condition, or disease condition it suffices if the method provides a positive indication that aids in diagnosis.

By "at risk of" is intended to mean at increased risk of, compared to a normal subject, or compared to a control group, e.g. a patient population. Thus a subject carrying a particular marker may have an increased risk for a specific disease, disorder, condition, medical condition, or disease condition and be identified as needing further testing. "Increased risk" or "elevated risk" mean any statistically significant increase in the probability, e.g., that the subject has the disease, disorder, condition, medical condition, or disease condition. The risk is preferably increased by at least 10%, more preferably at least 20%, and even more preferably at least 50% over the control group with which the comparison is being made.

The term "diagnosis," or "dx," refers to the identification of the nature and cause of a certain phenomenon. As used herein, a diagnosis typically refers to a medical diagnosis, which is the process of determining which disease, disorder, condition, medical condition, or disease condition explains a symptoms and signs. A diagnostic procedure, often a diagnostic test or assay, can be used to provide a diagnosis. A diagnosis can comprise detecting the presence of a disease, disorder, condition, medical condition, or disease condition or the risk of getting a disease, disorder, condition, medical condition, or disease condition.

The term "prognosis," or "px," as used herein refers to predicting the likely outcome of a current standing. For example, a prognosis can include the expected duration and course of a disease, disorder, condition, medical condition, or disease condition, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Non-limiting examples of samples or biological samples include cheek swab; mucus; whole blood, blood, serum; plasma; blood products, derivatives of blood products, urine; saliva; semen; lymph; fecal extract; sputum; other body fluid or biofluid; cell sample; and tissue sample, tissue extract, tissue biopsy, biopsy specimen, biopsy sample, etc. The term also includes a mixture of the above-mentioned samples or biological samples. The term "sample" also includes untreated or pretreated (or pre-processed) biological samples. In some embodiments, a sample or biological sample can comprise one or more cells from the subject. In some embodiments subject samples or biological samples comprise derivatives of blood products, including blood, plasma and serum. In some embodiments, a sample or biological sample can comprise one or more tissue samples from the subject. In some embodiments, the sample is a biological sample.

The terms "body fluid" or "bodily fluids" are liquids originating from inside the bodies of organisms. Bodily fluids include amniotic fluid, aqueous humour, vitreous humour, bile, whole blood, blood, serum, plasma, breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. Immunoglobulin G (IgG), the most abundant antibody subclass, may be found in all body fluids. "Biological sample" also includes a mixture of the above-mentioned body fluids. "Biological samples" may be untreated or pretreated (or pre-processed) biological samples.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaXis blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device. Additional sample collection procedures and devices include but are not limited to: a tissue sample collection device; standard collection/storage device (e.g., a collection/storage device for collection and/or storage of a sample (e.g., blood, plasma, serum, urine, etc.); a dried blood spot sampling device. In some embodiments, the Volumetric Absorptive Microsampling (VAMS™) samples can be stored and mailed, and an assay can be performed remotely.

Compounds

In various embodiments, the present invention provides a compound selected from:

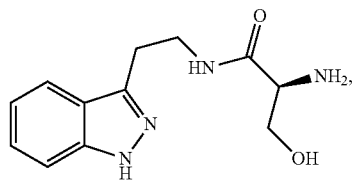 [SMILES: N[C@@H](CO)C(=O)NCCc1n[nH]c2ccccc12]

or a prodrug, isomer, dimer, enantiomer, derivative, or pharmaceutically acceptable salt thereof.

In various embodiments, the present invention provides a compound selected from:

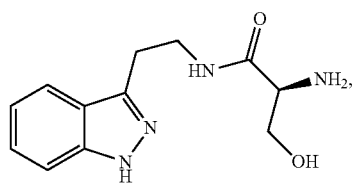 [SMILES: N[C@@H](CO)C(=O)NCCc1n[nH]c2ccccc12]

or any pharmaceutically acceptable salt thereof.

In various embodiments, the present invention provides a compound selected from:

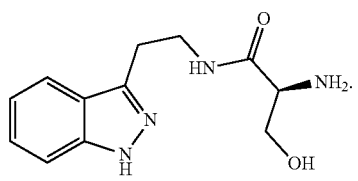 [SMILES: N[C@@H](CO)C(=O)NCCc1n[nH]c2ccccc12]

In various embodiments, the present invention provides a compound selected from:

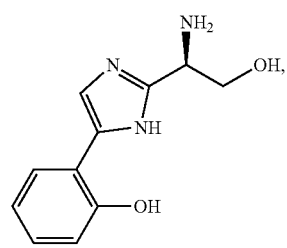 [SMILES: N[C@@H](CO)c1ncc(-c2ccccc2O)[nH]1]

or a prodrug, isomer, dimer, enantiomer, derivative, or pharmaceutically acceptable salt thereof.

In various embodiments, the present invention provides a compound selected from:

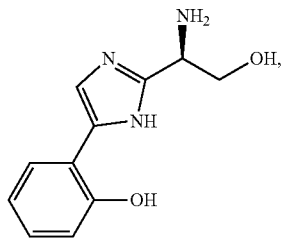 [SMILES: N[C@@H](CO)c1ncc(-c2ccccc2O)[nH]1]

or any pharmaceutically acceptable salt thereof.

In various embodiments, the present invention provides a compound selected from:

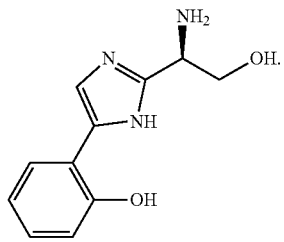 [SMILES: N[C@@H](CO)c1ncc(-c2ccccc2O)[nH]1]

Various embodiments of the present invention provide prodrugs, isomers, dimers, enantiomers, and derivatives of a compound selected from:

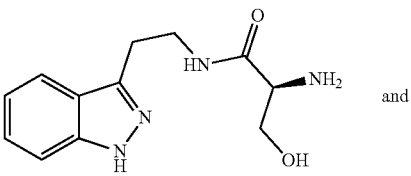 and

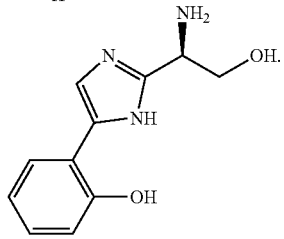

Various embodiments of the present invention provide prodrugs, isomers, dimers, enantiomers, and derivatives of a compound selected from:

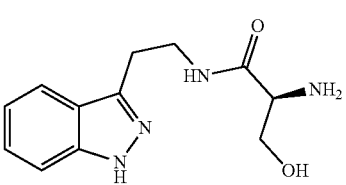 and

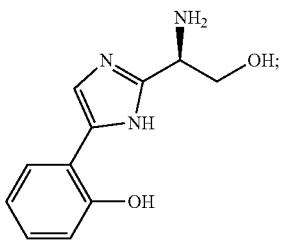

and any pharmaceutically acceptable salt thereof.

Various embodiments of the present invention provide prodrugs, isomers, dimers, enantiomers, and derivatives of a compound selected from:

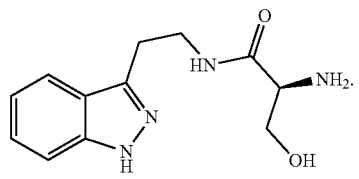 [SMILES: N[C@@H](CO)C(=O)NCCc1n[nH]c2ccccc12]

Various embodiments of the present invention provide prodrugs, isomers, dimers, enantiomers, and derivatives of a compound selected from:

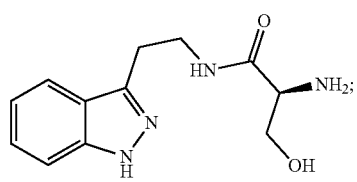 [SMILES: N[C@@H](CO)C(=O)NCCc1n[nH]c2ccccc12]

and any pharmaceutically acceptable salt thereof.

Various embodiments of the present invention provide prodrugs, isomers, dimers, enantiomers, and derivatives of a compound selected from:

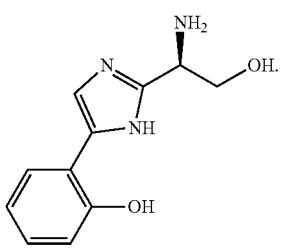 [SMILES: N[C@@H](CO)c1ncc(-c2ccccc2O)[nH]1]

Various embodiments of the present invention provide prodrugs, isomers, dimers, enantiomers, and derivatives of a compound selected from:

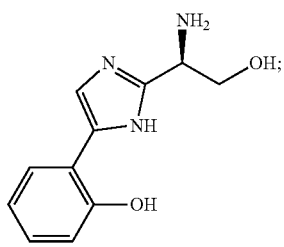 [SMILES: N[C@@H](CO)c1ncc(-c2ccccc2O)[nH]1]

and any pharmaceutically acceptable salt thereof.

In various embodiments, compounds of the present invention as disclosed herein may be synthesized using any synthetic method available to one of skill in the art. Non-limiting examples of synthetic methods used to prepare various embodiments of compounds of the present invention are disclosed in the Examples section herein.

Therapeutic Methods

In some embodiments, provided herein are methods for treating, inhibiting, reducing the severity of, delaying progression (slowing metastasis) of and/or preventing metastases of SCLC in a subject in need thereof. In one embodiment, the subject with SCLC overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of SCLC in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of SCLC in the subject.

In some embodiments, provided herein are methods for treating, inhibiting, reducing the severity of, delaying progression (slowing metastasis) of and/or preventing metastases of neuroblastoma in a subject in need thereof. In one embodiment, the subject with neuroblastoma overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of neuroblastoma in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of neuroblastoma in the subject.

In some embodiments, provided herein are methods for treating, inhibiting, reducing the severity of, delaying progression (slowing metastasis) of and/or preventing metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in a subject in need thereof. In one embodiment, the subject with neuroblastoma, small cell lung cancer (SCLC), large cell neuroendocrine cancer (LCNEC), large-cell carcinoma (LCC), squamous cell carcinoma (SqCC), or adenocarcinoma (AC) overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject.

Methods for Treating, Inhibiting, and/or Reducing the Severity of Small Cell Lung Cancer (SCLC)

In various embodiments, the present invention provides a method for treating, inhibiting, and/or reducing the severity of small cell lung cancer (SCLC) in a subject in need thereof, comprising providing an agent that inhibits expression or activity of ONECUT2; and administering a therapeutically effective amount of the agent to the subject so as to treat, inhibit, and/or reduce the severity of small cell lung cancer (SCLC) in the subject.

In various embodiments, the present invention provides a method for treating, inhibiting, and/or reducing the severity of small cell lung cancer (SCLC) in a subject in need thereof, comprising: providing a composition that comprises at least one agent that inhibits expression or activity of ONECUT2; and administering a therapeutically effective amount of the composition to the subject so as to treat, inhibit, and/or reduce the severity of small cell lung cancer (SCLC) in the subject.

In some embodiments, the small cell lung cancer (SCLC) overexpresses ONECUT2. In some embodiments, the composition is a pharmaceutical composition. In some embodiments, the method further comprises administering at least one additional anti-SCLC therapy to the subject. In some embodiments, the additional anti-SCLC therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-SCLC therapy are administered sequentially or simultaneously. In some embodiments, the composition and the anti-SCLC therapy are administered sequentially or simultaneously.

Methods for Diagnosing and Treating Small Cell Lung Cancer (SCLC)

In various embodiments, the present invention provides a method for diagnosing and treating small cell lung cancer (SCLC) in a subject, comprising: obtaining a sample from the subject; assaying the sample to determine the expression level of ONECUT2; diagnosing the subject with small cell lung cancer (SCLC) if the expression of ONECUT2 is increased relative to a reference value; and administering a treatment to the subject so as to treat the small cell lung cancer (SCLC), wherein the treatment comprises an agent that inhibits expression or activity of ONECUT2.

In various embodiments, the present invention provides a method for diagnosing and treating small cell lung cancer (SCLC) in a subject, comprising: obtaining a sample from the subject; assaying the sample to determine the expression level of ONECUT2; diagnosing the subject with small cell lung cancer (SCLC) if the expression of ONECUT2 is increased relative to a reference value; and administering a treatment to the subject so as to treat the small cell lung cancer (SCLC), wherein the treatment comprises a composition that comprises at least one agent that inhibits expression or activity of ONECUT2.

In some embodiments, the composition is a pharmaceutical composition. In some embodiments, the method further comprises administering at least one additional anti-SCLC therapy to the subject. In some embodiments, the additional anti-SCLC therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-SCLC therapy are administered sequentially or simultaneously. In some embodiments, the composition and the additional anti-SCLC therapy are administered sequentially or simultaneously. In some embodiments, the sample is selected from the group consisting of blood, plasma, urine, tissue, and combinations thereof. In some embodiments, the sample is obtained before, during, or after treatment for small cell lung cancer (SCLC). In some embodiments, the reference value is the mean or median level of ONECUT2 expression in a population of subjects that do not have small cell lung cancer (SCLC). In some embodiments, the reference value is the mean or median level of ONECUT2 expression in the subject, wherein the sample is obtained from the subject at an earlier time period. In some embodiments, the reference value is from a control subject, wherein the control subject does not have small cell lung cancer (SCLC).

Methods for Treating Small Cell Lung Cancer (SCLC)

In various embodiments, the present invention provides a method for treating small cell lung cancer (SCLC) in a subject, comprising: administering to the subject a therapeutically effective amount of at least one agent that inhibits expression or activity of ONECUT2, thereby treating small cell lung cancer (SCLC) in the subject.

In various embodiments, the present invention provides a method for treating small cell lung cancer (SCLC) in a subject, comprising: administering a treatment to the subject, wherein the treatment comprises a therapeutically effective amount of at least one agent that inhibits expression or activity of ONECUT2, thereby treating small cell lung cancer (SCLC) in the subject.

In various embodiments, the present invention provides a method for treating small cell lung cancer (SCLC) in a subject, comprising: administering to the subject a therapeutically effective amount of at least one composition that comprises at least one agent that inhibits expression or activity of ONECUT2, thereby treating small cell lung cancer (SCLC) in the subject.

In various embodiments, the present invention provides a method for treating small cell lung cancer (SCLC) in a subject, comprising: administering a treatment to the subject, wherein the treatment comprises a therapeutically effective amount of at least one composition that comprises at least one agent that inhibits expression or activity of ONECUT2, thereby treating small cell lung cancer (SCLC) in the subject.

In various embodiments, the present invention provides a method for treating small cell lung cancer in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating small cell lung cancer in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the small cell lung cancer (SCLC) overexpresses ONECUT2.

Methods for Inhibiting Small Cell Lung Cancer (SCLC)

In various embodiments, the present invention provides a method for inhibiting small cell lung cancer (SCLC) in a subject, comprising: administering to the subject a therapeutically effective amount of at least one agent that inhibits expression or activity of ONECUT2, thereby inhibiting small cell lung cancer (SCLC) in the subject.

In various embodiments, the present invention provides a method for inhibiting small cell lung cancer (SCLC) in a subject, comprising: administering a treatment to the subject, wherein the treatment comprises a therapeutically effective amount of at least one agent that inhibits expression or activity of ONECUT2, thereby inhibiting small cell lung cancer (SCLC) in the subject.

In various embodiments, the present invention provides a method for inhibiting small cell lung cancer (SCLC) in a subject, comprising: administering to the subject a therapeutically effective amount of at least one composition that comprises at least one agent that inhibits expression or activity of ONECUT2, thereby inhibiting small cell lung cancer (SCLC) in the subject.

In various embodiments, the present invention provides a method for inhibiting small cell lung cancer (SCLC) in a subject, comprising: administering a treatment to the subject, wherein the treatment comprises a therapeutically effective amount of at least one composition that comprises at least one agent that inhibits expression or activity of ONECUT2, thereby inhibiting small cell lung cancer (SCLC) in the subject.

In some embodiments, the at least one composition is at least one pharmaceutical composition. In some embodiments, the small cell lung cancer (SCLC) overexpresses ONECUT2.

Methods for Reducing the Severity of Small Cell Lung Cancer (SCLC)

In various embodiments, the present invention provides a method for reducing the severity of small cell lung cancer (SCLC) in a subject, comprising: administering to the subject a therapeutically effective amount of at least one agent that inhibits expression or activity of ONECUT2, thereby reducing the severity of small cell lung cancer (SCLC) in the subject.

In various embodiments, the present invention provides a method for reducing the severity of small cell lung cancer (SCLC) in a subject, comprising: administering a treatment to the subject, wherein the treatment comprises a therapeutically effective amount of at least one agent that inhibits expression or activity of ONECUT2, thereby reducing the severity of small cell lung cancer (SCLC) in the subject.

In various embodiments, the present invention provides a method for reducing the severity of small cell lung cancer (SCLC) in a subject, comprising: administering to the subject a therapeutically effective amount of at least one composition that comprises at least one agent that inhibits expression or activity of ONECUT2, thereby reducing the severity of small cell lung cancer (SCLC) in the subject.

In various embodiments, the present invention provides a method for reducing the severity of small cell lung cancer (SCLC) in a subject, comprising: administering a treatment to the subject, wherein the treatment comprises a therapeutically effective amount of at least one composition that comprises at least one agent that inhibits expression or activity of ONECUT2, thereby reducing the severity of small cell lung cancer (SCLC) in the subject.

In some embodiments, the at least one composition is at least one pharmaceutical composition. In some embodiments, the small cell lung cancer (SCLC) overexpresses ONECUT2.

Methods for Promoting Prophylaxis of Small Cell Lung Cancer

In various embodiments, the present invention provides a method for promoting prophylaxis of small cell lung cancer (SCLC) in a subject, comprising: administering to the subject a therapeutically effective amount of at least one agent that inhibits expression or activity of ONECUT2, thereby reducing the severity of small cell lung cancer (SCLC) in the subject.

In various embodiments, the present invention provides a method for promoting prophylaxis of small cell lung cancer (SCLC) in a subject, comprising: administering a treatment to the subject, wherein the treatment comprises a therapeutically effective amount of at least one agent that inhibits expression or activity of ONECUT2, thereby reducing the severity of small cell lung cancer (SCLC) in the subject.

In various embodiments, the present invention provides a method for promoting prophylaxis of small cell lung cancer (SCLC) in a subject, comprising: administering to the subject a therapeutically effective amount of at least one composition that comprises at least one agent that inhibits expression or activity of ONECUT2, thereby reducing the severity of small cell lung cancer (SCLC) in the subject.

In various embodiments, the present invention provides a method for promoting prophylaxis of small cell lung cancer (SCLC) in a subject, comprising: administering a treatment to the subject, wherein the treatment comprises a therapeutically effective amount of at least one composition that comprises at least one agent that inhibits expression or activity of ONECUT2, thereby reducing the severity of small cell lung cancer (SCLC) in the subject.

In some embodiments, the at least one composition is at least one pharmaceutical composition. In some embodiments, the small cell lung cancer (SCLC) overexpresses ONECUT2.

Methods for Treating, Inhibiting, Reducing the Severity of, Delaying Progression of and/or Preventing Metastases of Small Cell Lung Cancer (SCLC)

In various embodiments, the present invention provides a method of treating, inhibiting, reducing the severity of, delaying progression of and/or preventing metastases of small cell lung cancer in a subject, comprising: administering to the subject a therapeutically effective amount of at least one agent that inhibits expression or activity of ONECUT2, thereby treating, inhibiting, reducing the severity of, delaying progression of and/or preventing metastases of small cell lung cancer (SCLC) in the subject.

In various embodiments, the present invention provides a method of treating, inhibiting, reducing the severity of, delaying progression of and/or preventing metastases of small cell lung cancer in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of small cell lung cancer (SCLC) in the subject.

In various embodiments, the present invention provides a method of treating, inhibiting, reducing the severity of, delaying progression of and/or preventing metastases of small cell lung cancer in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of small cell lung cancer (SCLC) in the subject.

In various embodiments, the present invention provides a method of treating, inhibiting, reducing the severity of, delaying progression of and/or preventing metastases of small cell lung cancer in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of small cell lung cancer (SCLC) in the subject.

In some embodiments, the at least one composition is at least one pharmaceutical composition. In some embodiments, the small cell lung cancer (SCLC) overexpresses ONECUT2.

Methods for Treating, Inhibiting, and/or Reducing the Severity of Neuroblastoma

In various embodiments, the present invention provides a method for treating, inhibiting, and/or reducing the severity of neuroblastoma in a subject in need thereof, comprising providing an agent that inhibits expression or activity of ONECUT2; and administering a therapeutically effective amount of the agent to the subject so as to treat, inhibit, and/or reduce the severity of neuroblastoma in the subject.

In various embodiments, the present invention provides a method for treating, inhibiting, and/or reducing the severity of neuroblastoma in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, and/or reduce the severity of neuroblastoma in the subject.

In some embodiments, the neuroblastoma overexpresses ONECUT2. In some embodiments, the composition is a pharmaceutical composition. In some embodiments, the method further comprises administering at least one additional anti-neuroblastoma therapy to the subject. In some embodiments, the additional anti-neuroblastoma therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-neuroblastoma therapy are administered sequentially or simultaneously. In some embodiments, the composition and the anti-neuroblastoma therapy are administered sequentially or simultaneously.

Methods for Diagnosing and Treating Neuroblastoma

In various embodiments, the present invention provides a method for diagnosing and treating neuroblastoma in a subject, comprising: obtaining a sample from the subject; assaying the sample to determine the expression level of ONECUT2; diagnosing the subject with neuroblastoma if the expression of ONECUT2 is increased relative to a reference value; and administering a treatment to the subject so as to treat the neuroblastoma, wherein the treatment comprises an agent that inhibits expression or activity of ONECUT2.

In various embodiments, the present invention provides a method for diagnosing and treating neuroblastoma in a subject, comprising: obtaining a sample from the subject; assaying the sample to determine the expression level of ONECUT2; diagnosing the subject with neuroblastoma if the expression of ONECUT2 is increased relative to a reference value; and administering a treatment to the subject so as to treat the neuroblastoma, wherein the treatment comprises a composition that comprises at least one agent that inhibits expression or activity of ONECUT2, wherein the composition comprises at least one agent that inhibits expression or activity of ONECUT2

In some embodiments, the composition is a pharmaceutical composition. In some embodiments, the method further comprises administering at least one additional anti-neuroblastoma therapy to the subject. In some embodiments, the additional anti-neuroblastoma therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-neuroblastoma therapy are administered sequentially or simultaneously. In some embodiments, the composition and the additional anti-neuroblastoma therapy are administered sequentially or simultaneously. In some embodiments, the sample is selected from the group consisting of blood, plasma, urine, tissue, and combinations thereof. In some embodiments, the sample is obtained before, during, or after treatment for neuroblastoma. In some embodiments, the reference value is the mean or median level of ONECUT2 expression in a population of subjects that do not have neuroblastoma. In some embodiments, the reference value is the mean or median level of ONECUT2 expression in the subject, wherein the sample is obtained from the subject at an earlier time period. In some embodiments, the reference value is from a control subject, wherein the control subject does not have neuroblastoma.

Methods for Treating Neuroblastoma

In various embodiments, the present invention provides a method for treating neuroblastoma in a subject, comprising: administering to the subject a therapeutically effective amount of at least one agent that inhibits expression or activity of ONECUT2, thereby treating neuroblastoma in the subject.

In various embodiments, the present invention provides a method for treating neuroblastoma in a subject, comprising: administering a treatment to the subject, wherein the treatment comprises a therapeutically effective amount of at least one agent that inhibits expression or activity of ONECUT2, thereby treating neuroblastoma in the subject.

In various embodiments, the present invention provides a method for treating neuroblastoma in a subject, comprising: administering to the subject a therapeutically effective amount of at least one composition that comprises at least one agent that inhibits expression or activity of ONECUT2, thereby treating neuroblastoma in the subject.

In various embodiments, the present invention provides a method for treating neuroblastoma in a subject, comprising: administering a treatment to the subject, wherein the treatment comprises a therapeutically effective amount of at least one composition that comprises at least one agent that inhibits expression or activity of ONECUT2, thereby treating neuroblastoma in the subject.

In various embodiments, the present invention provides a method for treating neuroblastoma in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating neuroblastoma in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the neuroblastoma overexpresses ONECUT2.

Methods for Inhibiting Neuroblastoma

In various embodiments, the present invention provides a method for inhibiting neuroblastoma in a subject, comprising: administering to the subject a therapeutically effective amount of at least one agent that inhibits expression or activity of ONECUT2, thereby inhibiting neuroblastoma in the subject.

In various embodiments, the present invention provides a method for inhibiting neuroblastoma in a subject, comprising: administering a treatment to the subject, wherein the treatment comprises a therapeutically effective amount of at least one agent that inhibits expression or activity of ONECUT2, thereby inhibiting neuroblastoma in the subject.

In various embodiments, the present invention provides a method for inhibiting neuroblastoma in a subject, comprising: administering to the subject a therapeutically effective amount of at least one composition that comprises at least one agent that inhibits expression or activity of ONECUT2, thereby inhibiting neuroblastoma in the subject.

In various embodiments, the present invention provides a method for inhibiting neuroblastoma in a subject, comprising: administering a treatment to the subject, wherein the treatment comprises a therapeutically effective amount of at least one composition that comprises at least one agent that inhibits expression or activity of ONECUT2, thereby inhibiting neuroblastoma in the subject.

In some embodiments, the at least one composition is at least one pharmaceutical composition. In some embodiments, the neuroblastoma overexpresses ONECUT2.

Methods for Reducing the Severity of Neuroblastoma

In various embodiments, the present invention provides a method for reducing the severity of neuroblastoma in a subject, comprising: administering to the subject a therapeutically effective amount of at least one agent that inhibits expression or activity of ONECUT2, thereby reducing the severity of neuroblastoma in the subject.

In various embodiments, the present invention provides a method for reducing the severity of neuroblastoma in a subject, comprising: administering a treatment to the subject, wherein the treatment comprises a therapeutically effective amount of at least one agent that inhibits expression or activity of ONECUT2, thereby reducing the severity of neuroblastoma in the subject.

In various embodiments, the present invention provides a method for reducing the severity of neuroblastoma in a subject, comprising: administering to the subject a therapeutically effective amount of at least one composition that comprises at least one agent that inhibits expression or activity of ONECUT2, thereby reducing the severity of neuroblastoma in the subject.

In various embodiments, the present invention provides a method for reducing the severity of neuroblastoma in a subject, comprising: administering a treatment to the subject, wherein the treatment comprises a therapeutically effective amount of at least one composition that comprises at least one agent that inhibits expression or activity of ONECUT2, thereby reducing the severity of neuroblastoma in the subject.

In some embodiments, the at least one composition is at least one pharmaceutical composition. In some embodiments, the neuroblastoma overexpresses ONECUT2.

Methods for Promoting Prophylaxis of Neuroblastoma

In various embodiments, the present invention provides a method for promoting prophylaxis of neuroblastoma in a subject, comprising: administering to the subject a therapeutically effective amount of at least one agent that inhibits expression or activity of ONECUT2, thereby reducing the severity of neuroblastoma in the subject.

In various embodiments, the present invention provides a method for promoting prophylaxis of neuroblastoma in a subject, comprising: administering a treatment to the subject, wherein the treatment comprises a therapeutically effective amount of at least one agent that inhibits expression or activity of ONECUT2, thereby reducing the severity of neuroblastoma in the subject.

In various embodiments, the present invention provides a method for promoting prophylaxis of neuroblastoma in a subject, comprising: administering to the subject a therapeutically effective amount of at least one composition that comprises at least one agent that inhibits expression or activity of ONECUT2, thereby reducing the severity of neuroblastoma in the subject.

In various embodiments, the present invention provides a method for promoting prophylaxis of neuroblastoma in a subject, comprising: administering a treatment to the subject, wherein the treatment comprises a therapeutically effective amount of at least one composition that comprises at least one agent that inhibits expression or activity of ONECUT2, thereby reducing the severity of neuroblastoma in the subject.

In some embodiments, the at least one composition is at least one pharmaceutical composition. In some embodiments, the neuroblastoma overexpresses ONECUT2.

Methods for Treating, Inhibiting, Reducing the Severity of, Delaying Progression of and/or Preventing Metastases of Neuroblastoma In various embodiments, the present invention provides a method of treating, inhibiting, reducing the severity of, delaying progression of and/or preventing metastases of neuroblastoma in a subject, comprising: administering to the subject a therapeutically effective amount of at least one agent that inhibits expression or activity of ONECUT2, thereby treating, inhibiting, reducing the severity of, delaying progression of and/or preventing metastases of neuroblastoma in the subject.

In various embodiments, the present invention provides a method of treating, inhibiting, reducing the severity of, delaying progression of and/or preventing metastases of neuroblastoma in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of neuroblastoma in the subject.

In various embodiments, the present invention provides a method of treating, inhibiting, reducing the severity of, delaying progression of and/or preventing metastases of neuroblastoma in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of neuroblastoma in the subject.

In various embodiments, the present invention provides a method of treating, inhibiting, reducing the severity of, delaying progression of and/or preventing metastases of neuroblastoma in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of neuroblastoma in the subject.

In some embodiments, the at least one composition is at least one pharmaceutical composition. In some embodiments, the neuroblastoma overexpresses ONECUT2.

Methods for Treating, Inhibiting, Reducing the Severity of and/or Promoting Prophylaxis of Large Cell Neuroendocrine Cancer (LCNEC)

In various embodiments, the present invention provides a method for treating, inhibiting, reducing the severity of, and/or promoting prophylaxis of large cell neuroendocrine cancer (LCNEC) in a subject in need thereof, comprising providing an agent that inhibits expression or activity of ONECUT2; and administering a therapeutically effective amount of the agent to the subject so as to treat, inhibit, reduce the severity of, and/or promote prophylaxis of large cell neuroendocrine cancer (LCNEC) in the subject.

In various embodiments, the present invention provides a method for treating, inhibiting, reducing the severity of, and/or promoting prophylaxis large cell neuroendocrine cancer (LCNEC) in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of, and/or promote prophylaxis of large cell neuroendocrine cancer (LCNEC) in the subject.

In some embodiments, the large cell neuroendocrine cancer (LCNEC) overexpresses ONECUT2. In some embodiments, the composition is a pharmaceutical composition. In some embodiments, the method further comprises administering at least one additional anti-large cell neuroendocrine cancer (anti-LCNEC) therapy to the subject. In some embodiments, the additional anti-large cell neuroendocrine cancer (anti-LCNEC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-large cell neuroendocrine cancer (anti-LCNEC) therapy are administered sequentially or simultaneously. In some embodiments, the composition and the anti-large cell neuroendocrine cancer (anti-LCNEC) therapy are administered sequentially or simultaneously.

Methods for Diagnosing and Treating Large Cell Neuroendocrine Cancer (LCNEC)

In various embodiments, the present invention provides a method for diagnosing and treating large cell neuroendocrine cancer (LCNEC) in a subject, comprising: obtaining a sample from the subject; assaying the sample to determine the expression level of ONECUT2; diagnosing the subject with large cell neuroendocrine cancer (LCNEC) if the expression of ONECUT2 is increased relative to a reference value; and administering a treatment to the subject so as to treat the large cell neuroendocrine cancer (LCNEC), wherein the treatment comprises an agent that inhibits expression or activity of ONECUT2.

In various embodiments, the present invention provides a method for diagnosing and treating large cell neuroendocrine cancer (LCNEC) in a subject, comprising: obtaining a sample from the subject; assaying the sample to determine the expression level of ONECUT2; diagnosing the subject with large cell neuroendocrine cancer (LCNEC) if the expression of ONECUT2 is increased relative to a reference value; and administering a treatment to the subject so as to treat the large cell neuroendocrine cancer (LCNEC), wherein the treatment comprises a composition that comprises at least one agent that inhibits expression or activity of ONECUT2, wherein the composition comprises at least one agent that inhibits expression or activity of ONECUT2

In some embodiments, the composition is a pharmaceutical composition. In some embodiments, the method further comprises administering at least one additional anti-large cell neuroendocrine cancer (anti-LCNEC) therapy to the subject. In some embodiments, the additional anti-large cell neuroendocrine cancer (anti-LCNEC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administered to the subject for 1-5 days, 1-5 weeks, 1-5 months, or 1-5 years. In some embodiments, the agent and the additional anti-large cell neuroendocrine cancer (anti-LCNEC) therapy are administered sequentially or simultaneously. In some embodiments, the composition and the additional anti-large cell neuroendocrine cancer (anti-LCNEC) therapy are administered sequentially or simultaneously. In some embodiments, the sample is selected from the group consisting of blood, plasma, urine, tissue, and combinations thereof. In some embodiments, the sample is obtained before, during, or after treatment for large cell neuroendocrine cancer (LCNEC). In some embodiments, the reference value is the mean or median level of ONECUT2 expression in a population of subjects that do not have large cell neuroendocrine cancer (LCNEC). In some embodiments, the reference value is the mean or median level of ONECUT2 expression in the subject, wherein the sample is obtained from the subject at an earlier time period. In some embodiments, the reference value is from a control subject, wherein the control subject does not have large cell neuroendocrine cancer (LCNEC).

Methods for Treating Large Cell Neuroendocrine Cancer (LCNEC)

In various embodiments, the present invention provides a method for treating large cell neuroendocrine cancer (LCNEC) in a subject, comprising: administering to the subject a therapeutically effective amount of at least one agent that inhibits expression or activity of ONECUT2, thereby treating large cell neuroendocrine cancer (LCNEC) in the subject.

In various embodiments, the present invention provides a method for treating large cell neuroendocrine cancer (LCNEC) in a subject, comprising: administering a treatment to the subject, wherein the treatment comprises a therapeutically effective amount of at least one agent that inhibits expression or activity of ONECUT2, thereby treating large cell neuroendocrine cancer (LCNEC) in the subject.

In various embodiments, the present invention provides a method for treating large cell neuroendocrine cancer (LCNEC) in a subject, comprising: administering to the subject a therapeutically effective amount of at least one composition that comprises at least one agent that inhibits expression or activity of ONECUT2, thereby treating large cell neuroendocrine cancer (LCNEC) in the subject.

In various embodiments, the present invention provides a method for treating large cell neuroendocrine cancer (LCNEC) in a subject, comprising: administering a treatment to the subject, wherein the treatment comprises a therapeutically effective amount of at least one composition that comprises at least one agent that inhibits expression or activity of ONECUT2, thereby treating large cell neuroendocrine cancer (LCNEC) in the subject.

In various embodiments, the present invention provides a method for treating large cell neuroendocrine cancer (LCNEC) in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating large cell neuroendocrine cancer (LCNEC) in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the large cell neuroendocrine cancer (LCNEC) overexpresses ONECUT2.

Methods for Treating, Inhibiting, Reducing the Severity of, Delaying Progression of and/or Preventing Metastases of Large Cell Neuroendocrine Cancer (LCNEC)

In various embodiments, the present invention provides a method of treating, inhibiting, reducing the severity of, delaying progression of and/or preventing metastases of large cell neuroendocrine cancer (LCNEC) in a subject, comprising: administering to the subject a therapeutically effective amount of at least one agent that inhibits expression or activity of ONECUT2, thereby treating, inhibiting, reducing the severity of, delaying progression of and/or preventing metastases of large cell neuroendocrine cancer (LCNEC) in the subject.

In various embodiments, the present invention provides a method of treating, inhibiting, reducing the severity of, delaying progression of and/or preventing metastases of large cell neuroendocrine cancer (LCNEC) in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of large cell neuroendocrine cancer (LCNEC) in the subject.

In various embodiments, the present invention provides a method of treating, inhibiting, reducing the severity of, delaying progression of and/or preventing metastases of large cell neuroendocrine cancer (LCNEC) in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of large cell neuroendocrine cancer (LCNEC) in the subject.

In various embodiments, the present invention provides a method of treating, inhibiting, reducing the severity of, delaying progression of and/or preventing metastases of large cell neuroendocrine cancer (LCNEC) in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of large cell neuroendocrine cancer (LCNEC) in the subject.

In some embodiments, the at least one composition is at least one pharmaceutical composition. In some embodiments, the large cell neuroendocrine cancer (LCNEC) overexpresses ONECUT2.

Methods for Treating, Inhibiting, Reducing the Severity of and/or Promoting Prophylaxis of Large-Cell Carcinoma (LCC)

In various embodiments, the present invention provides a method for treating, inhibiting, reducing the severity of and/or promoting prophylaxis of large-cell carcinoma (LCC) in a subject in need thereof, comprising providing an agent that inhibits expression or activity of ONECUT2; and administering a therapeutically effective amount of the agent to the subject so as to treat, inhibit, reduce the severity of and/or promote prophylaxis of large-cell carcinoma (LCC) in the subject.

In various embodiments, the present invention provides a method for treating, inhibiting, reducing the severity of and/or promoting prophylaxis of large-cell carcinoma (LCC) in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of and/or promote prophylaxis of large-cell carcinoma (LCC) in the subject.

In some embodiments, the large-cell carcinoma (LCC) overexpresses ONECUT2. In some embodiments, the composition is a pharmaceutical composition. In some embodiments, the method further comprises administering at least one additional anti-large-cell carcinoma (anti-LCC) therapy to the subject. In some embodiments, the additional anti-large-cell carcinoma (anti-LCC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-large-cell carcinoma (anti-LCC) therapy are administered sequentially or simultaneously. In some embodiments, the composition and the anti-large-cell carcinoma (anti-LCC) therapy are administered sequentially or simultaneously.

Methods for Diagnosing and Treating Large-Cell Carcinoma (LCC)

In various embodiments, the present invention provides a method for diagnosing and treating large-cell carcinoma (LCC) in a subject, comprising: obtaining a sample from the subject; assaying the sample to determine the expression level of ONECUT2; diagnosing the subject with large-cell carcinoma (LCC) if the expression of ONECUT2 is increased relative to a reference value; and administering a treatment to the subject so as to treat the large-cell carcinoma (LCC), wherein the treatment comprises an agent that inhibits expression or activity of ONECUT2.

In various embodiments, the present invention provides a method for diagnosing and treating large-cell carcinoma (LCC) in a subject, comprising: obtaining a sample from the subject; assaying the sample to determine the expression level of ONECUT2; diagnosing the subject with large-cell carcinoma (LCC) if the expression of ONECUT2 is increased relative to a reference value; and administering a treatment to the subject so as to treat the large-cell carcinoma (LCC), wherein the treatment comprises a composition that comprises at least one agent that inhibits expression or activity of ONECUT2, wherein the composition comprises at least one agent that inhibits expression or activity of ONECUT2

In some embodiments, the composition is a pharmaceutical composition. In some embodiments, the method further comprises administering at least one additional anti-large-cell carcinoma (anti-LCC) therapy to the subject. In some embodiments, the additional anti-large-cell carcinoma (anti-LCC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-large-cell carcinoma (anti-LCC) therapy are administered sequentially or simultaneously. In some embodiments, the composition and the additional anti-large-cell carcinoma (anti-LCC) therapy are administered sequentially or simultaneously. In some embodiments, the sample is selected from the group consisting of blood, plasma, urine, tissue, and combinations thereof. In some embodiments, the sample is obtained before, during, or after treatment for large-cell carcinoma (LCC). In some embodiments, the reference value is the mean or median level of ONECUT2 expression in a population of subjects that do not have large-cell carcinoma (LCC). In some embodiments, the reference value is the mean or median level of ONECUT2 expression in the subject, wherein the sample is obtained from the subject at an earlier time period. In some embodiments, the reference value is from a control subject, wherein the control subject does not have large-cell carcinoma (LCC).

Methods for Treating Large-Cell Carcinoma (LCC)

In various embodiments, the present invention provides a method for treating large-cell carcinoma (LCC) in a subject, comprising: administering to the subject a therapeutically effective amount of at least one agent that inhibits expression or activity of ONECUT2, thereby treating large-cell carcinoma (LCC) in the subject.

In various embodiments, the present invention provides a method for treating large-cell carcinoma (LCC) in a subject, comprising: administering a treatment to the subject, wherein the treatment comprises a therapeutically effective amount of at least one agent that inhibits expression or activity of ONECUT2, thereby treating large-cell carcinoma (LCC) in the subject.

In various embodiments, the present invention provides a method for treating large-cell carcinoma (LCC) in a subject, comprising: administering to the subject a therapeutically effective amount of at least one composition that comprises at least one agent that inhibits expression or activity of ONECUT2, thereby treating large-cell carcinoma (LCC) in the subject.

In various embodiments, the present invention provides a method for treating large-cell carcinoma (LCC) in a subject, comprising: administering a treatment to the subject, wherein the treatment comprises a therapeutically effective amount of at least one composition that comprises at least one agent that inhibits expression or activity of ONECUT2, thereby treating large-cell carcinoma (LCC) in the subject.

In various embodiments, the present invention provides a method for treating large-cell carcinoma (LCC) in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating large-cell carcinoma (LCC) in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the large-cell carcinoma (LCC) overexpresses ONECUT2.

Methods for Treating, Inhibiting, Reducing the Severity of, Delaying Progression of and/or Preventing Metastases of Large-Cell Carcinoma (LCC)

In various embodiments, the present invention provides a method of treating, inhibiting, reducing the severity of, delaying progression of and/or preventing metastases of large-cell carcinoma (LCC) in a subject, comprising: administering to the subject a therapeutically effective amount of at least one agent that inhibits expression or activity of ONECUT2, thereby treating, inhibiting, reducing the severity of, delaying progression of and/or preventing metastases of large-cell carcinoma (LCC) in the subject.

In various embodiments, the present invention provides a method of treating, inhibiting, reducing the severity of, delaying progression of and/or preventing metastases of large-cell carcinoma (LCC) in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of large-cell carcinoma (LCC) in the subject.

In various embodiments, the present invention provides a method of treating, inhibiting, reducing the severity of, delaying progression of and/or preventing metastases of large-cell carcinoma (LCC) in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of large-cell carcinoma (LCC) in the subject.

In various embodiments, the present invention provides a method of treating, inhibiting, reducing the severity of, delaying progression of and/or preventing metastases of large-cell carcinoma (LCC) in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of large-cell carcinoma (LCC) in the subject.

In some embodiments, the at least one composition is at least one pharmaceutical composition. In some embodiments, the large-cell carcinoma (LCC) overexpresses ONECUT2.

Methods for Treating, Inhibiting, Reducing the Severity of and/or Promoting Prophylaxis of Squamous Cell Carcinoma (SqCC)

In various embodiments, the present invention provides a method for treating, inhibiting, reducing the severity of and/or promoting prophylaxis of squamous cell carcinoma (SqCC) in a subject in need thereof, comprising providing an agent that inhibits expression or activity of ONECUT2; and administering a therapeutically effective amount of the agent to the subject so as to treat, inhibit, reduce the severity of, and/or promote prophylaxis of squamous cell carcinoma (SqCC) in the subject.

In various embodiments, the present invention provides a method for treating, inhibiting, reducing the severity of and/or promoting prophylaxis of squamous cell carcinoma (SqCC) in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of, and/or promote prophylaxis of squamous cell carcinoma (SqCC) in the subject.

In some embodiments, the squamous cell carcinoma (SqCC) overexpresses ONECUT2. In some embodiments, the composition is a pharmaceutical composition. In some embodiments, the method further comprises administering at least one additional anti-squamous cell carcinoma (anti-SqCC) therapy to the subject. In some embodiments, the additional anti-squamous cell carcinoma (anti-SqCC) is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-squamous cell carcinoma (anti-SqCC) therapy are administered sequentially or simultaneously. In some embodiments, the composition and the anti-squamous cell carcinoma (anti-SqCC) therapy are administered sequentially or simultaneously.

Methods for Diagnosing and Treating Squamous Cell Carcinoma (SqCC)

In various embodiments, the present invention provides a method for diagnosing and treating squamous cell carcinoma (SqCC) in a subject, comprising: obtaining a sample from the subject; assaying the sample to determine the expression level of ONECUT2; diagnosing the subject with squamous cell carcinoma (SqCC) if the expression of ONECUT2 is increased relative to a reference value; and administering a treatment to the subject so as to treat the squamous cell carcinoma (SqCC), wherein the treatment comprises an agent that inhibits expression or activity of ONECUT2.

In various embodiments, the present invention provides a method for diagnosing and treating squamous cell carcinoma (SqCC) in a subject, comprising: obtaining a sample from the subject; assaying the sample to determine the expression level of ONECUT2; diagnosing the subject with squamous cell carcinoma (SqCC) if the expression of ONECUT2 is increased relative to a reference value; and administering a treatment to the subject so as to treat the squamous cell carcinoma (SqCC), wherein the treatment comprises a composition that comprises at least one agent that inhibits expression or activity of ONECUT2, wherein the composition comprises at least one agent that inhibits expression or activity of ONECUT2

In some embodiments, the composition is a pharmaceutical composition. In some embodiments, the method further comprises administering at least one additional anti-squamous cell carcinoma (anti-SqCC) therapy to the subject. In some embodiments, the additional anti-squamous cell carcinoma (anti-SqCC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-squamous cell carcinoma (anti-SqCC) therapy are administered sequentially or simultaneously. In some embodiments, the composition and the additional anti-squamous cell carcinoma (anti-SqCC) therapy are administered sequentially or simultaneously. In some embodiments, the sample is selected from the group consisting of blood, plasma, urine, tissue, and combinations thereof. In some embodiments, the sample is obtained before, during, or after treatment for squamous cell carcinoma (SqCC). In some embodiments, the reference value is the mean or median level of ONECUT2 expression in a population of subjects that do not have squamous cell carcinoma (SqCC). In some embodiments, the reference value is the mean or median level of ONECUT2 expression in the subject, wherein the sample is obtained from the subject at an earlier time period. In some embodiments, the reference value is from a control subject, wherein the control subject does not have squamous cell carcinoma (SqCC).

Methods for Treating Squamous Cell Carcinoma (SqCC)

In various embodiments, the present invention provides a method for treating squamous cell carcinoma (SqCC) in a subject, comprising: administering to the subject a therapeutically effective amount of at least one agent that inhibits expression or activity of ONECUT2, thereby treating squamous cell carcinoma (SqCC) in the subject.

In various embodiments, the present invention provides a method for treating squamous cell carcinoma (SqCC) in a subject, comprising: administering a treatment to the subject, wherein the treatment comprises a therapeutically effective amount of at least one agent that inhibits expression or activity of ONECUT2, thereby treating squamous cell carcinoma (SqCC) in the subject.

In various embodiments, the present invention provides a method for treating squamous cell carcinoma (SqCC) in a subject, comprising: administering to the subject a therapeutically effective amount of at least one composition that comprises at least one agent that inhibits expression or activity of ONECUT2, thereby treating squamous cell carcinoma (SqCC) in the subject.

In various embodiments, the present invention provides a method for treating squamous cell carcinoma (SqCC) in a subject, comprising: administering a treatment to the subject, wherein the treatment comprises a therapeutically effective amount of at least one composition that comprises at least one agent that inhibits expression or activity of ONECUT2, thereby treating squamous cell carcinoma (SqCC) in the subject.

In various embodiments, the present invention provides a method for treating squamous cell carcinoma (SqCC) in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating squamous cell carcinoma (SqCC) in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the squamous cell carcinoma (SqCC) overexpresses ONECUT2.

Methods for Treating, Inhibiting, Reducing the Severity of, Delaying Progression of and/or Preventing Metastases of Squamous Cell Carcinoma (SqCC)

In various embodiments, the present invention provides a method of treating, inhibiting, reducing the severity of, delaying progression of and/or preventing metastases of squamous cell carcinoma (SqCC) in a subject, comprising: administering to the subject a therapeutically effective amount of at least one agent that inhibits expression or activity of ONECUT2, thereby treating, inhibiting, reducing the severity of, delaying progression of and/or preventing metastases of squamous cell carcinoma (SqCC) in the subject.

In various embodiments, the present invention provides a method of treating, inhibiting, reducing the severity of, delaying progression of and/or preventing metastases of squamous cell carcinoma (SqCC) in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of squamous cell carcinoma (SqCC) in the subject.

In various embodiments, the present invention provides a method of treating, inhibiting, reducing the severity of, delaying progression of and/or preventing metastases of squamous cell carcinoma (SqCC) in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of squamous cell carcinoma (SqCC) in the subject.

In various embodiments, the present invention provides a method of treating, inhibiting, reducing the severity of, delaying progression of and/or preventing metastases of squamous cell carcinoma (SqCC) in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of squamous cell carcinoma (SqCC) in the subject.

In some embodiments, the at least one composition is at least one pharmaceutical composition. In some embodiments, the squamous cell carcinoma (SqCC) overexpresses ONECUT2.

Methods for Treating, Inhibiting, Reducing the Severity of and/or Promoting Prophylaxis of Adenocarcinoma (AC)

In various embodiments, the present invention provides a method for treating, inhibiting, reducing the severity of, and/or promoting prophylaxis of adenocarcinoma (AC) in a subject in need thereof, comprising providing an agent that inhibits expression or activity of ONECUT2; and administering a therapeutically effective amount of the agent to the subject so as to treat, inhibit, reduce the severity of, and/or promote prophylaxis of adenocarcinoma (AC) in the subject.

In various embodiments, the present invention provides a method for treating, inhibiting, reducing the severity of, and/or promoting prophylaxis of adenocarcinoma (AC) in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of, and/or promote prophylaxis of adenocarcinoma (AC) in the subject.

In some embodiments, the adenocarcinoma (AC) overexpresses ONECUT2. In some embodiments, the composition is a pharmaceutical composition. In some embodiments, the method further comprises administering at least one additional anti-adenocarcinoma (anti-AC) therapy to the subject. In some embodiments, the additional anti-adenocarcinoma (anti-AC) is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-adenocarcinoma (anti-AC) therapy are administered sequentially or simultaneously. In some embodiments, the composition and the anti-adenocarcinoma (anti-AC) therapy are administered sequentially or simultaneously.

Methods for Diagnosing and Treating Adenocarcinoma (AC)

In various embodiments, the present invention provides a method for diagnosing and treating adenocarcinoma (AC) in a subject, comprising: obtaining a sample from the subject; assaying the sample to determine the expression level of ONECUT2; diagnosing the subject with adenocarcinoma (AC) if the expression of ONECUT2 is increased relative to a reference value; and administering a treatment to the subject so as to treat the adenocarcinoma (AC), wherein the treatment comprises an agent that inhibits expression or activity of ONECUT2.

In various embodiments, the present invention provides a method for diagnosing and treating adenocarcinoma (AC) in a subject, comprising: obtaining a sample from the subject; assaying the sample to determine the expression level of ONECUT2; diagnosing the subject with adenocarcinoma (AC) if the expression of ONECUT2 is increased relative to a reference value; and administering a treatment to the subject so as to treat the adenocarcinoma (AC), wherein the treatment comprises a composition that comprises at least one agent that inhibits expression or activity of ONECUT2, wherein the composition comprises at least one agent that inhibits expression or activity of ONECUT2

In some embodiments, the composition is a pharmaceutical composition. In some embodiments, the method further comprises administering at least one additional anti-adenocarcinoma (anti-AC) therapy to the subject. In some embodiments, the additional anti-adenocarcinoma (anti-AC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-adenocarcinoma (anti-AC) therapy are administered sequentially or simultaneously. In some embodiments, the composition and the additional anti-adenocarcinoma (anti-AC) therapy are administered sequentially or simultaneously. In some embodiments, the sample is selected from the group consisting of blood, plasma, urine, tissue, and combinations thereof. In some embodiments, the sample is obtained before, during, or after treatment for adenocarcinoma (AC).

In some embodiments, the reference value is the mean or median level of ONECUT2 expression in a population of subjects that do not have adenocarcinoma (AC). In some embodiments, the reference value is the mean or median level of ONECUT2 expression in the subject, wherein the sample is obtained from the subject at an earlier time period. In some embodiments, the reference value is from a control subject, wherein the control subject does not have adenocarcinoma (AC).

Methods for Treating Adenocarcinoma (AC)

In various embodiments, the present invention provides a method for treating adenocarcinoma (AC) in a subject, comprising: administering to the subject a therapeutically effective amount of at least one agent that inhibits expression or activity of ONECUT2, thereby treating adenocarcinoma (AC) in the subject.

In various embodiments, the present invention provides a method for treating adenocarcinoma (AC) in a subject, comprising: administering a treatment to the subject, wherein the treatment comprises a therapeutically effective amount of at least one agent that inhibits expression or activity of ONECUT2, thereby treating adenocarcinoma (AC) in the subject.

In various embodiments, the present invention provides a method for treating adenocarcinoma (AC) in a subject, comprising: administering to the subject a therapeutically effective amount of at least one composition that comprises at least one agent that inhibits expression or activity of ONECUT2, thereby treating adenocarcinoma (AC) in the subject.

In various embodiments, the present invention provides a method for treating adenocarcinoma (AC) in a subject, comprising: administering a treatment to the subject, wherein the treatment comprises a therapeutically effective amount of at least one composition that comprises at least one agent that inhibits expression or activity of ONECUT2, thereby treating adenocarcinoma (AC) in the subject.

In various embodiments, the present invention provides a method for treating adenocarcinoma (AC) in a subject in whom an increase in the expression of ONECUT2 has been detected; and administering a treatment to the subject, wherein the treatment comprises a therapeutically effective amount of at least one agent that inhibits expression or activity of ONECUT2.

In various embodiments, the present invention provides a method for treating adenocarcinoma (AC) in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2.

In some embodiments, the adenocarcinoma (AC) overexpresses ONECUT2.

Methods for Treating, Inhibiting, Reducing the Severity of, Delaying Progression of and/or Preventing Metastases of Adenocarcinoma (AC)

In various embodiments, the present invention provides a method of treating, inhibiting, reducing the severity of, delaying progression of and/or preventing metastases of adenocarcinoma (AC) in a subject, comprising: administering to the subject a therapeutically effective amount of at least one agent that inhibits expression or activity of ONECUT2, thereby treating, inhibiting, reducing the severity of, delaying progression of and/or preventing metastases of adenocarcinoma (AC) in the subject.

In various embodiments, the present invention provides a method of treating, inhibiting, reducing the severity of, delaying progression of and/or preventing metastases of adenocarcinoma (AC) in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of adenocarcinoma (AC) in the subject.

In various embodiments, the present invention provides a method of treating, inhibiting, reducing the severity of, delaying progression of and/or preventing metastases of adenocarcinoma (AC) in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of adenocarcinoma (AC) in the subject.

In various embodiments, the present invention provides a method of treating, inhibiting, reducing the severity of, delaying progression of and/or preventing metastases of adenocarcinoma (AC) in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of adenocarcinoma (AC) in the subject.

In some embodiments, the at least one composition is at least one pharmaceutical composition. In some embodiments, the adenocarcinoma (AC) overexpresses ONECUT2.

Methods for Treating, Inhibiting, Reducing the Severity of and/or Promoting Prophylaxis of Cancer In various embodiments, the present invention provides a method for treating, inhibiting, reducing the severity of, and/or promoting prophylaxis of cancer in a subject in need thereof, comprising providing an agent that inhibits expression or activity of ONECUT2; and administering a therapeutically effective amount of the agent to the subject so as to treat, inhibit, reduce the severity of, and/or promote prophylaxis of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating, inhibiting, reducing the severity of, and/or promoting prophylaxis of cancer in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of, and/or promote prophylaxis of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the cancer overexpresses ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the composition is a pharmaceutical composition. In some embodiments, the method further comprises administering at least one additional anti-cancer therapy to the subject. In some embodiments, the additional anti-cancer is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administered to the subject for 1-5 days, 1-5 weeks, 1-5 months, or 1-5 years. In some embodiments, the agent and the additional anti-cancer therapy are administered sequentially or simultaneously. In some embodiments, the composition and the anti-cancer therapy are administered sequentially or simultaneously. In some embodiments, the anti-cancer therapy is selected from the group consisting of anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), anti-adenocarcinoma (anti-AC), and combinations thereof.

In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), and combinations thereof.

Methods for Diagnosing and Treating Cancer

In various embodiments, the present invention provides a method for diagnosing and treating cancer in a subject, comprising: obtaining a sample from the subject; assaying the sample to determine the expression level of ONECUT2; diagnosing the subject with cancer if the expression of ONECUT2 is increased relative to a reference value; and administering a treatment to the subject so as to treat the cancer, wherein the treatment comprises an agent that inhibits expression or activity of ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for diagnosing and treating cancer in a subject, comprising: obtaining a sample from the subject; assaying the sample to determine the expression level of ONECUT2; diagnosing the subject with cancer if the expression of ONECUT2 is increased relative to a reference value; and administering a treatment to the subject so as to treat the cancer, wherein the treatment comprises a composition that comprises at least one agent that inhibits expression or activity of ONECUT2, wherein the composition comprises at least one agent that inhibits expression or activity of ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the composition is a pharmaceutical composition. In some embodiments, the method further comprises administering at least one additional anti-cancer therapy to the subject. In some embodiments, the additional anti-cancer therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administered to the subject for 1-5 days, 1-5 weeks, 1-5 months, or 1-5 years. In some embodiments, the agent and the additional anti-cancer therapy are administered sequentially or simultaneously. In some embodiments, the composition and the additional anti-cancer therapy are administered sequentially or simultaneously. In some embodiments, the sample is selected from the group consisting of blood, plasma, urine, tissue, and combinations thereof. In some embodiments, the sample is obtained before, during, or after treatment for cancer. In some embodiments, the reference value is the mean or median level of ONECUT2 expression in a population of subjects that do not have cancer. In some embodiments, the reference value is the mean or median level of ONECUT2 expression in the subject, wherein the sample is obtained from the subject at an earlier time period. In some embodiments, the reference value is from a control subject, wherein the control subject does not have cancer. In some embodiments, the anti-cancer therapy is selected from the group consisting of anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), anti-adenocarcinoma (anti-AC), and combinations thereof.

In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), and combinations thereof.

In some embodiments, the cancer is not Non-Small Cell Lung Cancer (NSCLC). In some embodiments, the cancer is not adenocarcinoma (AC).

Methods for Treating Cancer

In various embodiments, the present invention provides a method for treating cancer in a subject, comprising: administering to the subject a therapeutically effective amount of at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating cancer in a subject, comprising: administering a treatment to the subject, wherein the treatment comprises a therapeutically effective amount of at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating cancer in a subject, comprising: administering to the subject a therapeutically effective amount of at least one composition that comprises at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating cancer in a subject, comprising: administering a treatment to the subject, wherein the treatment comprises a therapeutically effective amount of at least one composition that comprises at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating cancer in a subject in whom an increase in the expression of ONECUT2 has been detected; and administering a treatment to the subject, wherein the treatment comprises a therapeutically effective amount of at least one agent that inhibits expression or activity of ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating cancer in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the cancer overexpresses ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), and combinations thereof.

Methods for Treating, Inhibiting, Reducing the Severity of, Delaying Progression of and/or Preventing Metastases of Cancer In various embodiments, the present invention provides a method of treating, inhibiting, reducing the severity of, delaying progression of and/or preventing metastases of cancer in a subject, comprising: administering to the subject a therapeutically effective amount of at least one agent that inhibits expression or activity of ONECUT2, thereby treating, inhibiting, reducing the severity of, delaying progression of and/or preventing metastases of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of cancer in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of cancer in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of cancer in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the at least one composition is at least one pharmaceutical composition. In some embodiments, the cancer overexpresses ONECUT2, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the cancer is selected from the group consisting of neuroblastoma, small cell lung cancer (SCLC), large cell neuroendocrine cancer (LCNEC), large-cell carcinoma (LCC), squamous cell carcinoma (SqCC), and combinations thereof.

Methods for Treating, Inhibiting, Reducing the Severity of and/or Promoting Prophylaxis of Lung Cancer In various embodiments, the present invention provides a method for treating, inhibiting, reducing the severity of, and/or promoting prophylaxis of lung cancer in a subject in need thereof, comprising providing an agent that inhibits expression or activity of ONECUT2; and administering a therapeutically effective amount of the agent to the subject so as to treat, inhibit, reduce the severity of, and/or promote prophylaxis of lung cancer in the subject, wherein the cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating, inhibiting, reducing the severity of, and/or promoting prophylaxis of lung cancer in a subject in need thereof, comprising: providing a composition that comprises at least one agent that inhibits expression or activity of ONECUT2, wherein the composition comprises at least one agent that inhibits expression or activity of ONECUT2; and administering a therapeutically effective amount of the composition to the subject so as to treat, inhibit, reduce the severity of, and/or promote prophylaxis of lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the lung cancer overexpresses ONECUT2, wherein the cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the composition is a pharmaceutical composition. In some embodiments, the method further comprises administering at least one additional anti-lung cancer therapy to the subject. In some embodiments, the additional anti-lung cancer is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-lung cancer therapy are administered sequentially or simultaneously. In some embodiments, the composition and the anti-lung cancer therapy are administered sequentially or simultaneously. In some embodiments, the anti-lung cancer therapy is selected from the group consisting of anti-small cell lung cancer (anti-SCLC), anti-large cell neuroendocrine cancer (anti-LCNEC), anti-large-cell carcinoma (anti-LCC), anti-squamous cell carcinoma (anti-SqCC), anti-adenocarcinoma (anti-AC), and combinations thereof.

In some embodiments, the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the lung cancer is selected from the group consisting of small cell lung cancer (SCLC), large cell neuroendocrine cancer (LCNEC), large-cell carcinoma (LCC), squamous cell carcinoma (SqCC), and combinations thereof. In some embodiments, the lung cancer is selected from the group consisting of small cell lung cancer (SCLC), large cell neuroendocrine cancer (LCNEC), and combinations thereof.

Methods for Diagnosing and Treating Lung Cancer

In various embodiments, the present invention provides a method for diagnosing and treating lung cancer in a subject, comprising: obtaining a sample from the subject; assaying the sample to determine the expression level of ONECUT2; diagnosing the subject with lung cancer if the expression of ONECUT2 is increased relative to a reference value; and administering a treatment to the subject so as to treat the lung cancer, wherein the treatment comprises an agent that inhibits expression or activity of ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for diagnosing and treating lung cancer in a subject, comprising: obtaining a sample from the subject; assaying the sample to determine the expression level of ONECUT2; diagnosing the subject with lung cancer if the expression of ONECUT2 is increased relative to a reference value; and administering a treatment to the subject so as to treat the lung cancer, wherein the treatment comprises a composition that comprises at least one agent that inhibits expression or activity of ONECUT2, wherein the composition comprises at least one agent that inhibits expression or activity of ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the composition is a pharmaceutical composition. In some embodiments, the method further comprises administering at least one additional anti-lung cancer therapy to the subject. In some embodiments, the additional anti-lung cancer therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-lung cancer therapy are administered sequentially or simultaneously. In some embodiments, the composition and the additional anti-lung cancer therapy are administered sequentially or simultaneously. In some embodiments, the sample is selected from the group consisting of blood, plasma, urine, tissue, and combinations thereof. In some embodiments, the sample is obtained before, during, or after treatment for lung cancer. In some embodiments, the reference value is the mean or median level of ONECUT2 expression in a population of subjects that do not have lung cancer. In some embodiments, the reference value is the mean or median level of ONECUT2 expression in the subject, wherein the sample is obtained from the subject at an earlier time period. In some embodiments, the reference value is from a control subject, wherein the control subject does not have lung cancer. In some embodiments, the anti-cancer therapy is selected from the group consisting of anti-small cell lung cancer (anti-SCLC), anti-large cell neuroendocrine cancer (anti-LCNEC), anti-large-cell carcinoma (anti-LCC), anti-squamous cell carcinoma (anti-SqCC), anti-adenocarcinoma (anti-AC), and combinations thereof.

In some embodiments, the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the lung cancer is selected from the group consisting of small cell lung cancer (SCLC), large cell neuroendocrine cancer (LCNEC), large-cell carcinoma (LCC), squamous cell carcinoma (SqCC), and combinations thereof. In some embodiments, the lung cancer is selected from the group consisting of small cell lung cancer (SCLC), large cell neuroendocrine cancer (LCNEC), and combinations thereof.

In some embodiments, the lung cancer is not Non-Small Cell Lung Cancer (NSCLC). In some embodiments, the lung cancer is not adenocarcinoma (AC).

Methods for Treating Lung Cancer

In various embodiments, the present invention provides a method for treating lung cancer in a subject, comprising: administering to the subject a therapeutically effective amount of at least one agent that inhibits expression or activity of ONECUT2, thereby treating lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating lung cancer in a subject, comprising: administering a treatment to the subject, wherein the treatment comprises a therapeutically effective amount of at least one agent that inhibits expression or activity of ONECUT2, thereby treating lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating lung cancer in a subject, comprising: administering to the subject a therapeutically effective amount of at least one composition that comprises at least one agent that inhibits expression or activity of ONECUT2, thereby treating lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating lung cancer in a subject, comprising: administering a treatment to the subject, wherein the treatment comprises a therapeutically effective amount of at least one composition that comprises at least one agent that inhibits expression or activity of ONECUT2, thereby treating lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating lung cancer in a subject in whom an increase in the expression of ONECUT2 has been detected; and administering a treatment to the subject, wherein the treatment comprises a therapeutically effective amount of at least one agent that inhibits expression or activity of ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method for treating lung cancer in a subject in whom an increase in the expression of ONECUT2 has been detected; and administering a treatment to the subject, wherein the treatment comprises a therapeutically effective amount of at least one composition that comprises at least one agent that inhibits expression or activity of ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the lung cancer overexpresses ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the lung cancer is selected from the group consisting of small cell lung cancer (SCLC), large cell neuroendocrine cancer (LCNEC), large-cell carcinoma (LCC), squamous cell carcinoma (SqCC), and combinations thereof. In some embodiments, the lung cancer is selected from the group consisting of small cell lung cancer (SCLC), large cell neuroendocrine cancer (LCNEC), and combinations thereof.

Methods for Treating, Inhibiting, Reducing the Severity of, Delaying Progression of and/or Preventing Metastases of Lung Cancer In various embodiments, the present invention provides a method of treating, inhibiting, reducing the severity of, delaying progression of and/or preventing metastases of lung cancer in a subject, comprising: administering to the subject a therapeutically effective amount of at least one agent that inhibits expression or activity of ONECUT2, thereby treating, inhibiting, reducing the severity of, delaying progression of and/or preventing metastases of lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of lung cancer in a subject, comprising: administering a treatment to the subject, wherein the treatment comprises a therapeutically effective amount of at least one agent that inhibits expression or activity of ONECUT2, thereby treating, inhibiting, reducing the severity of, delaying progression of and/or preventing metastases of lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of lung cancer in a subject, comprising: administering to the subject a therapeutically effective amount of at least one composition that comprises at least one agent that inhibits expression or activity of ONECUT2, thereby treating, inhibiting, reducing the severity of, delaying progression of and/or preventing metastases of lung cancer in the subject, wherein the cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In various embodiments, the present invention provides a method of treating, inhibiting, reducing the severity of, delaying progression of and/or preventing metastases of lung cancer in a subject, wherein the treatment comprises a therapeutically effective amount of at least one composition that comprises at least one agent that inhibits expression or activity of ONECUT2, thereby treating, inhibiting, reducing the severity of, delaying progression of and/or preventing metastases of lung cancer in the subject, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the at least one composition is at least one pharmaceutical composition. In some embodiments, the lung cancer overexpresses ONECUT2, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the lung cancer is selected from the group consisting of small cell lung cancer (SCLC), large cell neuroendocrine cancer (LCNEC), large-cell carcinoma (LCC), squamous cell carcinoma (SqCC), and combinations thereof. In some embodiments, the lung cancer is selected from the group consisting of small cell lung cancer (SCLC), large cell neuroendocrine cancer (LCNEC), and combinations thereof.

Methods for Assessing the Efficacy of the Treatment

In various embodiments, the present invention provides a method for assessing the efficacy of the treatment, comprising detecting a level of small cell lung cancer specific markers in the subject, comparing the level of small cell lung cancer specific markers in the subject to a reference value, wherein a decrease in the level of small cell lung cancer specific markers in the subject relative to the reference value is indicative of the efficacy of the treatment.

In various embodiments, the present invention provides a method for assessing the efficacy of the treatment, comprising detecting a level of small cell lung cancer biomarkers in the subject, comparing the level of small cell lung cancer biomarkers in the subject to a reference value, wherein a decrease in the level of small cell lung cancer biomarkers in the subject relative to the reference value is indicative of the efficacy of the treatment.

In various embodiments, the present invention provides a method for assessing the efficacy of the treatment, comprising detecting a level of neuroblastoma specific markers in the subject, comparing the level of neuroblastoma specific markers in the subject to a reference value, wherein a decrease in the level of neuroblastoma specific markers in the subject relative to the reference value is indicative of the efficacy of the treatment.

In various embodiments, the present invention provides a method for assessing the efficacy of the treatment, comprising detecting a level of neuroblastoma biomarkers in the subject, comparing the level of neuroblastoma biomarkers in the subject to a reference value, wherein a decrease in the level of neuroblastoma biomarkers in the subject relative to the reference value is indicative of the efficacy of the treatment.

In various embodiments, the present invention provides a method for assessing the efficacy of the treatment, comprising detecting a level of large cell neuroendocrine cancer (LCNEC) specific markers in the subject, comparing the level of large cell neuroendocrine cancer (LCNEC) specific markers in the subject to a reference value, wherein a decrease in the level of large cell neuroendocrine cancer (LCNEC) specific markers in the subject relative to the reference value is indicative of the efficacy of the treatment.

In various embodiments, the present invention provides a method for assessing the efficacy of the treatment, comprising detecting a level of large cell neuroendocrine cancer (LCNEC) biomarkers in the subject, comparing the level of large cell neuroendocrine cancer (LCNEC) biomarkers in the subject to a reference value, wherein a decrease in the level of large cell neuroendocrine cancer (LCNEC) biomarkers in the subject relative to the reference value is indicative of the efficacy of the treatment.

In various embodiments, the present invention provides a method for assessing the efficacy of the treatment, comprising detecting a level of large-cell carcinoma (LCC) specific markers in the subject, comparing the level of neuroblastoma large-cell carcinoma (LCC) specific markers in the subject to a reference value, wherein a decrease in the level of large-cell carcinoma (LCC) specific markers in the subject relative to the reference value is indicative of the efficacy of the treatment.

In various embodiments, the present invention provides a method for assessing the efficacy of the treatment, comprising detecting a level of large-cell carcinoma (LCC) biomarkers in the subject, comparing the level of neuroblastoma large-cell carcinoma (LCC) biomarkers in the subject to a reference value, wherein a decrease in the level of large-cell carcinoma (LCC) biomarkers in the subject relative to the reference value is indicative of the efficacy of the treatment.

In various embodiments, the present invention provides a method for assessing the efficacy of the treatment, comprising detecting a level of squamous cell carcinoma (SqCC) specific markers in the subject, comparing the level of squamous cell carcinoma (SqCC) specific markers in the subject to a reference value, wherein a decrease in the level of squamous cell carcinoma (SqCC) specific markers in the subject relative to the reference value is indicative of the efficacy of the treatment.

In various embodiments, the present invention provides a method for assessing the efficacy of the treatment, comprising detecting a level of squamous cell carcinoma (SqCC) biomarkers in the subject, comparing the level of squamous cell carcinoma (SqCC) biomarkers in the subject to a reference value, wherein a decrease in the level of squamous cell carcinoma (SqCC) biomarkers in the subject relative to the reference value is indicative of the efficacy of the treatment.

In various embodiments, the present invention provides a method for assessing the efficacy of the treatment, comprising detecting a level of adenocarcinoma (AC) specific markers in the subject, comparing the level of adenocarcinoma (AC) specific markers in the subject to a reference value, wherein a decrease in the level of adenocarcinoma (AC) specific markers in the subject relative to the reference value is indicative of the efficacy of the treatment.

In various embodiments, the present invention provides a method for assessing the efficacy of the treatment, comprising detecting a level of adenocarcinoma (AC) biomarkers in the subject, comparing the level of adenocarcinoma (AC) biomarkers in the subject to a reference value, wherein a decrease in the level of adenocarcinoma (AC) biomarkers in the subject relative to the reference value is indicative of the efficacy of the treatment.

In various embodiments, the present inventon provides a method for assessing the efficacy of the treatment, comprising detecting a level of neuroblastoma, small cell lung cancer (SCLC), large cell neuroendocrine cancer (LCNEC), large-cell carcinoma (LCC), squamous cell carcinoma (SqCC), and/or adenocarcinoma (AC) specific markers in the subject to a reference value, wherein a decrease in the level of neuroblastoma, small cell lung cancer (SCLC), large cell neuroendocrine cancer (LCNEC), large-cell carcinoma (LCC), squamous cell carcinoma (SqCC), and/or adenocarcinoma (AC) specific markers in the subject relative to the reference value is indicative of the efficacy of the treatment.

In various embodiments, the present inventon provides a method for assessing the efficacy of the treatment, comprising detecting a level of neuroblastoma, small cell lung cancer (SCLC), large cell neuroendocrine cancer (LCNEC), large-cell carcinoma (LCC), squamous cell carcinoma (SqCC), and/or adenocarcinoma (AC) biomarkers in the subject to a reference value, wherein a decrease in the level of neuroblastoma, small cell lung cancer (SCLC), large cell neuroendocrine cancer (LCNEC), large-cell carcinoma (LCC), squamous cell carcinoma (SqCC), and/or adenocarcinoma (AC) biomarkers in the subject relative to the reference value is indicative of the efficacy of the treatment.

In some embodiments, the small cell lung cancer specific markers are ONECUT2. In some embodiments, the neuroblastoma specific markers are ONECUT2. In some embodiments, the large cell neuroendocrine cancer (LCNEC) specific markers are ONECUT2. In some embodiments, the large-cell carcinoma (LCC) specific markers are ONECUT2. In some embodiments, the squamous cell carcinoma (SqCC) specific markers are ONECUT2. In some embodiments, the adenocarcinoma (AC) specific markers are ONECUT2.

In some embodiments, the small cell lung cancer specific marker is a small cell lung cancer biomarker. In some embodiments, the neuroblastoma specific marker is a neuroblastoma biomarker. In some embodiments, the large cell neuroendocrine cancer (LCNEC) specific marker is a large cell neuroendocrine cancer biomarker. In some embodiments, the large-cell carcinoma (LCC) specific marker is a large-cell carcinoma biomarker. In some embodiments, the squamous cell carcinoma (SqCC) specific marker is a squamous cell carcinoma biomarker. In some embodiments, the adenocarcinoma (AC) specific marker is an adenocarcinoma biomarker.

In some embodiments, the small cell lung cancer biomarkers are ONECUT2. In some embodiments, the neuroblastoma biomarkers are ONECUT2. In some embodiments, the large cell neuroendocrine cancer biomarkers are ONECUT2. In some embodiments, the large-cell carcinoma biomarkers are ONECUT2. In some embodiments, the squamous cell carcinoma biomarkers are ONECUT2. In some embodiments, the adenocarcinoma biomarkers are ONECUT2.

In some embodiments, the agent that inhibits the expression or function of ONECUT2 for use with the therapeutic methods described herein is a direct inhibitor of ONECUT2. In some embodiments, the agent that inhibits the expression or function of ONECUT2 for use with the therapeutic methods described herein is an indirect inhibitor of ONECUT2, wherein the indirect inhibitor inhibits the binding partner of ONECUT2 thereby inhibiting ONECUT2. In one embodiment, ONECUT2 is inhibited by inhibiting KDM5B.

In exemplary embodiments, the agent that inhibits (directly or indirectly) the expression or function of ONECUT2 for use with the therapeutic methods described herein is any one or more of small molecule, a peptide, an antibody or a fragment thereof, a nucleic acid molecule, a protein-drug conjugate, or a combination thereof. In some embodiments, the antibody is selected from the group consisting of monoclonal antibody or fragment thereof, a polyclonal antibody or a fragment thereof, chimeric antibodies, humanized antibodies, human antibodies, and a single chain antibody.

In various embodiments of the present invention the agent for inhibiting the expression or activity or function of ONECUT2 or modulating the activity of ONECUT2 for use in the therapeutic methods described herein is a compound CSRM617:

COMPOUND CSRM617

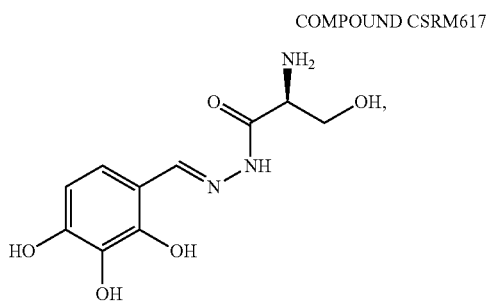 [SMILES: N[C@@H](CO)C(=O)N/N=C/c1ccc(O)c(O)c1O]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is compound CSRM617 or a pharmaceutically acceptable salt thereof:

COMPOUND CSRM617

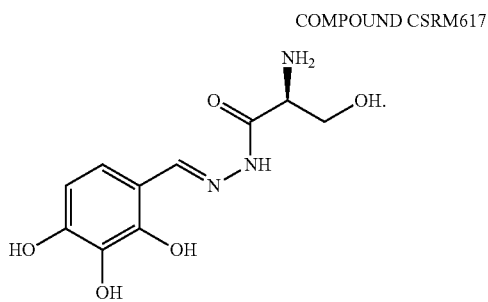 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is compound CSRM617:

COMPOUND CSRM617

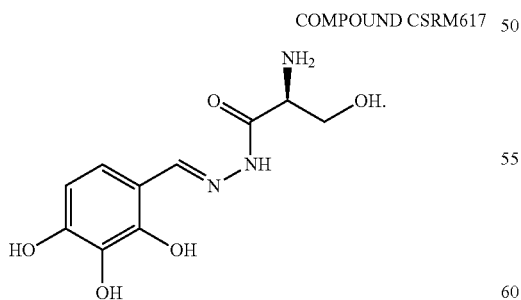

In various embodiments of the present invention the agent for inhibiting the expression or activity or function of ONECUT2 or modulating the activity of ONECUT2 for use in the therapeutic methods described herein is a compound of Formula I:

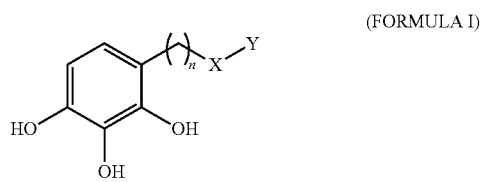 (FORMULA I)

or a prodrug, isomer, dimer, enantiomer, derivative, or pharmaceutically acceptable salt thereof, wherein:

n is 0, 1, 2, 3, 4 or 5;

X is NHC(O), C(O)NH, OC(O), C(O)O, C(O), or CH=N; and

Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula I:

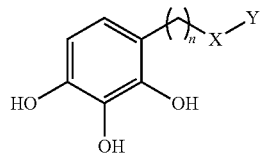 (FORMULA I)

wherein:

n is 0, 1, 2, 3, 4 or 5;

X is NHC(O), C(O)NH, OC(O), C(O)O, C(O), or CH=N;

Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula I:

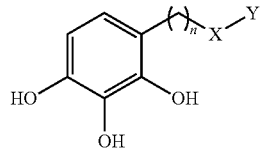 (FORMULA I)

wherein:

n is 0, 1, 2, 3, 4 or 5;

X is NHC(O), C(O)NH, OC(O), C(O)O, C(O), or CH=N;

Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula I:

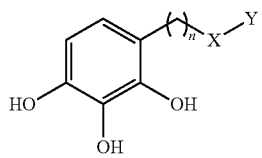

(FORMULA I)

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, C(O), or CH=N; and
Y is alkyl, heteroalkyl, cyclyl, heterocyclyl, aryl, or heteroaryl, each of which can be optionally substituted, provided that the compound is not

COMPOUND CSRM617

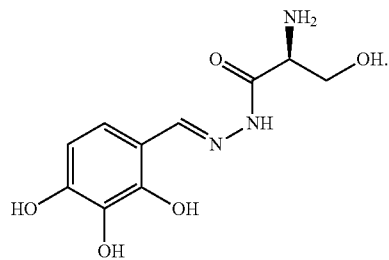

In various embodiments of the present invention the agent for inhibiting the expression or activity or function of ONECUT2 or modulating the activity of ONECUT2 for use in the therapeutic methods described herein is a compound of Formula I:

(FORMULA I)

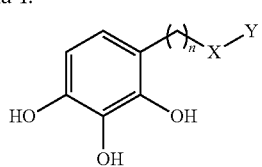

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted; and any pharmaceutically acceptable salt thereof, provided that the compound is not

COMPOUND CSRM617

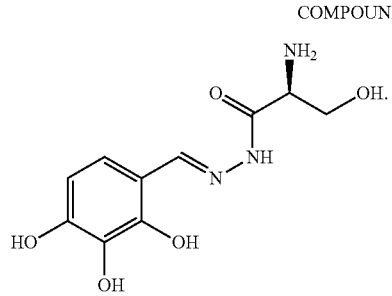

In various embodiments of the present invention the agent for inhibiting the expression or activity or function of ONECUT2 or modulating the activity of ONECUT2 for use in the therapeutic methods described herein is a compound of Formula I:

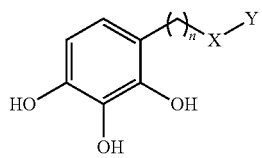

(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted, provided that the compound is not

COMPOUND CSRM617

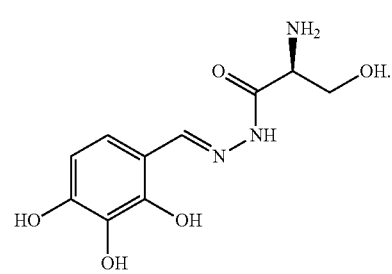

In various embodiments of the present invention the agent for inhibiting the expression or activity or function of ONECUT2 or modulating the activity of ONECUT2 for use in the therapeutic methods described herein is a compound of Formula II:

(FORMULA II)

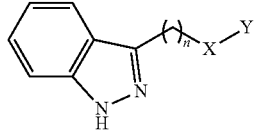

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula II:

(FORMULA II)

wherein:
n is 0, 1, 2, 3, 4 or 5;
X is NHC(O), C(O)NH, OC(O), C(O)O, or C(O);
Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula II:

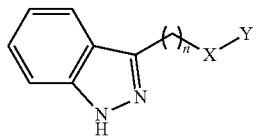

(FORMULA II)

wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula III:

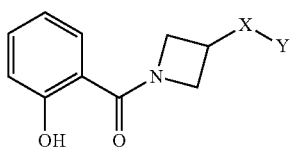

(FORMULA III)

or a prodrug, isomer, dimer, enantiomer, derivative, or pharmaceutically acceptable salt thereof, wherein:
X is NH, or O; and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula III:

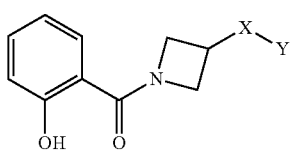

(FORMULA III)

wherein:
X is NH, or O;
Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula III:

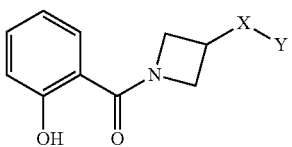

(FORMULA III)

wherein:
X is NH, or O; and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula IV:

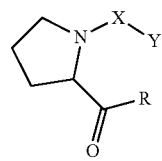

(FORMULA IV)

or a prodrug, isomer, dimer, enantiomer, derivative, or pharmaceutically acceptable salt thereof, wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5; and
R is H, CH$_3$, alkyl, NH$_2$, or OR', where R' is H, CH$_3$, or alkyl.

In various embodiments of the present invention the agent for inhibiting the expression or activity or function of ONECUT2 or modulating the activity of ONECUT2 for use in the therapeutic methods described herein is a compound of Formula IV:

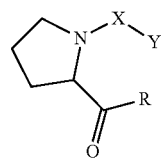

(FORMULA IV)

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5;
R is H, CH$_3$, alkyl, NH$_2$, or OR', where R' is H, CH$_3$, or alkyl; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula IV:

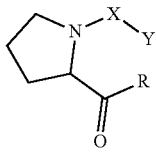

(FORMULA IV)

wherein:

X is C(O), C(O)(CH$_2$)$_m$O, or C(O)(CH$_2$)$_m$NH

Y is alkyl, heteroalkyl, cyclyl, heterocyclyl, aryl, or heteroaryl, each of which can be optionally substituted;

m is 0, 1, 2, 3, 4, or 5;

R is H, CH$_3$, alkyl, NH$_2$, or OR', where R' is H, CH$_3$, or alkyl.

In various embodiments of the present invention the agent for inhibiting the expression or activity or function of ONECUT2 or modulating the activity of ONECUT2 for use in the therapeutic methods described herein is a compound of Formula V:

(FORMULA V)

or a prodrug, isomer, dimer, enantiomer, derivative, or pharmaceutically acceptable salt thereof, wherein:

Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula V:

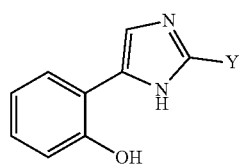

(FORMULA V)

wherein:

Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula V:

(FORMULA V)

wherein:

Y is alkyl, heteroalkyl, cyclyl, heterocyclyl, aryl, or heteroaryl, each of which can be optionally substituted.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Non-limiting examples of substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters),—CF$_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 2 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 2 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkenyl, and alkynyl" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. Non-limiting examples of $R_a$ and $R_b$ are each independently hydrogen, alkyl, substituted alkyl, alkenyl, or substituted alkenyl. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. For example, $C_6$-$C_{12}$ aryl includes aryls that have 6 to 12 carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a sub stituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. For example, $C_4$-$C_9$ heteroaryl includes heteroaryls that have 4 to 9 carbon atoms in the ring system. Heteroaryls include, but are not limited to, those derived from benzo[b] furan, benzo[b] thiophene, benzimidazole, imidazo[4,5-c] pyridine, quinazoline, thieno[2,3-c]pyridine, thieno[3,2-b] pyridine, thieno[2, 3-b]pyridine, indolizine, imidazo[1,2a] pyridine, quinoline, isoquinoline, phthalazine, quinoxaline, naphthyridine, quinolizine, indole, isoindole, indazole, indoline, benzoxazole, benzopyrazole, benzothiazole, imidazo[1, 5-a]pyridine, pyrazolo[1,5-a]pyridine, imidazo[1,2-a]pyrimidine, imidazo[1,2-c]pyrimidine, imidazo[1,5-a] pyrimidine, imidazo[1,5-c]pyrimidine, pyrrolo[2,3-b] pyridine, pyrrolo[2,3c]pyridine, pyrrolo[3,2-c]pyridine, pyrrolo[3,2-b]pyridine, pyrrolo[2,3-d]pyrimidine, pyrrolo [3,2-d]pyrimidine, pyrrolo [2,3-b]pyrazine, pyrazolo[1,5-a] pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a sub stituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cycyl are typically used where X and Y indicate the number of carbon atoms in the ring system. For example, $C_3$-$C_8$ cyclyl includes cyclyls that have 3 to 8 carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. For example, $C_4$-$C_9$ heterocyclyl includes heterocyclyls that have 4-9 carbon atoms in the ring system. In some embodiments, 1, 2 or 3 hydrogen atoms of each ring can be substituted by a sub stituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —NR$^N$—, —N$^+$(O$^-$)═, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring canbe such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —NH($C_1$-$C_{10}$alkyl), —N($C_1$-$C_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —$OCH_2CH_2OCH_3$, and the like.

The term "alkoxycarbonyl" means —C(O)O-(alkyl), such as —C(=O)$OCH_3$, —C(=O)$OCH_2CH_3$, and the like.

The term "alkoxyalkyl" means -(alkyl)-O-(alkyl), such as —$CH_2OCH_3$, —$CH_2OCH_2CH_3$, and the like.

The term "aryloxy" means —O-(aryl), such as —O-phenyl, —O-pyridinyl, and the like.

The term "arylalkyl" means -(alkyl)-(aryl), such as benzyl (i.e., —$CH_2$phenyl), —$CH_2$-pyrindinyl, and the like.

The term "arylalkyloxy" means —O-(alkyl)-(aryl), such as —O-benzyl, —O—$CH_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —$OCH_2$cyclohexyl, and the like.

The term "aminoalkoxy" means —O-(alkyl)-$NH_2$, such as —$OCH_2NH_2$, —$OCH_2CH_2NH_2$, and the like.

The term "mono- or di-alkylamino" means —NH(alkyl) or —N(alkyl)(alkyl), respectively, such as —$NHCH_3$, —$N(CH_3)_2$, and the like.

The term "mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —$NHCH_2$-pyridinyl, and the like.

The term "alkylamino" means —NH(alkyl), such as —$NHCH_3$, —$NHCH_2CH_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —$NHCH_2$-cyclohexyl, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —$CR_aR_bRc$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In some embodiments of compounds of Formula I or Formula II, n is 1, 2 or 3. In some embodiments of compounds of Formula I or Formula II, n is 2. In some embodiments of compounds of Formula I or Formula II, n is 1.

In some embodiments of compounds of Formula I or Formula II, X is NHC(O) or C(O)NH. In some embodiments of compounds of Formula I or Formula II, X is NHC(O). In some embodiments of compounds of Formula I or Formula II, X is C(O)NH.

In some embodiments of compounds of Formula I-Formula V, Y is an optionally substituted lower alkyl. In some embodiments of compounds of Formula I or II, Y is $C_1$-$C_6$ alkyl, 3-8 membered heterocyclyl, $C_6$-$C_8$ aryl, $C_3$-$C_8$ cyclyl, or 5-8 membered heteroaryl, each of which can be optionally substituted.

In some embodiments of compounds of Formula I-Formula V, Y can be an optionally substituted alkyl. In some embodiments, Y is alkyl optionally substituted with 1 or 2 substituents. In various embodiments, an optionally substituted alkyl is substituted with one or more substituents selected independently from the group consisting of amino, alkylamino, dialkylamino, hydroxyl, carbonyl (=O), NHOH, and amino substituted with an acyl group.

In some embodiments of compounds of Formula I-Formula V, Y can be an optionally substituted $C_1$-$C_4$ alkyl. In some embodiments, Y is $C_1$-$C_4$ alkyl optionally substituted with 1 or 2 substituents. In various embodiments, an optionally substituted $C_1$-$C_4$ alkyl is substituted with one or more substituents selected independently from the group consisting of amino, alkylamino, dialkylamino, hydroxyl, carbonyl (=O), NHOH, and amino substituted with an acyl group.

In various embodiments of compounds of Formula I-Formula V, Y is an ethyl, optionally substituted with two independently selected substituents.

In some embodiments of compounds of Formula I-Formula V, Y is an optionally substituted 6-membered heterocyclyl. In some embodiments, Y is a heterocyclyl optionally substituted with 1 or 2 substituents. In various embodiments, an optionally substituted heterocyclyl is substituted with one or more substituents selected independently from the group consisting of carbonyl (=O) and C(O)NH$_2$, halogen, carboxyl, and acyl. In some embodiments, Y is a heterocyclyl substituted with a carbonyl or C(O)NH$_2$ group.

In various embodiments of compounds of Formula I-Formula V, Y is a piperidine, optionally substituted with one substituent.

In various embodiments of compounds of Formula I-Formula V, Y is an optionally substituted aryl. Exemplary aryl for Y include, but are not limited to optionally substituted phenyl. In some embodiments, Y is an aryl optionally substituted with 1 or 2 substituents. In various embodiments, an optionally substituted aryl can be substituted with one or more substituents selected independently from the group consisting of C(O)NHOH, carbonyl (=O), C(O)NH$_2$, halogen, carboxyl, CF$_3$, hydroxyl, CH$_3$ and acyl. In some embodiments, Y is an aryl substituted with C(O)NHOH.

In various embodiments of compounds of Formula I-Formula V, Y is a phenyl, optionally substituted with one substituent.

In some embodiments of compounds of Formula I-Formula V, Y is —CH(NH$_2$)CH$_2$OH, —CH$_2$CH$_2$NHC(O)CH$_3$, —CH$_2$C(O)NHOH, piperidinecarbxamide, piperidone, or substituted phenyl.

In some embodiments of compounds of Formula I-Formula V, Y is

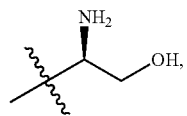 [SMILES: *[C@@H](N)CO]

—CH$_2$CH$_2$NHC(O)CH$_3$, —CH$_2$C(O)NHOH,

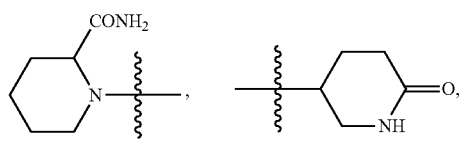

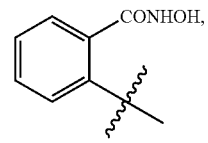

—NHC(O)CH(NH$_2$)CH$_2$OH, —C(O)CH(NH$_2$)CH$_2$OH, —C(O)CH(NH$_2$)CH$_2$OH, or —CH(NH$_2$)CH$_2$OH.

In some embodiments of compounds of Formula I-Formula V, Y is

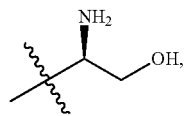 [SMILES: *[C@@H](N)CO]

—CH$_2$CH$_2$NHC(O)CH$_3$, —CH$_2$C(O)NHOH,

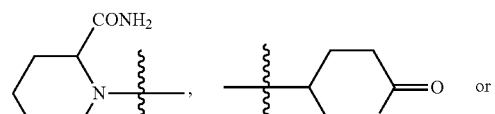

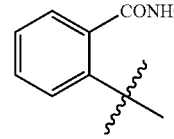

In some embodiments of compounds of Formula I-Formula V, Y is

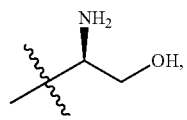 [SMILES: *[C@@H](N)CO]

—CH$_2$CH$_2$NHC(O)CH$_3$, —CH$_2$C(O)NHOH,

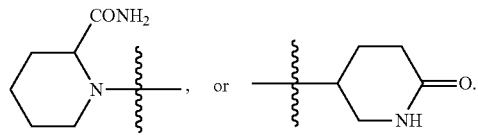 [SMILES: *N1CCCCC1C(N)=O ; "or" ; *C1CCC(=O)NC1]

In some embodiments of compounds of Formula I, Y is

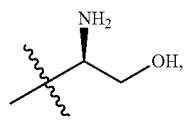 [SMILES: *[C@@H](N)CO]

—CH$_2$CH$_2$NHC(O)CH$_3$, —CH$_2$C(O)NHOH,

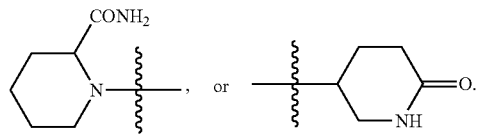 [SMILES: *N1CCCCC1C(N)=O ; "or" ; *C1CCC(=O)NC1]

In various embodiments of the present invention the agent for inhibiting the expression or activity or function of ONECUT2 or modulating the activity of ONECUT2 for use in the therapeutic methods described herein is a compound selected from:

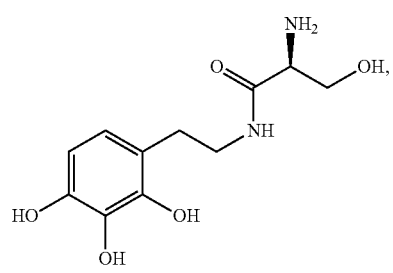 [SMILES: N[C@@H](CO)C(=O)NCCc1ccc(O)c(O)c1O]

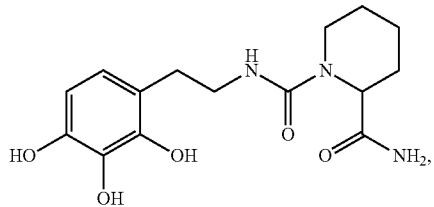

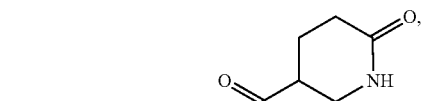

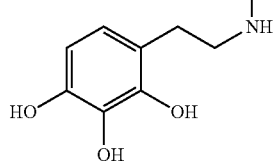

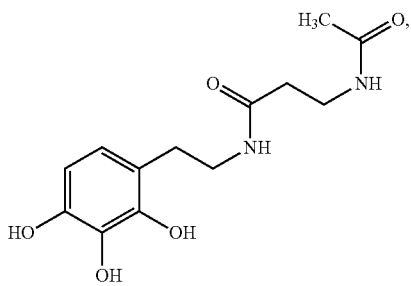

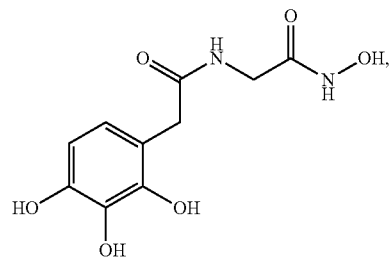

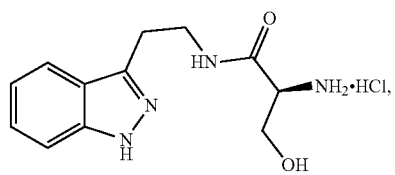

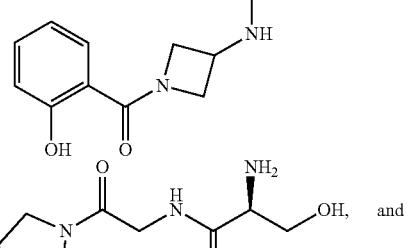

, and

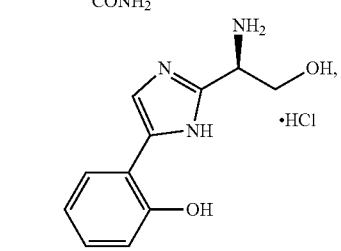

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

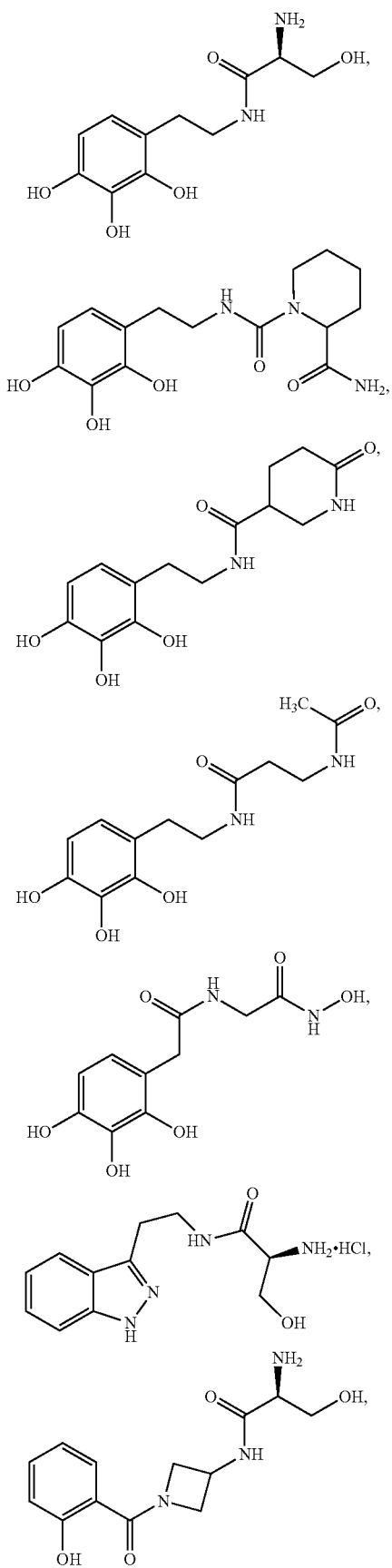
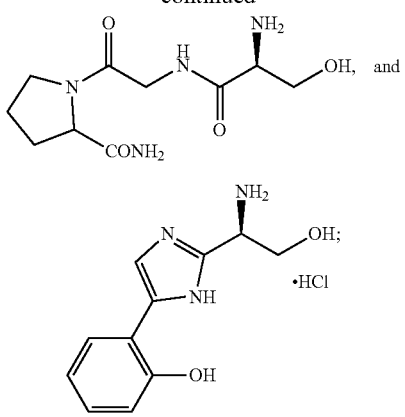
or any pharmaceutically acceptable salt thereof.
In various embodiments of the present invention the agent for inhibiting the expression or activity or function of ONECUT2 or modulating the activity of ONECUT2 for use in the therapeutic methods described herein is a compound selected from:
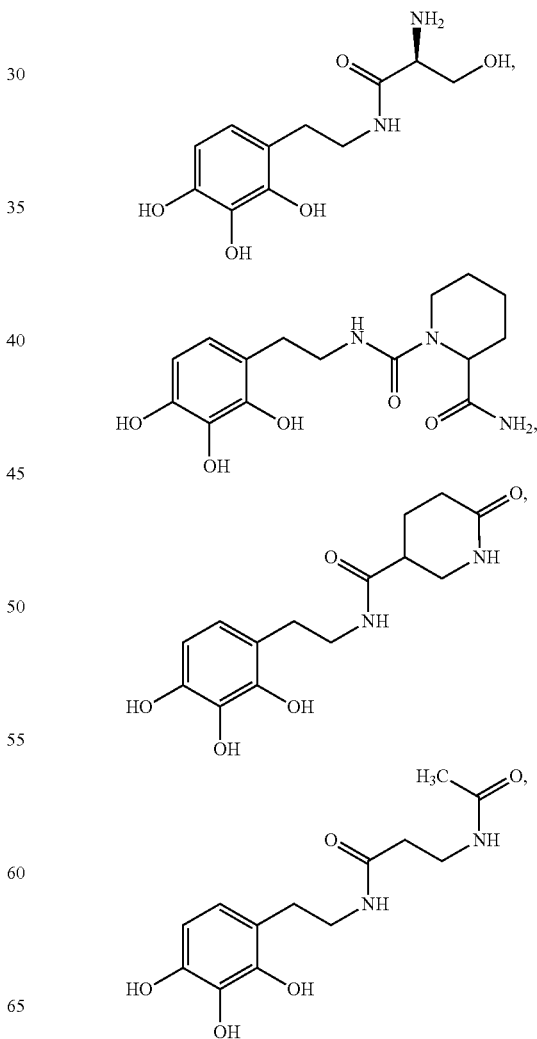

-continued

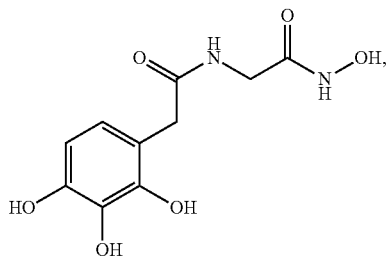

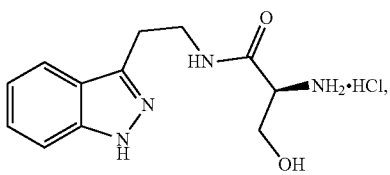

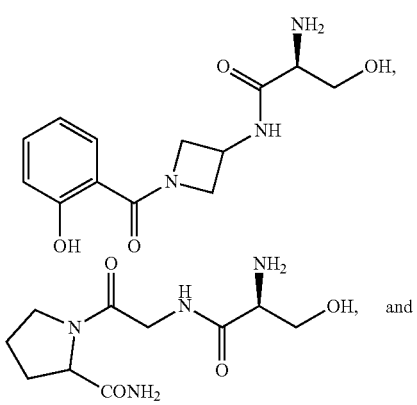

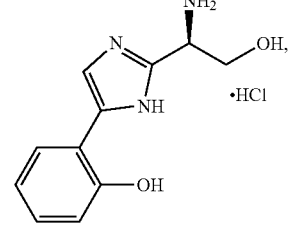

In various embodiments of the present invention the agent for inhibiting the expression or activity or function of ONECUT2 or modulating the activity of ONECUT2 for use in the therapeutic methods described herein is a compound selected from:

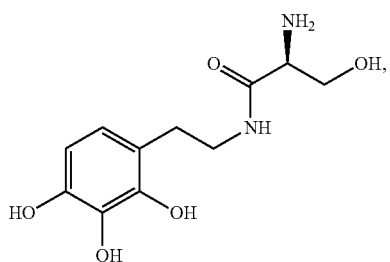 [SMILES: N[C@@H](CO)C(=O)NCCc1ccc(O)c(O)c1O]

-continued

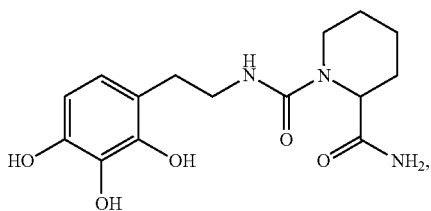

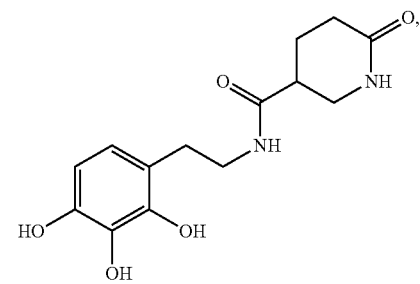

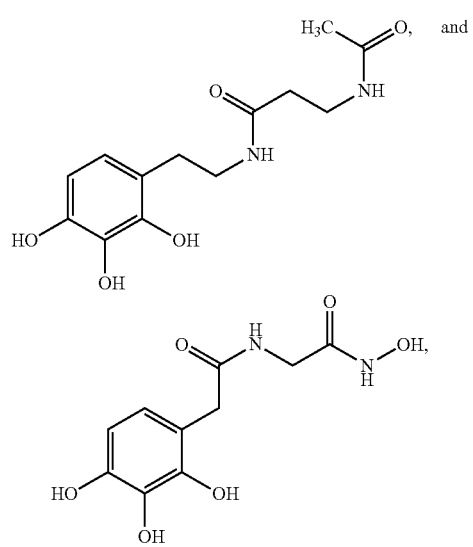

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

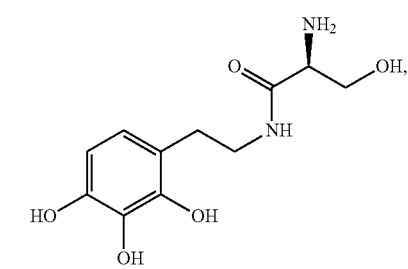

83
-continued

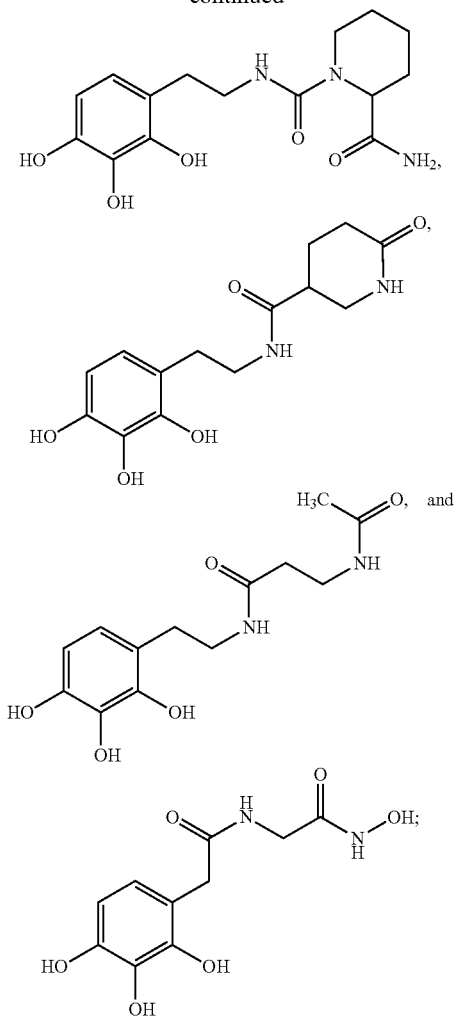

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

84
-continued

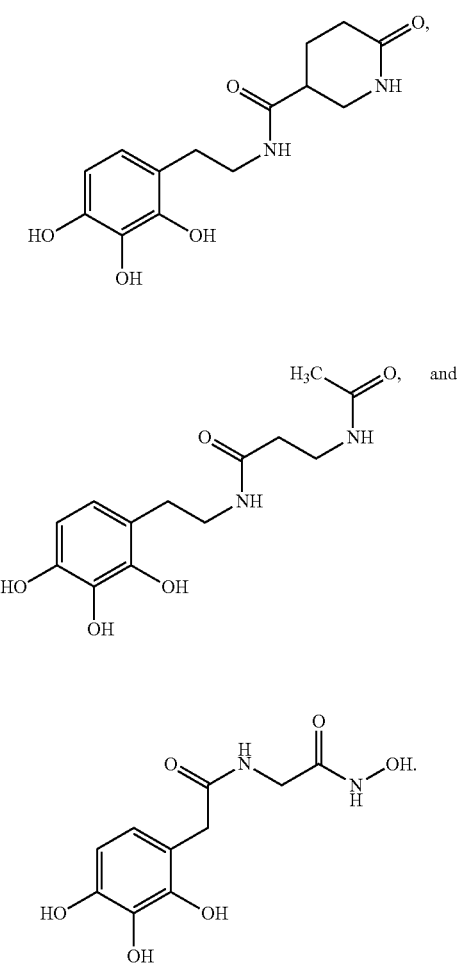

In various embodiments of the present invention the agent for inhibiting the expression or activity or function of ONECUT2 or modulating the activity of ONECUT2 for use in the therapeutic methods described herein is a compound selected from:

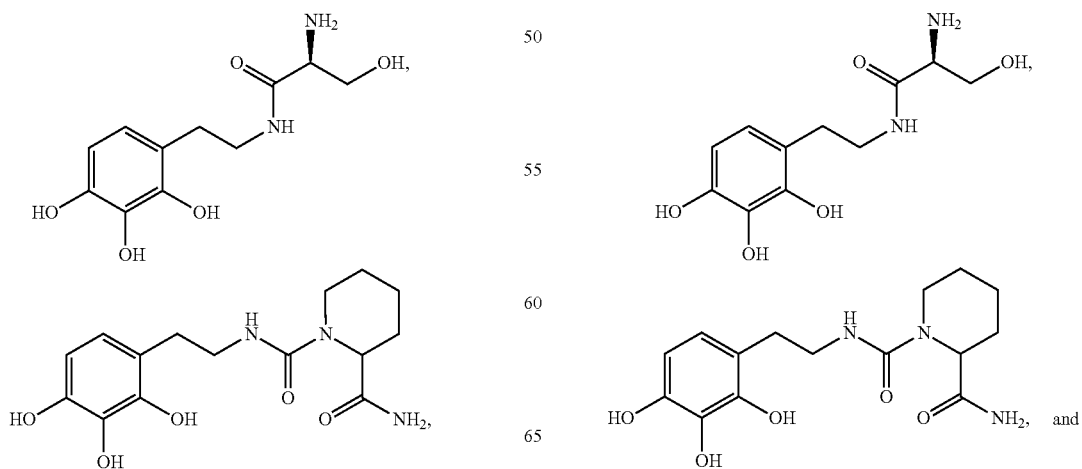

-continued

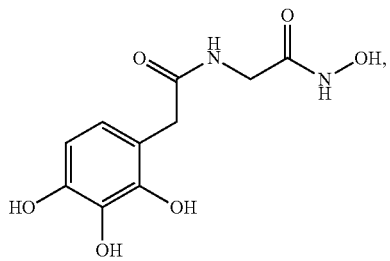

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

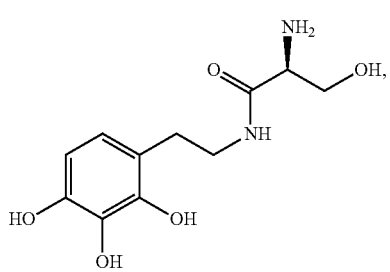

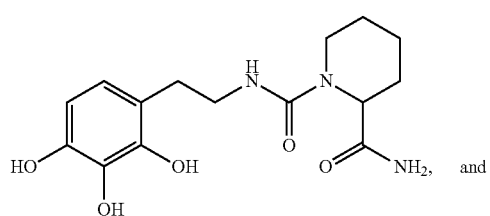

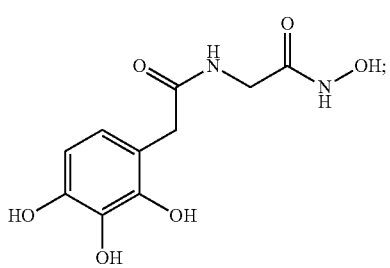

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

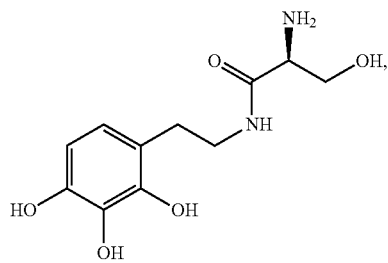

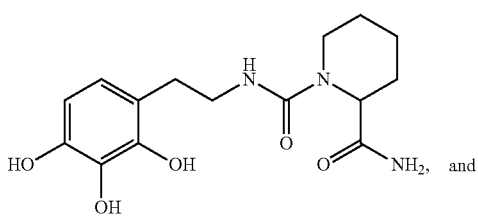

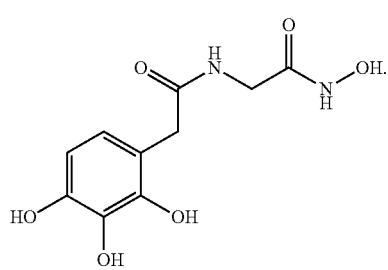

In various embodiments of the present invention the agent for inhibiting the expression or activity or function of ONECUT2 or modulating the activity of ONECUT2 for use in the therapeutic methods described herein is a compound selected from:

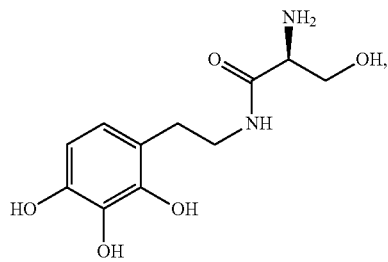

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

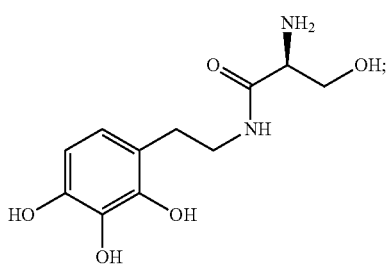

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

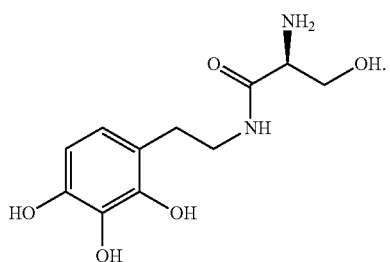 [SMILES: N[C@@H](CO)C(=O)NCCc1ccc(O)c(O)c1O]

In various embodiments of the present invention the agent for inhibiting the expression or activity or function of ONECUT2 or modulating the activity of ONECUT2 for use in the therapeutic methods described herein is a compound selected from:

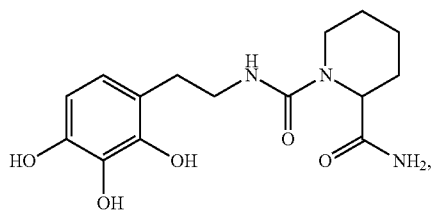

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

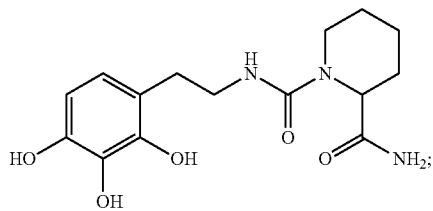

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

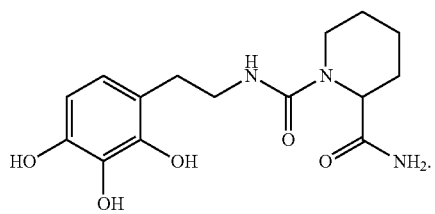 [SMILES: NC(=O)C1CCCCN1C(=O)NCCc1ccc(O)c(O)c1O]

In various embodiments of the present invention the agent for inhibiting the expression or activity or function of ONECUT2 or modulating the activity of ONECUT2 for use in the therapeutic methods described herein is a compound selected from:

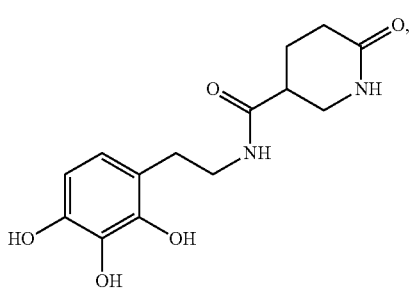 [SMILES: O=C1CCC(C(=O)NCCc2ccc(O)c(O)c2O)CN1]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

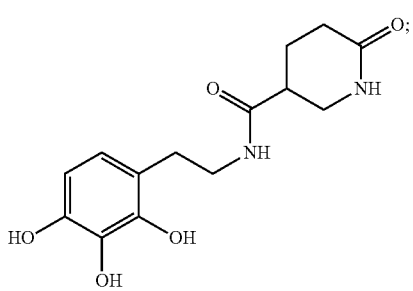 [SMILES: O=C1CCC(C(=O)NCCc2ccc(O)c(O)c2O)CN1]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

89

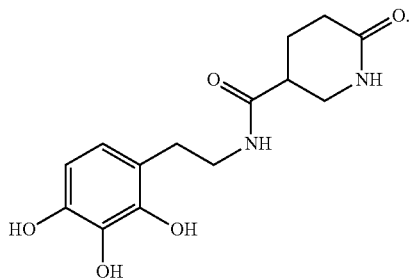 [SMILES: O=C1CCC(C(=O)NCCc2ccc(O)c(O)c2O)CN1]

In various embodiments of the present invention the agent for inhibiting the expression or activity or function of ONECUT2 or modulating the activity of ONECUT2 for use in the therapeutic methods described herein is a compound selected from:

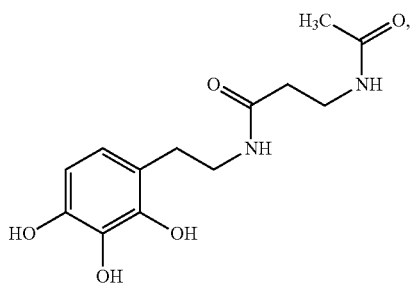 [SMILES: CC(=O)NCCC(=O)NCCc1ccc(O)c(O)c1O]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

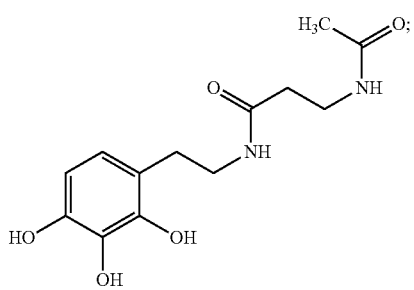 [SMILES: CC(=O)NCCC(=O)NCCc1ccc(O)c(O)c1O]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

90

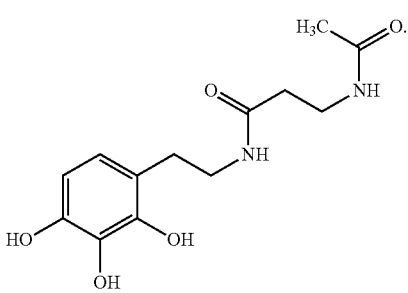 [SMILES: CC(=O)NCCC(=O)NCCc1ccc(O)c(O)c1O]

In various embodiments of the present invention the agent for inhibiting the expression or activity or function of ONECUT2 or modulating the activity of ONECUT2 for use in the therapeutic methods described herein is a compound selected from:

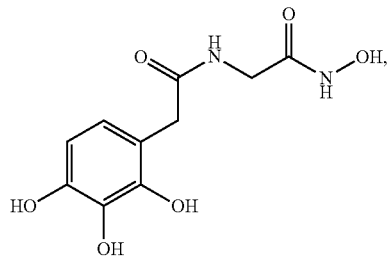

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

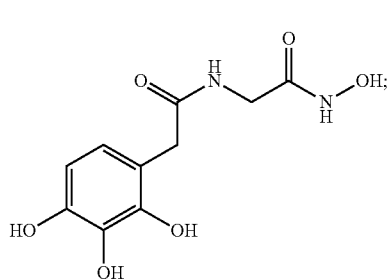 [SMILES: O=C(CNC(=O)Cc1ccc(O)c(O)c1O)NO]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

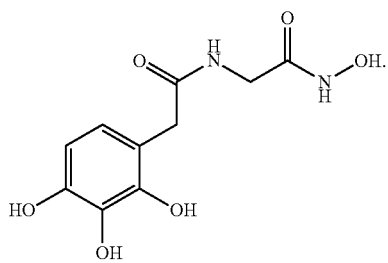 [SMILES: O=C(CNC(=O)Cc1ccc(O)c(O)c1O)NO]

In various embodiments of the present invention the agent for inhibiting the expression or activity or function of ONECUT2 or modulating the activity of ONECUT2 for use in the therapeutic methods described herein is a compound selected from:

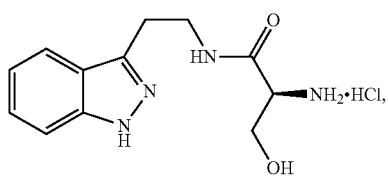

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

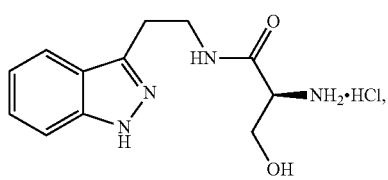

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

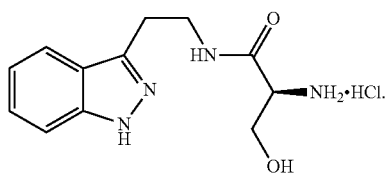

In various embodiments of the present invention the agent for inhibiting the expression or activity or function of ONECUT2 or modulating the activity of ONECUT2 for use in the therapeutic methods described herein is a compound selected from:

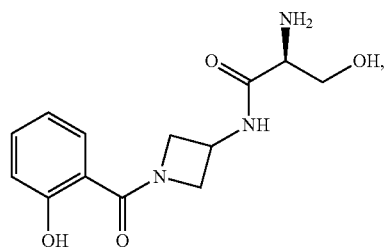 [SMILES: N[C@@H](CO)C(=O)NC1CN(C(=O)c2ccccc2O)C1]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

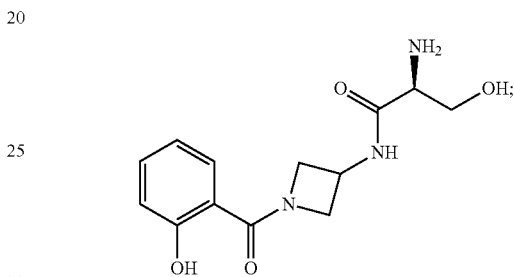

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

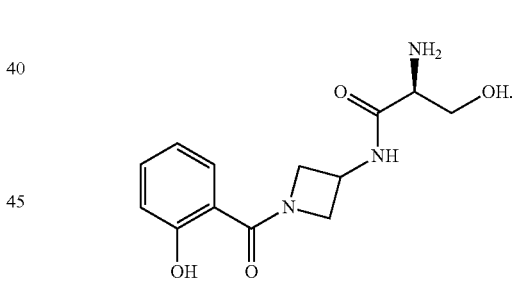

In various embodiments of the present invention the agent for inhibiting the expression or activity or function of ONECUT2 or modulating the activity of ONECUT2 for use in the therapeutic methods described herein is a compound selected from:

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

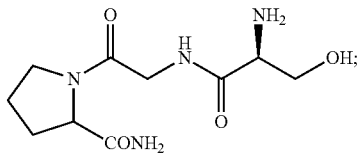

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

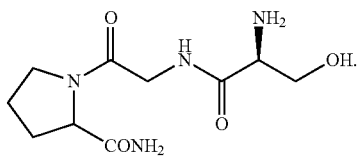 [SMILES: NC(=O)C1CCCN1C(=O)CNC(=O)[C@@H](N)CO]

In various embodiments of the present invention the agent for inhibiting the expression or activity or function of ONECUT2 or modulating the activity of ONECUT2 for use in the therapeutic methods described herein is a compound selected from:

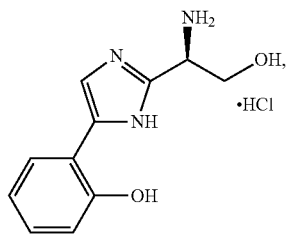 [SMILES: N[C@@H](CO)c1ncc(-c2ccccc2O)[nH]1 ; Cl]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

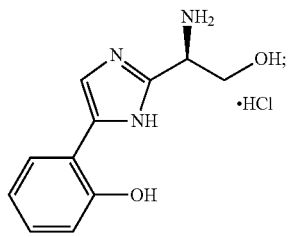 [SMILES: N[C@@H](CO)c1ncc(-c2ccccc2O)[nH]1 ; Cl]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

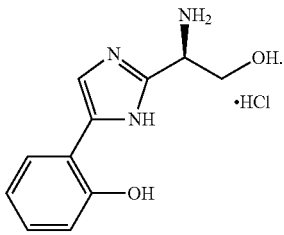 [SMILES: N[C@@H](CO)c1ncc(-c2ccccc2O)[nH]1 ; Cl]

In various embodiments of the present invention the agent for inhibiting the expression or activity or function of ONECUT2 or modulating the activity of ONECUT2 for use in the therapeutic methods described herein is a compound selected from:

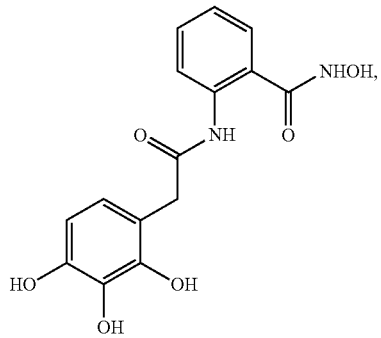

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

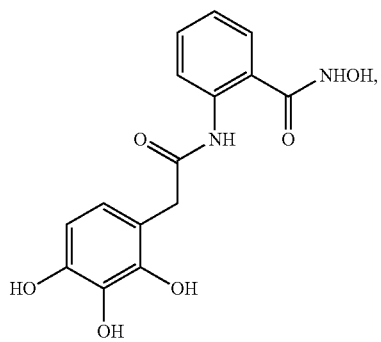

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

95

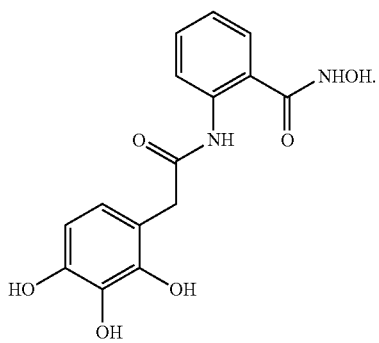

In various embodiments of the present invention the agent for inhibiting the expression or activity or function of ONECUT2 or modulating the activity of ONECUT2 for use in the therapeutic methods described herein is a compound having the structure:

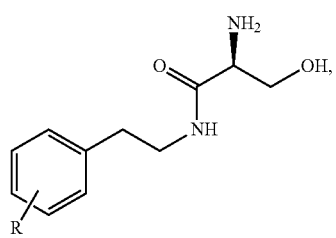

or a prodrug, isomer, dimer, enantiomer, derivative, or pharmaceutically acceptable salt thereof, wherein:
R is independently one or more of hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

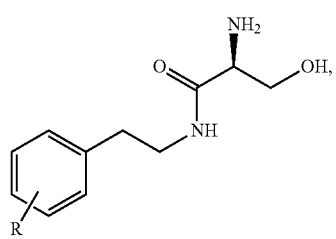

wherein:
R is independently one or more of hydrogen or optionally substituted substituent.

In various embodiments of the present invention the agent is a compound, prodrug, isomer, dimer, enantiomer, derivative, or pharmaceutically acceptable salt, selected from the group consisting of:

96

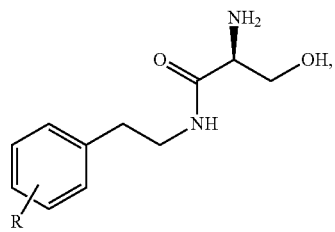

wherein:
R is independently one or more of hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

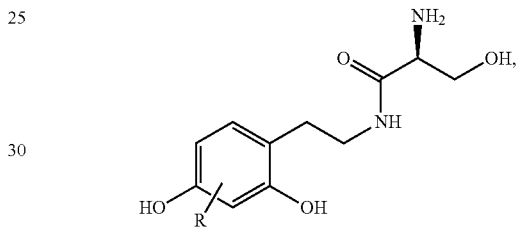

or a prodrug, isomer, dimer, enantiomer, derivative, or pharmaceutically acceptable salt thereof, wherein:
R is independently one or more of hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

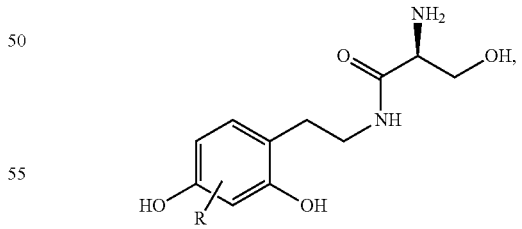

wherein:
R is independently one or more of hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

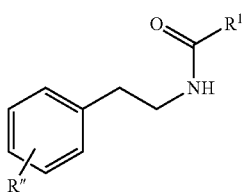

or a prodrug, isomer, dimer, enantiomer, derivative, or pharmaceutically acceptable salt thereof wherein:
R″ is independently one or more of hydrogen or optionally substituted substituent; and
$R^1$ is hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

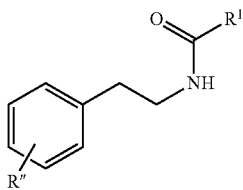

wherein:
R″ is independently one or more of hydrogen or optionally substituted substituent; and
$R^1$ is hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

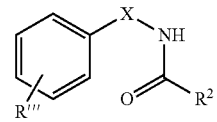

or a prodrug, isomer, dimer, enantiomer, derivative, or pharmaceutically acceptable salt thereof, wherein:
R‴ is independently one or more of hydrogen or optionally substituted substituent;
$R^2$ is hydrogen or optionally substituted substituent; and
X is NHC(O), C(O)NH, OC(O), C(O)O, C(O), or CH═N.

In various embodiments of the present invention the agent for inhibiting the expression or activity or function of ONECUT2 or modulating the activity of ONECUT2 for use in the therapeutic methods described herein is a compound having the structure:

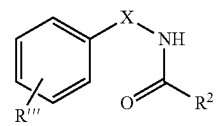

wherein:
R‴ is independently one or more of hydrogen or optionally substituted substituent;
$R^2$ is hydrogen or optionally substituted substituent; and
X is NHC(O), C(O)NH, OC(O), C(O)O, C(O), or CH═N.

In various embodiments of the present invention the agent for inhibiting the expression or activity or function of ONECUT2 or modulating the activity of ONECUT2 for use in the therapeutic methods described herein is a compound having the structure:

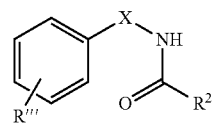

or a prodrug, isomer, dimer, enantiomer, derivative, or pharmaceutically acceptable salt thereof, wherein:
R‴ is independently one or more of hydrogen or optionally substituted substituent;
$R^2$ is hydrogen or optionally substituted substituent; and
X is NHC(O), C(O)NH, OC(O), C(O)O, C(O), or CH═N, provided that the compound is not

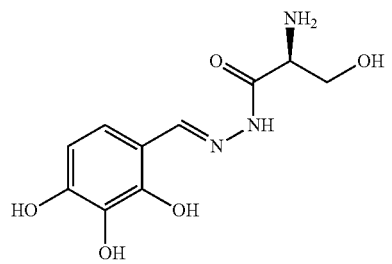

COMPOUND CSRM617

In various embodiments of the present invention the agent for inhibiting the expression or activity or function of ONECUT2 or modulating the activity of ONECUT2 for use in the therapeutic methods described herein is a compound having the structure:

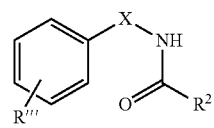

wherein:
R‴ is independently one or more of hydrogen or optionally substituted substituent;
$R^2$ is hydrogen or optionally substituted substituent; and
X is NHC(O), C(O)NH, OC(O), C(O)O, C(O), or CH═N, provided that the compound is not

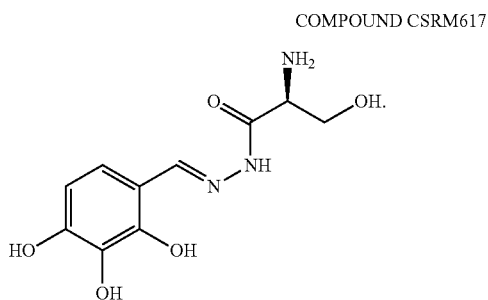 [SMILES: N[C@@H](CO)C(=O)N/N=C/c1ccc(O)c(O)c1O]

COMPOUND CSRM617

In various embodiments of the present invention the agent for inhibiting the expression or activity or function of ONECUT2 or modulating the activity of ONECUT2 is a compound having the structure:

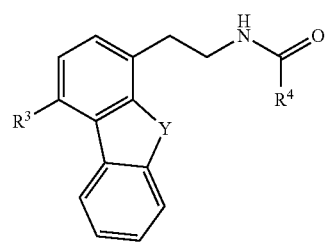

or a prodrug, isomer, dimer, enantiomer, derivative, or pharmaceutically acceptable salt thereof, wherein:

$R^3$ is hydrogen or optionally substituted substituent;
$R^4$ is hydrogen or optionally substituted substituent; and
Y is O or S.

In various embodiments of the present invention the agent for inhibiting the expression or activity or function of ONECUT2 or modulating the activity of ONECUT2 for use in the therapeutic methods described herein is a compound having the structure:

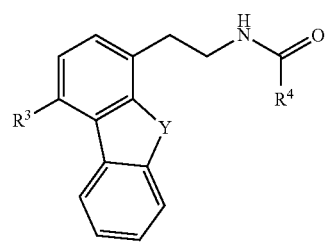

wherein:
$R^3$ is hydrogen or optionally substituted substituent;
$R^4$ is hydrogen or optionally substituted substituent; and
Y is O or S.

In various embodiments of the present invention the agent for inhibiting the expression or activity or function of ONECUT2 or modulating the activity of ONECUT2 for use in the therapeutic methods described herein is a compound having the structure:

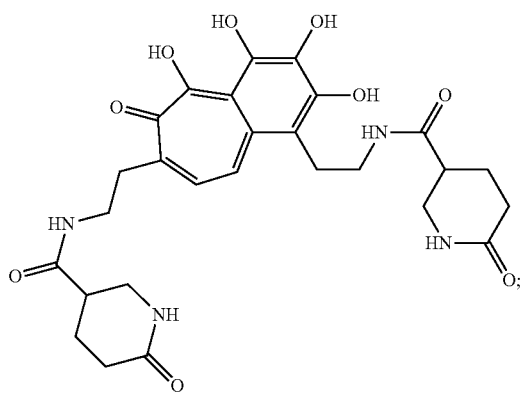 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound having the structure:

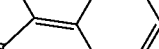

In various embodiments of the present invention the agent for inhibiting the expression or activity or function of ONECUT2 or modulating the activity of ONECUT2 for use in the therapeutic methods described herein is a compound selected from:

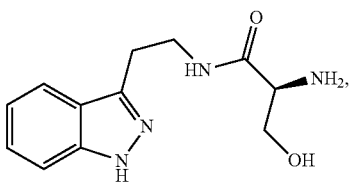 [SMILES: N[C@@H](CO)C(=O)NCCc1n[nH]c2ccccc12]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

101

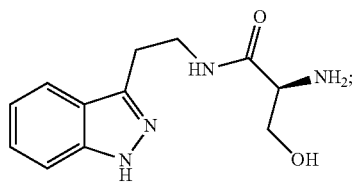 [SMILES: N[C@@H](CO)C(=O)NCCc1n[nH]c2ccccc12]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

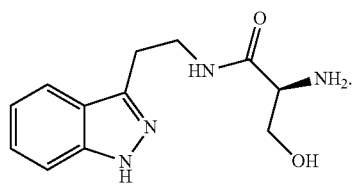

In various embodiments of the present invention the agent for inhibiting the expression or activity or function of ONECUT2 or modulating the activity of ONECUT2 for use in the therapeutic methods described herein is a compound selected from:

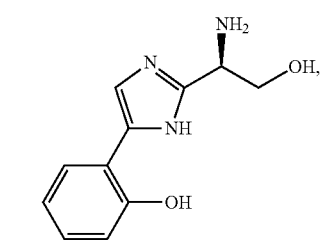 [SMILES: N[C@@H](CO)c1ncc(-c2ccccc2O)[nH]1]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

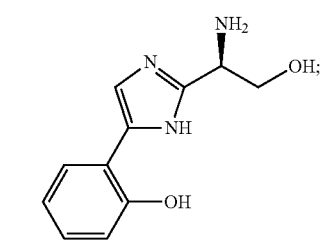 [SMILES: N[C@@H](CO)c1ncc(-c2ccccc2O)[nH]1]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

102

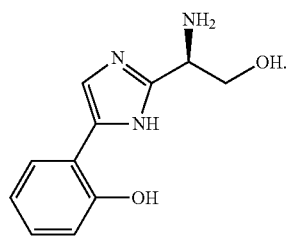 [SMILES: N[C@@H](CO)c1ncc(-c2ccccc2O)[nH]1]

In some embodiments, the agent is Compound CSRM617 of structure:

COMPOUND CSRM617

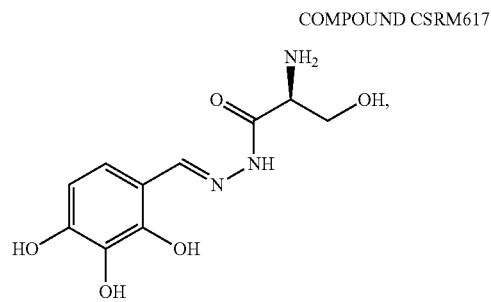 [SMILES: N[C@@H](CO)C(=O)N/N=C/c1ccc(O)c(O)c1O]

or a pharmacetucially acceptable salt thereof.

In some embodiments the agent is a compound, prodrug, isomer, dimer, enantiomer, derivative, or pharmaceutically acceptable salt, selected from the group consisting of:

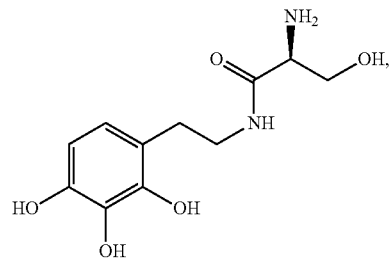

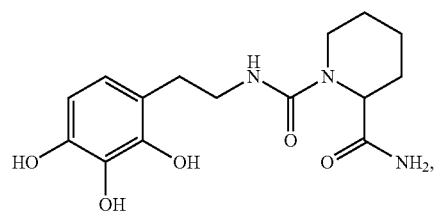

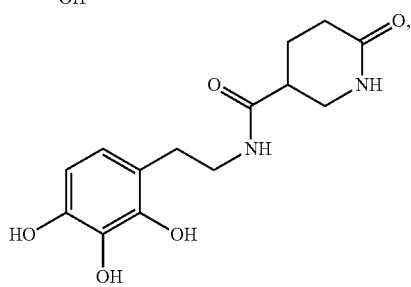

103
-continued

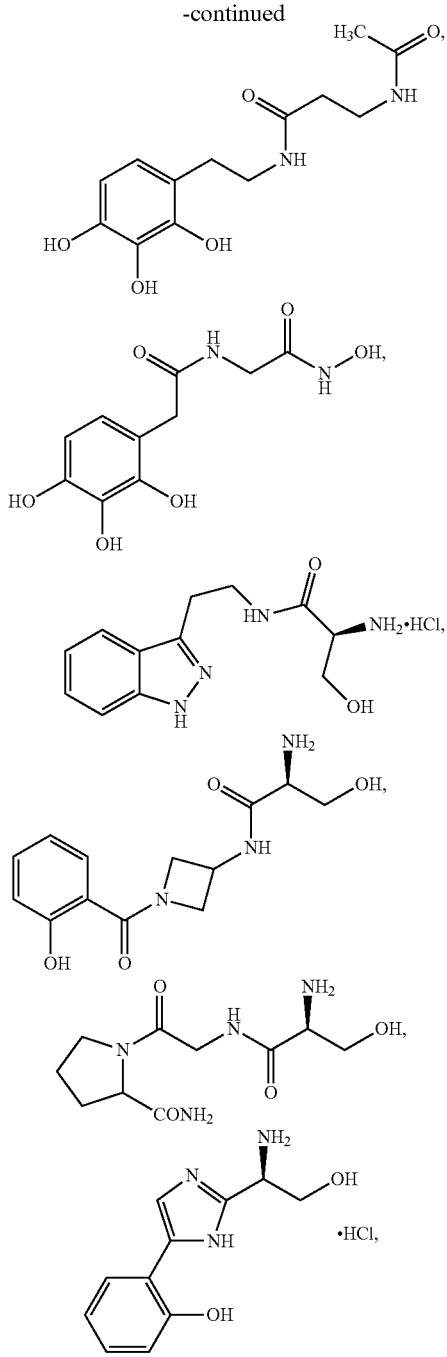

and combinations thereof.

In some embodiments, the agent is a compound, prodrug, isomer, dimer, enantiomer, derivative, or pharmaceutically acceptable salt, selected from the group consisting

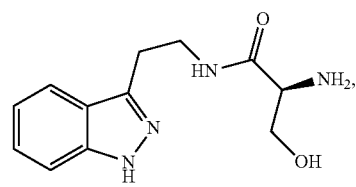

104
-continued

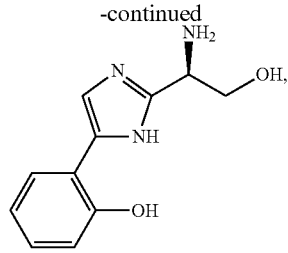

of and combinations thereof.

In some embodiments, the agent is a compound, prodrug, isomer, dimer, enantiomer, derivative, or pharmaceutically acceptable salt, selected from the group consisting of a compound of Formula I, a compound of Formula II, a compound of Formula III, a compound of Formula IV, a compound of Formula V, and combinations thereof.

In some embodiments, the agent is not compound CSRM617 of struture:

COMPOUND CSRM617

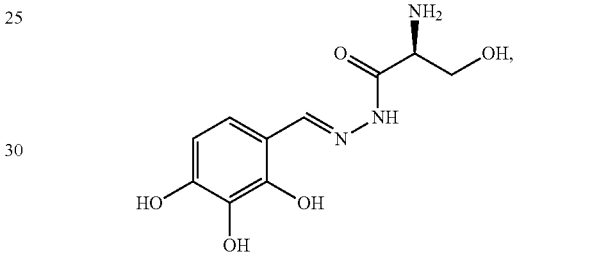

In various embodiments of the present invention, one or more agents and/or compounds for inhibiting the expression or activity or function of ONECUT2 or modulating the activity of ONECUT2 may be used in combination. In various embodiments of the present invention, agents and/or compounds for inhibiting the expression or activity or function of ONECUT2 or modulating the activity of ONECUT2 may be used in combination.

In some embodiments, the subject is undergoing androgen-deprivation therapy sequentially or simultaneously with administration of the agent described herein. In some embodiments, the agent that reduces or inhibits the expression or function of ONECUT2 (e.g., ONECUT2 protein and/or ONECUT2 gene) is administered 1-3 times per day or 1-7 times per week. In some embodiments, the agent that reduces or inhibits the expression or function of ONECUT2 (e.g., ONECUT2 protein and/or ONECUT2 gene) is administered for 1-5 days, 1-5 weeks, 1-5 months, or 1-5 years.

In some embodiments, the agent that inhibits the expression or activity or function of ONECUT2 or modulates the activity of ONECUT2 is administered 1-3 times per day or 1-7 times per week. In some embodiments, the agent that inhibits the expression or activity or function of ONECUT2 or modulates the activity of ONECUT2 is administered for 1-5 days, 1-5 weeks, 1-5 months, or 1-5 years.

In some embodiments, the therapeutically effective amount of the agent that inhibits the expression or activity or function of ONECUT2 or modulates the activity of ONECUT2 is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

Also provided herein is a method for assessing the efficacy of the therapeutic methods described herein which methods include administering an agent that inhibits expression or activity of ONECUT2. In some embodiments, the methods for assessing efficacy include detecting the level of SCLC or neuroblastoma specific markers in the subject that has undergone therapy with an agent that inhibits expression or activity of ONECUT2, wherein a decrease in the level of SCLC or neuroblastoma specific marker relative to the reference value indicates that the therapy with an agent that inhibits expression or activity of ONECUT2 is efficacious. In one embodiment, the reference value is the mean or median amount of the SCLC or neuroblastoma specific marker in the subject prior to starting treatment with the agent described herein.

Also provided herein is a method for assessing the efficacy of the therapeutic methods described herein which methods include administering an agent that inhibits expression or activity of ONECUT2. In some embodiments, the methods for assessing efficacy include detecting the level of neuroblastoma, small cell lung cancer (SCLC), large cell neuroendocrine cancer (LCNEC), large-cell carcinoma (LCC), squamous cell carcinoma (SqCC), or adenocarcinoma (AC) specific markers in the subject that has undergone therapy with an agent that inhibits expression or activity of ONECUT2, wherein a decrease in the level of neuroblastoma, small cell lung cancer (SCLC), large cell neuroendocrine cancer (LCNEC), large-cell carcinoma (LCC), squamous cell carcinoma (SqCC), or adenocarcinoma (AC) specific marker relative to the reference value indicates that the therapy with an agent that inhibits expression or activity of ONECUT2 is efficacious. In one embodiment, the reference value is the mean or median amount of the neuroblastoma, small cell lung cancer (SCLC), large cell neuroendocrine cancer (LCNEC), large-cell carcinoma (LCC), squamous cell carcinoma (SqCC), or adenocarcinoma (AC) specific marker in the subject prior to starting treatment with the agent described herein.

The agent reduces or inhibits the expression or function of ONECUT2 by a statistically significant amount. However, for avoidance of doubt, "reduced", "reduction" or "decrease" or "inhibit" in reference to expression of function of ONECUT2 means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level. In some embodiments, the reference level can be the level in absence of the agent.

The agent reduces or inhibits the expression or function of ONECUT2 gene by a statistically significant amount. However, for avoidance of doubt, "reduced", "reduction" or "decrease" or "inhibit" in reference to expression of function of ONECUT2 gene means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level. In some embodiments, the reference level can be the level in absence of the agent.

The agent reduces or inhibits the expression or function of ONECUT2 protein by a statistically significant amount. However, for avoidance of doubt, "reduced", "reduction" or "decrease" or "inhibit" in reference to expression of function of ONECUT2 protein means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level. In some embodiments, the reference level can be the level in absence of the agent.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptide. Measured or measurable parameters include clinically detectable markers of disease, for example, elevated or depressed levels of a biological marker, as well as parameters related to a clinically accepted scale of symptoms or markers for cancer (such SCLC or neuroblastoma). It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

In some embodiments, the method further comprises administration or treatment with one or more additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy to the subject in need thereof. In some embodiments, the additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

In some embodiments, the agent and the additional anti-SCLC or anti-neuroblastoma therapy are administered sequentially or simultaneously.

In some embodiments, the agent and the additional anti-neuroblastoma, anti-small cell lung cancer (anti-SCLC), anti-large cell neuroendocrine cancer (anti-LCNEC), antilarge-cell carcinoma (anti-LCC), anti-squamous cell carcinoma (anti-SqCC), or anti-adenocarcinoma (anti-AC) therapy are administered sequentially or simultaneously.

In some embodiments, the method further comprises administration or treatment with one or more anti-SCLC or anti-neuroblastoma therapeutic agents. In some such embodiments, the anti-SCLC or anti-neuroblastoma therapeutic agent is a chemotherapeutic agent, a growth inhibitor agent, an anti-angiogenesis agent, a cytotoxic agent, an anti-hormonal agent, a prodrug, or a cytokine.

In some embodiments, the method further comprises administration or treatment with one or more anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agents. In some such embodiments, the anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent is a chemotherapeutic agent, a growth inhibitor agent, an anti-angiogenesis agent, a cytotoxic agent, an anti-hormonal agent, a prodrug, or a cytokine.

In some embodiments, the method comprises co-administering the Compound CSRM617 and an anti-SCLC or anti-neuroblastoma therapeutic agent to the subject.

In some embodiments, the method comprises co-administering the Compound CSRM617 and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from Formula I-Formula V; and an anti-SCLC or anti-neuroblastoma therapeutic agent to the subject.

In some embodiments, the method comprises co-administering a compound selected from Formula I-Formula V; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from Formula I-Formula V; and an anti-SCLC or anti-neuroblastoma therapeutic agent to the subject, provided that the compound is not

COMPOUND CSRM617

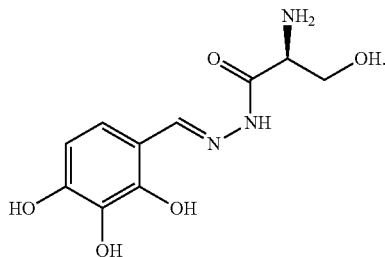

In some embodiments, the method comprises co-administering a compound selected from Formula I-Formula V; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject, provided that the compound is not

COMPOUND CSRM617

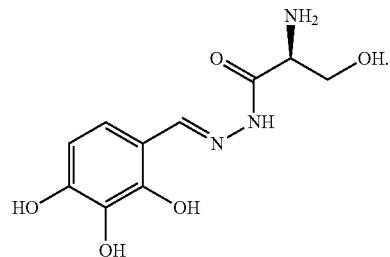

In some embodiments, the method comprises co-administering a compound selected from:

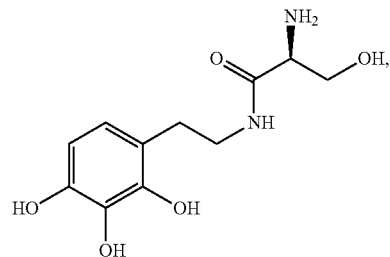

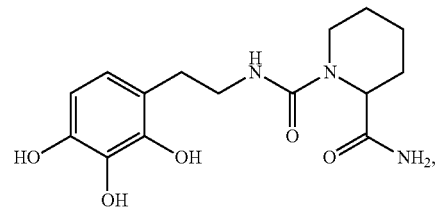

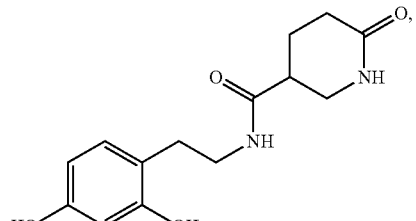

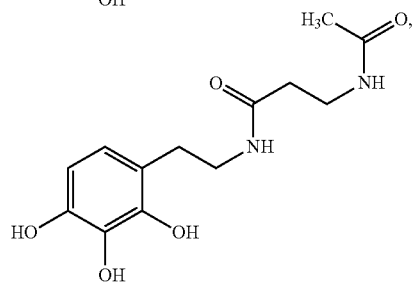

-continued
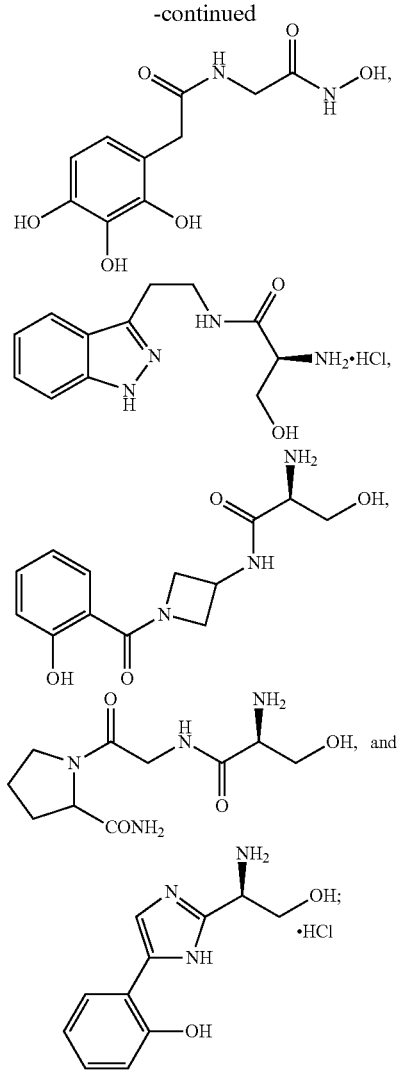
and an anti-SCLC or anti-neuroblastoma therapeutic agent to the subject.
In some embodiments, the method comprises co-administering a compound selected from:
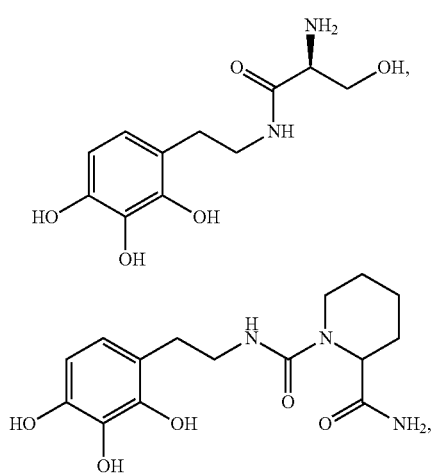
-continued
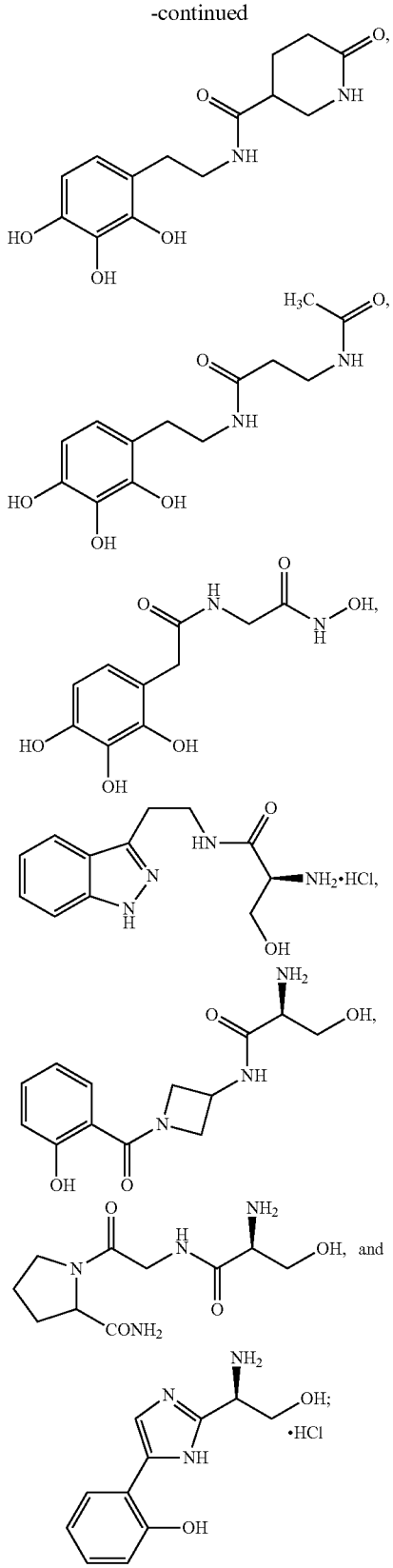
and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

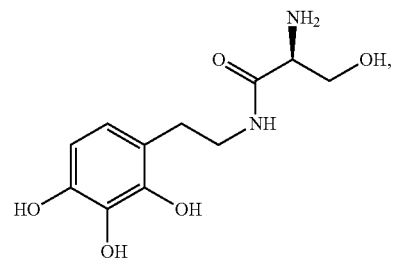

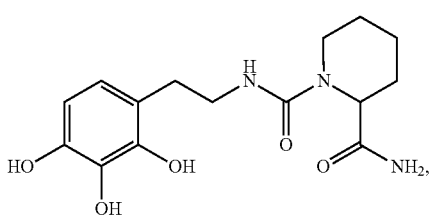

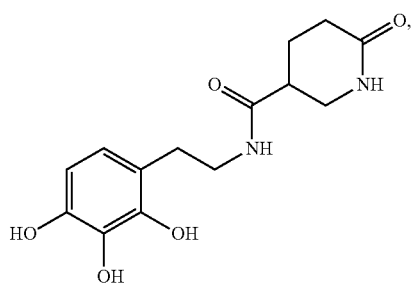

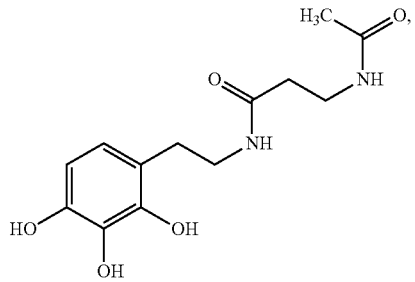

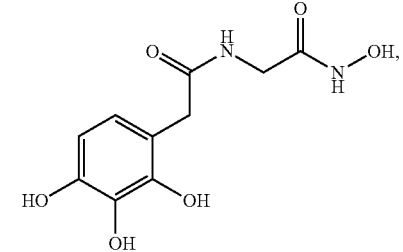

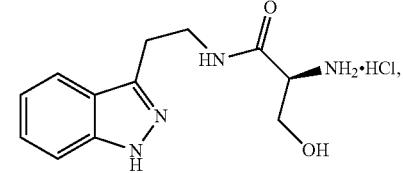

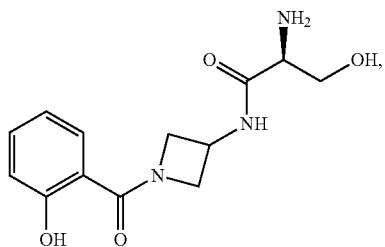

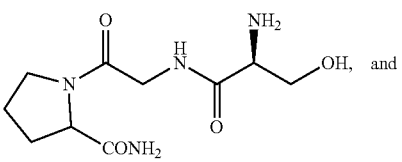

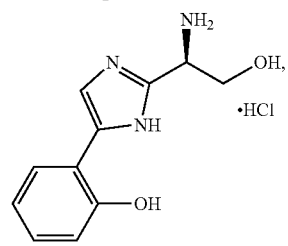

or any pharmaceutically acceptable salt thereof; and an anti-SCLC or anti-neuroblastoma therapeutic agent to the subject.

In some embodiments, the method comprises co-administering a compound selected from:

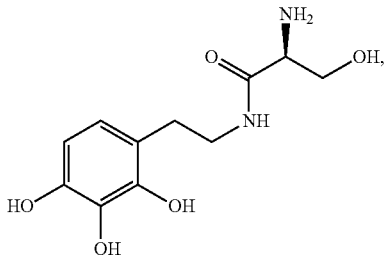 [SMILES: N[C@@H](CO)C(=O)NCCc1ccc(O)c(O)c1O]

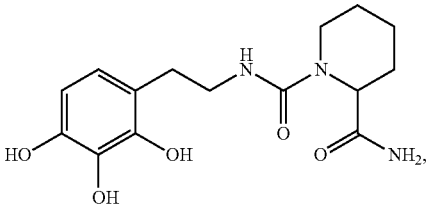

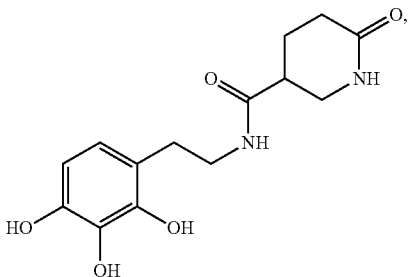

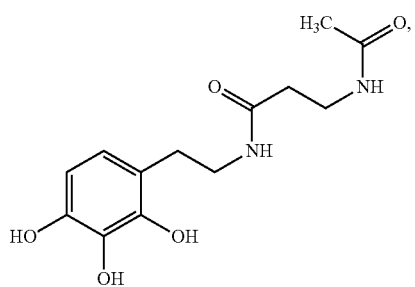

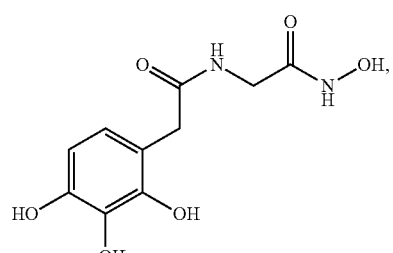

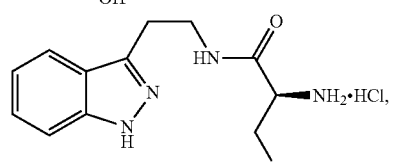

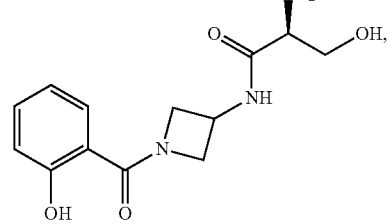

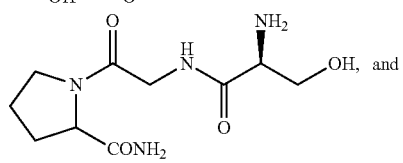

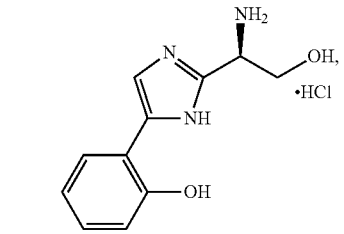

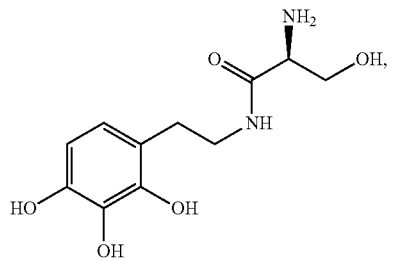 [SMILES: N[C@@H](CO)C(=O)NCCc1ccc(O)c(O)c1O]

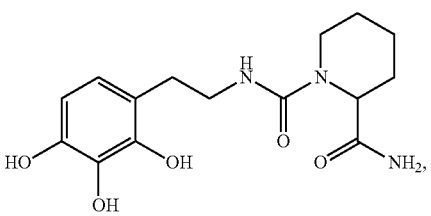

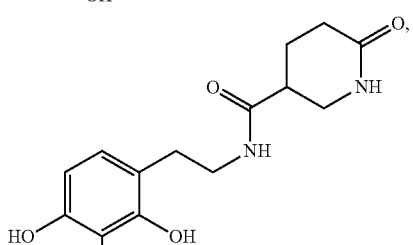

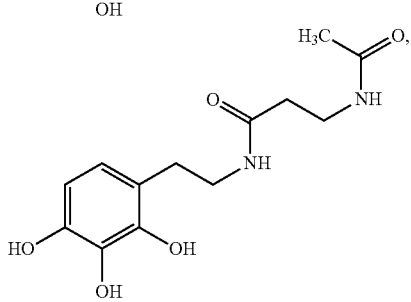

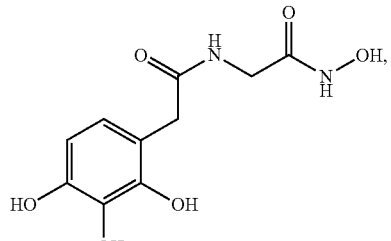

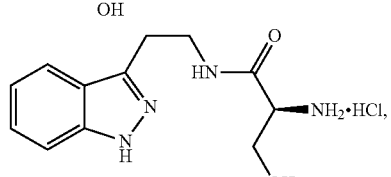

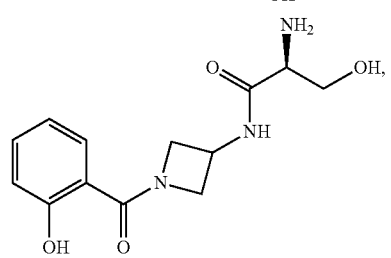

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

115

-continued

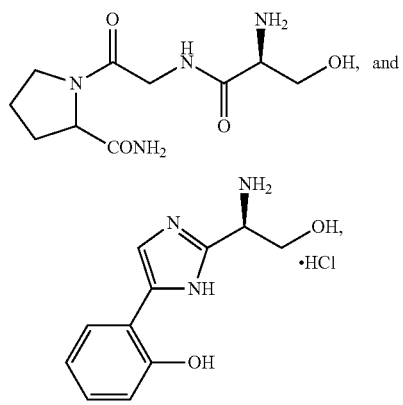

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

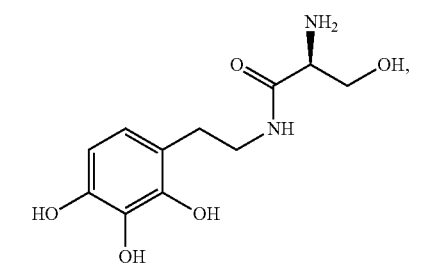 [SMILES: N[C@@H](CO)C(=O)NCCc1ccc(O)c(O)c1O]

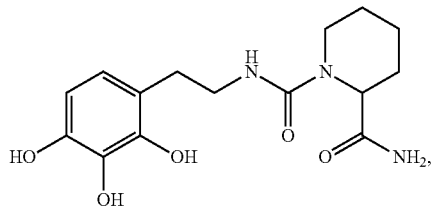

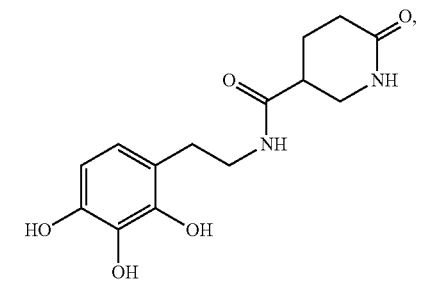

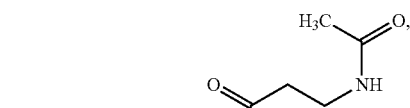

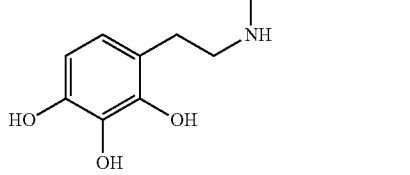

116

-continued

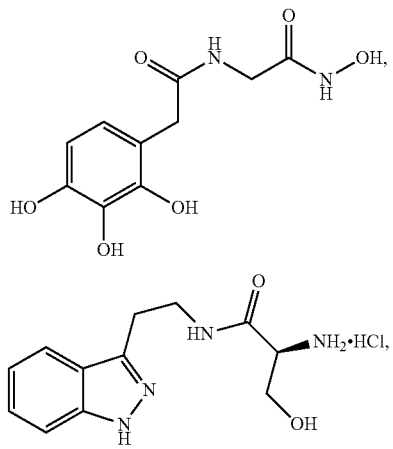

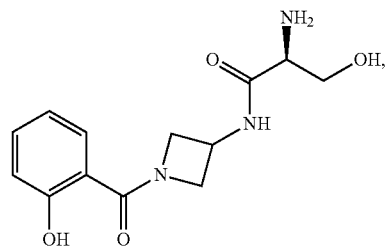

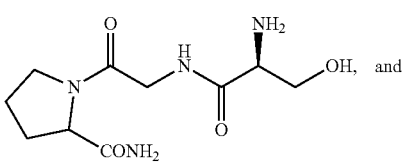

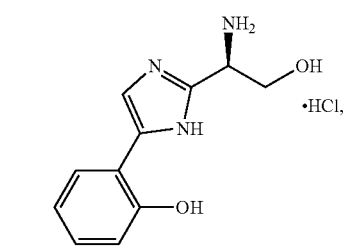

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

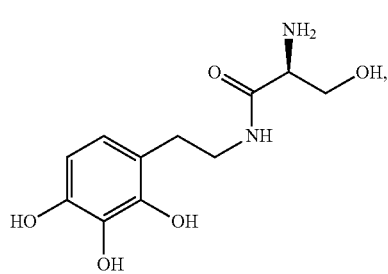

117

-continued

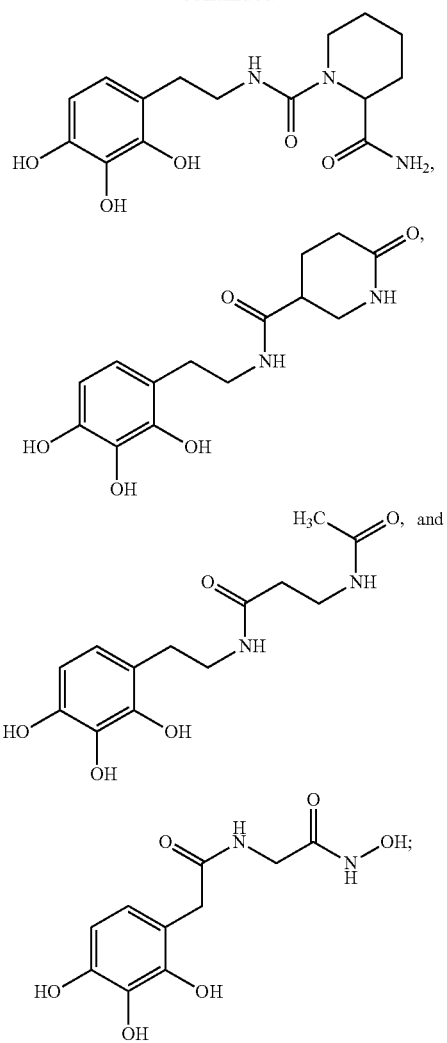

and an anti-SCLC or anti-neuroblastoma therapeutic agent to the subject.

In some embodiments, the method comprises co-administering a compound selected from:

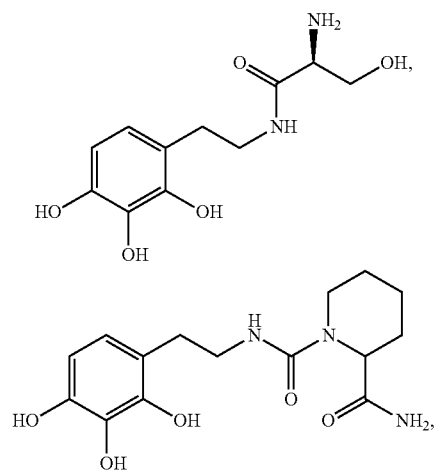

118

-continued

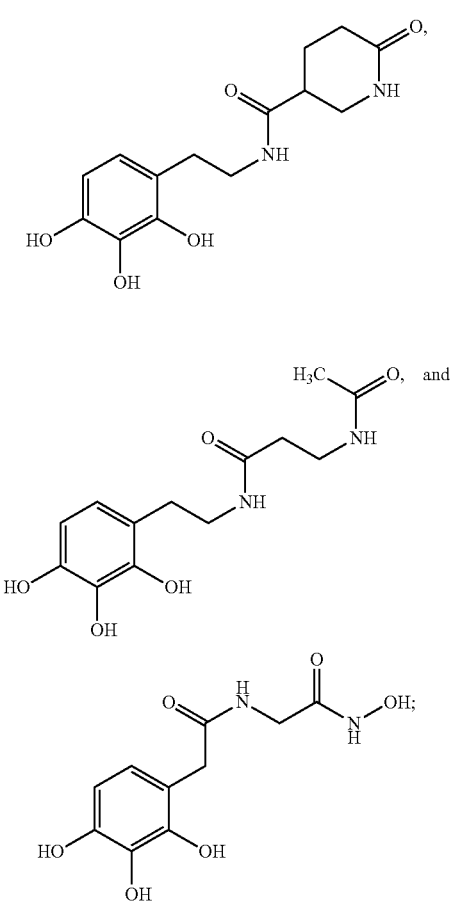

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

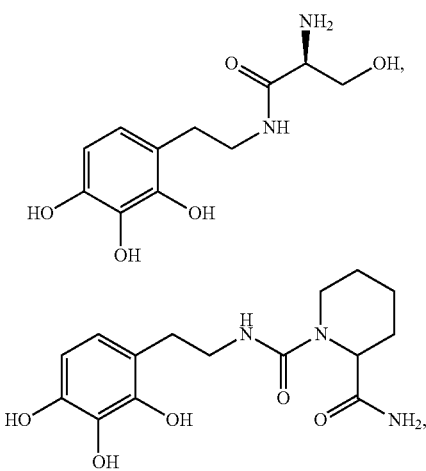

-continued

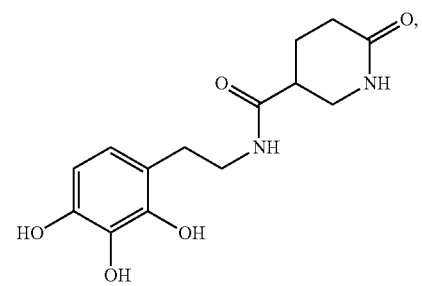

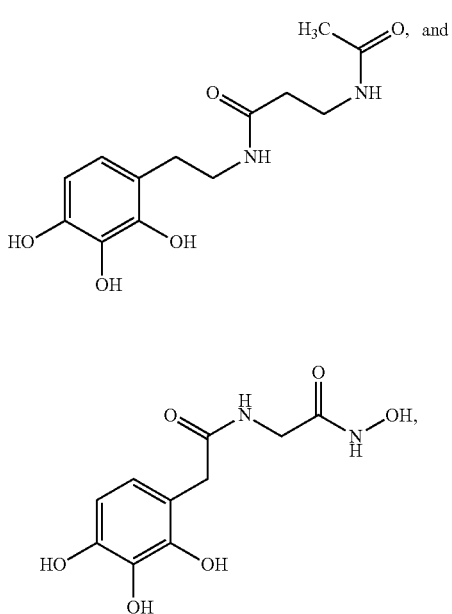

or any pharmaceutically acceptable salt thereof; and an anti-SCLC or anti-neuroblastoma therapeutic agent to the subject.

In some embodiments, the method comprises co-administering a compound selected from:

-continued or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

121
-continued

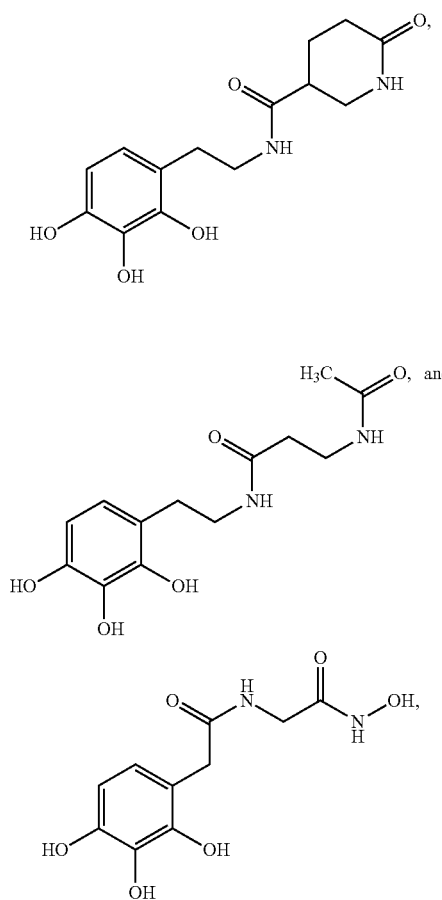

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

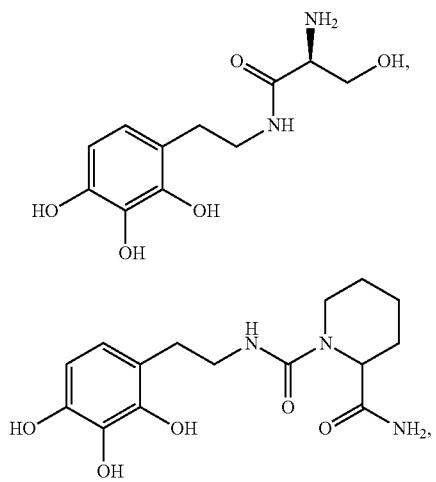

122
-continued

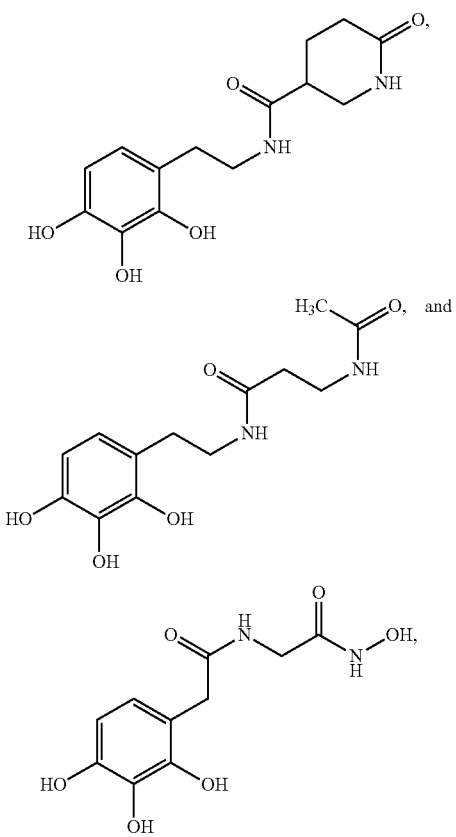

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

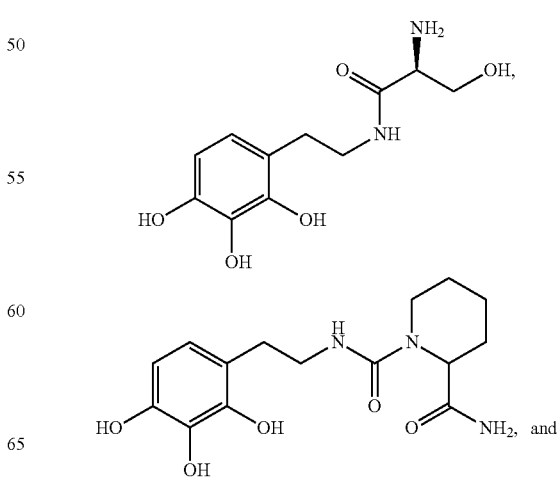

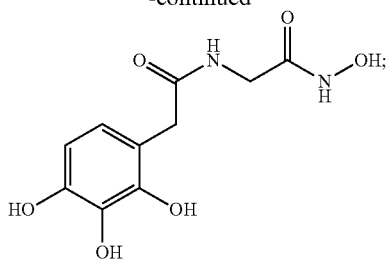

and an anti-SCLC or anti-neuroblastoma therapeutic agent to the subject.

In some embodiments, the method comprises co-administering a compound selected from:

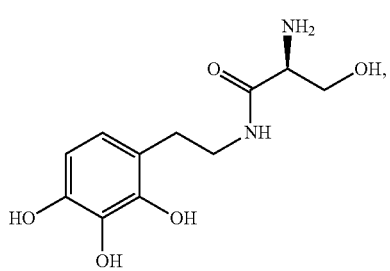 [SMILES: N[C@@H](CO)C(=O)NCCc1ccc(O)c(O)c1O]

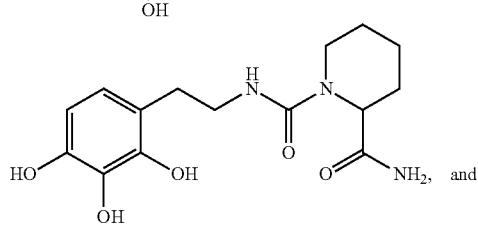

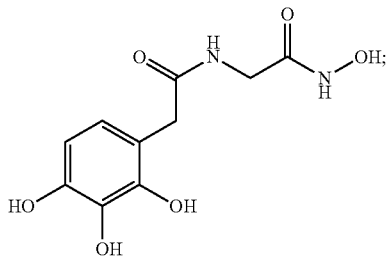

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

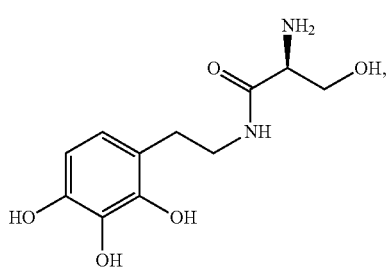

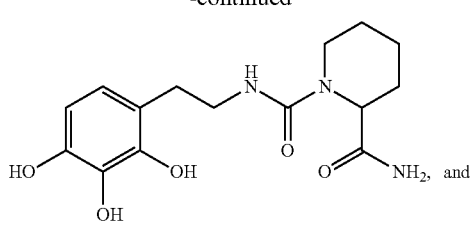

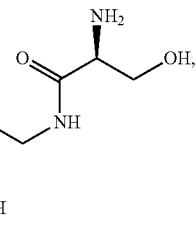

or any pharmaceutically acceptable salt thereof; and an anti-SCLC or anti-neuroblastoma therapeutic agent to the subject.

In some embodiments, the method comprises co-administering a compound selected from:

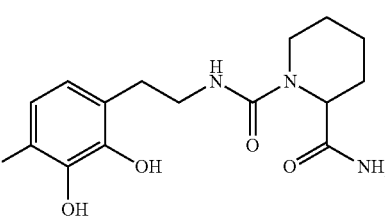

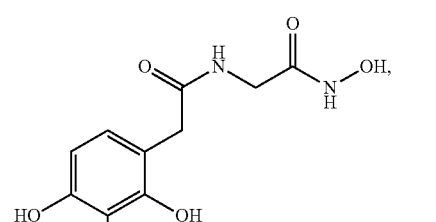

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

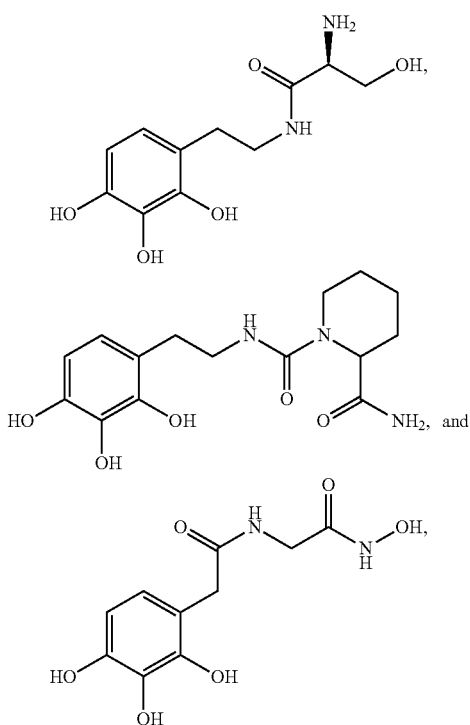

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

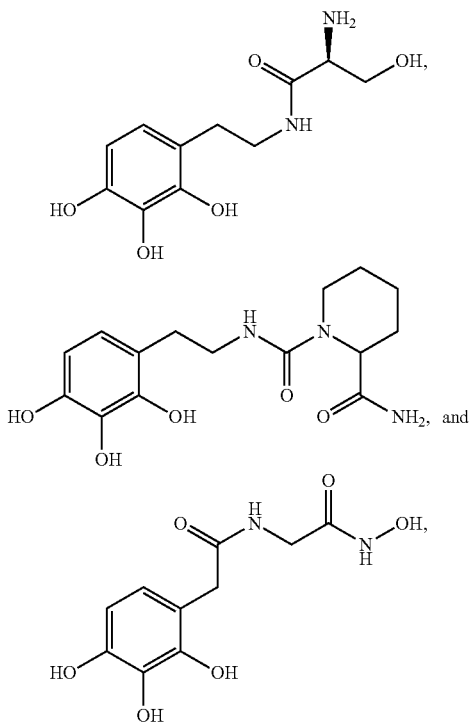

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

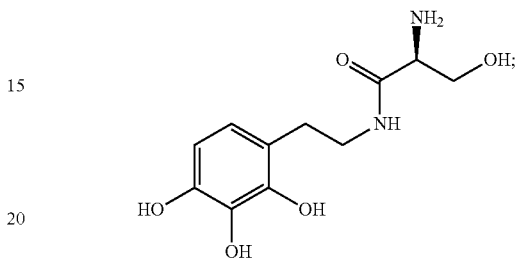

and an anti-SCLC or anti-neuroblastoma therapeutic agent to the subject.

In some embodiments, the method comprises co-administering a compound selected from:

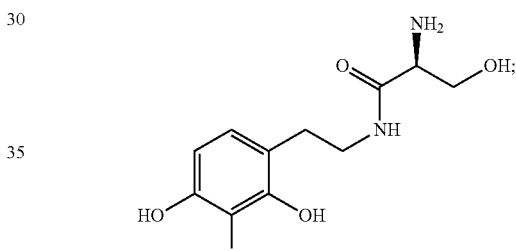

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

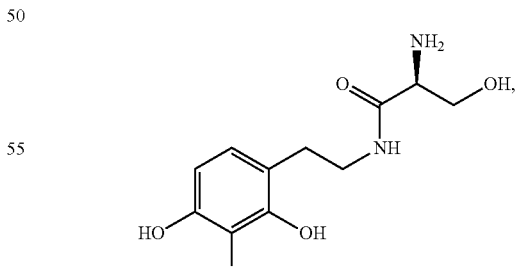

or any pharmaceutically acceptable salt thereof; and an anti-SCLC or anti-neuroblastoma therapeutic agent to the subject.

In some embodiments, the method comprises co-administering a compound selected from:

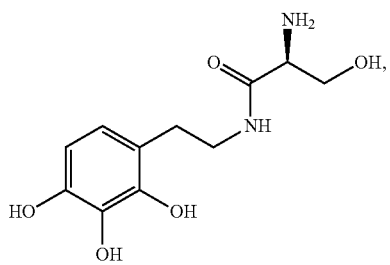

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

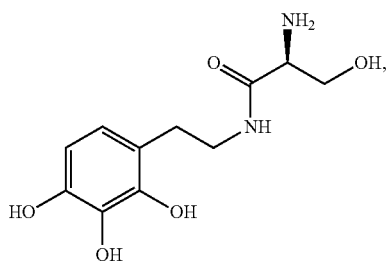 [SMILES: N[C@@H](CO)C(=O)NCCc1ccc(O)c(O)c1O]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

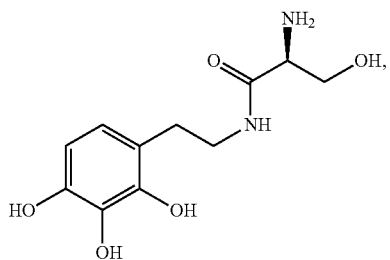 [SMILES: N[C@@H](CO)C(=O)NCCc1ccc(O)c(O)c1O]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

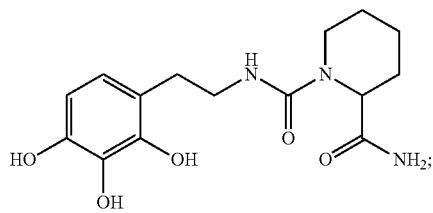 [SMILES: NC(=O)C1CCCCN1C(=O)NCCc1ccc(O)c(O)c1O]

and an anti-SCLC or anti-neuroblastoma therapeutic agent to the subject.

In some embodiments, the method comprises co-administering a compound selected from:

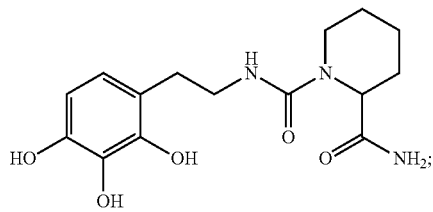 [SMILES: NC(=O)C1CCCCN1C(=O)NCCc1ccc(O)c(O)c1O]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

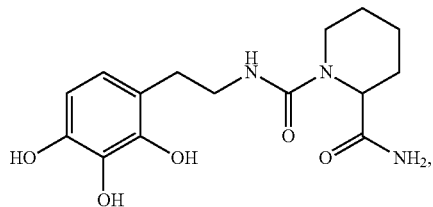 [SMILES: NC(=O)C1CCCCN1C(=O)NCCc1ccc(O)c(O)c1O]

or any pharmaceutically acceptable salt thereof; and an anti-SCLC or anti-neuroblastoma therapeutic agent to the subject.

In some embodiments, the method comprises co-administering a compound selected from:

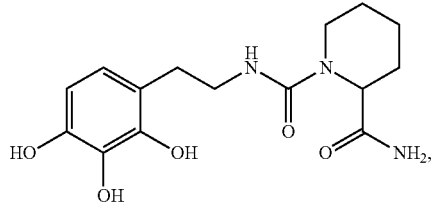 [SMILES: NC(=O)C1CCCCN1C(=O)NCCc1ccc(O)c(O)c1O]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

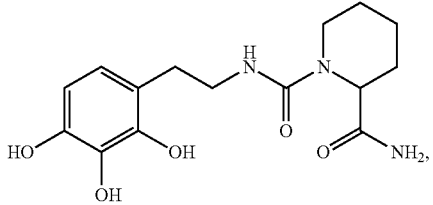

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

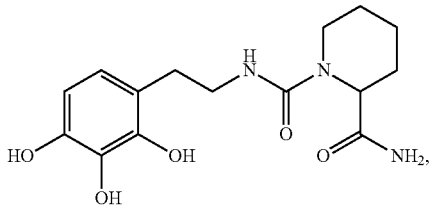

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

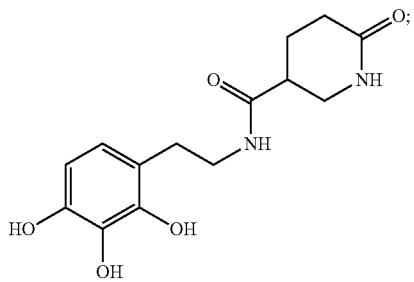 [SMILES: O=C1CCC(C(=O)NCCc2ccc(O)c(O)c2O)CN1]

and an anti-SCLC or anti-neuroblastoma therapeutic agent to the subject.

In some embodiments, the method comprises co-administering a compound selected from:

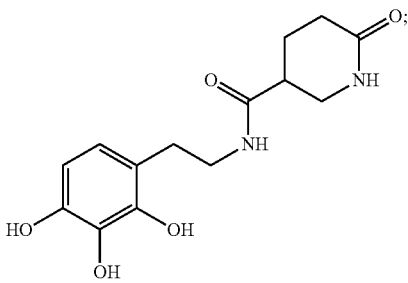 [SMILES: O=C1CCC(C(=O)NCCc2ccc(O)c(O)c2O)CN1]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

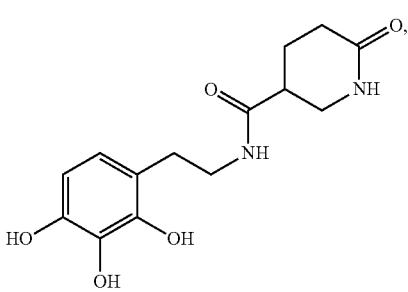 [SMILES: O=C1CCC(C(=O)NCCc2ccc(O)c(O)c2O)CN1]

or any pharmaceutically acceptable salt thereof; and an anti-SCLC or anti-neuroblastoma therapeutic agent to the subject.

In some embodiments, the method comprises co-administering a compound selected from:

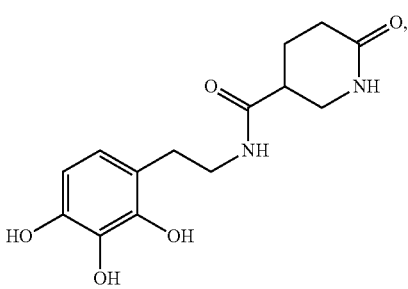 [SMILES: O=C1CCC(C(=O)NCCc2ccc(O)c(O)c2O)CN1]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

131

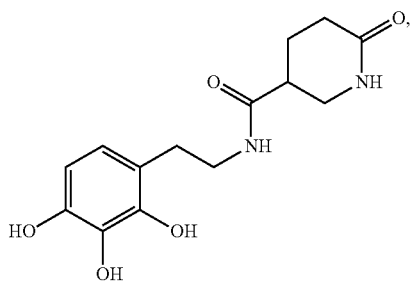 [SMILES: O=C1CCC(C(=O)NCCc2ccc(O)c(O)c2O)CN1]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

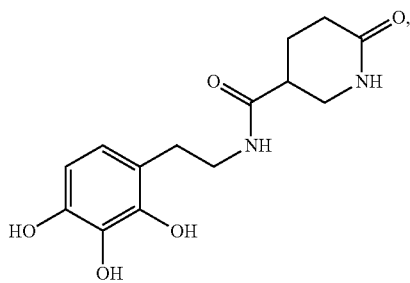 [SMILES: O=C1CCC(C(=O)NCCc2ccc(O)c(O)c2O)CN1]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

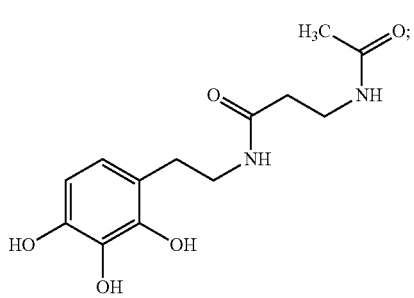 [SMILES: CC(=O)NCCC(=O)NCCc1ccc(O)c(O)c1O]

and an anti-SCLC or anti-neuroblastoma therapeutic agent to the subject.

In some embodiments, the method comprises co-administering a compound selected from:

132

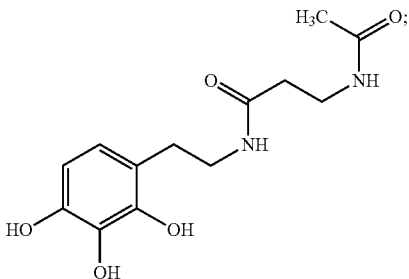 [SMILES: CC(=O)NCCC(=O)NCCc1ccc(O)c(O)c1O]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

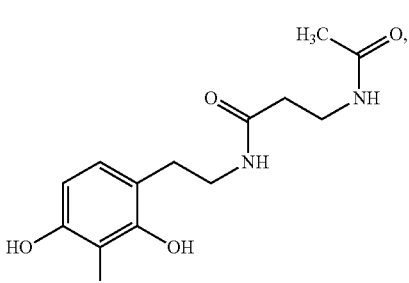

or any pharmaceutically acceptable salt thereof; and an anti-SCLC or anti-neuroblastoma therapeutic agent to the subject.

In some embodiments, the method comprises co-administering a compound selected from:

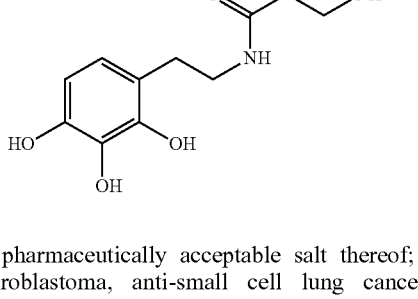

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

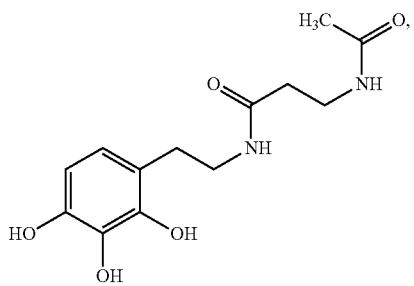 [SMILES: CC(=O)NCCC(=O)NCCc1ccc(O)c(O)c1O]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

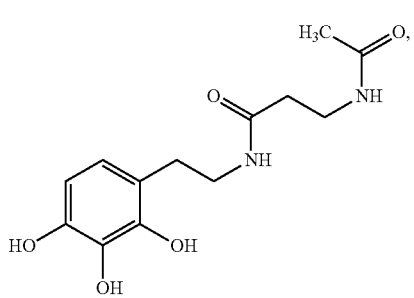 [SMILES: CC(=O)NCCC(=O)NCCc1ccc(O)c(O)c1O]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

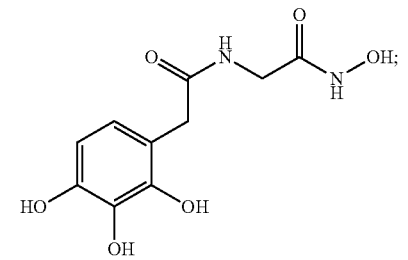 [SMILES: O=C(CNC(=O)Cc1ccc(O)c(O)c1O)NO]

and an anti-SCLC or anti-neuroblastoma therapeutic agent to the subject.

In some embodiments, the method comprises co-administering a compound selected from:

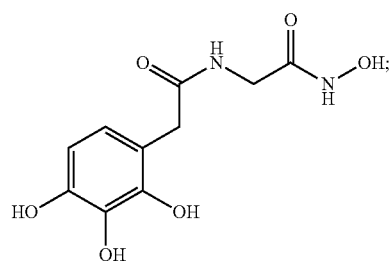 [SMILES: O=C(CNC(=O)Cc1ccc(O)c(O)c1O)NO]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

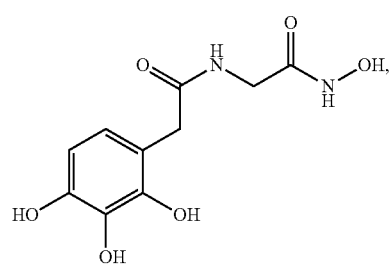

or any pharmaceutically acceptable salt thereof; and an anti-SCLC or anti-neuroblastoma therapeutic agent to the subject.

In some embodiments, the method comprises co-administering a compound selected from:

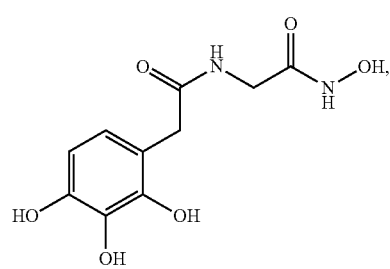 [SMILES: O=C(CNC(=O)Cc1ccc(O)c(O)c1O)NO]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

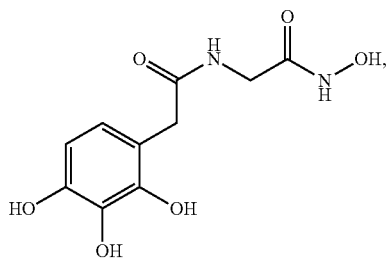 [SMILES: O=C(CNC(=O)Cc1ccc(O)c(O)c1O)NO]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

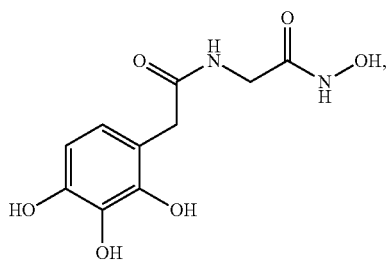 [SMILES: O=C(CNC(=O)Cc1ccc(O)c(O)c1O)NO]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

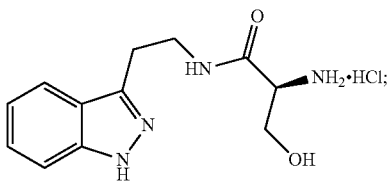

and an anti-SCLC or anti-neuroblastoma therapeutic agent to the subject.

In some embodiments, the method comprises co-administering a compound selected from:

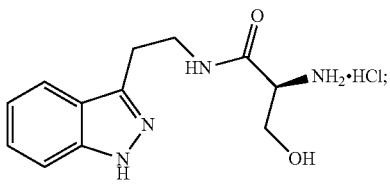

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

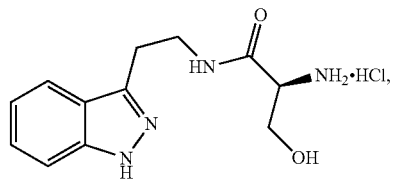

or any pharmaceutically acceptable salt thereof; and an anti-SCLC or anti-neuroblastoma therapeutic agent to the subject.

In some embodiments, the method comprises co-administering a compound selected from:

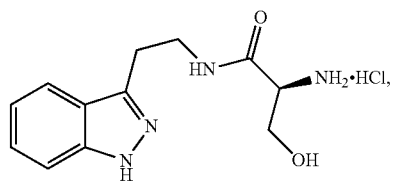

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

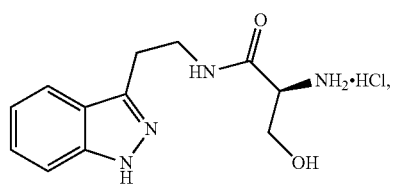

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

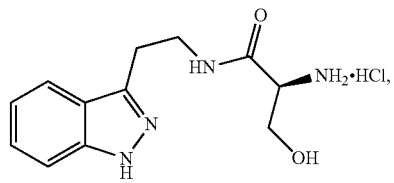

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

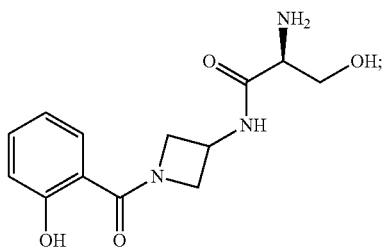 [SMILES: N[C@@H](CO)C(=O)NC1CN(C(=O)c2ccccc2O)C1]

and an anti-SCLC or anti-neuroblastoma therapeutic agent to the subject.

In some embodiments, the method comprises co-administering a compound selected from:

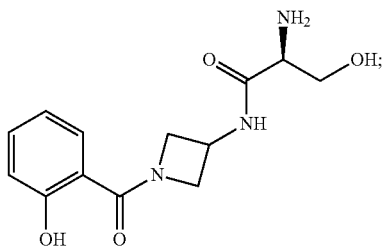 [SMILES: N[C@@H](CO)C(=O)NC1CN(C(=O)c2ccccc2O)C1]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

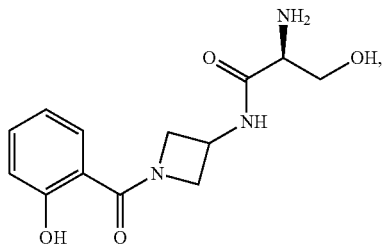 [SMILES: N[C@@H](CO)C(=O)NC1CN(C(=O)c2ccccc2O)C1]

or any pharmaceutically acceptable salt thereof; and an anti-SCLC or anti-neuroblastoma therapeutic agent to the subject.

In some embodiments, the method comprises co-administering a compound selected from:

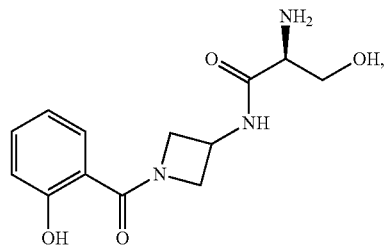 [SMILES: N[C@@H](CO)C(=O)NC1CN(C(=O)c2ccccc2O)C1]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

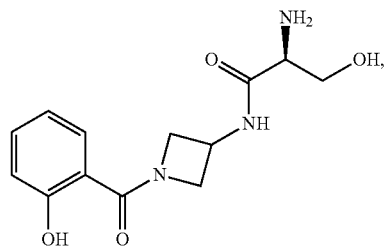 [SMILES: N[C@@H](CO)C(=O)NC1CN(C(=O)c2ccccc2O)C1]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

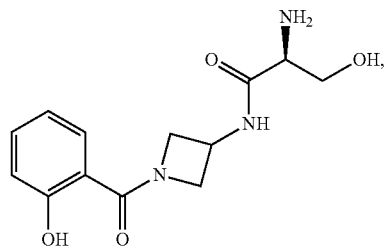 [SMILES: N[C@@H](CO)C(=O)NC1CN(C(=O)c2ccccc2O)C1]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

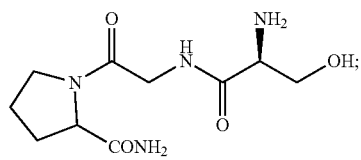 [SMILES: NC(=O)C1CCCN1C(=O)CNC(=O)[C@@H](N)CO]

and an anti-SCLC or anti-neuroblastoma therapeutic agent to the subject.

In some embodiments, the method comprises co-administering a compound selected from:

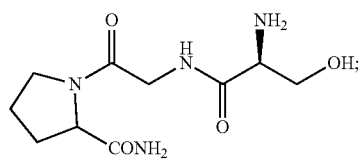

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

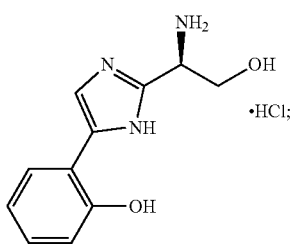

or any pharmaceutically acceptable salt thereof; and an anti-SCLC or anti-neuroblastoma therapeutic agent to the subject.

In some embodiments, the method comprises co-administering a compound selected from:

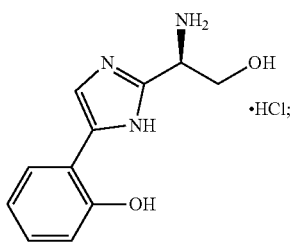

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

and an anti-SCLC or anti-neuroblastoma therapeutic agent to the subject.

In some embodiments, the method comprises co-administering a compound selected from:

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

141

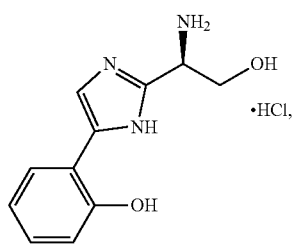

or any pharmaceutically acceptable salt thereof; and an anti-SCLC or anti-neuroblastoma therapeutic agent to the subject.

In some embodiments, the method comprises co-administering a compound selected from:

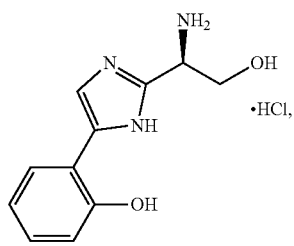

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

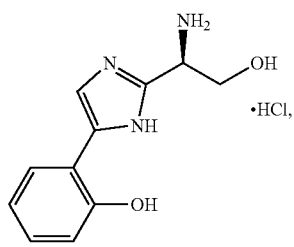

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

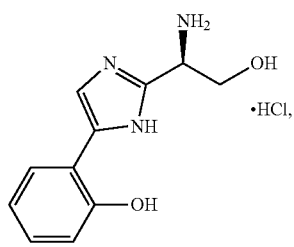

142 or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

COMPOUND CSRM617

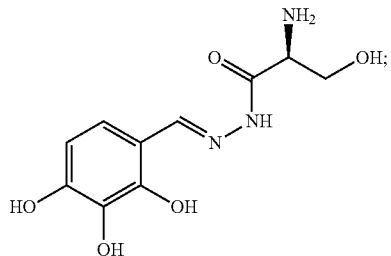

and an anti-SCLC or anti-neuroblastoma therapeutic agent to the subject.

In some embodiments, the method comprises co-administering a compound selected from:

COMPOUND CSRM617

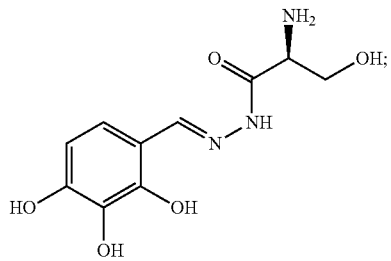

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

COMPOUND CSRM617

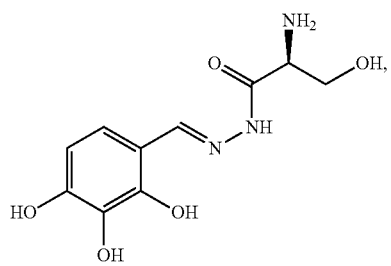

or any pharmaceutically acceptable salt thereof; and an anti-SCLC or anti-neuroblastoma therapeutic agent to the subject.

In some embodiments, the method comprises co-administering a compound selected from:

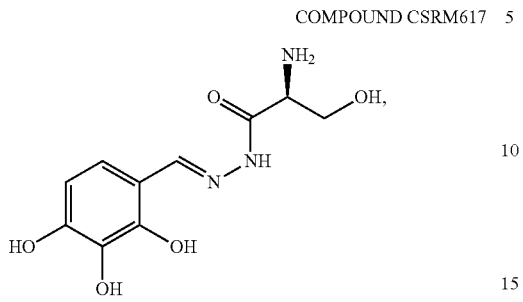

COMPOUND CSRM617 or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

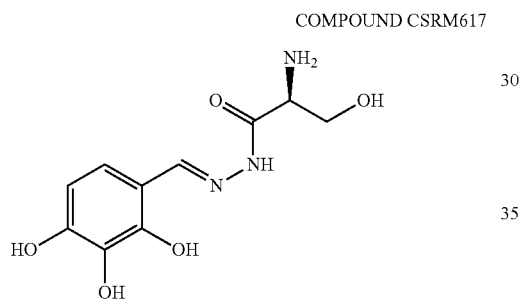

COMPOUND CSRM617 or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

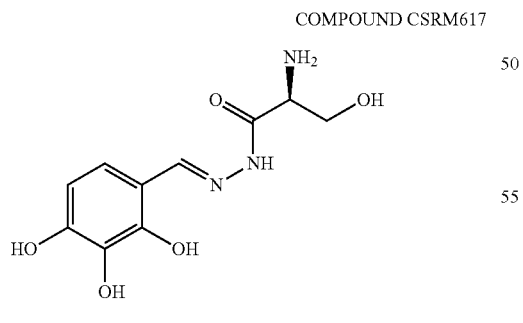

COMPOUND CSRM617 or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

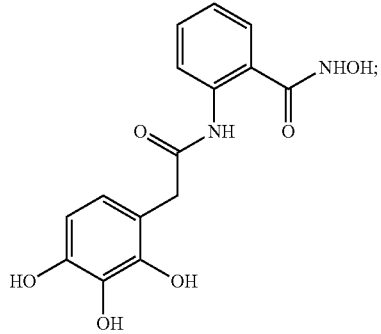

and an anti-SCLC or anti-neuroblastoma therapeutic agent to the subject.

In some embodiments, the method comprises co-administering a compound selected from:

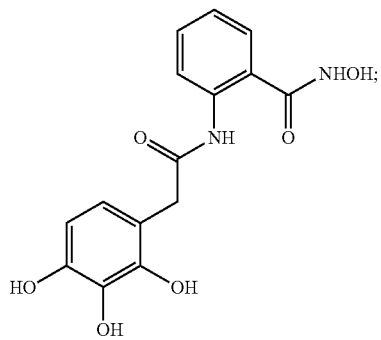

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

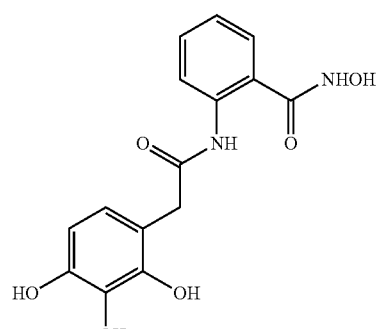

or any pharmaceutically acceptable salt thereof; and an anti-SCLC or anti-neuroblastoma therapeutic agent to the subject.

In some embodiments, the method comprises co-administering a compound selected from:

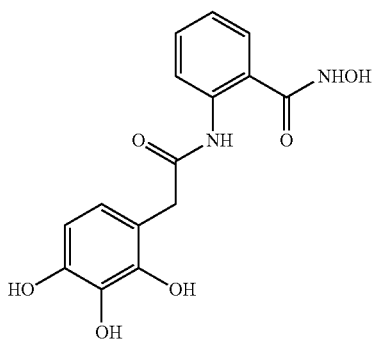

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

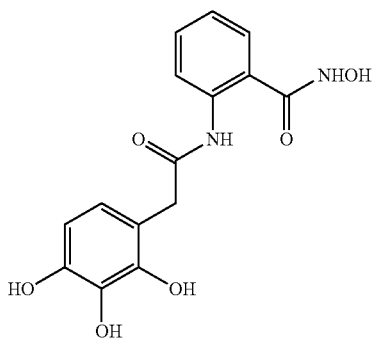

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

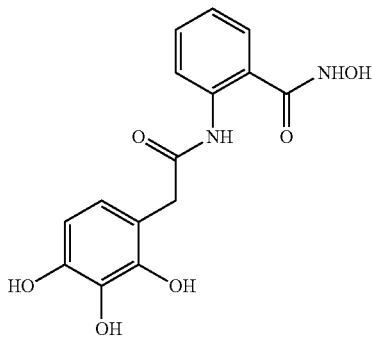

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

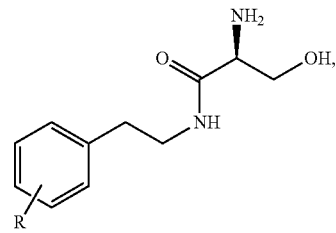

or a prodrug, isomer, dimer, enantiomer, derivative, or pharmaceutically acceptable salt thereof, wherein:

R is independently one or more of hydrogen or optionally substituted substituent; and and an anti-SCLC or anti-neuroblastoma therapeutic agent to the subject.

In some embodiments, the method comprises co-administering a compound having the structure:

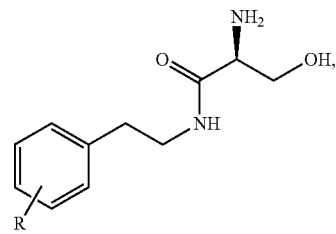

or a prodrug, isomer, dimer, enantiomer, derivative, or pharmaceutically acceptable salt thereof, wherein: R is independently one or more of hydrogen or optionally substituted substituent; and and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

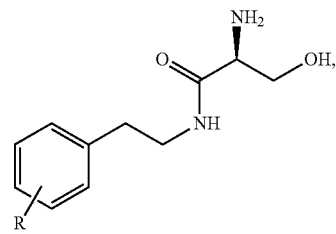

wherein:

R is independently one or more of hydrogen or optionally substituted substituent; and an anti-SCLC or anti-neuroblastoma therapeutic agent to the subject.

In some embodiments, the method comprises co-administering a compound having the structure:

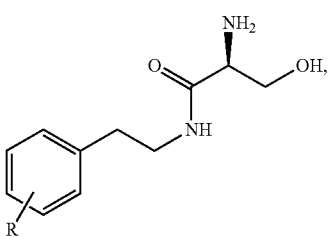

wherein:

R is independently one or more of hydrogen or optionally substituted substituent; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

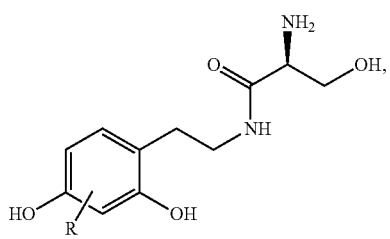

or a prodrug, isomer, dimer, enantiomer, derivative, or pharmaceutically acceptable salt thereof, wherein:

R is independently one or more of hydrogen or optionally substituted substituent; and an anti-SCLC or anti-neuroblastoma therapeutic agent to the subject.

In some embodiments, the method comprises co-administering a compound having the structure:

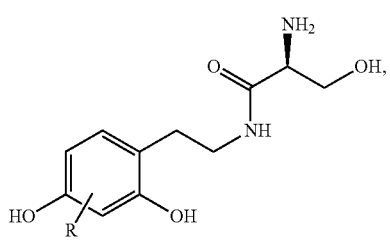

or a prodrug, isomer, dimer, enantiomer, derivative, or pharmaceutically acceptable salt thereof, wherein:

R is independently one or more of hydrogen or optionally substituted substituent; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

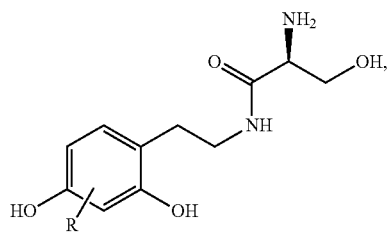

wherein:

R is independently one or more of hydrogen or optionally substituted substituent; and an anti-SCLC or anti-neuroblastoma therapeutic agent to the subject.

In some embodiments, the method comprises co-administering a compound having the structure:

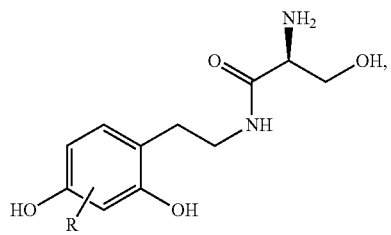

wherein:

R is independently one or more of hydrogen or optionally substituted substituent; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

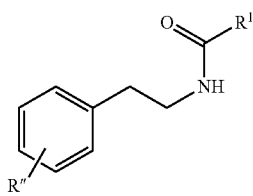

or a prodrug, isomer, dimer, enantiomer, derivative, or pharmaceutically acceptable salt thereof wherein:

R" is independently one or more of hydrogen or optionally substituted substituent; and R' is hydrogen or optionally substituted substituent; and an anti-SCLC or anti-neuroblastoma therapeutic agent to the subject.

In some embodiments, the method comprises co-administering a compound having the structure:

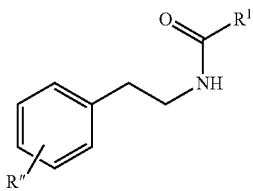

or a prodrug, isomer, dimer, enantiomer, derivative, or pharmaceutically acceptable salt thereof wherein:

R'' is independently one or more of hydrogen or optionally substituted substituent; and R' is hydrogen or optionally substituted substituent; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

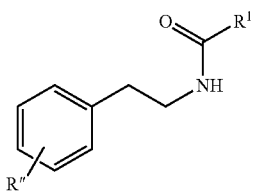

wherein:

R'' is independently one or more of hydrogen or optionally substituted substituent; and R$^1$ is hydrogen or optionally substituted substituent; and an anti-SCLC or anti-neuroblastoma therapeutic agent to the subject.

In some embodiments, the method comprises co-administering a compound having the structure:

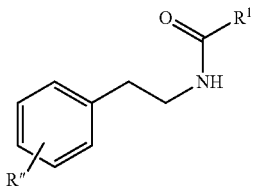

wherein:

R'' is independently one or more of hydrogen or optionally substituted substituent; and R$^1$ is hydrogen or optionally substituted substituent; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

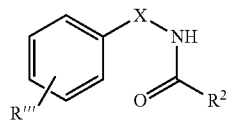

or prodrug, isomer, dimer, enantiomer, derivative, or pharmaceutically acceptable salt thereof, wherein:

R''' is independently one or more of hydrogen or optionally substituted substituent;

R$^2$ is hydrogen or optionally substituted substituent; and

X is NHC(O), C(O)NH, OC(O), C(O)O, C(O), or CH=N; and an anti-SCLC or anti-neuroblastoma therapeutic agent to the subject.

In some embodiments, the method comprises co-administering a compound having the structure:

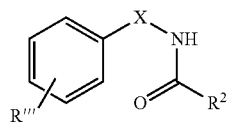

or prodrug, isomer, dimer, enantiomer, derivative, or pharmaceutically acceptable salt thereof, wherein:

R''' is independently one or more of hydrogen or optionally substituted substituent;

R$^2$ is hydrogen or optionally substituted substituent; and

X is NHC(O), C(O)NH, OC(O), C(O)O, C(O), or CH=N; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

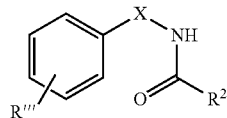

wherein:

R''' is independently one or more of hydrogen or optionally substituted substituent;

R$^2$ is hydrogen or optionally substituted substituent; and

X is NHC(O), C(O)NH, OC(O), C(O)O, C(O), or CH=N; and an anti-SCLC or anti-neuroblastoma therapeutic agent to the subject.

In some embodiments, the method comprises co-administering a compound having the structure:

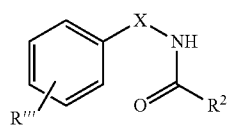

wherein:

R''' is independently one or more of hydrogen or optionally substituted substituent;

R$^2$ is hydrogen or optionally substituted substituent; and

X is NHC(O), C(O)NH, OC(O), C(O)O, C(O), or CH=N;
and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

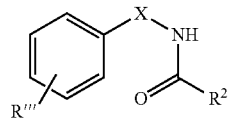

or prodrug, isomer, dimer, enantiomer, derivative, or pharmaceutically acceptable salt thereof, wherein:

R''' is independently one or more of hydrogen or optionally substituted substituent;

$R^2$ is hydrogen or optionally substituted substituent; and

X is NHC(O), C(O)NH, OC(O), C(O)O, C(O), or CH=N; and an anti-SCLC or anti-neuroblastoma therapeutic agent to the subject, provided that the compound is not

COMPOUND CSRM617

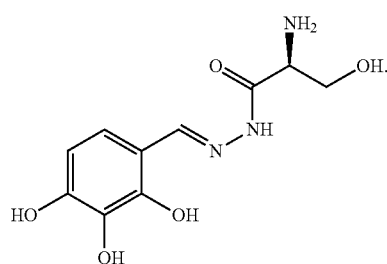

In some embodiments, the method comprises co-administering a compound having the structure:

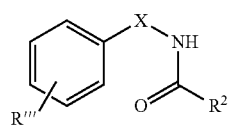

or prodrug, isomer, dimer, enantiomer, derivative, or pharmaceutically acceptable salt thereof, wherein:

R''' is independently one or more of hydrogen or optionally substituted substituent;

$R^2$ is hydrogen or optionally substituted substituent; and

X is NHC(O), C(O)NH, OC(O), C(O)O, C(O), or CH=N; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject, provided that the compound is not

COMPOUND CSRM617

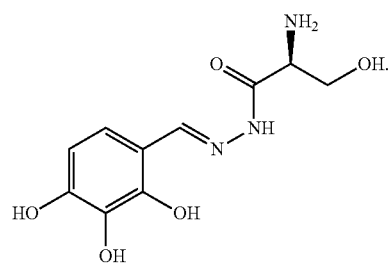

In some embodiments, the method comprises co-administering a compound having the structure:

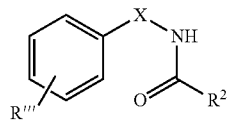

wherein:
R''' is independently one or more of hydrogen or optionally substituted substituent;

$R^2$ is hydrogen or optionally substituted substituent; and

X is NHC(O), C(O)NH, OC(O), C(O)O, C(O), or CH=N; and an anti-SCLC or anti-neuroblastoma therapeutic agent to the subject, provided that the compound is not

COMPOUND CSRM617

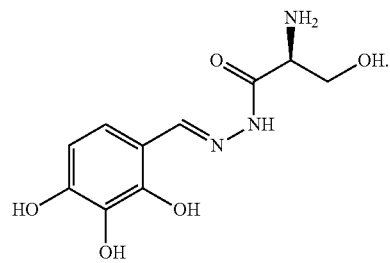

In some embodiments, the method comprises co-administering a compound having the structure:

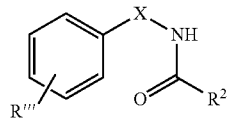

wherein:
R''' is independently one or more of hydrogen or optionally substituted substituent;

$R^2$ is hydrogen or optionally substituted substituent; and

X is NHC(O), C(O)NH, OC(O), C(O)O, C(O), or CH=N; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject, provided that the compound is not

COMPOUND CSRM617

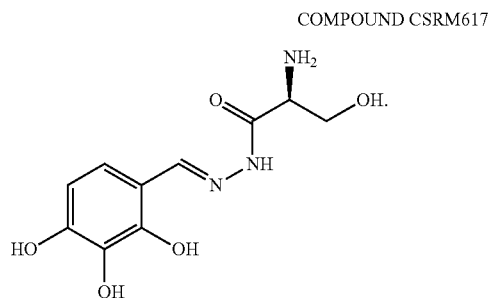 [SMILES: N[C@@H](CO)C(=O)N/N=C/c1ccc(O)c(O)c1O]

In some embodiments, the method comprises co-administering a compound having the structure:

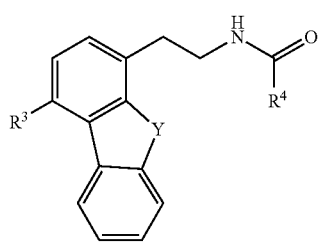

or a prodrug, an isomer, a dimer, an enantiomer, a derivative, or a pharmaceutically acceptable salt thereof, wherein:
$R^3$ is hydrogen or optionally substituted substituent;
$R^4$ is hydrogen or optionally substituted substituent; and
Y is O or S; and an anti-SCLC or anti-neuroblastoma therapeutic agent to the subject.

In some embodiments, the method comprises co-administering a compound having the structure:

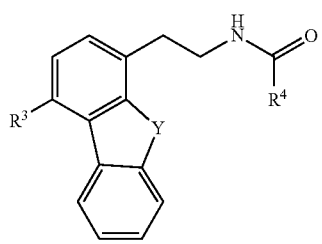

or a prodrug, an isomer, a dimer, an enantiomer, a derivative, or a pharmaceutically acceptable salt thereof, wherein:
$R^3$ is hydrogen or optionally substituted substituent;
$R^4$ is hydrogen or optionally substituted substituent; and
Y is O or S; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound having the structure:

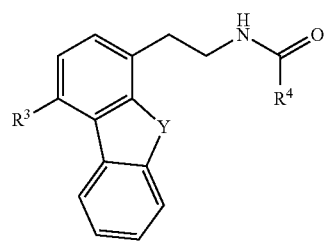

wherein:
$R^3$ is hydrogen or optionally substituted substituent;
$R^4$ is hydrogen or optionally substituted substituent; and
Y is O or S; and an anti-SCLC or anti-neuroblastoma therapeutic agent to the subject.

In some embodiments, the method comprises co-administering a compound having the structure:

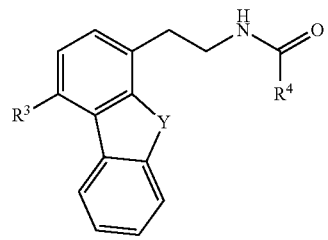

wherein:
$R^3$ is hydrogen or optionally substituted substituent;
$R^4$ is hydrogen or optionally substituted substituent; and
Y is O or S; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

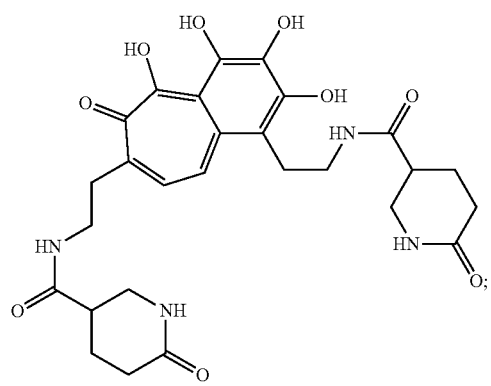 [SMILES: O=C1CCC(C(=O)NCCc2ccc3c(CCNC(=O)C4CCC(=O)NC4)c(O)c(O)c(O)c3c(O)c2=O)CN1]

and an anti-SCLC or anti-neuroblastoma therapeutic agent to the subject.

In some embodiments, the method comprises co-administering a compound selected from:

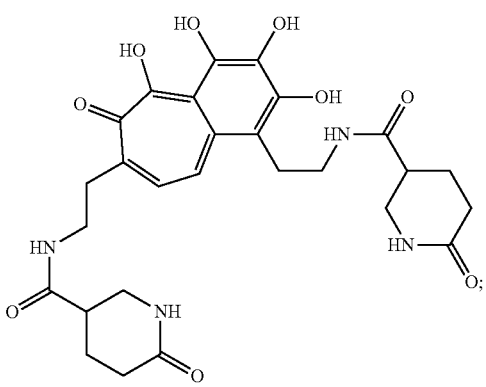 [SMILES: O=C1CCC(C(=O)NCCc2ccc3c(CCNC(=O)C4CCC(=O)NC4)c(O)c(O)c(O)c3c(O)c2=O)CN1]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

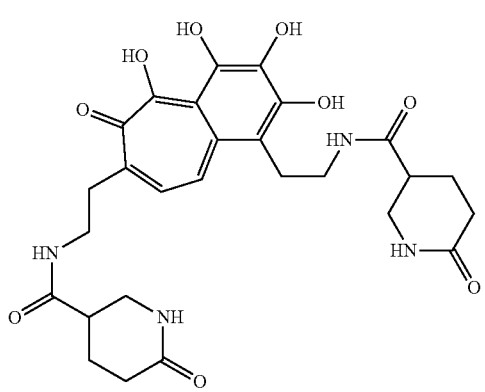 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof; and an anti-SCLC or anti-neuroblastoma therapeutic agent to the subject.

In some embodiments, the method comprises co-administering a compound selected from:

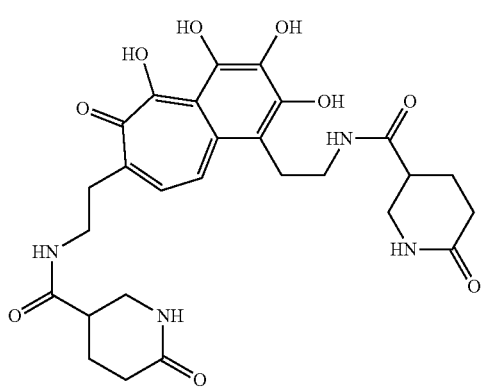 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

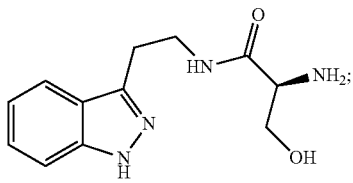 [SMILES: N[C@@H](CO)C(=O)NCCc1n[nH]c2ccccc12]

and an anti-SCLC or anti-neuroblastoma therapeutic agent to the subject.

In some embodiments, the method comprises co-administering a compound selected from:

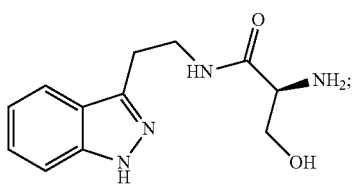 [SMILES: N[C@@H](CO)C(=O)NCCc1n[nH]c2ccccc12]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

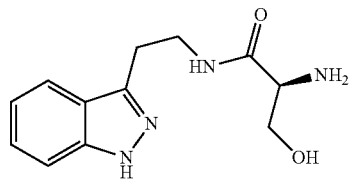 [SMILES: N[C@@H](CO)C(=O)NCCc1n[nH]c2ccccc12]

or any pharmaceutically acceptable salt thereof; and an anti-SCLC or anti-neuroblastoma therapeutic agent to the subject.

In some embodiments, the method comprises co-administering a compound selected from:

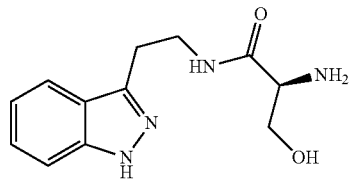 [SMILES: N[C@@H](CO)C(=O)NCCc1n[nH]c2ccccc12]

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

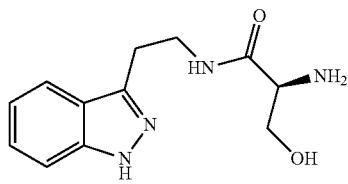 [SMILES: N[C@@H](CO)C(=O)NCCc1n[nH]c2ccccc12]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

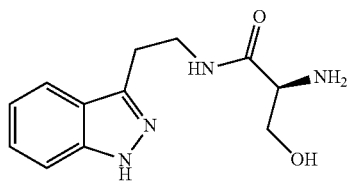 [SMILES: N[C@@H](CO)C(=O)NCCc1n[nH]c2ccccc12]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

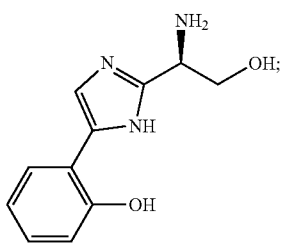 [SMILES: N[C@@H](CO)c1ncc(-c2ccccc2O)[nH]1]

and an anti-SCLC or anti-neuroblastoma therapeutic agent to the subject.

In some embodiments, the method comprises co-administering a compound selected from:

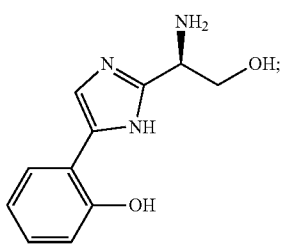 [SMILES: N[C@@H](CO)c1ncc(-c2ccccc2O)[nH]1]

and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

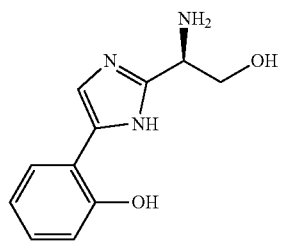 [SMILES: N[C@@H](CO)c1ncc(-c2ccccc2O)[nH]1]

or any pharmaceutically acceptable salt thereof; and an anti-SCLC or anti-neuroblastoma therapeutic agent to the subject.

In some embodiments, the method comprises co-administering a compound selected from:

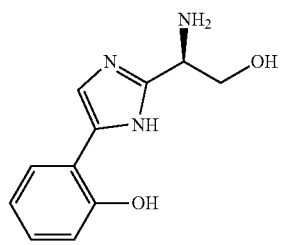

or any pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

In some embodiments, the method comprises co-administering a compound selected from:

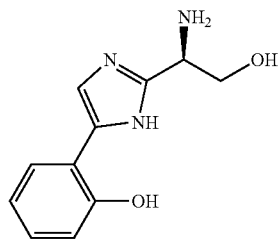 [SMILES: N[C@@H](CO)c1ncc(-c2ccccc2O)[nH]1]

or a prodrug, an isomer, a dimer, an enantiomer, a derivative, or a pharmaceutically acceptable salt thereof; and an anti-SCLC or anti-neuroblastoma therapeutic agent to the subject.

In some embodiments, the method comprises co-administering a compound selected from:

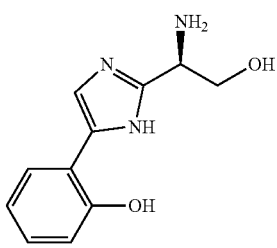 [SMILES: N[C@@H](CO)c1ncc(-c2ccccc2O)[nH]1]

or a prodrug, an isomer, a dimer, an enantiomer, a derivative, or a pharmaceutically acceptable salt thereof; and an anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapeutic agent to the subject.

As used herein, the terms "anti-SCLC therapeutic agent" or "anti-neuroblastoma therapeutic agent" refer to any compound (including its analogs, derivatives, prodrugs and pharmaceutically salts) or composition which can be used to treat SCLC or neuroblastoma. Anti-SCLC or anti-neuroblastoma compounds for use in the present invention include, but are not limited to, inhibitors of topoisomerase I and II, alkylating agents, microtubule inhibitors (e.g., taxol), and angiogenesis inhibitors. Exemplary anti-SCLC or anti-neuroblastoma compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levami sole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-SCLC or anti-neuroblastoma agent is a paclitaxel-carbohydrate conjugate, e.g., a paclitaxel-glucose conjugate, as described in U.S. Pat. No. 6,218,367, content of which is incorporated herein by reference in its entirety.

As used herein, the terms "anti-neuroblastoma", "anti-small cell lung cancer (anti-SCLC)", "anti-large cell neuroendocrine cancer (anti-LCNEC)", "anti-large-cell carcinoma (anti-LCC)", "anti-squamous cell carcinoma (anti-SqCC)", or "anti-adenocarcinoma (anti-AC)" refer to any compound (including its analogs, derivatives, prodrugs and pharmaceutically salts) or composition which can be used to treat neuroblastoma, small cell lung cancer (SCLC), large cell neuroendocrine cancer (LCNEC), large-cell carcinoma (LCC), squamous cell carcinoma (SqCC), or adenocarcinoma (AC). "Anti-cancer", "anti-lung cancer", "anti-neuroblastoma", "anti-small cell lung cancer (anti-SCLC)", "anti-large cell neuroendocrine cancer (anti-LCNEC)", "anti-large-cell carcinoma (anti-LCC)", "anti-squamous cell carcinoma (anti-SqCC)", or "anti-adenocarcinoma (anti-AC)" compounds for use in the present invention include, but are not limited to, inhibitors of topoisomerase I and II, alkylating agents, microtubule inhibitors (e.g., taxol), and angiogenesis inhibitors. Exemplary "anti-cancer", "anti-lung cancer", "anti-neuroblastoma", "anti-small cell lung cancer (anti-SCLC)", "anti-large cell neuroendocrine cancer (anti-LCNEC)", "anti-large-cell carcinoma (anti-LCC)", "anti-squamous cell carcinoma (anti-SqCC)", or "anti-adenocarcinoma (anti-AC)" compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the "anti-cancer", "anti-lung cancer", "anti-neuroblastoma", "anti-small cell lung cancer (anti-SCLC)", "anti-large cell neuroendocrine cancer (anti-LCNEC)", "anti-large-cell carcinoma (anti-LCC)", "anti-squamous cell carcinoma (anti-SqCC)", or "anti-adenocarcinoma (anti-AC)" agent is a paclitaxel-carbohydrate conjugate, e.g., a paclitaxel-glucose conjugate, as described in U.S. Pat. No. 6,218,367, content of which is incorporated herein by reference in its entirety.

The methods of the invention are especially useful in combination with anti-SCLC or anti-neuroblastoma treatments that involve administering a second drug that acts in a different phase of the cell cycle.

The methods of the invention are especially useful in combination with anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) treatments that involve administering a second drug that acts in a different phase of the cell cycle.

Pharmaceutical Compositions of the Invention

In various embodiments, the present invention provides pharmaceutical compositions for use in the methods described herein.

Various embodiments of the present invention provide a pharmaceutical composition for use in the methods described herein comprising a compound selected from:

COMPOUND CSRM617

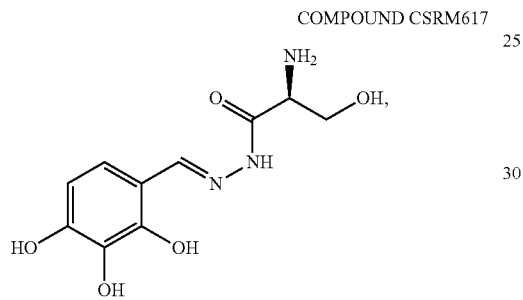

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

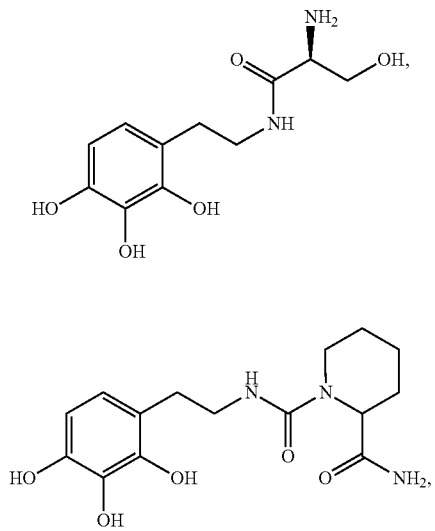

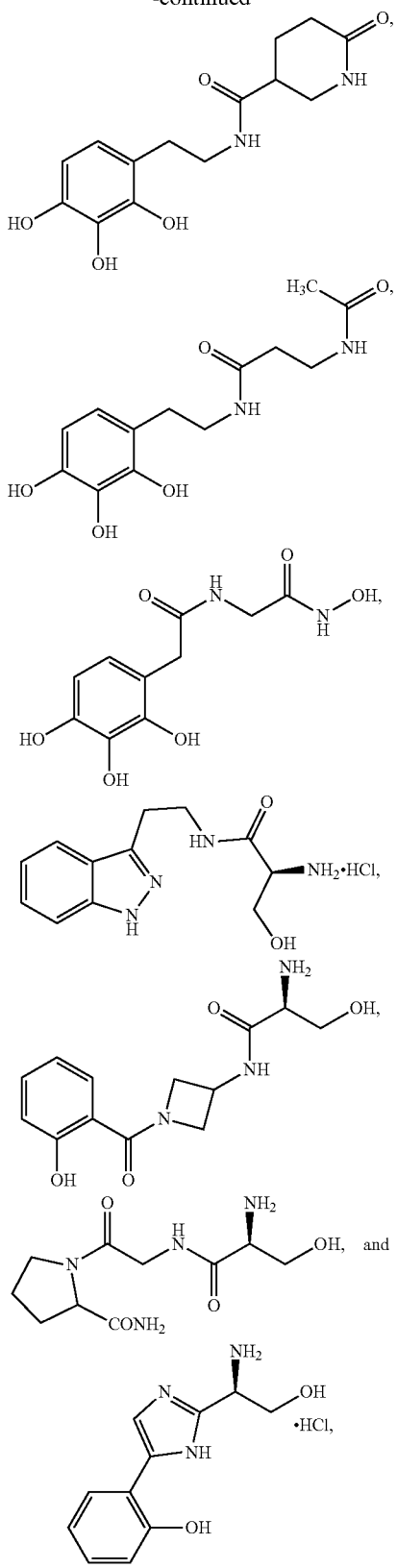

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

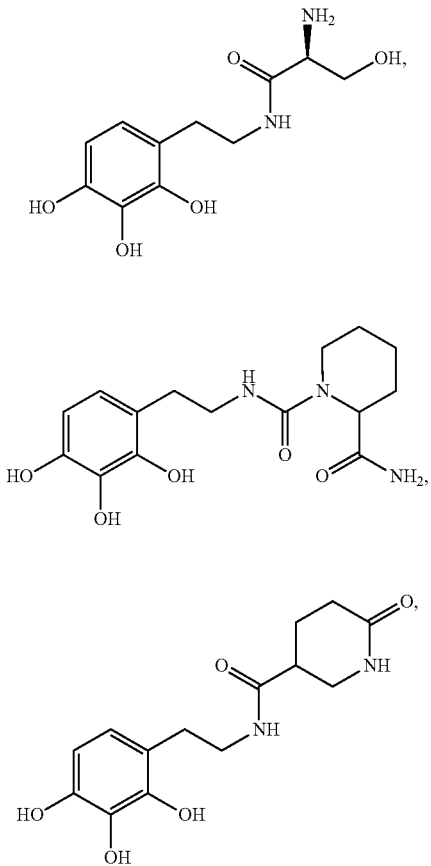

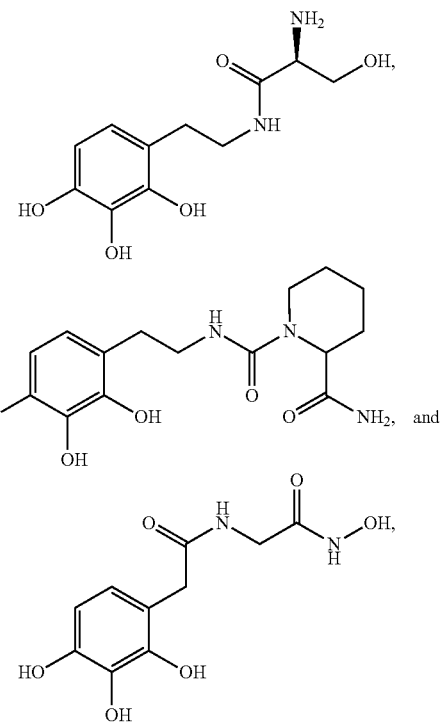

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

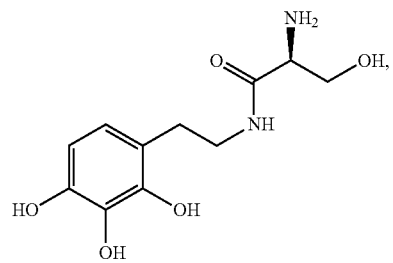 [SMILES: N[C@@H](CO)C(=O)NCCc1ccc(O)c(O)c1O]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

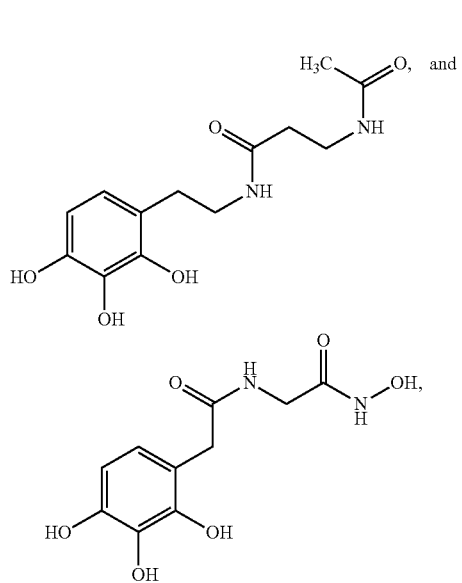

or a prodrug, isomer, dimer, enantiomer, derivative, or pharmaceutically acceptable salt thereof; and a pharmaceutical composition for use in the methods described herein comprising a compound selected from:

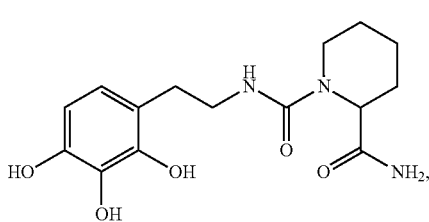 [SMILES: NC(=O)C1CCCCN1C(=O)NCCc1ccc(O)c(O)c1O]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

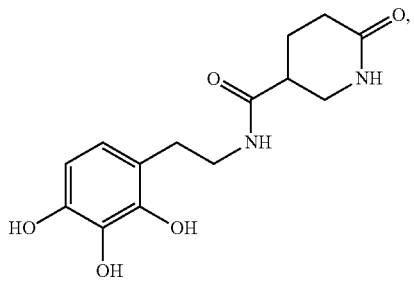 [SMILES: O=C1CCC(C(=O)NCCc2ccc(O)c(O)c2O)CN1]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

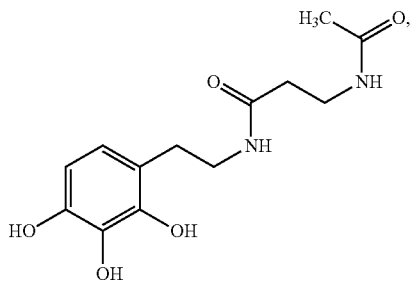 [SMILES: CC(=O)NCCC(=O)NCCc1ccc(O)c(O)c1O]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

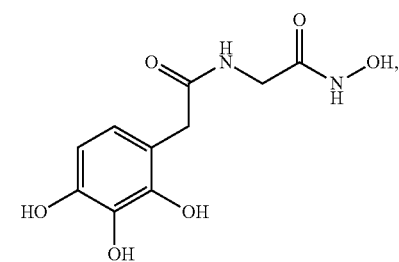 [SMILES: O=C(CNC(=O)Cc1ccc(O)c(O)c1O)NO]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

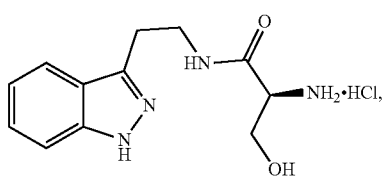

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

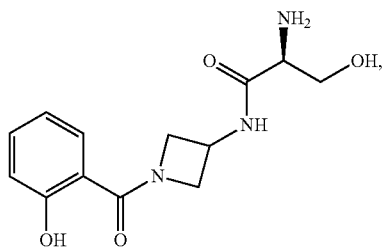 [SMILES: N[C@@H](CO)C(=O)NC1CN(C(=O)c2ccccc2O)C1]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

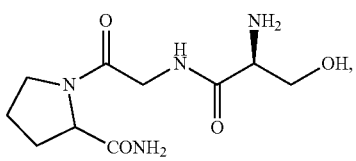 [SMILES: NC(=O)C1CCCN1C(=O)CNC(=O)[C@@H](N)CO]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

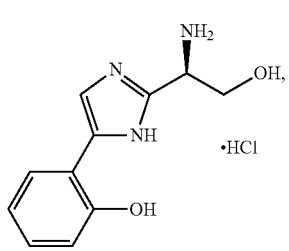 [SMILES: N[C@@H](CO)c1ncc(-c2ccccc2O)[nH]1 ; Cl]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

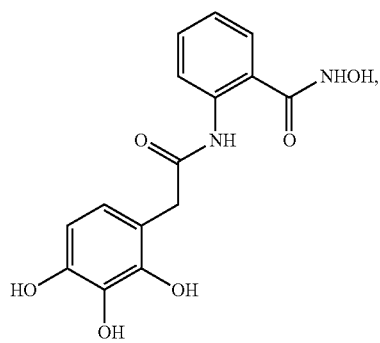

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

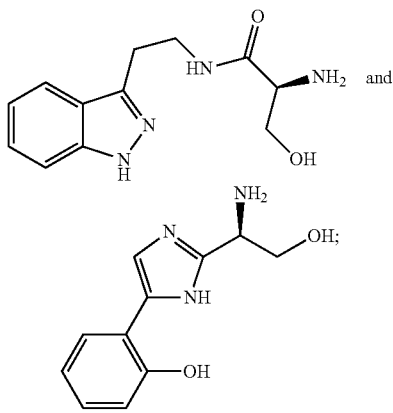

and a pharmaceutically acceptable excipient or carrier.

Various embodiments of the present invention provide a pharmaceutical composition for use in the methods described herein comprising a compound selected from:

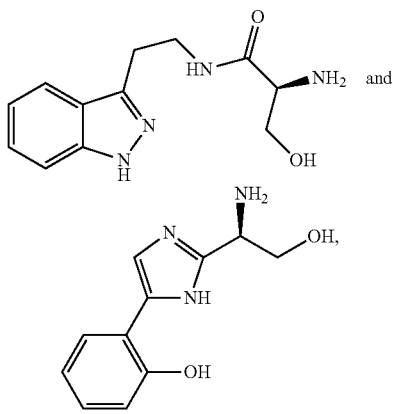

or any pharmaceutically acceptable salt thereof; and a pharmaceutically acceptable excipient or carrier.

Various embodiments of the present invention provide a pharmaceutical composition for use in the methods described herein comprising a compound selected from:

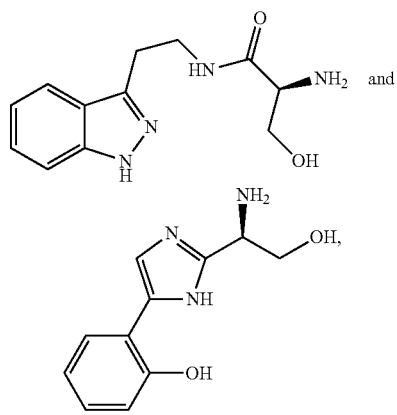

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

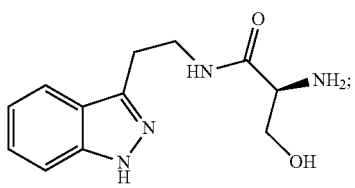 [SMILES: N[C@@H](CO)C(=O)NCCc1n[nH]c2ccccc12]

and a pharmaceutically acceptable excipient or carrier.

Various embodiments of the present invention provide a pharmaceutical composition for use in the methods described herein comprising a compound selected from:

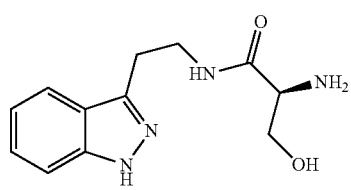 [SMILES: N[C@@H](CO)C(=O)NCCc1n[nH]c2ccccc12]

or any pharmaceutically acceptable salt thereof; and a pharmaceutically acceptable excipient or carrier.

Various embodiments of the present invention provide a pharmaceutical composition for use in the methods described herein comprising a compound selected from:

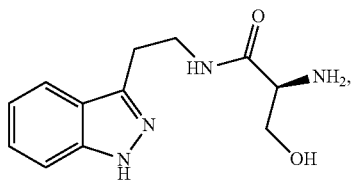 [SMILES: N[C@@H](CO)C(=O)NCCc1n[nH]c2ccccc12]

or a prodrug, isomer, dimer, enantiomer, derivative, or pharmaceutically acceptable salt thereof; and a pharmaceutically acceptable excipient or carrier.

Various embodiments of the present invention provide a pharmaceutical composition for use in the methods described herein comprising a compound selected from:

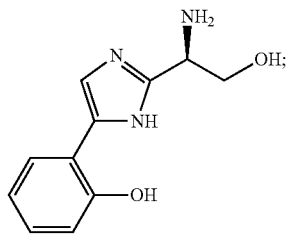 [SMILES: N[C@@H](CO)c1ncc(-c2ccccc2O)[nH]1]

and a pharmaceutically acceptable excipient or carrier.

Various embodiments of the present invention provide a pharmaceutical composition for use in the methods described herein comprising a compound selected from:

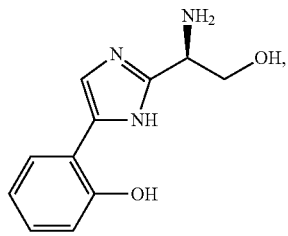 [SMILES: N[C@@H](CO)c1ncc(-c2ccccc2O)[nH]1]

or any pharmaceutically acceptable salt thereof; and a pharmaceutically acceptable excipient or carrier.

Various embodiments of the present invention provide a pharmaceutical composition for use in the methods described herein comprising a compound selected from:

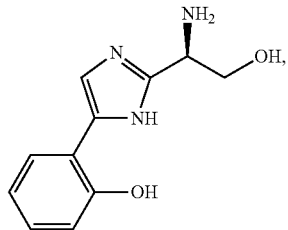 [SMILES: N[C@@H](CO)c1ncc(-c2ccccc2O)[nH]1]

or a prodrug, isomer, dimer, enantiomer, derivative, or pharmaceutically acceptable salt thereof; and a pharmaceutically acceptable excipient or carrier Various embodiments of the present invention provide a pharmaceutical composition for use in the methods described herein comprising a compound of Formula I:

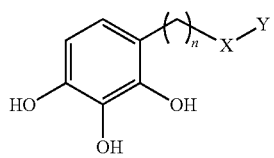
(FORMULA I)

or a prodrug, isomer, dimer, enantiomer, derivative, or pharmaceutically acceptable salt thereof; and a pharmaceutically acceptable excipient or carrier, wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted.

Various embodiments of the present invention provide a pharmaceutical composition for use in the methods described herein comprising a compound of Formula I:

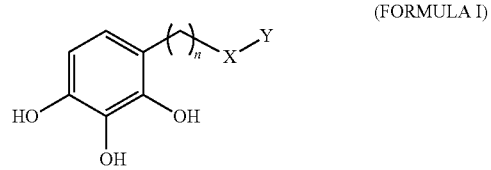
(FORMULA I)

or a prodrug, isomer, dimer, enantiomer, derivative, or pharmaceutically acceptable salt thereof; and a pharmaceutically acceptable excipient or carrier, wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted, provided that the compound is not

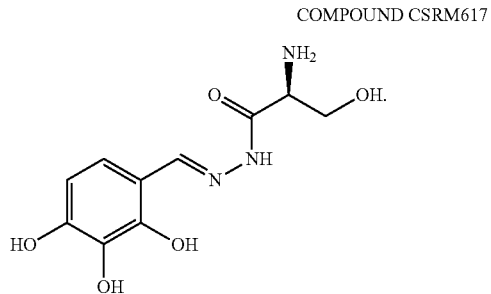 [SMILES: N[C@@H](CO)C(=O)N/N=C/c1ccc(O)c(O)c1O]
COMPOUND CSRM617

Various embodiments of the present invention provide a pharmaceutical composition for use in the methods described herein comprising a compound of Formula II:

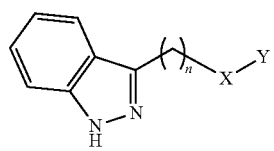
(FORMULA II)

or a prodrug, isomer, dimer, enantiomer, derivative, or pharmaceutically acceptable salt thereof; and a pharmaceutically acceptable excipient or carrier, wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted.

Various embodiments of the present invention provide a pharmaceutical composition for use in the methods described herein comprising a compound of Formula III:

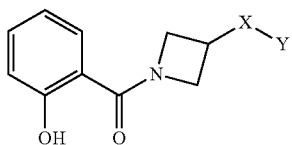

(FORMULA III)

or a prodrug, isomer, dimer, enantiomer, derivative, or pharmaceutically acceptable salt thereof; and a pharmaceutically acceptable excipient or carrier, wherein: X is NH, or O; Y is alkyl, heteroalkyl, cyclyl, heterocyclyl, aryl, or heteroaryl, each of which can be optionally substituted.

Various embodiments of the present invention provide a pharmaceutical composition for use in the methods described herein comprising a compound of Formula IV:

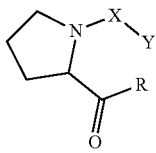

(FORMULA IV)

or a prodrug, isomer, dimer, enantiomer, derivative, or pharmaceutically acceptable salt thereof; and a pharmaceutically acceptable excipient or carrier, wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl.

Various embodiments of the present invention provide a pharmaceutical composition for use in the methods described herein comprising a compound of Formula V:

(FORMULA V)

or a prodrug, isomer, dimer, enantiomer, derivative, or pharmaceutically acceptable salt thereof; and a pharmaceutically acceptable excipient or carrier, wherein: Y is alkyl, heteroalkyl, cyclyl, heterocyclyl, aryl, or heteroaryl, each of which can be optionally substituted.

Various embodiments of the present invention provide a pharmaceutical composition for use in the methods described herein comprising a compound having the structure:

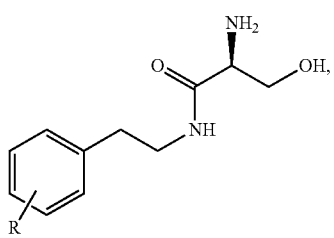

or a prodrug, an isomer, dimer, enantiomer, derivative, or pharmaceutically acceptable salt thereof; and a pharmaceutically acceptable excipient or carrier, wherein:

R is independently one or more of hydrogen or optionally substituted substituent.

Various embodiments of the present invention provide a pharmaceutical composition for use in the methods described herein comprising a compound having the structure:

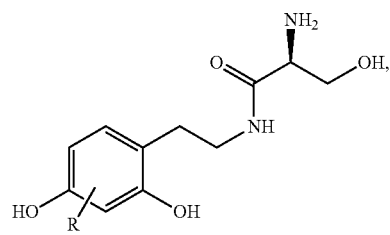

or a prodrug, isomer, dimer, enantiomer, derivative, or pharmaceutically acceptable salt thereof; and a pharmaceutically acceptable excipient or carrier, wherein:

R is independently one or more of hydrogen or optionally substituted substituent Various embodiments of the present invention provide a pharmaceutical composition for use in the methods described herein comprising a compound having the structure:

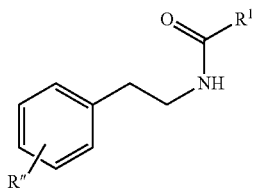

or a prodrug, isomer, dimer, enantiomer, derivative, or pharmaceutically acceptable salt thereof; and a pharmaceutically acceptable excipient or carrier, wherein: R" is independently one or more of hydrogen or optionally substituted substituent; and R$^1$ is hydrogen or optionally substituted substituent.

Various embodiments of the present invention provide a pharmaceutical composition for use in the methods described herein comprising a compound having the structure:

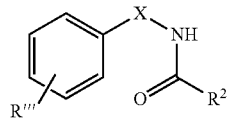

or a prodrug, isomer, dimer, enantiomer, derivative, or pharmaceutically acceptable salt thereof; and a pharmaceutically acceptable excipient or carrier, wherein: R'" is independently one or more of hydrogen or optionally substituted substituent; R$^2$ is hydrogen or optionally substituted substituent; and X is NHC(O), C(O)NH, OC(O), C(O)O, C(O), or CH=N.

Various embodiments of the present invention provide a pharmaceutical composition for use in the methods described herein comprising a compound having the structure:

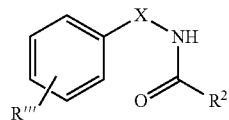

or a prodrug, isomer, dimer, enantiomer, derivative, or pharmaceutically acceptable salt thereof; and a pharmaceutically acceptable excipient or carrier, wherein: R''' is independently one or more of hydrogen or optionally substituted substituent; $R^2$ is hydrogen or optionally substituted substituent; and X is NHC(O), C(O)NH, OC(O), C(O)O, C(O), or CH=N, provided that the compound is not

COMPOUND CSRM617

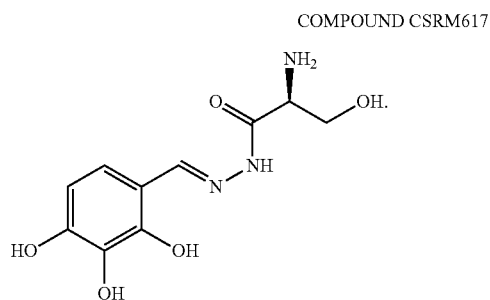 [SMILES: N[C@@H](CO)C(=O)N/N=C/c1ccc(O)c(O)c1O]

Various embodiments of the present invention provide a pharmaceutical composition for use in the methods described herein comprising a compound having the structure:

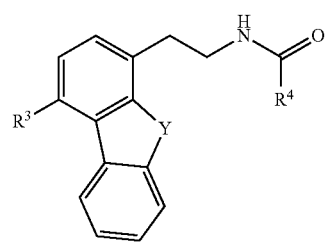

or prodrug, isomer, dimer, enantiomer, derivative, or pharmaceutically acceptable salt thereof; and a pharmaceutically acceptable excipient or carrier, wherein: $R^3$ is hydrogen or optionally substituted substituent; $R^4$ is hydrogen or optionally substituted substituent; and
Y is O or S.

Various embodiments of the present invention provide a pharmaceutical composition for use in the methods described herein comprising a compound selected from:

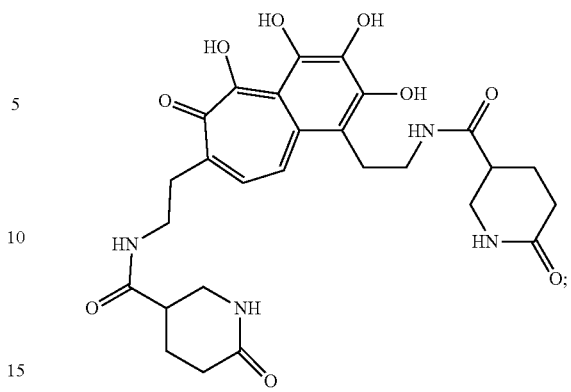

and a pharmaceutically acceptable excipient or carrier

Various embodiments of the present invention provide a pharmaceutical composition for use in the methods described herein comprising a compound selected from:

or any pharmaceutically acceptable salt thereof; and a pharmaceutically acceptable excipient or carrier.

For administration to a subject, the agents for modulating activity of ONECUT2 (e.g, ONECUT2 protein and/or ONECUT2 gene) can be provided in pharmaceutically acceptable compositions. These pharmaceutically acceptable compositions comprise an agent capable of modulating activity of ONECUT2 (e.g., ONECUT2 protein and/or ONECUT2 gene) formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, contents of all of which are herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The phrase "therapeutically effective amount" as used herein means that amount of an agent, compound, material, or composition comprising the same which is effective for producing some desired therapeutic effect in at least a sub-population of cells in an animal at a reasonable benefit/risk ratio applicable to a medical treatment. Determination of a therapeutically effective amount is well within the capability of those skilled in the art. Generally, a therapeutically effective amount can vary with the subject's history, age, condition, as well as the severity and type of the medical condition in the subject.

The amount of the ONECUT2 modulating agent that can be combined with a carrier material to produce a single dosage form will generally be that amount of the agent that produces a therapeutic effect. Generally, out of one hundred percent, this amount will range from about 0.01% to 99% of agent, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg,8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that agent or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

"Contacting" as used here with reference to contacting a cell with an agent (e.g., a compound disclosed herein) refers to any method that is suitable for placing the agent on, in or adjacent to a target cell. For example, when the cells are in vitro, contact the cells with the agent can comprise adding the agent to culture medium containing the cells. For example, when the cells are in vivo, contacting the cells with the agent can comprise administering the agent to the subject.

As used herein, the term "administering" refers to the placement of an agent or a composition as disclosed herein into a subject by a method or route which results in at least partial localization of the agents or composition at a desired site such that a desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

"Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres, nanoparticles comprised of proteineous or non-proteineous components or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the various aspects described herein, the compositions are administered by intravenous infusion or injection.

A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs",Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which are herein incorporated by reference in its entirety.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "co-administer" refers to administration of two or more therapies or two or more therapeutic agents (e.g., Compound CSRM617 and an additional anti-SCLC or an anti-neuroblastoma therapy; a compound of Formula I-Formula V and an additional anti-SCLC or an anti-neuroblastoma; or an agent or compound disclosed herein for inhibiting the expression or function of ONECUT2 or modulating the activity of ONECUT2, and an additional anti-SCLC or an anti-neuroblastoma therapy) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. For example, when the Compound CSRM617 and the additional anti-SCLC or anti-neuroblastoma therapy are administered in different pharmaceutical compositions or at different times, routes of administration can be same or different. For example, when the compound of Formula I-Formula V and additional anti-SCLC or anti-neuroblastoma therapy are administered in different pharmaceutical compositions or at different times, routes of administration can be same or different. For example, when the agent or compound disclosed herein for inhibiting the expression or function of ONECUT2 or modulating the activity of ONECUT2, and an additional anti-SCLC or anti-neuroblastoma therapy are administered in different pharmaceutical compositions or at different times, routes of administration can be same or different.

As used herein, the term "co-administer" refers to administration of two or more therapies or two or more therapeutic agents (e.g., Compound CSRM617 and an additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC)

therapy; a compound of Formula I-Formula V and an additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC); or an agent or compound disclosed herein for inhibiting the expression or function of ONECUT2 or modulating the activity of ONECUT2, and an additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. For example, when the Compound CSRM617 and the additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy are administered in different pharmaceutical compositions or at different times, routes of administration can be same or different. For example, when the compound of Formula I-Formula V and additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy are administered in different pharmaceutical compositions or at different times, routes of administration can be same or different. For example, when the agent or compound disclosed herein for inhibiting the expression or function of ONECUT2 or modulating the activity of ONECUT2, and an additional anti-neuroblastoma, anti-small cell lung cancer (anti-SCLC), anti-large cell neuroendocrine cancer (anti-LCNEC), anti-large-cell carcinoma (anti-LCC), anti-squamous cell carcinoma (anti-SqCC), or anti-adenocarcinoma (anti-AC) therapy are administered in different pharmaceutical compositions or at different times, routes of administration can be same or different.

Kits

In various embodiments, the present invention provides a kit for treating SCLC or neuroblastoma. The kit comprises components to treat SCLC or neuroblastoma in the subject and instructions for use.

In various embodiments, the present invention provides a kit for treating neuroblastoma, small cell lung cancer (SCLC), large cell neuroendocrine cancer (LCNEC), large-cell carcinoma (LCC), squamous cell carcinoma (SqCC), or adenocarcinoma (AC). The kit comprises components to treat neuroblastoma, small cell lung cancer (SCLC), large cell neuroendocrine cancer (LCNEC), large-cell carcinoma (LCC), squamous cell carcinoma (SqCC), or adenocarcinoma (AC) in the subject and instructions for use.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat SCLC or neuroblastoma. Optionally, the kit also contains other useful components, such as, measuring tools, diluents, buffers, pharmaceutical compositions, pharmaceutically acceptable carriers, syringes or other useful paraphernalia as will be readily recognized by those of skill in the art.

Instructions for use may be included in the kit. "Instructions for use" typically include a tangible expression describing the technique to be employed in using the components of the kit to effect a desired outcome, such as to treat neuroblastoma, small cell lung cancer (SCLC), large cell neuroendocrine cancer (LCNEC), large-cell carcinoma (LCC), squamous cell carcinoma (SqCC), or adenocarcinoma (AC). Optionally, the kit also contains other useful components, such as, measuring tools, diluents, buffers, pharmaceutical compositions, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In various embodiments, the present invention provides a kit for for treating SCLC or neuroblastoma in a subject, the kit comprising an agent that inhibits expression or activity of ONECUT2. In some embodiments, the kit further comprises instructions for using the kit.

In various embodiments, the present invention provides a kit for for treating neuroblastoma, small cell lung cancer (SCLC), large cell neuroendocrine cancer (LCNEC), large-cell carcinoma (LCC), squamous cell carcinoma (SqCC), or adenocarcinoma (AC) in a subject, the kit comprising an agent that inhibits expression or activity of ONECUT2. In some embodiments, the kit further comprises instructions for using the kit.

In various embodiments, the present invention provides a kit for treating, inhibiting, reducing the severity of, and/or promoting prophylaxis of small cell lung cancer (SCLC) in a subject, the kit comprising: a therapeutically effective amount of at least one agent that inhibits expression or activity of ONECUT2; and instructions for using the kit to to treat, inhibit, reduce the severity of, and/or promote prophylaxix of small cell lung cancer in the subject.

In various embodiments, the present invention provides a kit for treating, inhibiting, reducing the severity of, and/or promoting prophylaxis of neuroblastoma, small cell lung cancer (SCLC), large cell neuroendocrine cancer (LCNEC), large-cell carcinoma (LCC), squamous cell carcinoma (SqCC), or adenocarcinoma (AC) in a subject, the kit comprising: a therapeutically effective amount of at least one agent that inhibits expression or activity of ONECUT2; and instructions for using the kit to to treat, inhibit, reduce the severity of, and/or promote prophylaxix of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject.

In various embodiments, the present invention provides a kit for treating, inhibiting, reducing the severity of, and/or promoting prophylaxis of small cell lung cancer (SCLC) in a subject, the kit comprising: a composition that comprises at least one agent that inhibits expression or activity of ONECUT2; and instructions for using the kit to to treat, inhibit, reduce the severity of, and/or promote prophylaxix of small cell lung cancer in the subject.

In various embodiments, the present invention provides a kit for treating, inhibiting, reducing the severity of, and/or promoting prophylaxis of neuroblastoma, small cell lung cancer (SCLC), large cell neuroendocrine cancer (LCNEC), large-cell carcinoma (LCC), squamous cell carcinoma (SqCC), or adenocarcinoma (AC) in a subject, the kit comprising: a composition that comprises at least one agent that inhibits expression or activity of ONECUT2; and instructions for using the kit to to treat, inhibit, reduce the severity of, and/or promote prophylaxis of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject.

In various embodiments, the present invention provides a kit for treating, inhibiting, reducing the severity of, delaying progression of and/or preventing metastases of small cell lung cancer (SCLC) in a subject, the kit comprising: a therapeutically effective amount of at least one agent that inhibits expression or activity of ONECUT2; and instructions for using the kit to to treat, inhibit, reduce the severity of, delaying progression of and/or preventing metastases of small cell lung cancer in the subject.

In various embodiments, the present invention provides a kit for treating, inhibiting, reducing the severity of, delaying progression of and/or preventing metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in a subject, the kit comprising: a therapeutically effective amount of at least one agent that inhibits expression or activity of ONECUT2; and instructions for using the kit to to treat, inhibit, reduce the severity of, delaying progression of and/or preventing metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject.

In various embodiments, the present invention provides a kit for treating, inhibiting, reducing the severity of, delaying progression of and/or preventing metastases of small cell lung cancer (SCLC) in a subject, the kit comprising: a composition that comprises at least one agent that inhibits expression or activity of ONECUT2; and instructions for using the kit to to treat, inhibit, reduce the severity of, delaying progression of and/or preventing metastases of small cell lung cancer in the subject.

In various embodiments, the present invention provides a kit for treating, inhibiting, reducing the severity of, delaying progression of and/or preventing metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in a subject, the kit comprising: a composition that comprises at least one agent that inhibits expression or activity of ONECUT2; and instructions for using the kit to to treat, inhibit, reduce the severity of, delaying progression of and/or preventing metastases of neuroblastoma, small cell lung cancer (SCLC), large cell neuroendocrine cancer (LCNEC), large-cell carcinoma (LCC), squamous cell carcinoma (SqCC), or adenocarcinoma (AC) in the subject.

In various embodiments, the present invention provides a kit for treating, inhibiting, reducing the severity of, and/or promoting prophylaxis of neuroblastoma in a subject, the kit comprising: a therapeutically effective amount of at least one agent that inhibits expression or activity of ONECUT2; and instructions for using the kit to to treat, inhibit, reduce the severity of, and/or promote prophylaxix of neuroblastoma in the subject.

In various embodiments, the present invention provides a kit for treating, inhibiting, reducing the severity of, and/or promoting prophylaxis of neuroblastoma in a subject, the kit comprising: a composition that comprises at least one agent that inhibits expression or activity of ONECUT2; and instructions for using the kit to to treat, inhibit, reduce the severity of, and/or promote prophylaxix of neuroblastoma in the subject.

In various embodiments, the present invention provides a kit for treating, inhibiting, reducing the severity of, delaying progression of and/or preventing metastases of neuroblastoma in a subject, the kit comprising: a therapeutically effective amount of at least one agent that inhibits expression or activity of ONECUT2; and instructions for using the kit to to treat, inhibit, reduce the severity of, delaying progression of and/or preventing metastases of neuroblastoma in the subject.

In various embodiments, the present invention provides a kit for treating, inhibiting, reducing the severity of, delaying progression of and/or preventing metastases of neuroblastoma in a subject, the kit comprising: a composition that comprises at least one agent that inhibits expression or activity of ONECUT2; and instructions for using the kit to to treat, inhibit, reduce the severity of, delaying progression of and/or preventing metastases of neuroblastoma in the subject.

Assays

Assay for Small Cell Lung Cancer (SCLC)

In various embodiments, the present invention provides an assay for determining the likelihood of small cell lung cancer (SCLC) in a subject, comprising: obtaining a sample from the subject; assaying the sample to determine the expression level of ONECUT2; and determining that the subject has increased likelihood of small cell lung cancer (SCLC) if the expression of ONECUT2 is increased relative to a reference value, or determining that the subject has decreased likelihood of small cell lung cancer (SCLC) if the expression of ONECUT2 is decreased relative to the reference value.

In some embodiments, the sample is selected from the group consisting of blood, plasma, urine, tissue, and combinations thereof. In some embodiments, the sample is obtained before, during, or after treatment for small cell lung cancer (SCLC). In some embodiments, the reference value is the mean or median level of ONECUT2 expression in a population of subjects that do not have small cell lung cancer (SCLC). In some embodiments, the reference value is the mean or median level of ONECUT2 expression in the subject, wherein the sample is obtained from the subject at an earlier time period. In some embodiments, the reference value is from a control subject, wherein the control subject does not have small cell lung cancer (SCLC).

Assay for Neuroblastoma

In various embodiments, the present invention provides an assay for determining the likelihood of neuroblastoma in a subject, comprising: obtaining a sample from the subject; assaying the sample to determine the expression level of ONECUT2; and determining that the subject has increased likelihood of neuroblastoma if the expression of ONECUT2 is increased relative to a reference value, or determining that the subject has decreased likelihood of neuroblastoma if the expression of ONECUT2 is decreased relative to the reference value.

In some embodiments, the sample is selected from the group consisting of blood, plasma, urine, tissue, and combinations thereof. In some embodiments, the sample is obtained before, during, or after treatment for neuroblastoma. In some embodiments, the reference value is the mean or median level of ONECUT2 expression in a population of subjects that do not have neuroblastoma. In some embodiments, the reference value is the mean or median level of ONECUT2 expression in the subject, wherein the sample is obtained from the subject at an earlier time period. In some embodiments, the reference value is from a control subject, wherein the control subject does not have neuroblastoma.

Assay for Cancer

In various embodiments, the present invention provides an assay for determining the likelihood of cancer in a subject, comprising: obtaining a sample from the subject; assaying the sample to determine the expression level of ONECUT2; and determining that the subject has increased likelihood of cancer if the expression of ONECUT2 is increased relative to a reference value, or determining that the subject has decreased likelihood of cancer if the expression of ONECUT2 is decreased relative to the reference value, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the sample is selected from the group consisting of blood, plasma, urine, tissue, and combinations thereof. In some embodiments, the sample is obtained before, during, or after treatment for cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the reference value is the mean or median level of ONECUT2 expression in a population of subjects that do not have cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the reference value is the mean or median level of ONECUT2 expression in the subject, wherein the sample is obtained from the subject at an earlier time period. In some embodiments, the reference value is from a control subject, wherein the control subject does not have cancer, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

Assay for Lung Cancer

In various embodiments, the present invention provides an assay for determining the likelihood of lung cancer in a subject, comprising: obtaining a sample from the subject; assaying the sample to determine the expression level of ONECUT2; and determining that the subject has increased likelihood of lung cancer if the expression of ONECUT2 is increased relative to a reference value, or determining that the subject has decreased likelihood of cancer if the expression of ONECUT2 is decreased relative to the reference value, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

In some embodiments, the sample is selected from the group consisting of blood, plasma, urine, tissue, and combinations thereof. In some embodiments, the sample is obtained before, during, or after treatment for lung cancer, wherein the cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the reference value is the mean or median level of ONECUT2 expression in a population of subjects that do not have lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof. In some embodiments, the reference value is the mean or median level of ONECUT2 expression in the subject, wherein the sample is obtained from the subject at an earlier time period. In some embodiments, the reference value is from a control subject, wherein the control subject does not have lung cancer, wherein the lung cancer is selected from the group consisting of small cell lung cancer (SCLC), large cell neuroendocrine cancer (LCNEC), large-cell carcinoma (LCC), squamous cell carcinoma (SqCC), adenocarcinoma (AC), and combinations thereof.

Various Non-Limiting Embodiments of the Invention

Various embodiments of the invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject. In some embodiments, the agent is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the antibody is selected from the group consisting of monoclonal antibody or fragment thereof, a polyclonal antibody or a fragment thereof, chimeric antibodies, humanized antibodies, human antibodies, and a single chain antibody. In some embodiments, agents that target OC2 indirectly target OC2, for example by targeting OC2 interacting proteins like KDM5B. In some embodiments, the agent is Compound CSRM617 of structure:

COMPOUND CSRM617

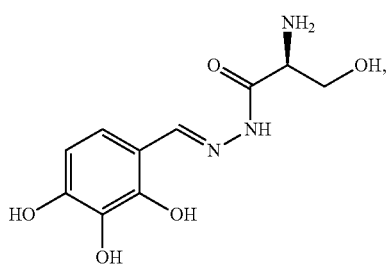

or a pharmacetucially acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-SCLC or anti-neuroblastoma therapy are administered sequentially or simultaneously.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from a compound of Formula I:

(FORMULA I)

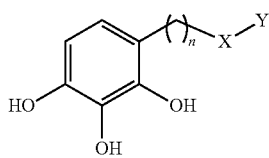

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the compound of Formula I is not

COMPOUND CSRM617

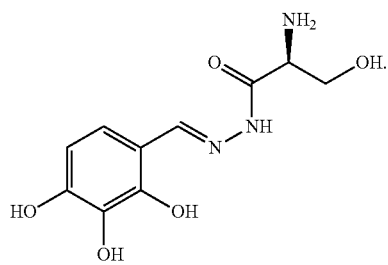

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from a compound of Formula II:

(FORMULA II)

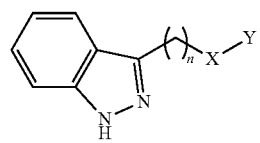

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from a compound of Formula III:

(FORMULA III)

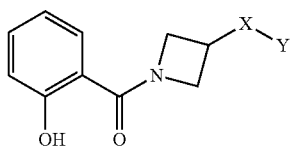

wherein: X is NH, or O; Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from a compound of Formula IV:

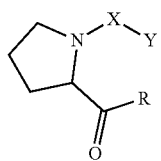

(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl; and any pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from a compound of Formula V:

(FORMULA V)

wherein: Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from:

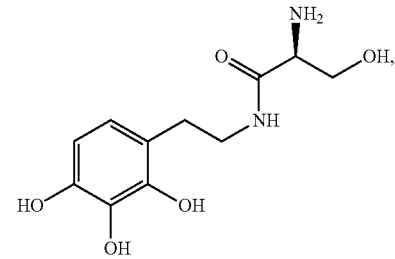

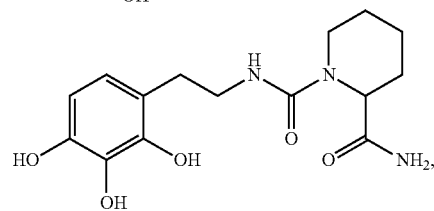

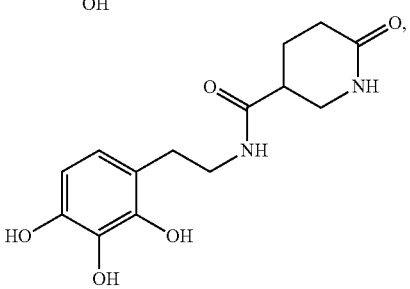

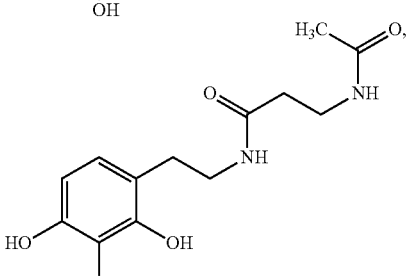

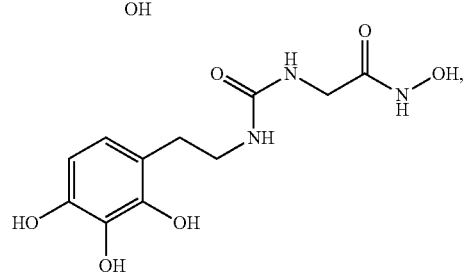

-continued

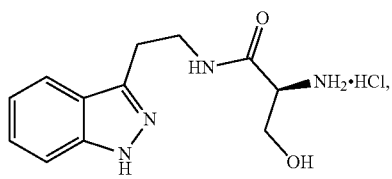

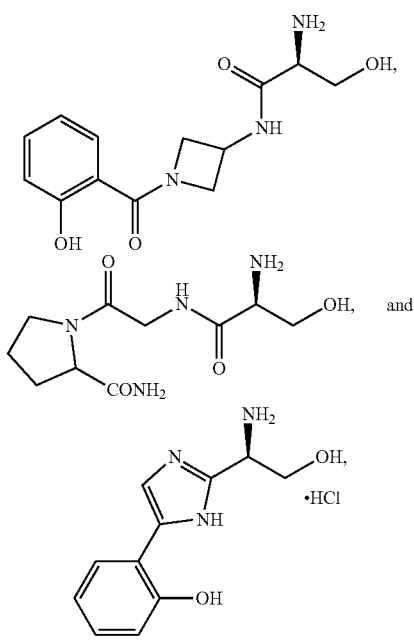

or a pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide an assay for determining the prognosis of SCLC or neuroblastoma in a subject in need thereof comprising: obtaining a sample from the subject having or suspected of having SCLC or neuroblastoma; assaying the sample to determine the expression level of ONECUT2; and determining that the subject has poor prognosis if the expression of ONECUT2 is increased relative to a reference value. In some embodiments, the sample is blood, plasma, urine, tissue or combinations thereof. In some embodiments, the sample is obtained before, during or after treatment for SCLC or neuroblastoma. In some embodiments, the subject is human. In some embodiments, the reference value is the mean or median level of ONECUT2 expression in a population of subjects that do not have SCLC or neuroblastoma. In some embodiments, the reference value is the mean or median level of ONECUT2 expression in a population of subjects that have SCLC or neuroblastoma and have been treated for SCLC or neuroblastoma. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have ONECUT2 overexpressing SCLC or neuroblastoma and have undergone or are undergoing treatment for the SCLC. In some embodiments, the expression of ONECUT2 is increased 2-fold, 3-fold, 4-fold, 5-fold, 10-fold, 20-fold, 50-fold, or 100-fold relative to a reference value.

Various embodiments of the present invention provide a compound selected from:

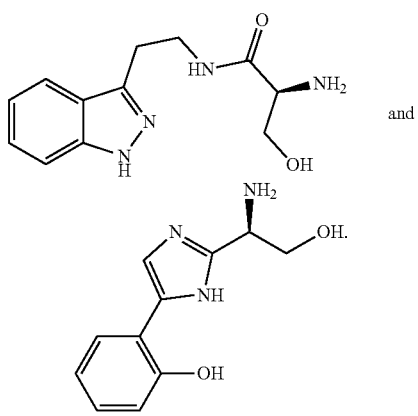

Various embodiments of the present invention provide a compound selected from:

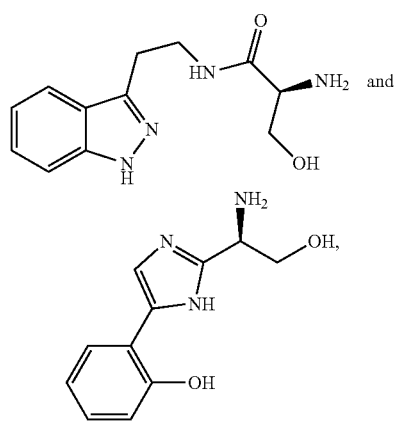

or a prodrug, isomer, dimer, enantiomer, derivative, or pharmaceutically acceptable salt thereof.

Various embodiments of the present invention provide a pharmaceutical composition comprising a compound selected from:

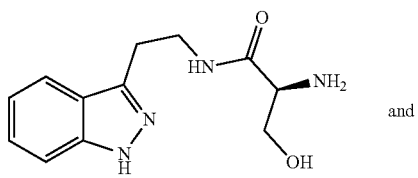

-continued

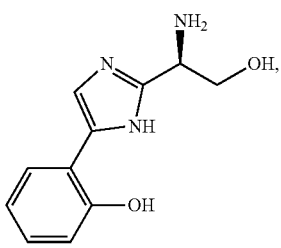

or a pharmaceutically acceptable salt thereof; and a pharmaceutically acceptable excipient or carrier.

Various embodiments of the present invention provide a method for treating, inhibiting and/or reducing the severity of SCLC or neuroblastoma in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from:

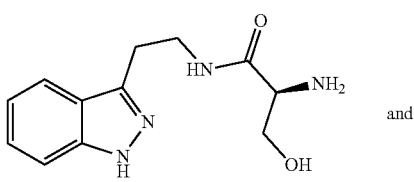

and

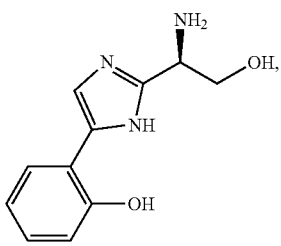

or a pharmaceutically acceptable salt thereof. In some embodiments, the method further comprises administration or treatment with one or more additional anti-SCLC or anti-neuroblastoma therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Some embodiments of the present invention can be defined as any of the following numbered paragraphs:

1. A method for treating SCLC or neuroblastoma in a subject in need thereof, comprising providing an agent that inhibits expression or activity of ONECUT2 and administering a therapeutically effective amount of the agent so as to treat SCLC or neuroblastoma that overexpress ONECUT2 in the subject.

2. The method of paragraph 1, wherein the agent is Compound CSRM617 of structure:

COMPOUND CSRM617

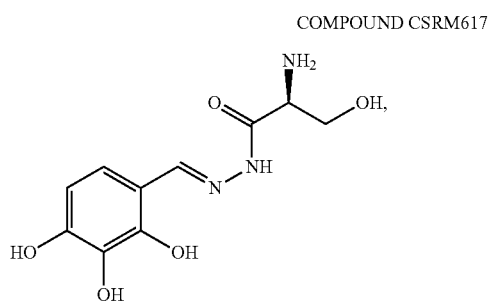 [SMILES: N[C@@H](CO)C(=O)N/N=C/c1ccc(O)c(O)c1O]

or a pharmacetucially acceptable salt thereof.

3. The method of paragraph 1, wherein the method further comprises administration or treatment with one or more additional anti-SCLC or anti-neuroblastoma therapy to the subject in need thereof.
4. The method of paragraph 3, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.
5. The method of paragraph 1, wherein the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.
6. The method of paragraph 1, wherein the subject is human.
7. The method of paragraph 1, wherein the agent is administered to the subject 1-3 times per day or 1-7 times per week.
8. The method of paragraph 1, wherein the agent is administrated to the subject for 1-5 days, 1-5 weeks, 1-5 months, or 1-5 years.
9. The method of paragraph 4, wherein the agent and the additional anti-SCLC or anti-neuroblastoma therapy are administered sequentially or simultaneously.
10. A method for treating, inhibiting and/or reducing the severity of SCLC or neuroblastoma that overexpress ONECUT2 in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from:

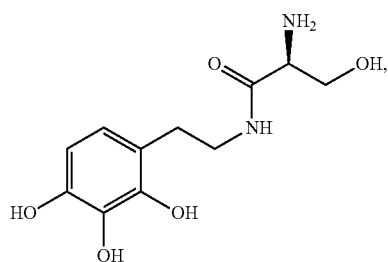

-continued

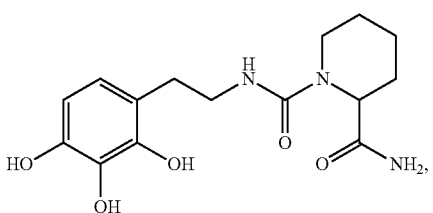

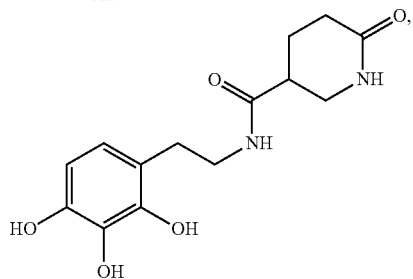

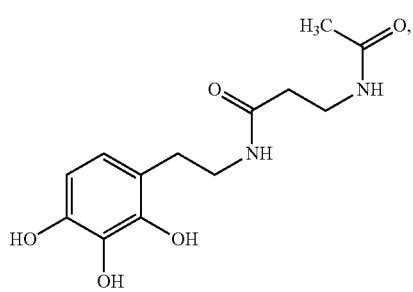

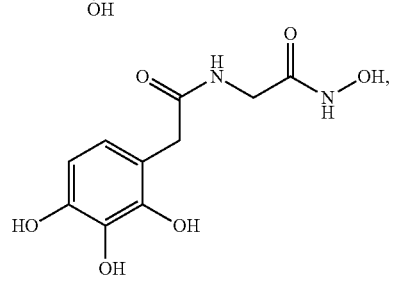

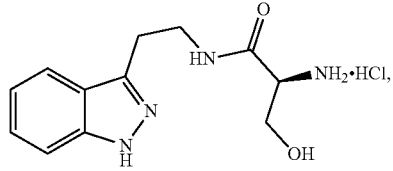

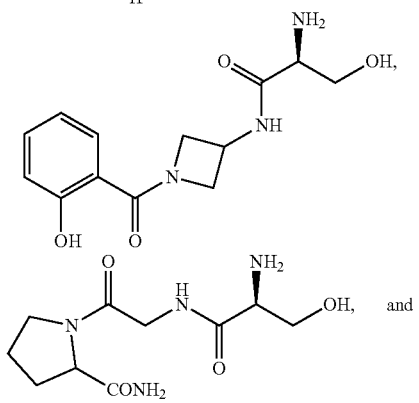 and

-continued

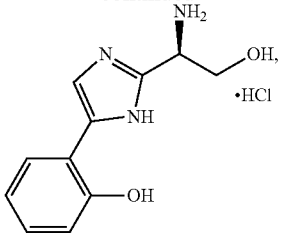

or a pharmaceutically acceptable salt thereof.

11. The method of paragraph 10, wherein the method further comprises administration or treatment with one or more additional anti-SCLC or anti-neuroblastoma therapy to the subject in need thereof.

12. The method of paragraph 11, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

13. A method for treating, inhibiting and/or reducing the severity of SCLC or neuroblastoma that overexpress ONECUT2 in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is Compound CSRM617 of structure:

COMPOUND CSRM617

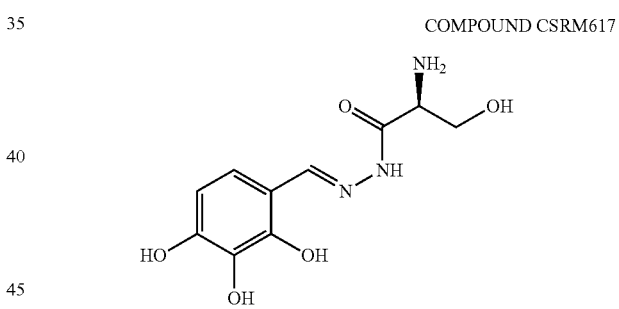

or a pharmacetucially acceptable salt thereof.

14. The method of paragraph 13, wherein the method further comprises administration or treatment with one or more additional anti-SCLC or anti-neuroblastoma therapy to the subject in need thereof.

15. The method of paragraph 14, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

16. A method for treating, inhibiting and/or reducing the severity of SCLC or neuroblastoma that overexpress ONECUT2 in a subject in need thereof, comprising providing an agent that inhibits expression or activity of ONECUT2 and administering a therapeutically effective amount of the agent so as to treat, inhibit and/or reduce the severity of SCLC or neuroblastoma in the subject, wherein the agent is selected from:

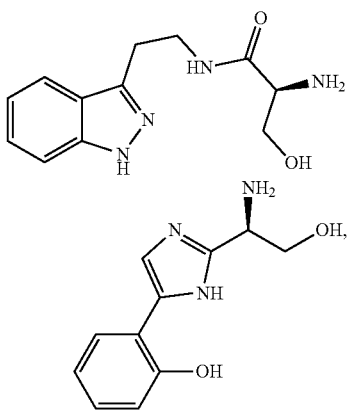

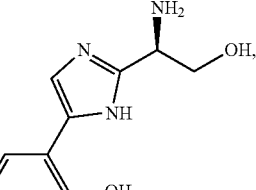

or a pharmacetucially acceptable salt thereof.

17. The method of paragraph 16, wherein the method further comprises administration or treatment with one or more additional anti-SCLC or anti-neuroblastoma therapy to the subject in need thereof.
18. The method of paragraph 17, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Some embodiments of the present invention can be defined as any of the following numbered paragraphs:

19. A method for treating cancer in a subject, comprising: administering to the subject a therapeutically effective amount of at least one agent that inhibits expression or activity of ONECUT2, thereby treating cancer in the subject, wherein the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.
20. The method of paragraph 19, wherein the cancer overexpresses ONECUT2.
21. The method of paragraph 19, wherein the neuroblastoma, small cell lung cancer (SCLC), large cell neuroendocrine cancer (LCNEC), large-cell carcinoma (LCC), squamous cell carcinoma (SqCC), adenocarcinoma (AC) each individually overexpress ONECUT2.
22. The method of paragraph 19, wherein the agent is Compound CSRM617 of structure:

COMPOUND CSRM617

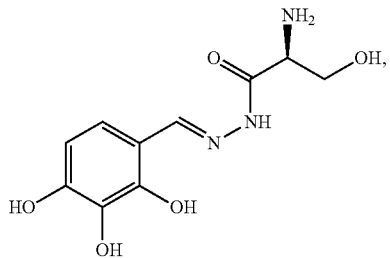

or a pharmacetucially acceptable salt thereof.

23. The method of paragraph 19, wherein the agent is a compound selected from:

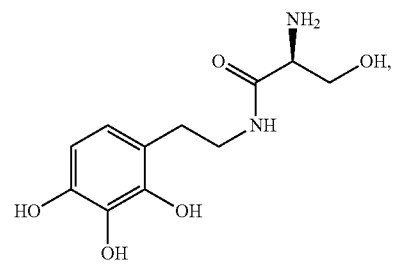

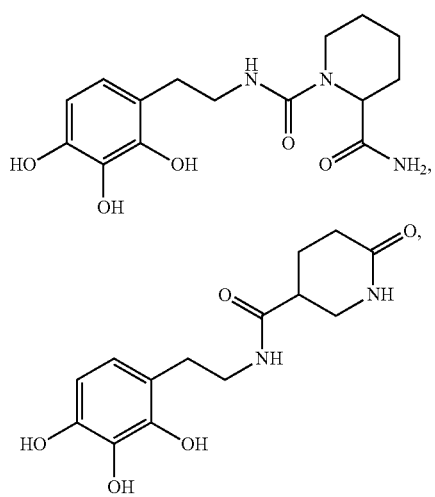

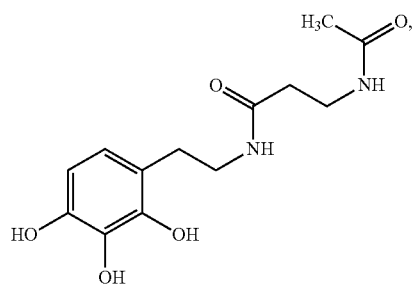

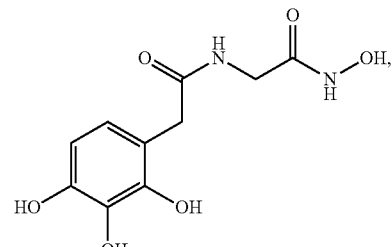

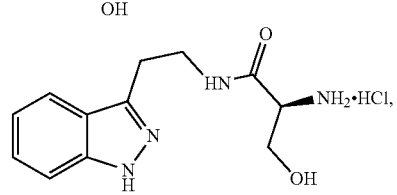

-continued

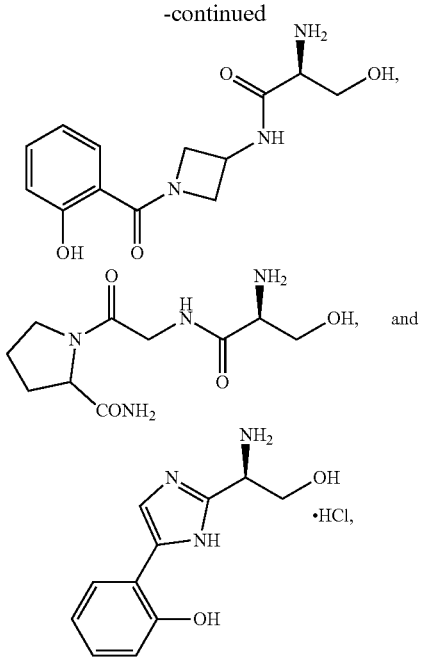

or a prodrug, isomer, dimer, enantiomer, derivative, or pharmaceutically acceptable salt thereof.

24. The method of paragraph 19, wherein the agent is a compound having the structure:

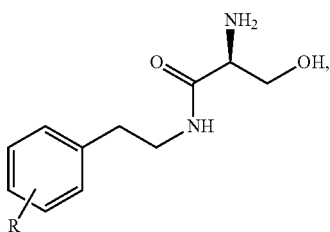

or a prodrug, isomer, dimer, enantiomer, derivative, or pharmaceutically acceptable salt thereof, wherein:

R is independently one or more of hydrogen or optionally substituted substituent.

25. The method of paragraph 19, wherein the agent is a compound having the structure:

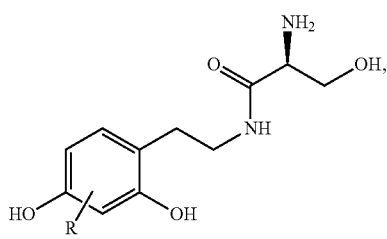

or a prodrug, isomer, dimer, enantiomer, derivative, or pharmaceutically acceptable salt thereof, wherein:

R is independently one or more of hydrogen or optionally substituted substituent.

26. The method of paragraph 19, wherein the agent is a compound having the structure:

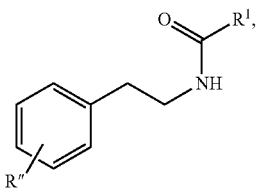

or a prodrug, isomer, dimer, enantiomer, derivative, or pharmaceutically acceptable salt thereof wherein:

R" is independently one or more of hydrogen or optionally substituted substituent; and $R^1$ is hydrogen or optionally substituted substituent.

27. The method of paragraph 19, wherein the agent is a compound having the structure:

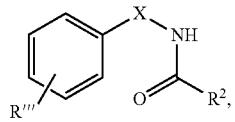

or a prodrug, isomer, dimer, enantiomer, derivative, or pharmaceutically acceptable salt thereof, wherein:

R''' is independently one or more of hydrogen or optionally substituted substituent;

$R^2$ is hydrogen or optionally substituted substituent; and

X is NHC(O), C(O)NH, OC(O), C(O)O, C(O), or CH=N.

28. The method of paragraph 19, wherein the agent is a compound having the structure:

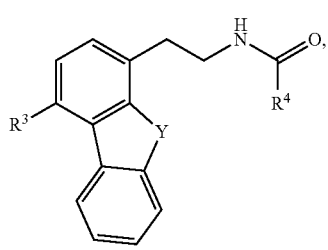

or a prodrug, isomer, dimer, enantiomer, derivative, or pharmaceutically acceptable salt thereof, wherein:

$R^3$ is hydrogen or optionally substituted substituent;

$R^4$ is hydrogen or optionally substituted substituent; and

Y is O or S.

29. The method of paragraph 19, wherein the agent is a compound having the structure:

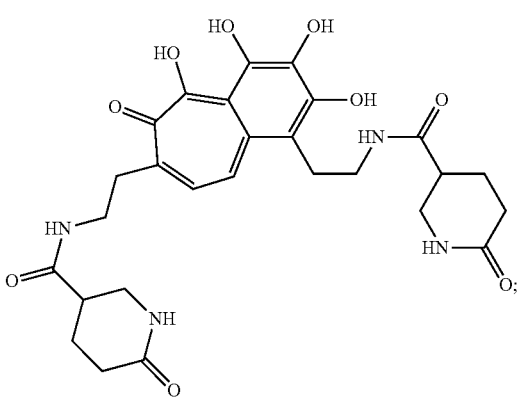 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

30. The method of paragraph 19, wherein the agent is a compound having the structure:

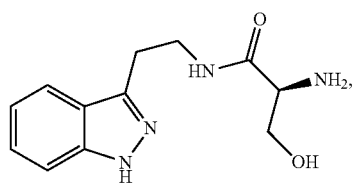 [SMILES: N[C@@H](CO)C(=O)NCCc1n[nH]c2ccccc12]

or a prodrug, isomer, dimer, enantiomer, derivative, or pharmaceutically acceptable salt thereof.

31. The method of paragraph 19, wherein the agent is a compound having the structure:

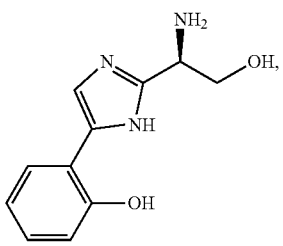 [SMILES: N[C@@H](CO)c1ncc(-c2ccccc2O)[nH]1]

or a prodrug, isomer, dimer, enantiomer, derivative, or pharmaceutically acceptable salt thereof.

32. The method of paragraph 19, wherein the agent is a compound selected from the group consisting of a compound of Formula I, a compound of Formula II, a compound of Formula III, a compound of Formula IV, and a compound of Formula V, or a prodrug, isomer, dimer, enantiomer, derivative, or pharmaceutically acceptable salt thereof.

33. The method of paragraph 19, wherein ONECUT2 is selected from the group consisting of ONECUT2 gene, ONECUT2 protein, and combinations thereof.

34. A method for treating small cell lung cancer (SCLC) or neuroblastoma in a subject in need thereof, comprising providing an agent that inhibits expression or activity of ONECUT2; and administering a therapeutically effective amount of the agent so as to treat SCLC or neuroblastoma in the subject.

35. A method for treating, inhibiting, reducing the severity of and/or promoting prophylaxis of small cell lung cancer (SCLC) or neuroblastoma in a subject in need thereof, comprising providing an agent that inhibits expression or activity of ONECUT2; and administering a therapeutically effective amount of the agent so as to treat, inhibit, reduce the severity of and/or promoting prophylaxis of small cell lung cancer (SCLC) or neuroblastoma in the subject.

36. A method of treating, inhibiting, reducing the severity of, delaying progression of and/or preventing metastases of small cell lung cancer (SCLC) or neuroblastoma in a subject, comprising: providing at least one agent that inhibits expression or activity of ONECUT2; administering to the subject a therapeutically effective amount of the at least one agent, thereby treating, inhibiting, reducing the severity of, delaying progression of and/or preventing metastases of small cell lung cancer (SCLC) or neuroblastoma in the subject.

37. The method of any one of paragraphs 16-18, further comprising administering at least one additional anti-SCLC therapy or at least one additional anti-neuroblastoma therapy to the subject.

38. The method of paragraph 37, wherein the additional anti-SCLC therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

39. The method of paragraph 37, wherein the additional anti-neuroblastoma therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

40. The method of any one of paragraphs 19, 34-36, wherein the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

41. The method of any one of paragraphs 19, 34-36, wherein the subject is human.

42. The method of any one of paragraphs 19, 34-36, wherein the agent is administered to the subject 1-3 times per day or 1-7 times per week.

43. The method of any one of paragraphs 19, 34-36, wherein the agent is administrated to the subject for 1-5 days, 1-5 weeks, 1-5 months, or 1-5 years.

44. The method of paragraph 37, wherein the agent and the additional anti-SCLC therapy or the anti-neuroblastoma therapy are administered sequentially or simultaneously.

45. The method of any one of paragraphs 34-36, wherein the small cell lung cancer (SCLC) overexpresses ONECUT2.

46. The method of any one of paragraphs 34-36, wherein the neuroblastoma overexpresses ONECUT2.

47. The method of any one of paragraphs 34-36, wherein the agent is Compound CSRM617 of structure:

COMPOUND CSRM617

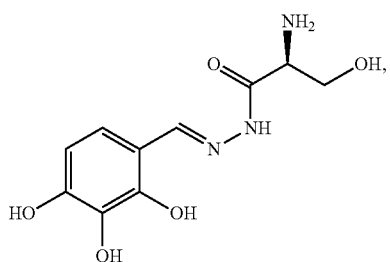

or a pharmacetucially acceptable salt thereof.

48. The method of any one of paragraphs 34-36, wherein the agent is a compound selected from:

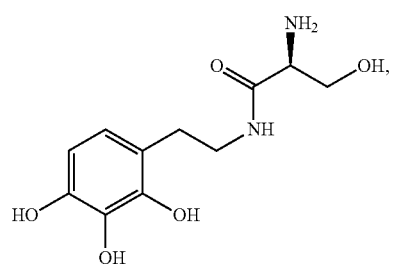

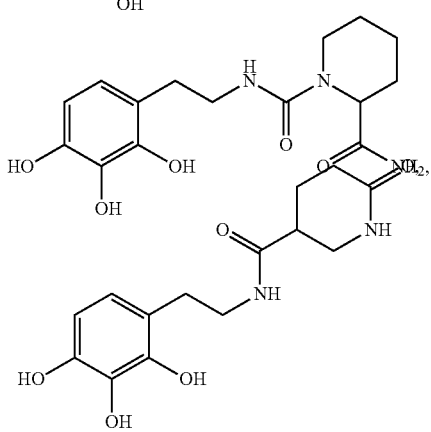

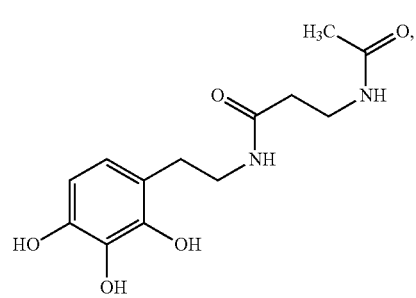

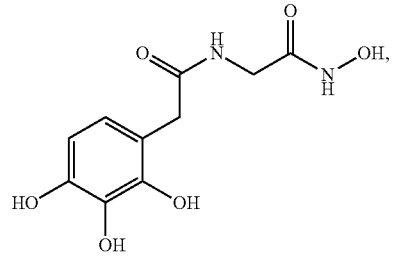

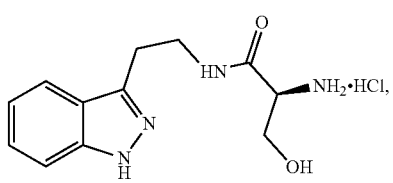

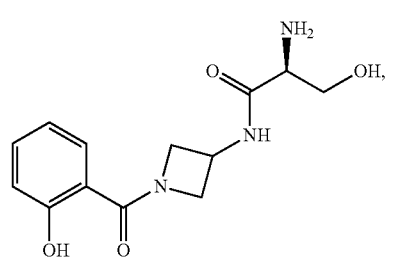

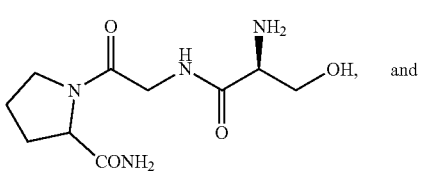

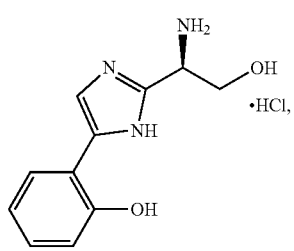

or a prodrug, isomer, dimer, enantiomer, derivative, or pharmaceutically acceptable salt thereof.

49. The method of any one of paragraphs 34-36, wherein the agent is a compound having the structure:

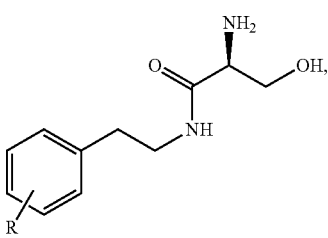

or a prodrug, isomer, dimer, enantiomer, derivative, or pharmaceutically acceptable salt thereof, wherein:

R is independently one or more of hydrogen or optionally substituted substituent.

50. The method of any one of paragraphs 34-36, wherein the agent is a compound having the structure:

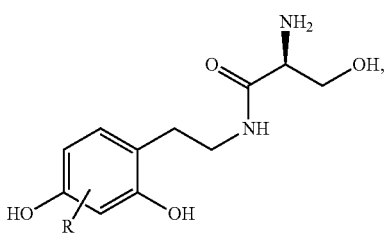

or a prodrug, isomer, dimer, enantiomer, derivative, or pharmaceutically acceptable salt thereof, wherein:
R is independently one or more of hydrogen or optionally substituted substituent.

51. The method of any one of paragraphs 34-36, wherein the agent is a compound having the structure:

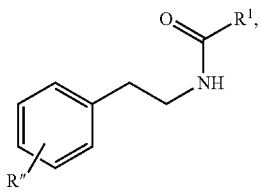

or a prodrug, isomer, dimer, enantiomer, derivative, or pharmaceutically acceptable salt thereof wherein:
R" is independently one or more of hydrogen or optionally substituted substituent; and
$R^1$ is hydrogen or optionally substituted substituent.

52. The method of any one of paragraphs 34-36, wherein the agent is a compound having the structure:

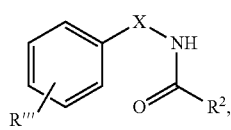

or a prodrug, isomer, dimer, enantiomer, derivative, or pharmaceutically acceptable salt thereof, wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N.

53. The method of any one of paragraphs 34-36, wherein the agent is a compound having the structure:

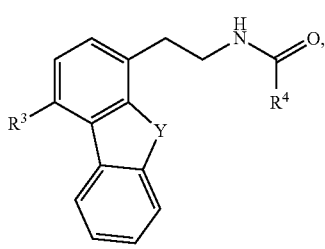

or a prodrug, isomer, dimer, enantiomer, derivative, or pharmaceutically acceptable salt thereof, wherein:

$R^3$ is hydrogen or optionally substituted substituent;
$R^4$ is hydrogen or optionally substituted substituent; and
Y is O or S.

54. The method of any one of paragraphs 34-36, wherein the agent is a compound having the structure:

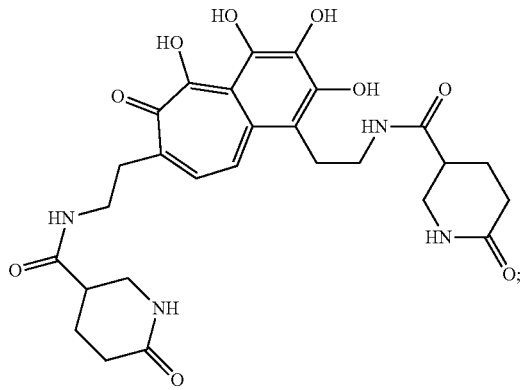 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

55. The method of any one of paragraphs 34-36, wherein the agent is a compound having the structure:

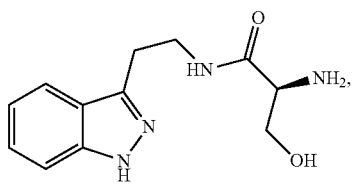 [SMILES: N[C@@H](CO)C(=O)NCCc1n[nH]c2ccccc12]

or a prodrug, isomer, dimer, enantiomer, derivative, or pharmaceutically acceptable salt thereof.

56. The method of any one of paragraphs 34-36, wherein the agent is a compound having the structure:

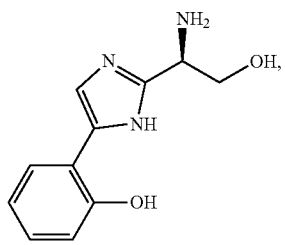 [SMILES: N[C@@H](CO)c1ncc(-c2ccccc2O)[nH]1]

or a prodrug, isomer, dimer, enantiomer, derivative, or pharmaceutically acceptable salt thereof.

57. The method of any one of paragraphs 34-36, wherein the agent is a compound selected from the group consisting of a compound of Formula I, a compound of Formula II, a compound of Formula III, a compound of Formula IV, and a compound of Formula V, or a prodrug, isomer, dimer, enantiomer, derivative, or pharmaceutically acceptable salt thereof.

58. The method of any one of paragraphs 34-36, wherein ONECUT2 is selected from the group consisting of ONECUT2 gene, ONECUT2 protein, and combinations thereof.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Unless otherwise noted, reagents and solvents were used as received from commercial suppliers. Nuclear magnetic resonance spectra were obtained on a Bruker AC 300, a Bruker AV 300 spectrometer, or on a Bruker AV 500 spectrometer. Spectra are given in ppm (δ) and coupling constants, J, are reported in Hertz. Tetramethylsilane was used as an internal standard for proton spectra. Flash chromatography often utilized the Isco Combiflash $R_f$ MPLC system. Mass spectra and LC/MS data reported using the Waters Aquity system as outlined in LC/MS Conditions "Method A" as the default.

HPLC Conditions:
Method A
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 223 nm
Method A Gradient

| Time (min) | Flow (mL/min) | % A | % B |
|---|---|---|---|
| 0.0 | 1.0 | 95.0 | 5.0 |
| 20.0 | 1.0 | 5.0 | 95.0 |
| 27.0 | 1.0 | 5.0 | 95.0 |

Method B
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method B Gradient

| Time (min) | Flow (mL/min) | % A | % B |
|---|---|---|---|
| 0.0 | 1.0 | 95.0 | 5.0 |
| 20.0 | 1.0 | 5.0 | 95.0 |
| 27.0 | 1.0 | 5.0 | 95.0 |

Method C
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method C Gradient

| Time (min) | Flow (mL/min) | % A | % B |
|---|---|---|---|
| 0.0 | 1.0 | 95.0 | 5.0 |
| 20.0 | 1.0 | 50.0 | 50.0 |
| 27.0 | 1.0 | 50.0 | 50.0 |

Method D
Column: Luna C18(2) column (150×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method D Gradient

| Time (min) | Flow (mL/min) | % A | % B |
|---|---|---|---|
| 0.0 | 1.0 | 90.0 | 10.0 |
| 15.0 | 1.0 | 0.0 | 100.0 |
| 20.0 | 1.0 | 0.0 | 100.0 |

LC/MS Conditions:
Method A (Default)
Instrument: Waters Acquity, SQ Detector
Column: Acquity UPLC BEH C18 (2.1 mm×50 mm)
Mobile Phase A: Water containing 0.1% v/v Formic Acid
Mobile Phase B: Acetonitrile containing 0.1% v/v Formic Acid
UV Detection: 254 nm
MS Detection: ESI
Method A Gradient

| Time (min) | Flow (mL/min) | % A | % B |
|---|---|---|---|
| 0.0 | 0.5 | 98.0 | 2.0 |
| 2.25 | 0.5 | 5.0 | 95.0 |
| 3.0 | 0.5 | 5.0 | 95.0 |

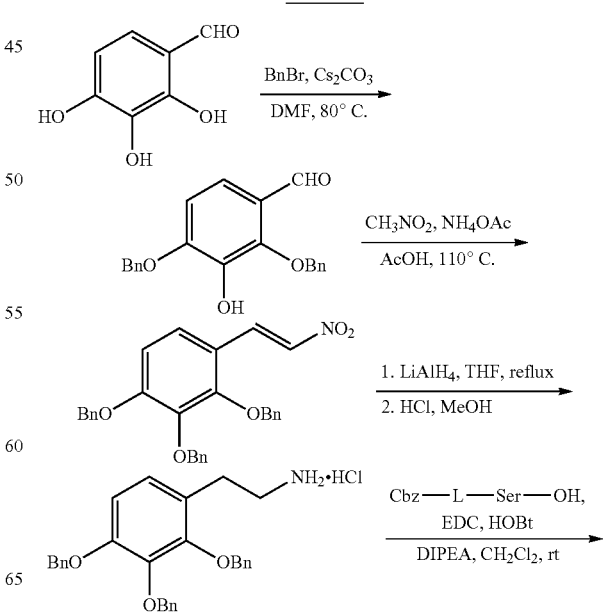

Scheme 1.

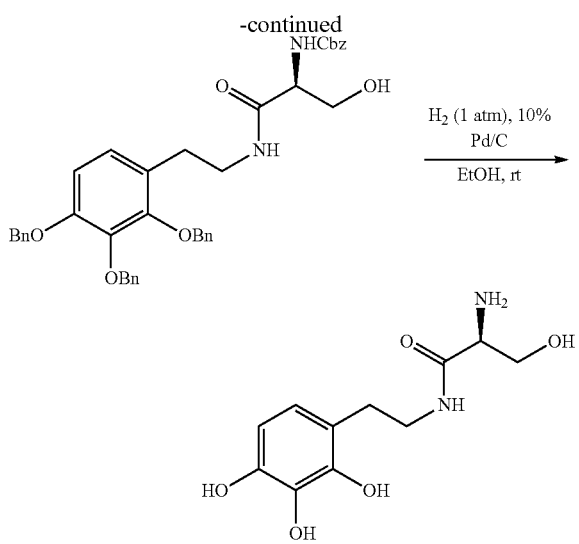

Preparation of 2,3,4-Tris(benzyloxy)benzaldehyde

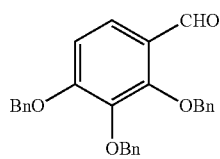 [SMILES: O=Cc1ccc(OCc2ccccc2)c(OCc2ccccc2)c1OCc1ccccc1]

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 $[C_{28}H_{24}O_4+H]^+$.

Preparation of (E)-(((4-(2-Nitrovinyl)benzene-1,2,3-triyl)tris(oxy))tris(methylene)) tribenzene

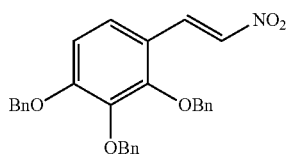 [SMILES: O=[N+]([O-])/C=C/c1ccc(OCc2ccccc2)c(OCc2ccccc2)c1OCc1ccccc1]

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 $[C_{29}H_{25}NO_5+H]^+$.

Preparation of 2-(2,3,4-Tris(benzyloxy)phenyl)ethanamine hydrochloride

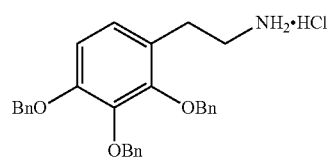

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of (S)-Benzyl (3-hydroxy-1-oxo-1-((2,3,4-tris(benzyloxy)phenethyl) amino) propan-2-yl)carbamate

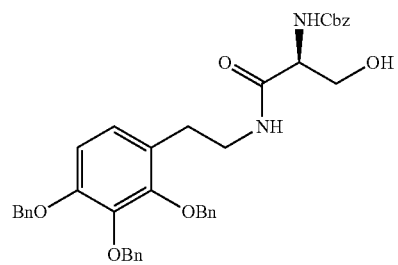 [SMILES: O=C(N[C@@H](CO)C(=O)NCCc1ccc(OCc2ccccc2)c(OCc2ccccc2)c1OCc1ccccc1)OCc1ccccc1]

A suspension of 2-(2,3,4-tris(benzyloxy)phenyl)ethanamine hydrochloride (246 mg, 0.517 mmol) and (S)-2-(((benzyloxy)carbonyl)amino)-3-hydroxypropanoic acid (150 mg, 0.627 mmol) in methylene chloride (10 mL) was treated with 1-ethyl-3-(3-dimethylaminopropyl)carbodiimide (119 mg, 0.621 mmol), hydroxybenzotriazole (87 mg, 0.64 mmol), and N,N-diisopropylethylamine (0.30 mL, 1.7 mmol). The mixture was stirred under a nitrogen atmosphere for 16 h. After this time, the reaction mixture was diluted with methylene chloride (25 mL); washed with water (25 mL), saturated sodium bicarbonate (25 mL), and brine (25 mL); dried over sodium sulfate; filtered; and concentrated under reduced pressure. The crude residue was purified by column chromatography (silica gel, 0-50% ethyl acetate/methylene chloride) to provide (S)-benzyl (3-hydroxy-1-oxo-1-((2,3,4-tris(benzyloxy)phenethyl)amino)propan-2-yl) carbamate (195 mg, 57%) as a white solid: $^1$H NMR (300 MHz, DMSO-d$_6$) δ 7.93 (t, J=5.0 Hz, 1H), 7.49-7.29 (m, 20H), 7.14 (d, J=8.4 Hz, 1H), 6.88 (s, 2H), 5.11 (s, 2H), 5.03-4.97 (m, 6H), 4.82 (t, J=5.6 Hz, 1H), 4.05-3.98 (m, 1H), 3.61-3.46 (m, 2H), 3.26-3.19 (m, 2H), 2.65 (t, J=6.8 Hz, 2H); ESI MS m/z 661 [C$_{40}$H$_{40}$N$_2$O$_7$+H]+.

Preparation of (S)-2-Amino-3-hydroxy-N-(2,3,4-trihydroxyphenethyl) propanamide

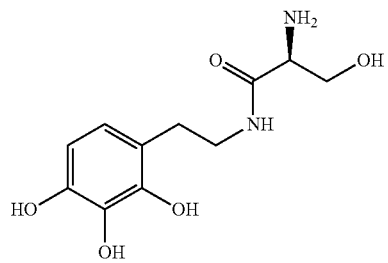 [SMILES: N[C@@H](CO)C(=O)NCCc1ccc(O)c(O)c1O]

A solution of (S)-benzyl (3-hydroxy-1-oxo-1-((2,3,4-tris(benzyloxy)phenethyl)amino)propan-2-yl)carbamate (195 mg, 0.295 mmol) in ethyl acetate (10 mL) and ethanol (10 mL) was bubbled with nitrogen gas for 10 min. The solution was treated with 10% palladium on carbon (28 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was dissolved in methanol and concentrated under reduced pressure (3x) and freeze dried from water to provide (S)-2-amino-3-hydroxy-N-(2,3,4-trihydroxyphenethyl)propanamide, (74 mg, 98%) as a fluffy, off-white solid: $^1$H NMR (300 MHz, DMSO-d$_6$) δ 8.79 (br s, 1H), 7.82 (t, J=5.7 Hz, 1H), 6.33 (d, J=8.1 Hz, 1H), 6.20 (d, J=8.1 Hz, 1H), 4.70 (br s, 1H), 3.49 (dd, J=10.5, 4.5 Hz, 1H), 3.38-3.32 (m, 1H, partially obscured by water peak), 3.22-3.14 (m, 3H), 2.55 (t, J=7.5 Hz, 2H, partially obscured by solvent peak), 4 exchangeable protons not observed; ESI MS m/z 257 [C$_{11}$H$_{16}$N$_2$O$_5$+H]$^+$; HPLC (Method A) 96.1% (AUC), t$_R$=5.92 min.

Scheme 2.

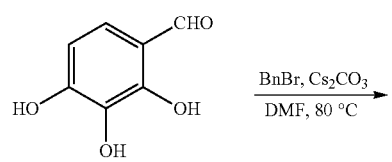

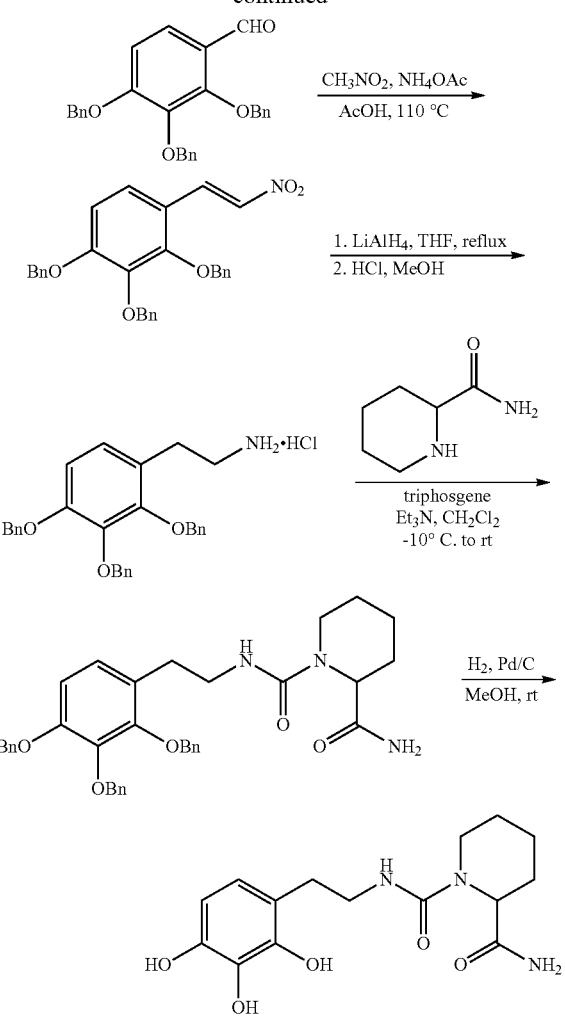

Preparation of 2,3,4-Tris(benzyloxy)benzaldehyde

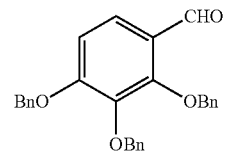

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 [C$_{28}$H$_{24}$O$_4$+H]$^+$.

Preparation of (E)-(((4-(2-Nitrovinyl)benzene-1,2,3-triyl)tris(oxy))tris (methylene)) tribenzene

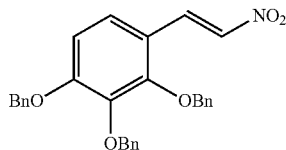 [SMILES: O=[N+]([O-])/C=C/c1ccc(OCc2ccccc2)c(OCc2ccccc2)c1OCc1ccccc1]

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 [$C_{29}H_{25}NO_5$+H]$^+$.

Preparation of 2-(2,3,4-Tris(benzyloxy)phenyl)ethanamine hydrochloride

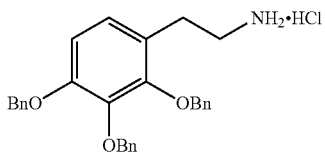

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 [$C_{29}H_{29}NO_3$+H]$^+$.

Preparation of $N^1$-(2,3,4-Tris(benzyloxy)phenethyl)piperidine-1,2-dicarboxamide

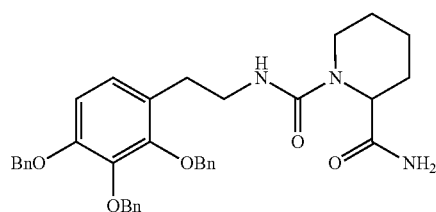 [SMILES: NC(=O)C1CCCCN1C(=O)NCCc1ccc(OCc2ccccc2)c(OCc2ccccc2)c1OCc1ccccc1]

A mixture of 2-(2,3,4-tris(benzyloxy)phenyl)ethanamine hydrochloride (250 mg, 0.525 mmol), piperidine-2-carboxamide (90 mg, 0.70 mmol) and triethylamine (0.50 mL, 3.6 mmol) in methylene chloride (8 mL) was cooled to −10° C. (ice/methanol bath) under a nitrogen atmosphere. Triphosgene (105 mg, 0.354 mmol) was added in one portion, and the mixture was stirred at −10° C. to room temperature over 2.5 h. After this time, the mixture was diluted with ethyl acetate and washed with 10% citric acid, water, and brine. The organic extract was dried over sodium sulfate, filtered, and concentrated. The residue was purified by column chromatography (silica gel, 0-100% ethyl acetate/heptane) to provide $N^1$-(2,3,4-tris(benzyloxy)phenethyl)piperidine-1,2-dicarboxamide (130 mg, 42%): ESI MS m/z 594 [$C_{36}H_{39}N_3O_5$+H]$^+$.

Preparation of $N^1$-(2,3,4-Trihydroxyphenethyl)piperidine-1,2-dicarboxamide

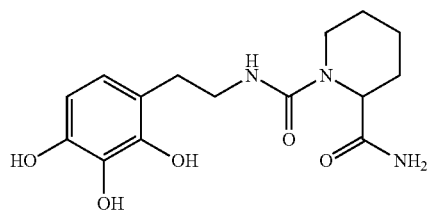 [SMILES: NC(=O)C1CCCCN1C(=O)NCCc1ccc(O)c(O)c1O]

A mixture of $N^1$-(2,3,4-tris(benzyloxy)phenethyl)piperidine-1,2-dicarboxamide (355 mg, 0.599 mmol) and palladium (10% on carbon, 200 mg) in methanol (20 mL) was stirred at room temperature under balloon pressure hydrogen for 3 h. After this time, the reaction mixture was purged with nitrogen and filtered over diatomaceous earth. The filtrate was concentrated under reduced pressure. The residue was purified by column chromatography (silica gel, 0-10% methanol/methylene chloride) and freeze dried from water to provide $N^1$-(2,3,4-trihydroxyphenethyl)piperidine-1,2-dicarboxamide, (99 mg, 51%) as a white solid: $^1$H NMR (300 MHz, DMSO-$d_6$) δ 8.76 (s, 1H), 8.32 (s, 1H), 8.13 (s, 1H), 7.09 (s, 1H), 6.95 (s, 1H), 6.48 (t, J=5.0 Hz, 1H), 6.32 (d, J=8.2 Hz, 1H), 6.19 (d, J=8.2 Hz, 1H), 4.63 (d, J=3.8 Hz, 1H), 3.69 (d, J=12.2 Hz, 1H), 3.17-3.02 (m, 2H), 3.02-2.90 (m, 1H), 2.56 (t, J=8.0 Hz, 2H), 2.06 (d, J=12.6 Hz, 1H), 1.59-1.20 (m, 5H); ESI MS m/z 324 [$C_{15}H_{21}N_3O_5$+H]$^+$; HPLC (Method B) 95.0% (AUC), $t_R$=8.95 min.

Scheme 3.

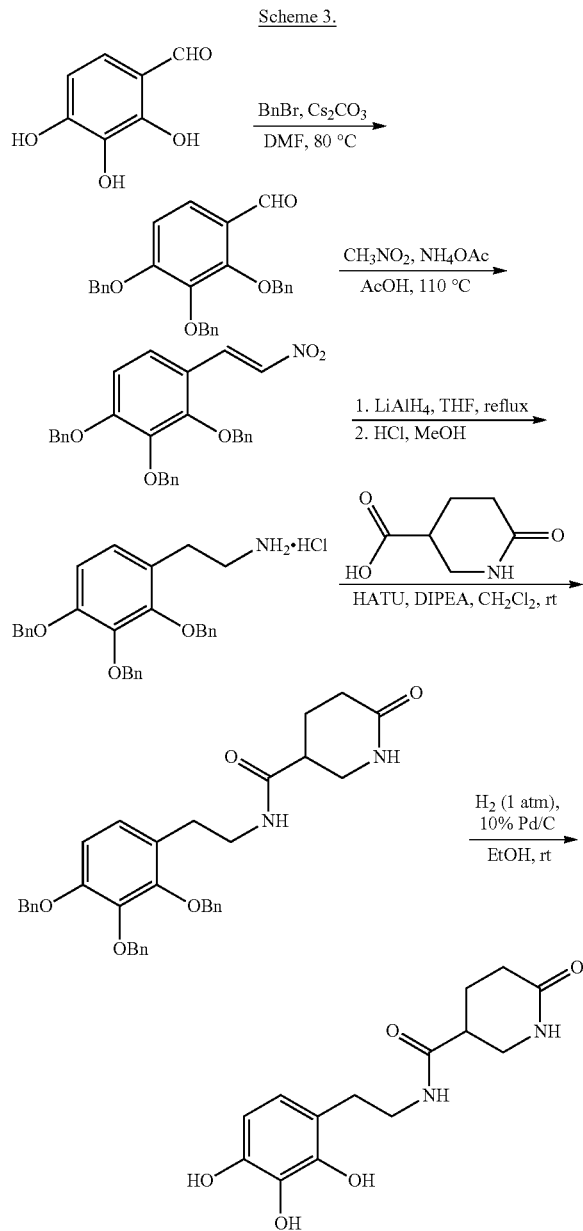

Preparation of 2,3,4-Tris(benzyloxy)benzaldehyde

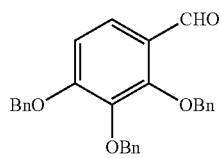

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 $[C_{28}H_{24}O_4+H]^+$.

Preparation of (E)-(((4-(2-Nitrovinyl)benzene-1,2,3-triyl)tris(oxy))tris (methylene)) tribenzene A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 $[C_{29}H_{25}NO_5+H]^+$.

Preparation of 2-(2,3,4-Tris(benzyloxy)phenyl)ethanamine hydrochloride

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of 6-Oxo-N-(2,3,4-tris(benzyloxy)phenethyl)piperidine-3-carboxamide

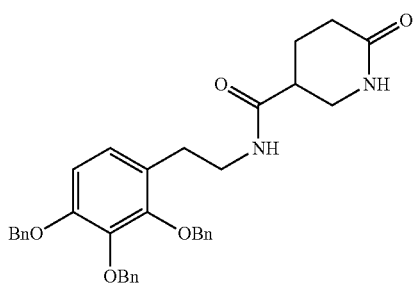 [SMILES: O=C1CCC(C(=O)NCCc2ccc(OCc3ccccc3)c(OCc3ccccc3)c2OCc2ccccc2)CN1]

A suspension of 2-(2,3,4-tris(benzyloxy)phenyl)ethanamine hydrochloride (461 mg, 0.968 mmol) and 6-oxopiperidine-3-carboxylic acid (166 mg, 1.16 mmol) in methylene chloride (10 mL) was treated with (1-[bis(dimethylamino)methylene]-1H-1,2,3-triazolo[4,5-b]pyridinium 3-oxide hexafluorophosphate) (442 mg, 1.16 mmol) and N,N-diisopropylethylamine (0.56 mL, 3.2 mmol). The mixture was stirred under a nitrogen atmosphere for 16 h. After this time, the reaction mixture was diluted with methylene chloride (25 mL); washed with 10% citric acid (25 mL), saturated sodium bicarbonate (25 mL), and brine (25 mL); dried over sodium sulfate; filtered; and concentrated under reduced pressure. The crude residue was purified by column chromatography (silica gel, 0-10% methanol/methylene chloride) to provide 6-oxo-N-(2,3,4-tris(benzyloxy)phenethyl)piperidine-3-carboxamide (430 mg, 79%) as a white solid: $^1$H NMR (300 MHz, DMSO-$d_6$) δ 7.98 (t, J=5.7 Hz, 1H), 7.50-7.29 (m, 16H), 6.91-6.86 (m, 2H), 5.13 (s, 2H), 5.00 (s, 2H), 4.99 (s, 2H), 3.24-3.14 (m, 4H), 2.65 (t, J=7.2 Hz, 2H), 2.49-2.43 (m, 1H, partially obscured by solvent peak), 2.16-2.09 (m, 2H), 1.84-1.70 (m, 2H); ESI MS m/z 565 $[C_{35}H_{36}N_2O_5+H]^+$.

Preparation of 6-Oxo-N-(2,3,4-trihydroxyphenethyl)piperidine-3-carboxamide

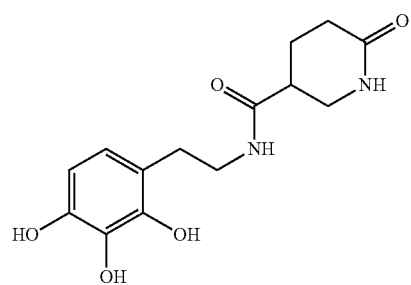 [SMILES: O=C1CCC(C(=O)NCCc2ccc(O)c(O)c2O)CN1]

A solution of 6-oxo-N-(2,3,4-tris(benzyloxy)phenethyl)piperidine-3-carboxamide (428 mg, 0.758 mmol) in ethanol (15 mL) was bubbled with nitrogen gas for 10 min. The solution was treated with 10% palladium on carbon (63 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was purified by column chromatography (silica gel, 1-10% methanol/methylene chloride) and freeze dried from acetonitrile/water to provide 6-oxo-N-(2,3,4-trihydroxyphenethyl)piperidine-3-carboxamide, (110 mg, 49%) as a fluffy white solid: $^1$H NMR (300 MHz, DMSO-$d_6$) δ 8.82 (s, 1H), 8.16 (s, 2H), 7.93 (t, J=5.4 Hz, 1H), 7.42 (br s, 1H), 6.30 (d, J=8.1 Hz, 1H), 6.19 (d, J=8.1 Hz, 1H), 3.18-3.13 (m, 4H), 2.56-2.45 (m, 3H, partially obscured by solvent peak), 2.22-2.05 (m, 2H), 1.88-1.68 (m, 2H); ESI MS m/z 295 $[C_{14}H_{18}N_2O_5+H]^+$; HPLC (Method B) 96.6% (AUC), $t_R$=7.50 min.

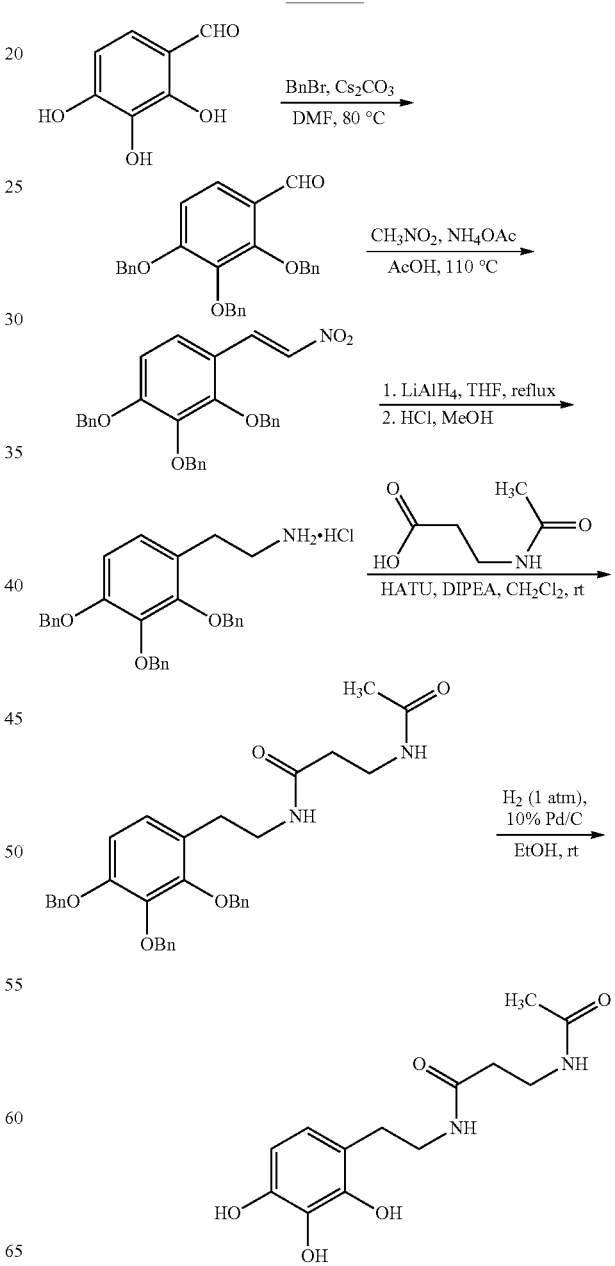

Scheme 4.

Preparation of 2,3,4-Tris(benzyloxy)benzaldehyde

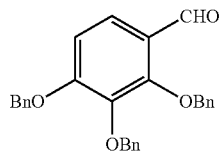

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 $[C_{28}H_{24}O_4+H]^+$.

Preparation of (E)-(((4-(2-Nitrovinyl)benzene-1,2,3-triyl)tris(oxy))tris (methylene)) tribenzene

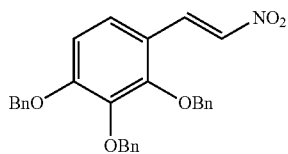 [SMILES: O=[N+]([O-])/C=C/c1ccc(OCc2ccccc2)c(OCc2ccccc2)c1OCc1ccccc1]

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 $[C_{29}H_{25}NO_5+H]^+$.

Preparation of 2-(2,3,4-Tris(benzyloxy)phenyl)ethanamine hydrochloride

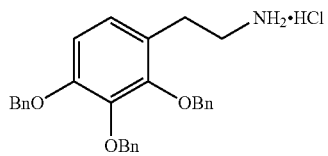

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of 3-Acetamido-N-(2,3,4-tris(benzyloxy)phenethyl)propanamide

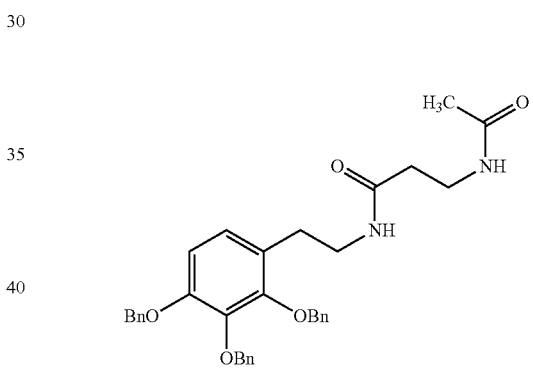

A suspension of 2-(2,3,4-tris(benzyloxy)phenyl)ethanamine hydrochloride (289 mg, 0.607 mmol) and 3-acetamidopropanoic acid (96 mg, 0.73 mmol) in methylene chloride (6 mL) was treated with (1-[bis(dimethylamino)methylene]-1H-1,2,3-triazolo[4,5-b]pyridinium 3-oxide hexafluorophosphate) (278 mg, 0.731 mmol) and N,N-diisopropylethylamine (0.35 mL, 2.0 mmol). The mixture was stirred under a nitrogen atmosphere for 16 h. After this time, the reaction mixture was diluted with methylene chloride (25 mL); washed with 10% citric acid (25 mL), saturated sodium bicarbonate (25 mL), and brine (25 mL); dried over sodium sulfate; filtered; and concentrated under reduced pressure. The crude residue was purified by column chromatography (silica gel, 0-10% methanol/methylene chloride) to provide 3-acetamido-N-(2,3,4-tris(benzyloxy)phenethyl)propanamide (193 mg, 58%) as a white solid: $^1$H NMR (300 MHz, DMSO-$d_6$) δ 7.92 (t, J=5.7 Hz, 1H), 7.84 (t, J=5.7 Hz, 1H), 7.50-7.29 (m, 15H), 6.89 (s, 2H), 5.13 (s, 2H), 5.00 (s, 2H), 4.99 (s, 2H), 3.21-3.16 (m, 4H), 2.65 (t, J=7.5 Hz, 2H), 2.19 (t, J=7.1 Hz, 2H), 1.76 (s, 3H); ESI MS m/z 553 $[C_{34}H_{36}N_2O_5+H]^+$.

Preparation of 3-Acetamido-N-(2,3,4-trihydroxyphenethyl)propanamide

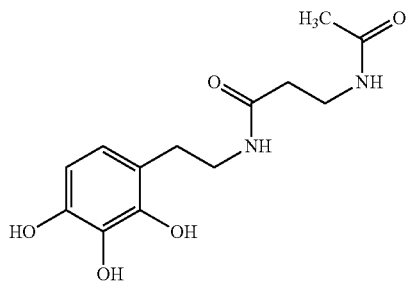

A solution of 3-acetamido-N-(2,3,4-tris(benzyloxy)phenethyl)propanamide (190 mg, 0.344 mmol) in ethyl acetate (4 mL) and ethanol (4 mL) was bubbled with nitrogen gas for 10 min. The solution was treated with 10% palladium on carbon (27 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was purified by column chromatography (silica gel, 1-10% methanol/methylene chloride) and freeze dried from water to provide 3-acetamido-N-(2,3,4-trihydroxyphenethyl)propanamide, (59 mg, 61%) as a fluffy white solid: $^1$H NMR (300 MHz, DMSO-$d_6$) δ 8.82 (s, 1H), 8.16 (s, 2H), 7.87-7.82 (m, 2H), 6.31 (d, J=8.1 Hz, 1H), 6.19 (d, J=8.1 Hz, 1H), 3.23-3.11 (m, 4H), 2.56-2.50 (m, 2H, partially obscured by solvent peak), 2.19 (t, J=6.9 Hz, 2H), 1.77 (s, 3H); ESI MS m/z 283 [$C_{13}H_{18}N_2O_5$+H]$^+$; HPLC (Method B) 96.6% (AUC), $t_R$=7.50 min.

Scheme 5.

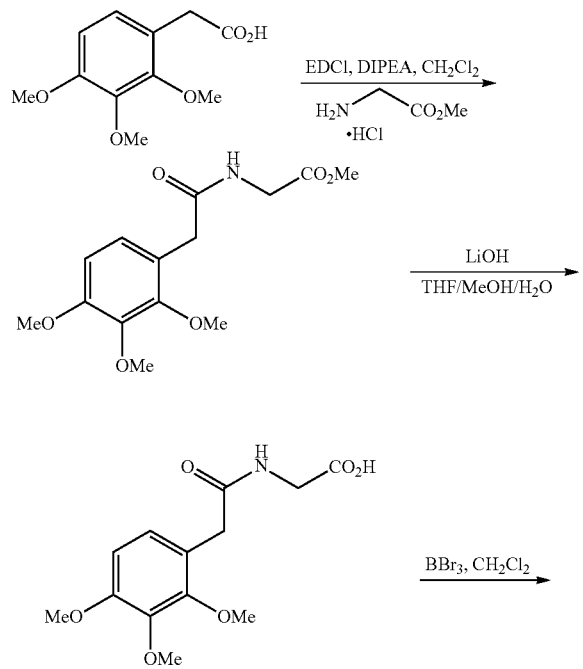

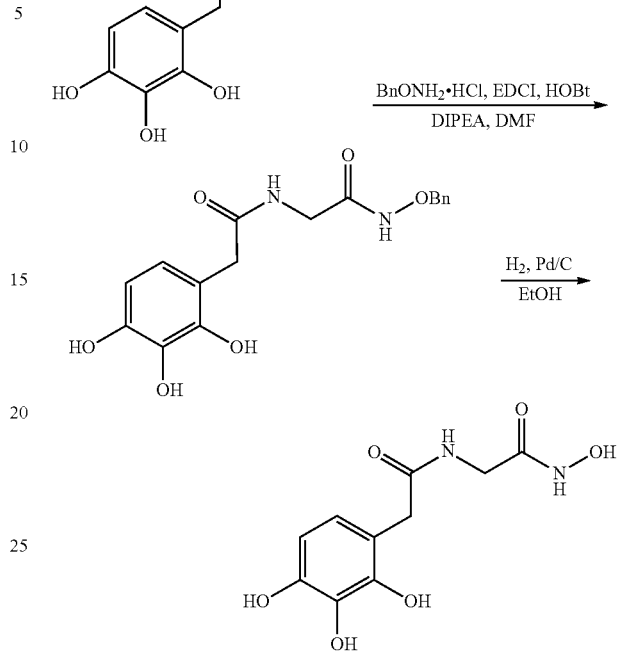

Preparation of Methyl 2-(2-(2,3,4-Trimethoxyphenyl)acetamido)acetate

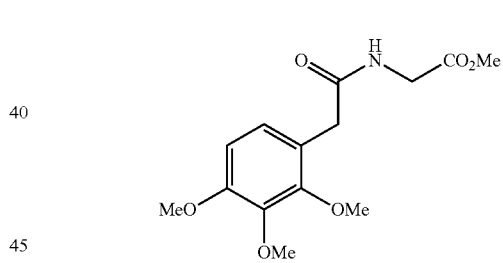

A solution of 2-(2,3,4-trimethoxyphenyl)acetic acid (500 mg, 2.21 mmol), glycine hydrochloride (277 mg, 2.21 mmol) and diisopropylethylamine (686 mg, 5.30 mmol) in methylene chloride (25 mL) was cooled in an ice bath and treated with N-(3-dimethylaminopropyl)-N'-ethylcarbodiimide hydrochloride (636 mg, 3.32 mmol). The mixture was stirred at room temperature for 4 h. After this time, the reaction mixture was treated with water (40 mL) and extracted with ethyl acetate (2×40 mL). The combined organics were washed with 2 N hydrochloric acid (10 mL), saturated aqueous sodium bicarbonate (50 mL), and water (50 mL); dried over sodium sulfate; filtered; and concentrated under reduced pressure to provide methyl 2-(2-(2,3,4-trimethoxyphenyl)acetamido)acetate (392 mg, 59%) as a white solid: $^1$H NMR (300 MHz, CDCl$_3$) δ 6.94 (d, J=8.4 Hz, 1H), 6.65 (d, J=8.4 Hz, 1H), 6.32 (br s, 1H), 4.00 (d, J=5.1 Hz, 2H), 3.93 (s, 3H), 3.88 (s, 3H), 3.86 (s, 3H), 3.72 (s, 3H), 3.55 (s, 2H).

Preparation of 2-(2-(2,3,4-Trimethoxyphenyl)acetamido)acetic Acid

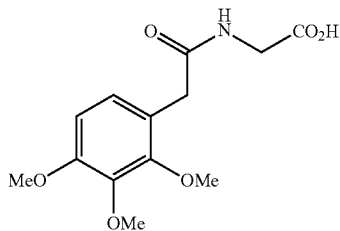 [SMILES: COc1ccc(CC(=O)NCC(=O)O)c(OC)c1OC]

Methyl 2-(2-(2,3,4-trimethoxyphenyl)acetamido)acetate (392 mg, 1.32 mmol), lithium hydroxide (126 mg, 5.27 mmol), tetrahydrofuran (5 mL), methanol (5 mL) and water (5 mL) were combined and stirred at room temperature for 2 h. After this time, the reaction mixture was concentrated under reduced pressure, and the residue was acidified to pH 2 with 2 N hydrochloric acid. The resulting suspension was extracted with ethyl acetate (2×20 mL). The combined organics were washed with brine (50 mL), dried over sodium sulfate, filtered, and concentrated under reduced pressure to provide 2-(2-(2,3,4-trimethoxyphenyl)acetamido)acetic acid (375 mg, 100%) as a white solid: $^1$H NMR (300 MHz, CDCl$_3$) δ 6.93 (d, J=8.4 Hz, 1H), 6.65 (d, J=8.4 Hz, 1H), 6.42 (br s, 1H), 4.03 (d, J=5.4 Hz, 2H), 3.93 (s, 3H), 3.88 (s, 3H), 3.86 (s, 3H), 3.56 (s, 2H), CO2H proton not observed.

Preparation of 2-(2-(2,3,4-Trihydroxyphenyl)acetamido)acetic Acid

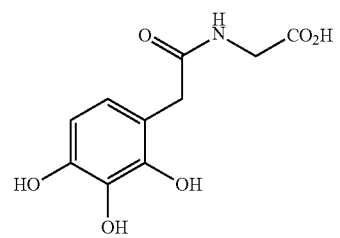 [SMILES: O=C(O)CNC(=O)Cc1ccc(O)c(O)c1O]

A solution of 2-(2-(2,3,4-trimethoxyphenyl)acetamido)acetic acid (375 mg, 1.32 mmol) in methylene chloride (40 mL) was cooled in an ice bath and treated dropwise with a 1.0 M solution of boron tribromide in methylene chloride (6.62 mL, 6.62 mmol). After addition was complete, the mixture was stirred at 0° C. for 4 min, and water (20 mL) was added slowly. The resulting suspension was extracted with ethyl acetate (2×20 mL). The combined organics were washed with brine (50 mL), dried over sodium sulfate, filtered, and concentrated under reduced pressure to provide 2-(2-(2,3,4-trihydroxyphenyl)acetamido)acetic acid (321 mg, 100%) as a white solid: $^1$H NMR (300 MHz, DMSO-d$_6$) δ 6.37 (d, J=8.4 Hz, 1H), 6.21 (d, J=8.4 Hz, 1H), 3.72 (m, 2H), 3.38 (m, 2H), 5 exchangeable protons not observed.

Preparation of N-(Benzyloxy)-2-(2-(2,3,4-trihydroxyphenyl)acetamido)acetamide

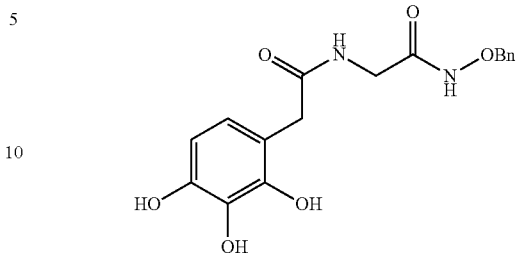

A solution of 2-(2-(2,3,4-trihydroxyphenyl)acetamido)acetic acid (300 mg, 1.24 mmol), benzylhydroxylamine hydrochloride (397 mg, 2.49 mmol) and diisopropylethylamine (322 mg, 2.49 mmol) in N,N-dimethylformamide (10 mL) was treated with N-(3-dimethylaminopropyl)-N'-ethylcarbodiimide hydrochloride (477 mg, 2.49 mmol) and 1-hydroxybenzotriazole hydrate (336 mg, 2.49 mmol), and the mixture was stirred at room temperature for 16 h. After this time, the reaction mixture was treated with water (40 mL) and extracted with ethyl acetate (2×40 mL). The combined organics were dried over sodium sulfate, filtered, and concentrated under reduced pressure. The residue was purified by reversed phase column chromatography (50 g C18 column, 10-100% acetonitrile/water) to provide N-(benzyloxy)-2-(2-(2,3,4-trihydroxyphenyl)acetamido)acetamide (170 mg, 39%) as a white solid: $^1$H NMR (300 MHz, CD$_3$OD) δ 7.45-7.35 (m, 5H), 6.50 (d, J=8.1 Hz, 1H), 6.34 (d, J=8.1 Hz, 1H), 4.84 (s, 2H), 3.76 (s, 2H), 3.50 (s, 2H), 5 exchangeable protons not observed; ESI MS m/z 345 [C$_{17}$H$_{18}$N$_2$O$_6$–H]$^-$.

Preparation of N-Hydroxy-2-(2-(2,3,4-trihydroxyphenyl)acetamido)acetamide

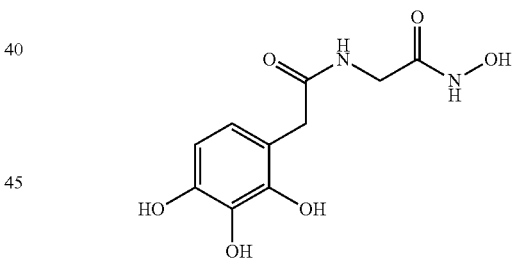

A solution of N-(benzyloxy)-2-(2-(2,3,4-trihydroxyphenyl)acetamido)acetamide (170 mg, 0.491 mmol) in ethanol (5 mL) was sparged with nitrogen gas for 30 min. The solution was treated with 5% palladium on carbon (100 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure and the residue was purified by reversed phase column chromatography (50 g C18 column, 2-100% acetonitrile/water) to provide N-hydroxy-2-(2-(2,3,4-trihydroxyphenyl)acetamido)acetamide, (55 mg, 43%) as an off-white solid: $^1$H NMR (300 MHz, DMSO-d$_6$) δ 10.50 (br s, 1H), 9.02 (br s, 1H), 8.83 (br s, 1H), 8.78 (br s, 1H), 8.14 (m, 2H), 6.36 (d, J=8.4 Hz, 1H), 6.21 (d, J=8.4 Hz, 1H), 3.60 (d, J=5.7 Hz, 2H), 3.35 (s, 2H); ESI MS m/z 257 [C$_{10}$H$_{12}$N$_2$O$_6$+H]$^+$; HPLC (Method C) 96.5% (AUC), tR=5.18 min.

Scheme 6.

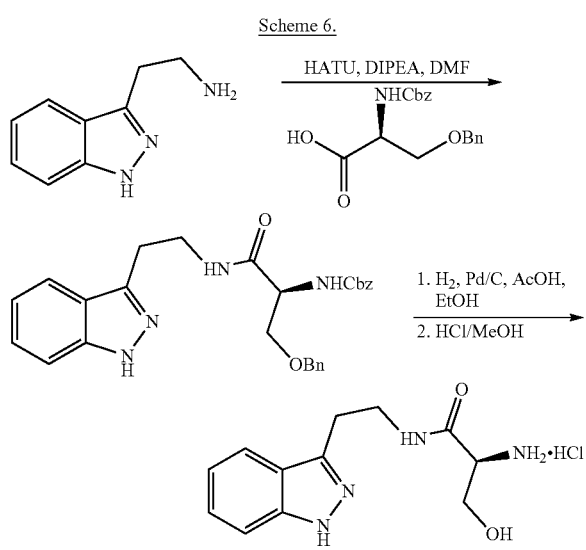

Preparation of (S)-Benzyl (1-((2-(1H-indazol-3-yl)ethyl)amino)-3-(benzyloxy)-1-oxopropan-2-yl)carbamate

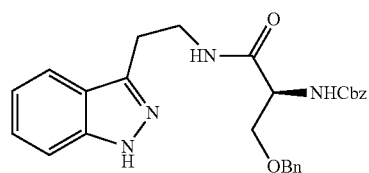 [SMILES: O=C(N[C@@H](COCc1ccccc1)C(=O)NCCc1n[nH]c2ccccc12)OCc1ccccc1]

A solution of 2-(1H-indazol-3-yl)ethanamine (240 mg, 1.49 mmol), (S)-3-(benzyloxy)-2-(((benzyloxy)carbonyl)amino)propanoic acid (981 mg, 2.98 mmol) and diisopropylethylamine (578 mg, 4.47 mmol) in N,N-dimethylformamide (20 mL) was cooled to −10° C. and treated with O-(7-azabbenzotriazol-1-yl)-N,N,N',N'-tetramethyluronium hexafluorophosphate (1.70 g, 4.47 mmol). The mixture was stirred at −10° C. for 1 h. After this time, the reaction mixture was treated with water (40 mL) and extracted with ethyl acetate (2×40 mL). The combined organics were washed with saturated aqueous sodium bicarbonate (40 mL), water (40 mL), and brine (40 mL); dried over sodium sulfate; filtered; and concentrated under reduced pressure. The residue was purified by column chromatography (40 g silica column, 0-100% ethyl acetate/heptane) to provide (S)-benzyl (1-((2-(1H-indazol-3-yl)ethyl)amino)-3-(benzyloxy)-1-oxopropan-2-yl)carbamate (535 mg, 75%) as a white solid: ESI MS m/z 473 $[C_{27}H_{28}N_4O_4+H]^+$.

Preparation of (S)—N-(2-(1H-Indazol-3-yl)ethyl)-2-amino-3-hydroxypropanamide hydrochloride

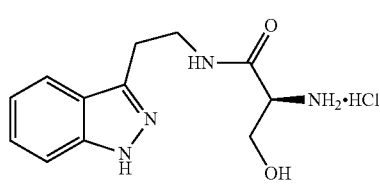

A solution of (S)-benzyl (1-((2-(1H-indazol-3-yl)ethyl)amino)-3-(benzyloxy)-1-oxopropan-2-yl)carbamate (300 mg, 0.887 mmol) and acetic acid (1 mL) in ethanol (20 mL) was sparged with nitrogen gas for 30 min. The solution was treated with 5% palladium on carbon (100 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure and the residue was purified by reversed phase column chromatography (50 g C18 column, 2-100% acetonitrile/water). The resulting solid was treated with a 1.5 M solution of hydrogen chloride in methanol (2 mL) and concentrated under reduced pressure to provide (S)—N-(2-(1H-indazol-3-yl)ethyl)-2-amino-3-hydroxypropanamide hydrochloride, (71 mg, 28%) as an off-white solid: $^1$H NMR (300 MHz, DMSO-$d_6$) δ 12.78 (br s, 1H), 8.59 (t, J=5.7 Hz, 1H), 8.14 (br s, 3H), 7.74 (d, J=8.1 Hz, 1H), 7.48 (d, J=8.4 Hz, 1H), 7.33 (t, J=8.1 Hz, 1H), 7.09 (t, J=8.4 Hz, 1H), 3.75-3.44 (m, 5H), 3.08 (t, J=6.9 Hz, 2H), OH proton not observed; ESI MS m/z 249 $[C_{12}H_{16}N_4O_2+H]^+$; HPLC (Method B) 96.5% (AUC), $t_R$=5.18 min.

Scheme 7.

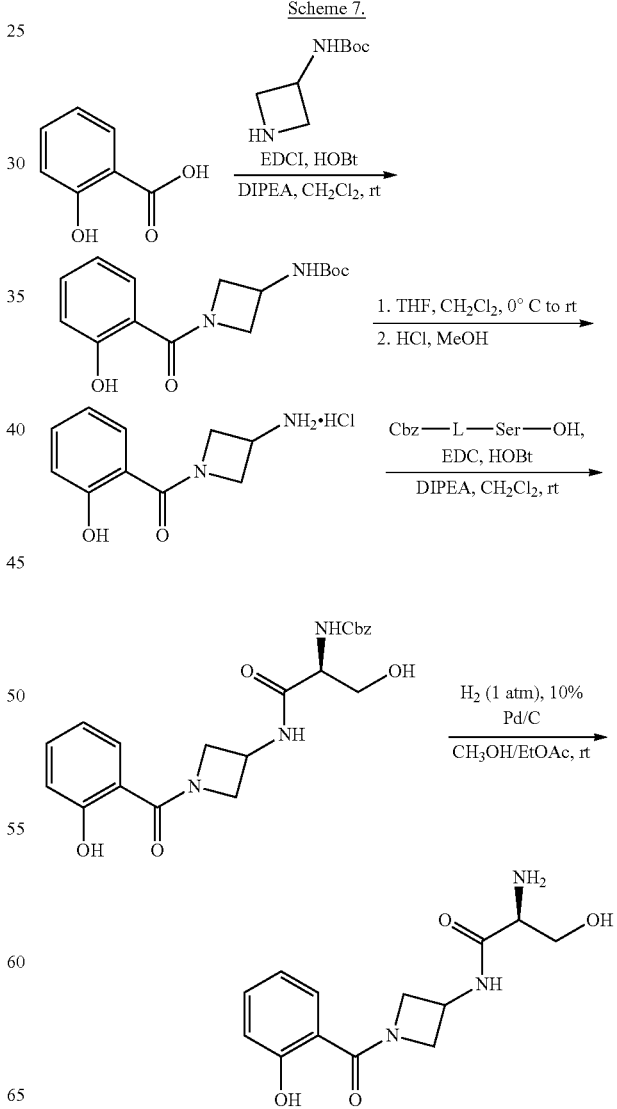

Preparation of tert-Butyl (1-(2-hydroxybenzoyl)azetidin-3-yl)carbamate

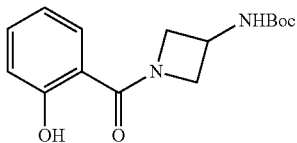 [SMILES: CC(C)(C)OC(=O)NC1CN(C(=O)c2ccccc2O)C1]

A solution of 2-hydroxybenzoic acid (640 mg, 4.63 mmol) in methylene chloride (20 mL) was treated with 1-ethyl-3-(3-dimethylaminopropyl)carbodiimide (1.4 mL, 8.1 mmol), hydroxybenzotriazole (938 mg, 6.95 mmol), and (tert-butyl azetidin-3-ylcarbamate (997 mg, 5.79 mmol) and stirred under a nitrogen atmosphere for 16 h. After this time, the reaction mixture was diluted with ethyl acetate (125 mL), washed with saturated sodium bicarbonate (50 mL) and brine (25 mL), dried over sodium sulfate, decanted, and concentrated under reduced pressure. The crude residue was purified by column chromatography (silica gel, 5-30% ethyl acetate/hexanes) to provide tert-butyl (1-(2-hydroxybenzoyl)azetidin-3-yl)carbamate (800 mg, 59%) as a white solid: $^1$H NMR (300 MHz, DMSO-$d_6$) δ 11.76 (s, 1H), 7.62 (d, J=6.3 Hz, 1H), 7.40-7.34 (m, 2H), 6.91-6.83 (m, 2H), 4.58 (br s, 1H), 4.33-4.21 (m, 3H), 3.92 (br s, 1H), 1.39 (s, 9H); ESI MS m/z 293 $[C_{15}H_{20}N_2O_4+H]^+$.

Preparation of (3-Aminoazetidin-1-yl)(2-hydroxyphenyl)methanone hydrochloride

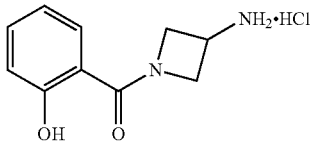

A solution of tert-butyl (1-(2-hydroxybenzoyl)azetidin-3-yl)carbamate (800 mg, 2.73 mmol) in methylene chloride (30 mL) was cooled in an ice bath and treated with trifluoroacetic acid (15 mL). The ice bath was removed, and the mixture was stirred at ambient temperature under a nitrogen atmosphere for 1 h. The mixture was concentrated under reduced pressure. The residue was treated with a ~1.2 M solution of hydrogen chloride in methanol (25 mL) and concentrated under reduced pressure. The hydrogen chloride treatment was repeated a second time to provide (3-aminoazetidin-1-yl)(2-hydroxyphenyl)methanone hydrochloride (679 mg, quantitative) as an off-white sticky solid: ESI MS m/z 193 $[C_{10}H_{12}N_2O_2+H]^+$.

Preparation of (S)-Benzyl (3-hydroxy-1-((1-(2-hydroxybenzoyl)azetidin-3-yl)amino)-1-oxopropan-2-yl)carbamate

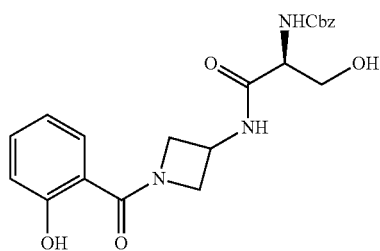 [SMILES: O=C(N[C@@H](CO)C(=O)NC1CN(C(=O)c2ccccc2O)C1)OCc1ccccc1]

A solution of (3-aminoazetidin-1-yl)(2-hydroxyphenyl)methanone hydrochloride (315 mg, 1.38 mmol) in methylene chloride (15 mL) was cooled in an ice bath and treated with N,N-diisopropylethylamine (0.36 mL, 2.1 mmol), 1-ethyl-3-(3-dimethylaminopropyl)carbodiimide (0.30 mL, 1.7 mmol), hydroxybenzotriazole (232 mg, 1.72 mmol), and (S)-2-(((benzyloxy)carbonyl)amino)-3-hydroxypropanoic acid (413 mg, 1.72 mmol). The ice bath was removed, and the mixture was stirred under a nitrogen atmosphere for 16 h. After this time, the reaction mixture was diluted with methylene chloride (30 mL), washed with saturated sodium bicarbonate (20 mL) and brine (20 mL), dried over sodium sulfate, decanted, and concentrated under reduced pressure. The crude residue was purified by column chromatography (silica gel, 0-75% ethyl acetate/methylene chloride) to provide (S)-benzyl (3-hydroxy-1-((1-(2-hydroxybenzoyl)azetidin-3-yl)amino)-1-oxopropan-2-yl)carbamate (200 mg, 35%) as a white solid: $^1$H NMR (500 MHz, DMSO-$d_6$) δ 11.74 (s, 1H), 8.63 (d, J=6.5 Hz, 1H), 7.40-7.30 (m, 6H), 7.17 (d, J=8.0 Hz, 1H), 6.92-6.85 (m, 2H), 5.07-5.00 (m, 2H), 4.86 (t, J=5.5 Hz, 1H), 4.63-4.53 (m, 2H), 4.33-4.23 (m, 2H), 4.04-3.98 (m, 2H), 3.61-3.54 (s, 2H), 1 exchangeable proton not observed; ESI MS m/z 414 $[C_{21}H_{23}N_3O_6+H]^+$.

Preparation of (S)-2-Amino-3-hydroxy-N-(1-(2-hydroxybenzoyl)azetidin-3-yl)propanamide

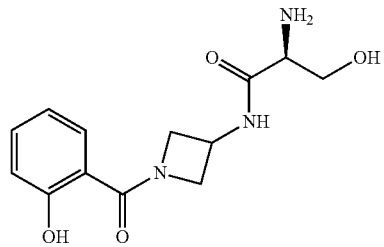 [SMILES: N[C@@H](CO)C(=O)NC1CN(C(=O)c2ccccc2O)C1]

A solution of (S)-benzyl (3-hydroxy-1-((1-(2-hydroxybenzoyl)azetidin-3-yl)amino)-1-oxopropan-2-yl)carbamate (183 mg, 0.443 mmol) in methanol (20 mL) and ethyl acetate (20 mL) was flushed with nitrogen gas and treated with 10% palladium on carbon (50 mg). The reaction vessel was flushed with hydrogen gas, and the reaction mixture was stirred under a hydrogen atmosphere (balloon) for 16 h. After this time, the reaction mixture was filtered over diatomaceous earth. The filtrate was concentrated under reduced pressure. The residue was purified by column chromatography (silica gel, 0-100% [90:9:1 methylene chloride/methanol/ammonium hydroxide]/methylene chloride) and freeze dried from acetonitrile/water to provide (S)-2-amino-3-hydroxy-N-(1-(2-hydroxybenzoyl)azetidin-3-yl)propanamide, (96 mg, 78%) as a fluffy white solid: $^1$H NMR (500 MHz, DMSO-$d_6$) δ 11.79 (br s, 1H), 8.53 (s, 1H), 7.41-7.35 (m, 2H), 6.91-6.84 (m, 2H), 4.71-4.55 (m, 3H), 4.28 (br s, 2H), 4.00 (br s, 1H), 3.47-3.40 (m, 2H), 3.19 (t, J=5.0 Hz, 1H), 1.75 (br s, 2H); ESI MS m/z 280 $[C_{13}H_{17}N_3O_4+H]^-$; HPLC (Method D) >99% (AUC), $t_R$=6.08 min.

Scheme 8.

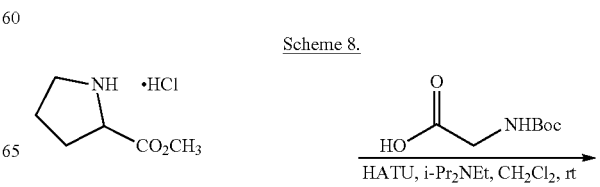

-continued

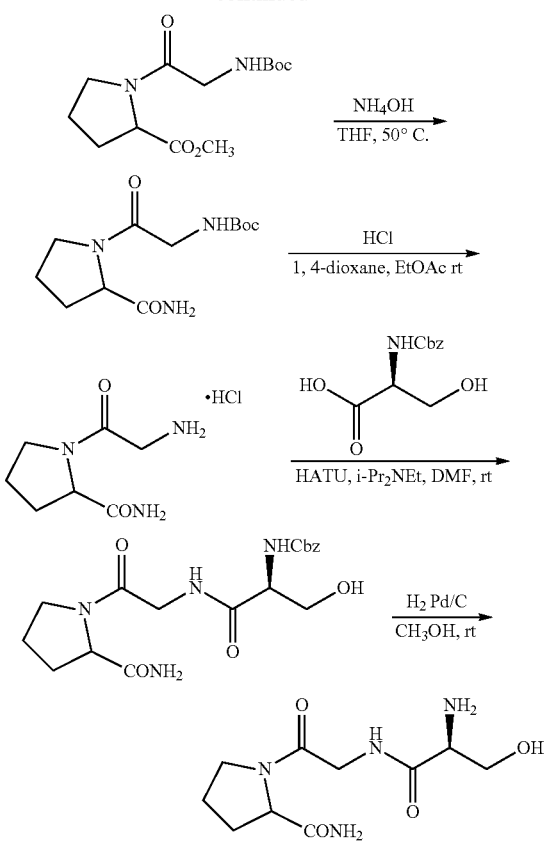

Preparation of Methyl 1-(2-((tert-butoxycarbonyl)amino) acetyl)pyrrolidine-2-carboxylate

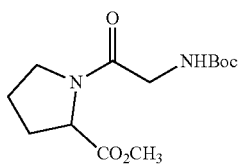

A mixture of N-Boc-glycine (2.30 g, 13.1 mmol) and methyl pyrrolidine-2-carboxylate hydrochloride (2.00 g, 12.1 mmol) in methylene chloride (25 mL) at room temperature was treated with N,N-diisopropylethylamine (4.25 mL, 24.4 mmol) followed by (1-[bis(dimethylamino)methylene]-1H-1,2,3-triazolo[4,5-b]pyridinium 3-oxide hexafluorophosphate) (5.00 g, 13.1 mmol). The mixture was stirred at room temperature for 18 h. After this time, the reaction mixture was diluted with methylene chloride and sequentially washed with water, saturated ammonium chloride, saturated sodium bicarbonate, water, and brine. The organic extract was dried over sodium sulfate, filtered, and concentrated to obtain crude methyl 1-(2-((tert-butoxycarbonyl)amino)acetyl)pyrrolidine-2-carboxylate (3.9 g), which was used in the next step without purification: ESI MS m/z 287 $[C_{13}H_{22}N_2O_5+H]^+$.

Preparation of tert-Butyl (2-(2-carbamoylpyrrolidin-1-yl)-2-oxoethyl)carbamate

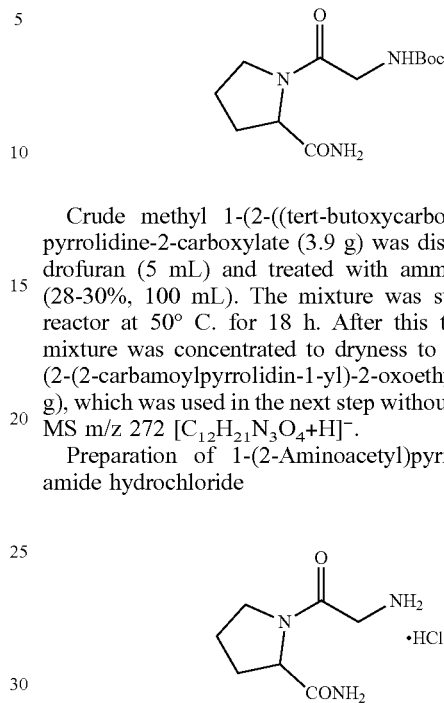

Crude methyl 1-(2-((tert-butoxycarbonyl)amino)acetyl) pyrrolidine-2-carboxylate (3.9 g) was dissolved in tetrahydrofuran (5 mL) and treated with ammonium hydroxide (28-30%, 100 mL). The mixture was stirred in a sealed reactor at 50° C. for 18 h. After this time, the reaction mixture was concentrated to dryness to provide tert-butyl (2-(2-carbamoylpyrrolidin-1-yl)-2-oxoethyl)carbamate (3.6 g), which was used in the next step without purification: ESI MS m/z 272 $[C_{12}H_{21}N_3O_4+H]^-$.

Preparation of 1-(2-Aminoacetyl)pyrrolidine-2-carboxamide hydrochloride

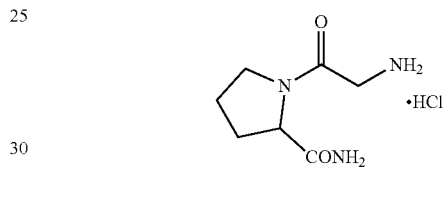

A solution of crude tert-butyl (2-(2-carbamoylpyrrolidin-1-yl)-2-oxoethyl)carbamate (3.6 g) in ethyl acetate (12 mL) was treated with a 4 M solution of hydrogen chloride in 1,4-dioxane (10 mL) and stirred at room temperature for 1.5 h. After this time, heptane (10 mL) was added to obtain a precipitate that was collected by filtration to provide 1-(2-aminoacetyl)pyrrolidine-2-carboxamide hydrochloride (2.5 g): ESI MS m/z 172 $[C_7H_{13}N_3O_2+H]^+$.

Preparation of Benzyl ((2S)-1-((2-(2-carbamoylpyrrolidin-1-yl)-2-oxoethyl)amino)-3-hydroxy-1-oxopropan-2-yl) carbamate

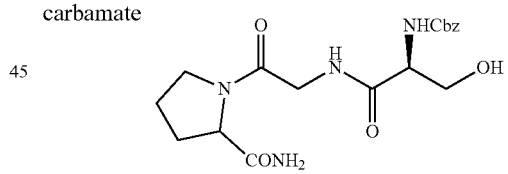

A mixture of crude 1-(2-aminoacetyl)pyrrolidine-2-carboxamide hydrochloride (2.5 g) and N-Cbz-L-serine (1.5 g, 6.2 mmol) in N,N-dimethylformamide (18 mL) at room temperature was treated with N,N-diisopropylethylamine (2.5 mL, 14 mmol) followed by (1-[bis(dimethylamino) methylene]-1H-1,2,3-triazolo[4,5-b]pyridinium 3-oxide hexafluorophosphate) (5.00 g, 13.1 mmol). The mixture was stirred at room temperature for 18 h. After this time, the reaction mixture was diluted with ethyl acetate and washed with 0.5 N hydrochloric acid. The aqueous layer was extracted three more times with ethyl acetate, and the organic extracts were combined, dried over sodium sulfate, and concentrated. The residue was purified by reversed phase column chromatography (50 g C18 column, 3-60% acetonitrile/water) to provide benzyl ((2S)-1-((2-(2-carbamoylpyrrolidin-1-yl)-2-oxoethyl)amino)-3-hydroxy-1-oxopropan-2-yl)carbamate (80 mg, 6% over four steps): ESI MS m/z 393 $[C_{18}H_{24}N_4O_6+H]^9$.

Preparation of 1-(2-((S)-2-Amino-3-hydroxypropanamido)acetyl)pyrrolidine-2-carboxamide

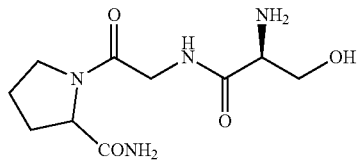 [SMILES: NC(=O)C1CCCN1C(=O)CNC(=O)[C@@H](N)CO]

A mixture of benzyl ((2S)-1-((2-(2-carbamoylpyrrolidin-1-yl)-2-oxoethyl)amino)-3-hydroxy-1-oxopropan-2-yl)carbamate (135 mg, 0.344 mmol) and palladium (10% on carbon, 80 mg) in methanol (12 mL) was stirred under balloon pressure hydrogen for 2 h. After this time, the reaction mixture was purged with nitrogen, and the catalyst was removed by filtration. The filtrate was concentrated, and the residue was dissolved in water and freeze dried to provide 1-(2-((S)-2-amino-3-hydroxypropanamido)acetyl)pyrrolidine-2-carboxamide, (82 mg, 92%) as a white solid as a mixture of diastereomers: $^1$H NMR (300 MHz, DMSO-$d_6$) δ 8.10 (s, 1H), 7.59 (s, 0.3H), 7.28 (s, 0.7H), 7.21 (s, 0.3H), 6.95 (s, 0.7H), 4.77 (broad s, 1H), 4.32 (dd, J=8.4, 2.4 Hz, 0.3H), 4.23-4.16 (m, 0.7H), 3.99-3.83 (m, 1.7 H)3.61-3.37 (m, 4.3H), 3.27-3.13 (m, 1H), 2.25-1.66 (m, 6H); ESI MS m/z 259 $[C_{10}H_{18}N_4O_4+H]^+$.

Scheme 9.

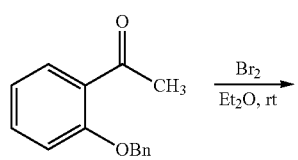

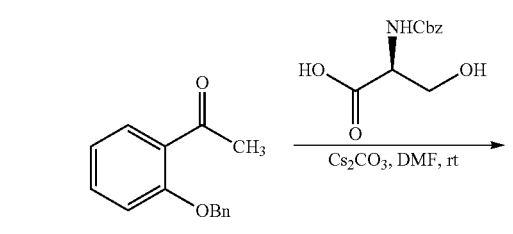

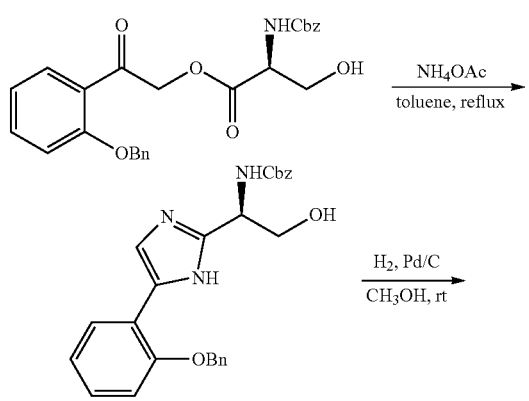

Preparation of 1-(2-(Benzyloxy)phenyl)-2-bromoethanone

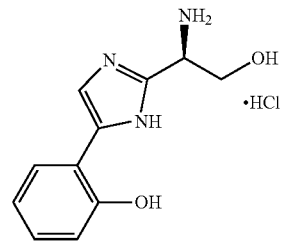

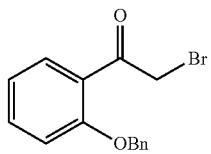 [SMILES: O=C(CBr)c1ccccc1OCc1ccccc1]

Bromine (0.7 mL, 13.7 mmol) was added dropwise to a solution of 1-(2-(benzyloxy)phenyl)ethanone (3.00 g, 13.3 mmol) in diethyl ether (100 mL), and the mixture was stirred at room temperature for 2 h. After this time, the mixture was washed with saturated sodium bicarbonate, water, and brine. The organic extract was dried over sodium sulfate, filtered and concentrated to dryness to provide 1-(2-(benzyloxy)phenyl)-2-bromoethanone (3.80 g, 94%): ESI MS m/z 305 $[C_{15}H_{13}BrO_2+H]^+$.

Preparation of (S)-2-(2-(Benzyloxy)phenyl)-2-oxoethyl 2-(((benzyloxy)carbonyl)amino)-3-hydroxypropanoate

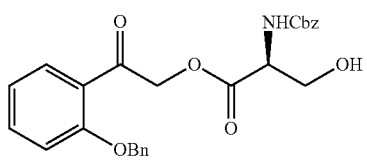 [SMILES: O=C(N[C@@H](CO)C(=O)OCC(=O)c1ccccc1OCc1ccccc1)OCc1ccccc1]

A mixture of 1-(2-(benzyloxy)phenyl)-2-bromoethanone (1.80 g, 5.90 mmol), (S)-2-(((benzyloxy)carbonyl)amino)-3-hydroxypropanoic acid (1.60 g, 6.69 mmol), and cesium carbonate (1.40 g, 4.30 mmol) in N,N-dimethylformamide (15 mL) was stirred at room temperature for 2 h. After this time, the mixture was diluted with ethyl acetate and washed with 1 N hydrochloric acid, water, 5% lithium chloride, and brine. The organic extract was dried over sodium sulfate, filtered, and concentrated. The residue was purified by column chromatography (80 g silica, 0-100% ethyl acetate/heptane) to provide (S)-2-(2-(benzyloxy)phenyl)-2-oxoethyl 2-(((benzyloxy)carbonyl)amino)-3-hydroxypropanoate (2.04 g, 75%): ESI MS m/z 464 $[C_{26}H_{25}NO_7+H]^+$.

235

Preparation of (R)-Benzyl (1-(5-(2-(benzyloxy)phenyl)-1H-imidazol-2-yl)-2-hydroxyethyl)carbamate

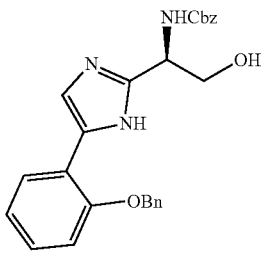 [SMILES: O=C(N[C@@H](CO)c1ncc(-c2ccccc2OCc2ccccc2)[nH]1)OCc1ccccc1]

A mixture of (S)-2-(2-(benzyloxy)phenyl)-2-oxoethyl 2-(((benzyloxy)carbonyl)amino)-3-hydroxypropanoate (1.95 g, 4.21 mmol) and ammonium acetate (2.20 g, 28.6 mmol) in toluene (100 mL) was stirred at reflux in a flask equipped with a Dean-Stark trap for 10 h. After this time, the mixture was cooled to room temperature, diluted with ethyl acetate, and washed with water and brine. The organic extract was dried over sodium sulfate, filtered, and concentrated. The residue was purified by column chromatography (120 g silica, 0-8% methanol/dichloromethane) to provide (R)-benzyl (1-(5-(2-(benzyloxy)phenyl)-1H-imidazol-2-yl)-2-hydroxyethyl)carbamate (0.89 g, 48%): ESI MS m/z 444 $[C_{26}H_{25}N_3O_4+H]^+$.

Preparation of (R)-2-(2-(1-Amino-2-hydroxyethyl)-1H-imidazol-5-yl)phenol hydrochloride

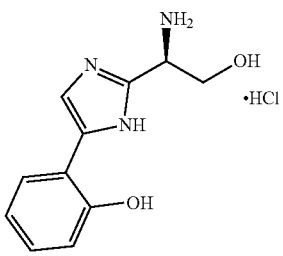 [SMILES: N[C@@H](CO)c1ncc(-c2ccccc2O)[nH]1 ; Cl]

A mixture of (R)-benzyl (1-(5-(2-(benzyloxy)phenyl)-1H-imidazol-2-yl)-2-hydroxyethyl)carbamate (440 mg, 0.99 mmol) and palladium (10% on carbon, 120 mg) in methanol (16 mL) was stirred under balloon pressure hydrogen for 5 h. After this time, the reaction mixture was purged with nitrogen, the catalyst was removed by filtration, and the filtrate was concentrated to dryness to obtain the product as a free base (200 mg, 92%). A portion of the material (105 mg) was dissolved in methanol (2 mL) and treated with a 1.25 M solution of hydrogen chloride in methanol (1 mL). The solution was concentrated to dryness, and the residue was dissolved in water and freeze dried to provide (R)-2-(2-(1-amino-2-hydroxyethyl)-1H-imidazol-5-yl)phenol hydrochloride, as an off-white solid: $^1$H NMR (300 MHz, DMSO-$d_6$) δ 9.09 (broad s, 3H), 7.97 (s, 1H), 7.84 (dd, J=7.8, 1.2 Hz, 1H), 7.23 (t, J=7.2 Hz, 1H), 7.05 (d, J=8.0 Hz, 1H), 6.93 (t, J=7.5 Hz, 1H), 4.87-4.72 (m, 1H), 4.07-3.94 (m, 2H), 3 exchangeable protons not observed; ESI MS m/z 220 $[C_{11}H_{13}N_3O_2+H]^+$; HPLC (Method B) >99% (AUC), $t_R$=8.01 min.

Example 2

Additional derivatives of Compound CSRM617 are prepared. These additional derivatives of Compound CSRM617 are studied to assess specificity of the chemical analogs for OC2 and effectiveness in inhibiting the actions of this protein and/or gene. Various studies we perform include in silico and high throughput screening using the UCLA Molecular Shared Screening Resource (MSSR), followed by optimization using homology modeling.

As shown in Scheme 10, in various embodiments we prepare and test several analogs of Compound 122 in which the 2,3,4-trihydroxylphenyl unit is replaced with other substituted phenyl units, wherein the sub stituents include, but are not limited to, one or more of F, Cl, OMe, OH, and/or combinations thereof. In the various embodiments of Scheme 1, the phenethylamine (2) is reacted with a protected serine (3) to give, after deprotection, the desired amide (4). We test various embodiments of amide (4) for inhibiting expression or activity of ONECUT2. Tests for biological activity and selectivity include growth inhibition assays, gene expression profiling, and SPR.

Scheme 10.

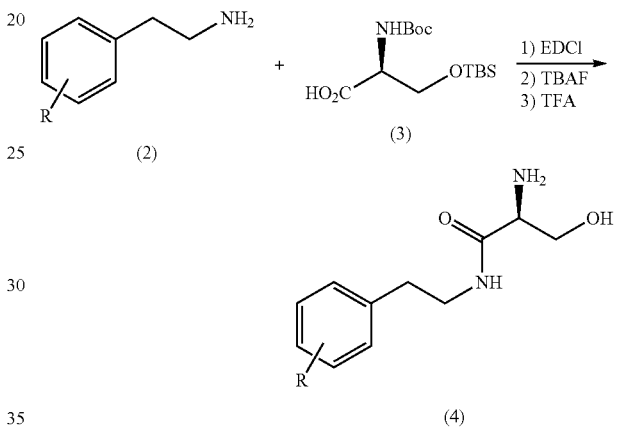

R = independently one or more of hydrogen or optionally substituted substituent

As shown in Scheme 11, in various embodiments we prepare and test various other compounds based on phenethylamine (2). In the various embodiments of Scheme 11, the phenethylamine (2) is reacted with various carboxylic acids to give, after deprotection, the desired amide (5). We test various embodiments of amide (5) for inhibiting expression or activity of ONECUT2. Tests for biological activity and selectivity include growth inhibition assays, gene expression profiling, and SPR.

Scheme 11.

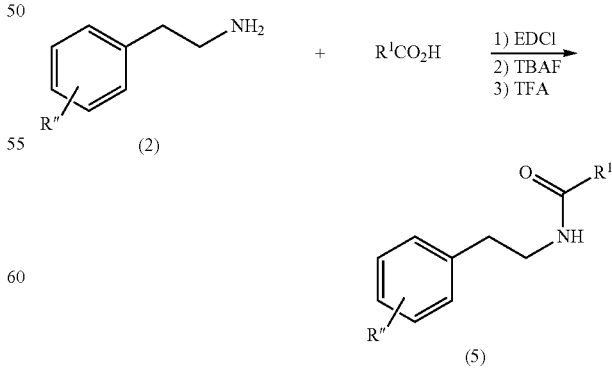

R″ = independently one or more of hydrogen or optionally substituted substituent
$R^1$ = hydrogen or optionally substituted substituent As shown in Scheme 12, in various embodiments we prepare and test various compounds having the structure of amide (6). We test various embodiments of amide (6) for inhibiting expression or activity of ONECUT2. Tests for biological activity and selectivity include growth inhibition assays, gene expression profiling, and SPR.

Scheme 12.

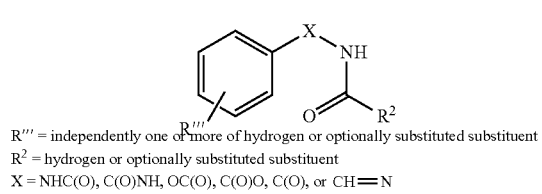

(6)

R''' = independently one or more of hydrogen or optionally substituted substituent
R² = hydrogen or optionally substituted substituent
X = NHC(O), C(O)NH, OC(O), C(O)O, C(O), or CH=N As shown in Scheme 13, in various embodiments we prepare and test various compounds having the structure of amide (7). We test various embodiments of amide (7) for inhibiting expression or activity of ONECUT2. Tests for biological activity and selectivity include growth inhibition assays, gene expression profiling, and SPR.

Scheme 13.

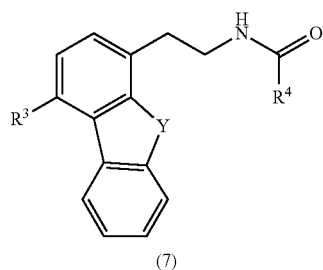

(7)

R³ = hydrogen or optionally substituted substituent
R⁴ = hydrogen or optionally substituted substituent
Y = O or S As shown in Scheme 14, we prepared dimer (8) which was identified by LC/MS. In various embodiments we test the compound having the structure of dimer (8). We test various embodiments of dimer (8) for inhibiting expression or activity of ONECUT2. Tests for biological activity and selectivity include growth inhibition assays, gene expression profiling, and SPR.

Scheme 14.

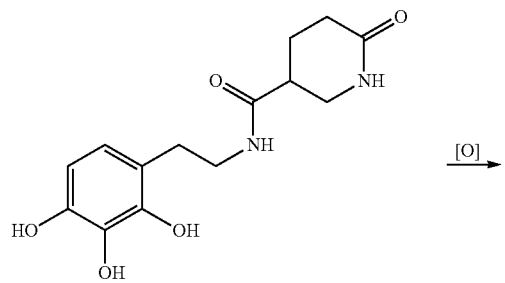

Compound 848
Exact Mass: 294.12
Molecular Weight: 294.30

[O]

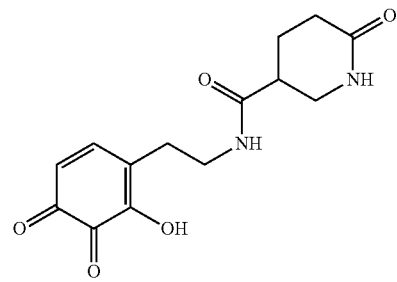

-continued

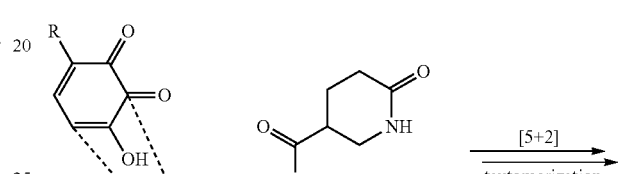

$\xrightarrow{[5+2]}$ tautomerization

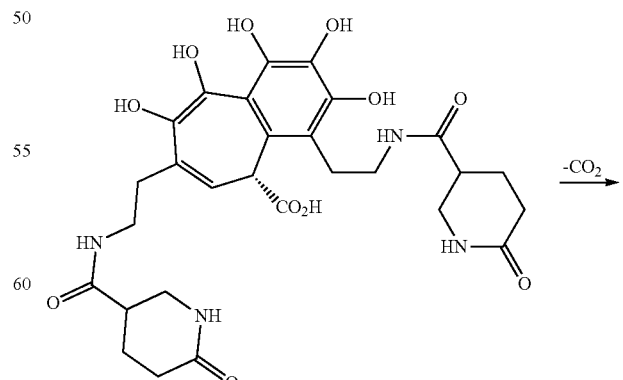

Exact Mass: 602.22
Molecular Weight: 602.59

$-CO_2$

-continued

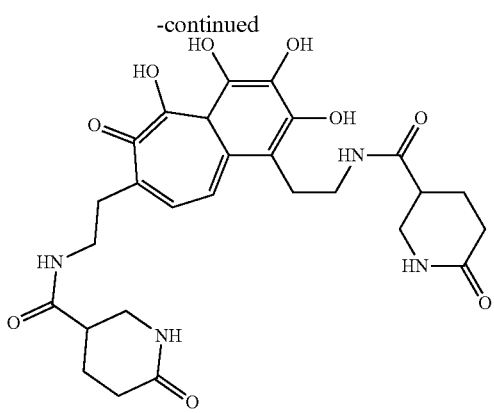

Dimer (8)
Exact Mass: 556.22
Molecular Weight: 556.56

Example 3

Compound CSRM617 was prepared according to known methods,

COMPOUND CSRM617

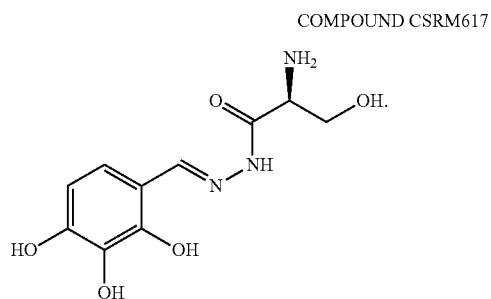 [SMILES: N[C@@H](CO)C(=O)N/N=C/c1ccc(O)c(O)c1O]

Example 4

Figure 2:
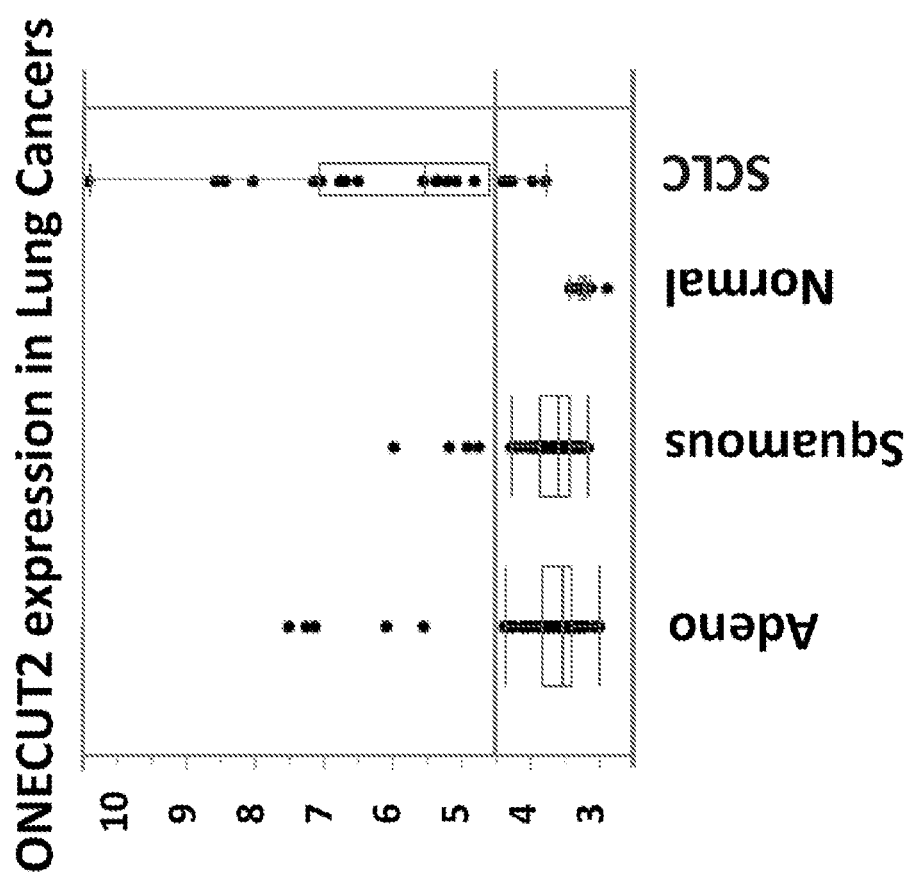
FIG. 2 depicts in accordance with various embodiments of the invention, ONECUT2 expression is highest in SCLC clinical samples relative to normal lung or other lung tumors.
Figure 4:
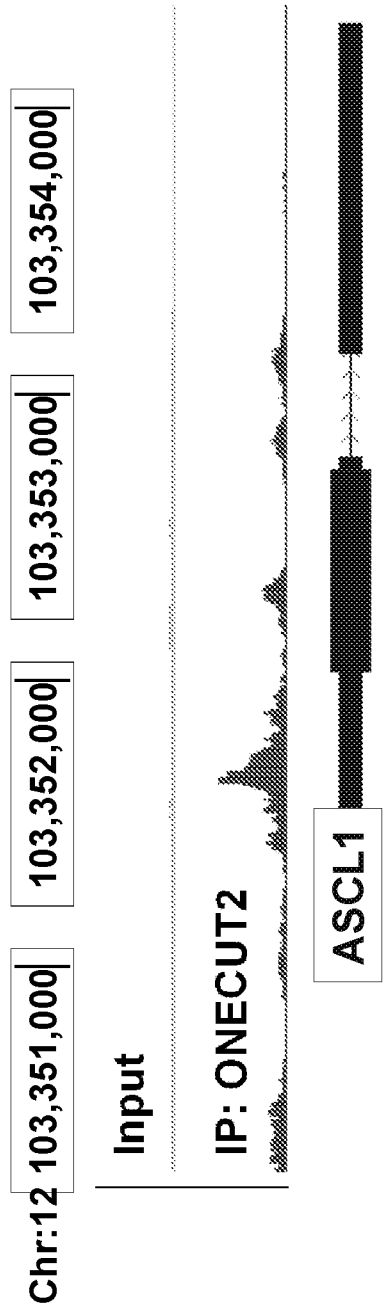
FIG. 4 depicts in accordance with various embodiments of the invention, ONECUT2 binds to the ASCL1 promoter. Genome browser view of ChIPseq data in 22Rv1 cells showing OC2 binding to the ASCL1 gene promoter.
Figure 5:
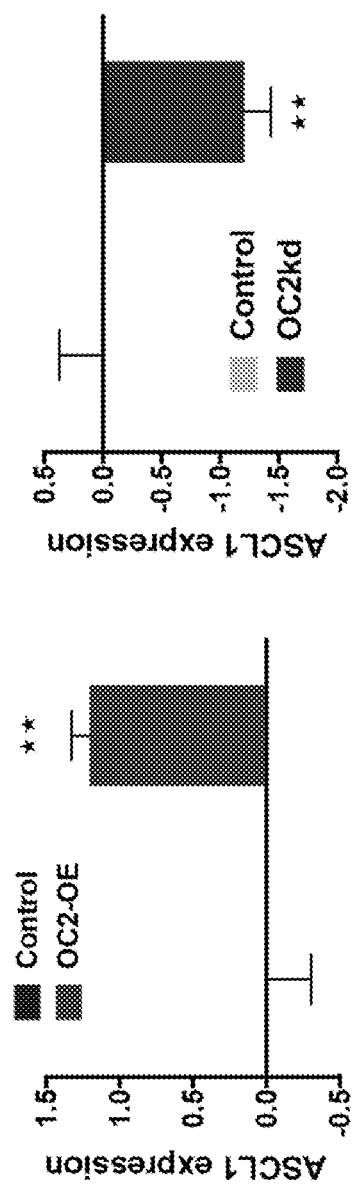
FIG. 5 depicts in accordance with various embodiments of the invention, ONECUT2 activates ASCL1 gene expression. Expression of ASCL1 after enforced OC2 expression (left) or silencing (right) in prostate cancer cell lines.
Figure 6:
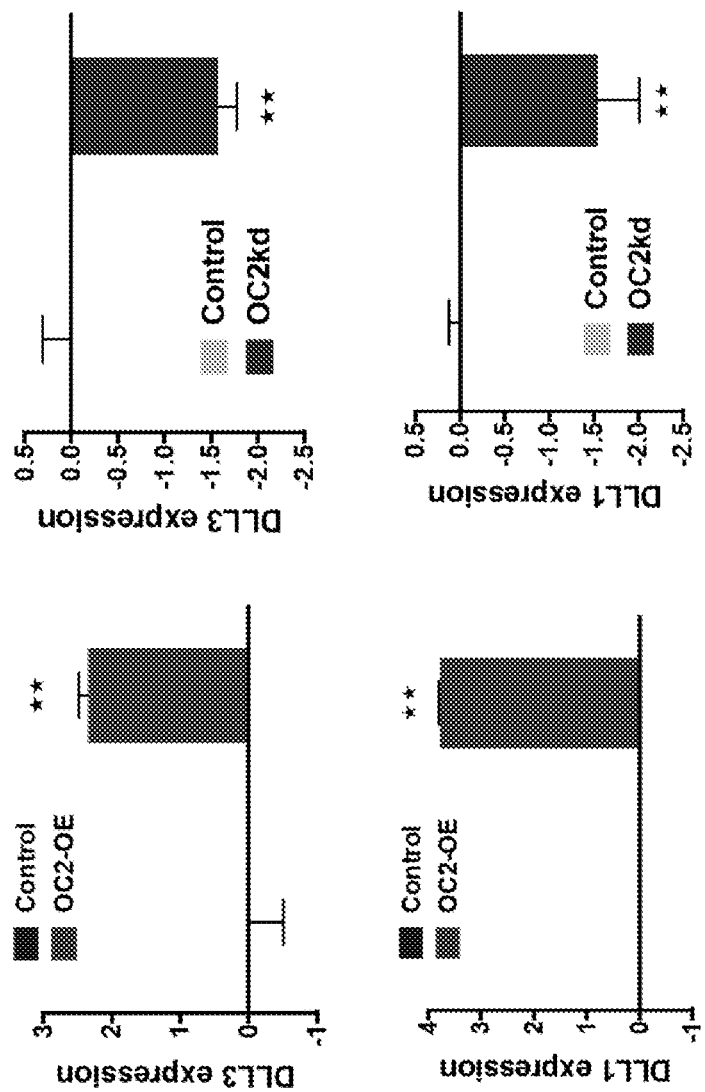
FIG. 6 depicts in accordance with various embodiments of the invention, ONECUT2 regulates ASCL1 target genes. Expression of the ASCL1 target genes DLL3 (up) and DLL1 (down) after enforced OC2 expression (left) or silencing (right) in prostate cancer cell lines.
Figure 7:
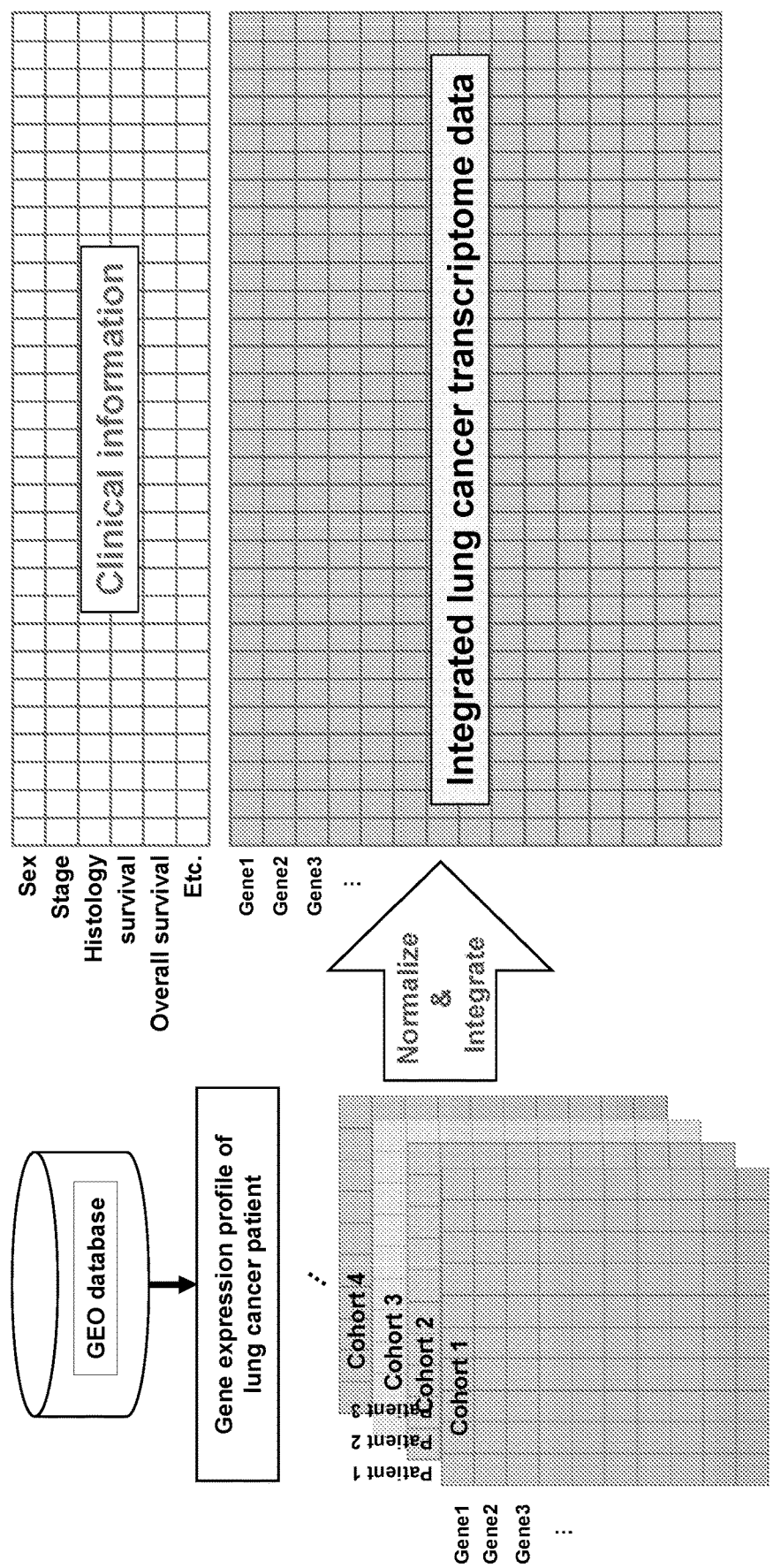
FIG. 7 depicts in accordance with various embodiments of the invention, scheme of assembling lung cancer transcriptome data sets by MCQ method. We collected and integrated transcriptome and clinical data of 459 patients from 6 cohorts.
Figure 8:
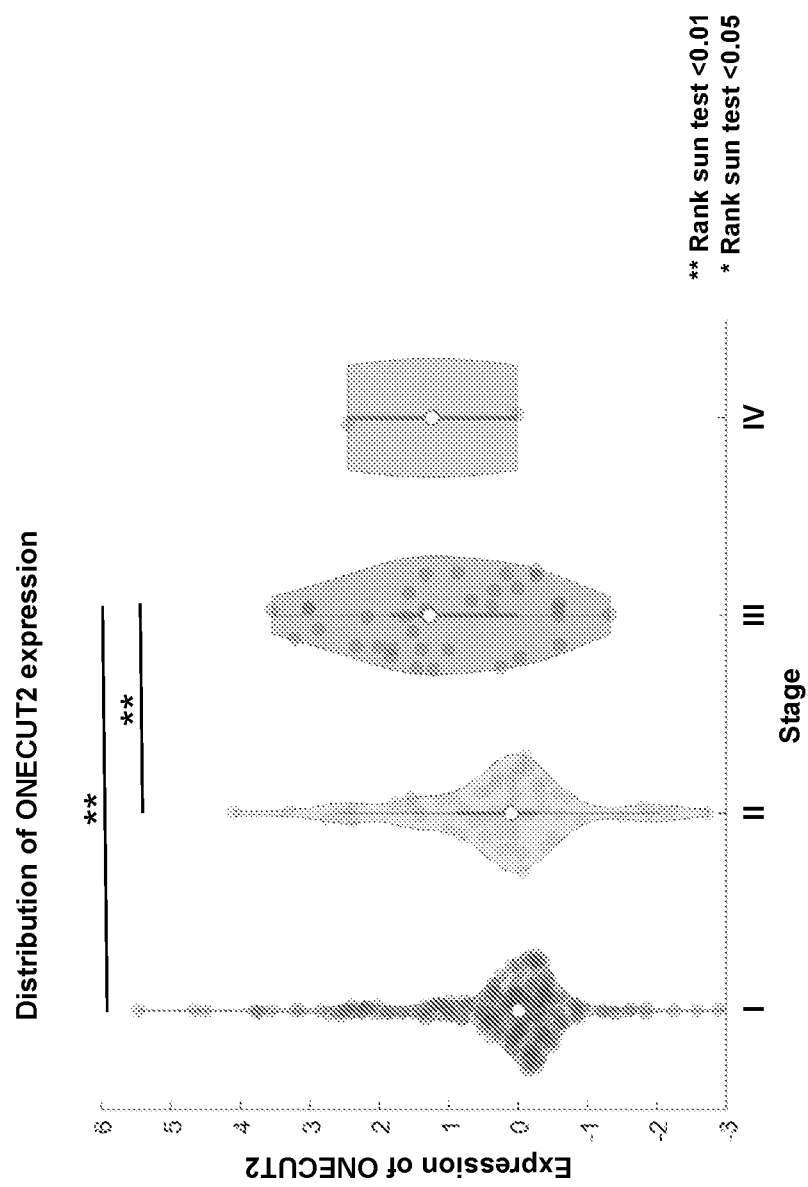
FIG. 8 depicts in accordance with various embodiments of the invention, distribution of ONECUT2 expression. ONECUT2 expression increased in high grade tumors from lung cancer patients.
Figure 9:
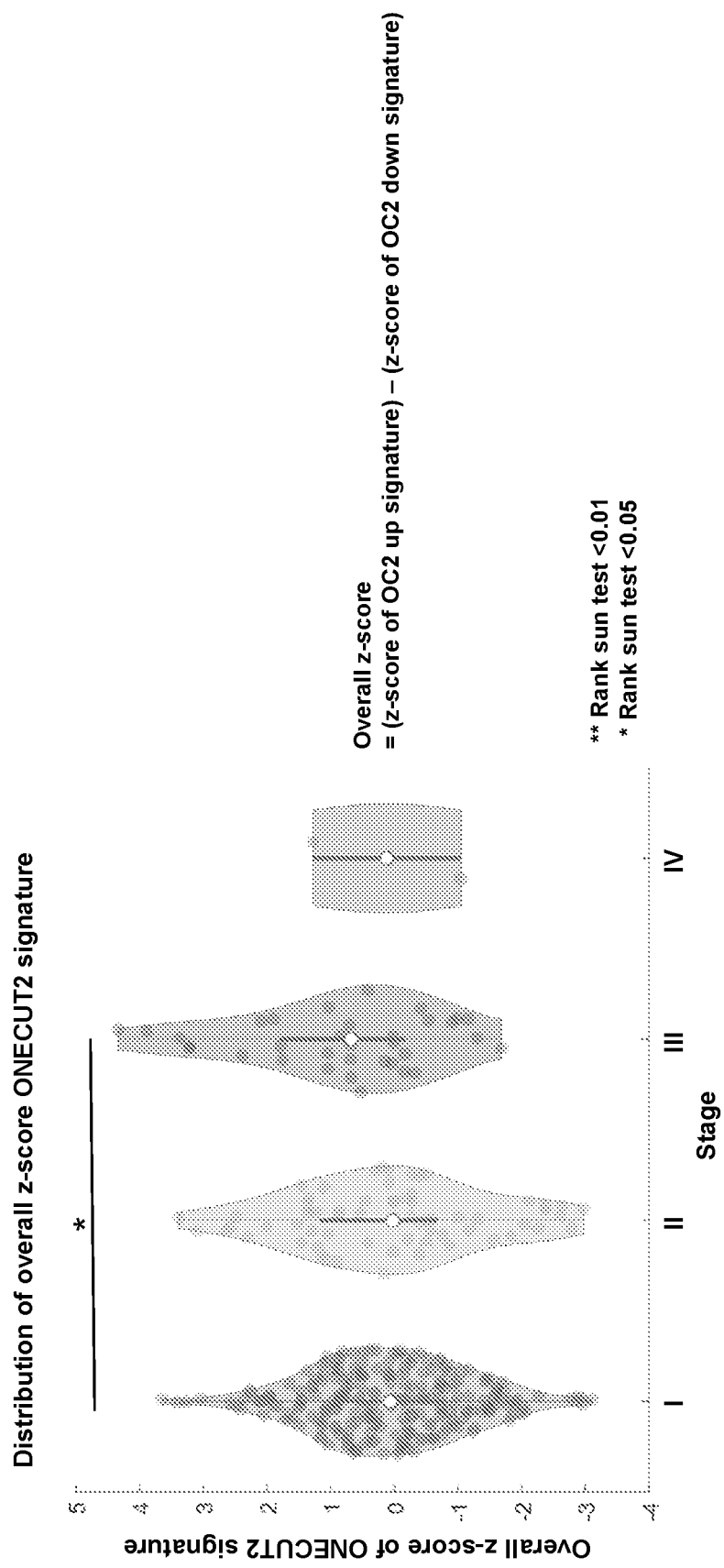
FIG. 9 depicts in accordance with various embodiments of the invention, distribution of overall z-score ONECUT2 signature. ONECUT2 activity increased in high grade tumors from lung cancer patients.
Figure 10:
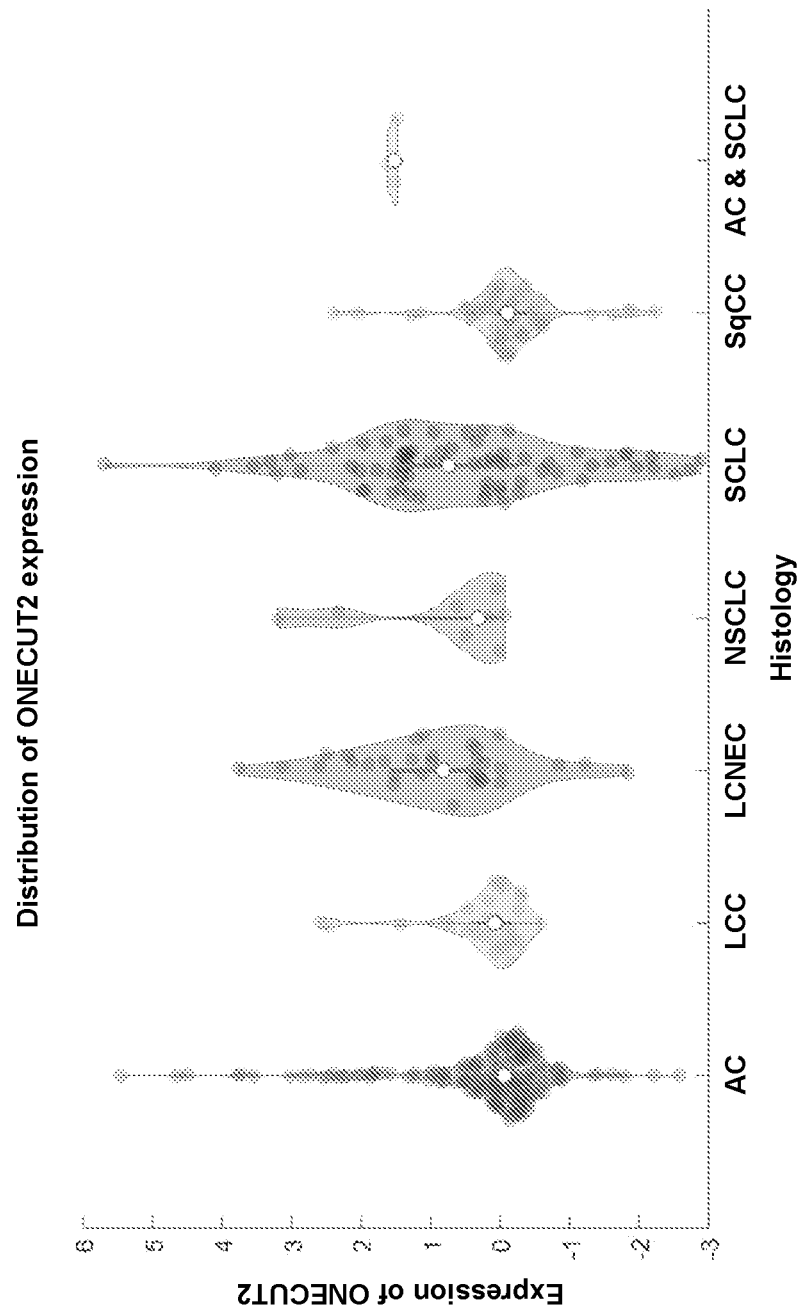
FIG. 10 depicts in accordance with various embodiments of the invention, distribution of ONECUT2 expression. ONECUT2 expression is highly variable in large cell neurodendocrine cancer (LCNEC) and small cell lung cancer (SCLC). Small cell lung cancer (SCLC), large cell neuroendocrine cancer (LCNEC), large-cell carcinoma (LCC), squamous cell carcinoma (SqCC), adenocarcinoma (AC), Non-Small Cell Lung Cancer (NSCLC).

FIG. 1 that ONECUT2 RNA expression is highest in small cell lung cancer (SCLC) and neuroblastoma cell lines. FIG. 2 depicts that ONECUT2 expression is highest in SCLC clinical samples relative to normal lung or other lung tumors. FIG. 3 depicts that ONECUT2 and ASCL1 mRNA expression is positively correlated in SCLC cohorts. FIG. 4 depicts that ONECUT2 binds to the ASCL1 promoter. Genome browser view of ChIPseq data in 22Rv1 cells showing OC2 binding to the ASCL1 gene promoter. FIG. 5 depicts that ONECUT2 activates ASCL1 gene expression. FIG. 6 that ONECUT2 regulates ASCL1 target genes.

Three distinct SCLC molecular subtypes have been defined by differential expression of the transcription factors ASCL1 and NEUROD1. The most common subtype, described as 'classic', is defined by high expression of ASCL1. ASCL1, but not NEUROD1, is required in vivo for tumor formation in mouse models of SCLC. ASCL1 regulates oncogenic genes, including RET, MYCL1 and SOX2. ASCL1 also regulates multiple genes in the NOTCH pathway including DLL3 and DLL1.

OC2 expression is highest in SCLC relative to any other cancer cell line or lung tumor. We find ASCL1 and OC2 significantly positively correlated in human SCLC. Our results also show that OC2 is a positive regulator of ASCL1 expression by direct binding to the ACL1 promoter. We also have evidence of perturbation of ASCL1 target genes such as DLL3, DLL1 or RET when we manipulate OC2 levels.

OC2 lies directly upstream of ASCL1, and is coordinately expressed with ASCL1 in human SCLC. We have shown that OC2 can be inhibited with a small molecule that suppresses metastasis in mice. Therefore, inhibiting OC2 provides a novel strategy for inhibiting this demonstrated SCLC oncogene in the major SCLC subtype.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for treating cancer in a subject, comprising: administering to the subject a therapeutically effective amount of an agent that inhibits expression or activity of ONECUT2, thereby treating cancer in the subject, wherein the agent is a compound selected from the group consisting of:

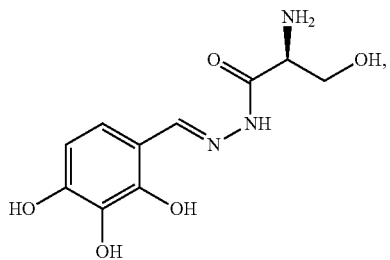

-continued

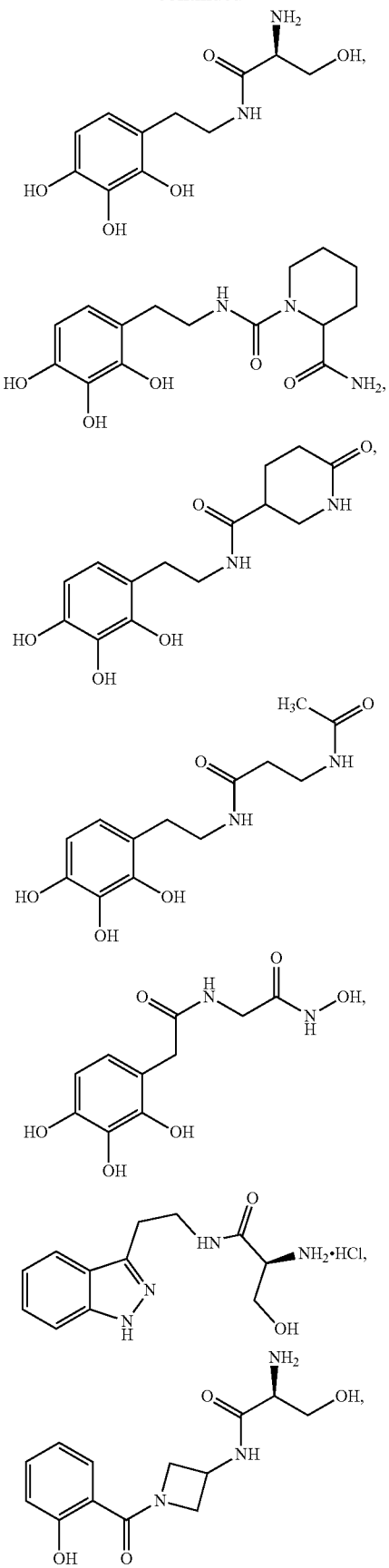

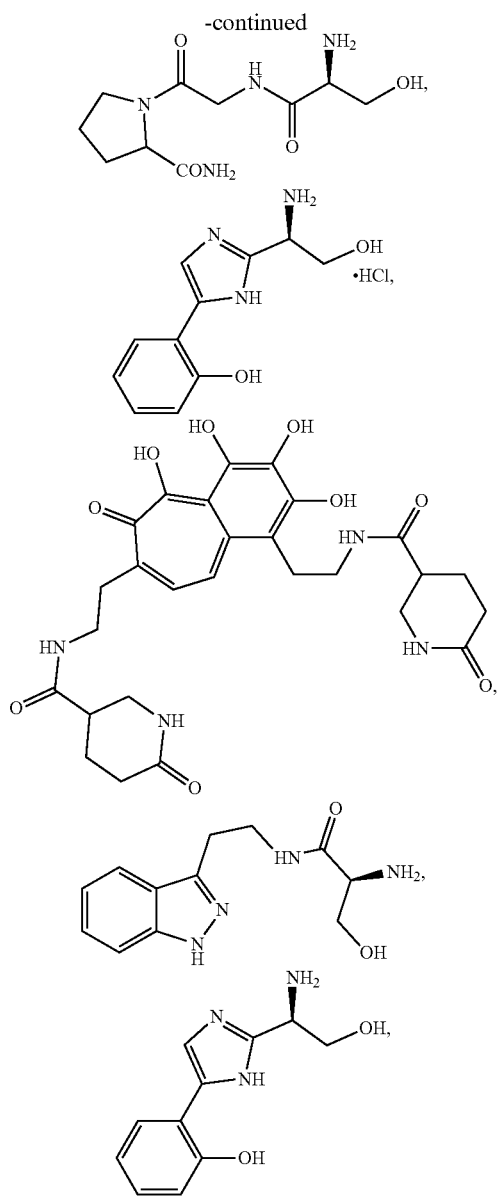

and a prodrug, enantiomer, and a pharmaceutically acceptable salt thereof;

wherein the cancer overexpresses ONECUT2 in the subject, and the cancer is selected from the group consisting of neuroblastoma, small cell lung cancer (SCLC), large cell neuroendocrine cancer (LCNEC), large-cell carcinoma (LCC), squamous cell carcinoma (SqCC), adenocarcinoma (AC), and combinations thereof.

2. The method of claim 1, wherein ONECUT2 is selected from the group consisting of ONECUT2 gene, ONECUT2 protein, and combinations thereof.

3. A method for treating small cell lung cancer (SCLC) or neuroblastoma in a subject in need thereof, comprising providing an agent that inhibits expression or activity of ONECUT2; and administering a therapeutically effective amount of the agent so as to treat SCLC or neuroblastoma in the subject, wherein SCLC or neuroblastoma overexpresses ONECUT2 in the subject, and the agent is a compound of Formula I:

(FORMULA I)

or a prodrug, isomer, enantiomer, or pharmaceutically acceptable salt thereof;
wherein
n is 0, 1, 2, or 3;
X is NHC(O), C(O)NH, or CH=N; and
Y is —CH$_2$C(O)NHOH, —CH$_2$CH$_2$NHC(O)CH$_3$, —NHC(O)CH(NH$_2$)CH$_2$OH, 4. A method for treating, inhibiting, reducing the severity of and/or promoting prophylaxis of and/or delaying progression of metastases of small cell lung cancer (SCLC) or neuroblastoma in a subject in need thereof, comprising providing an agent that inhibits expression or activity of ONECUT2, wherein the agent is a compound of Formula I:

(FORMULA I)

or a prodrug, isomer, enantiomer, or pharmaceutically acceptable salt thereof;
wherein
n is 0, 1, 2, or 3;
X is NHC(O), C(O)NH, or CH=N; and
Y is —CH$_2$C(O)NHOH, —CH$_2$CH$_2$NHC(O)CH$_3$, —NHC(O)CH(NH$_2$)CH$_2$OH, and
administering a therapeutically effective amount of the agent so as to treat, inhibit, reduce the severity of and/or promoting prophylaxis of and/or delaying progression of metastases of small cell lung cancer (SCLC) or neuroblastoma in the subject, wherein SCLC or neuroblastoma overexpresses ONECUT2 in the subject.

5. The method of claim 3, further comprising administering at least one additional anti-SCLC therapy or at least one additional anti-neuroblastoma therapy to the subject.

6. The method of claim 5, wherein the additional anti-SCLC therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

7. The method of claim 5, wherein the additional anti-neuroblastoma therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

8. The method of claim 3, wherein the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

9. The method of claim 3, wherein the agent is administered to the subject 1-3 times per day or 1-7 times per week.

10. The method of claim 3, wherein the agent is administrated to the subject for 1-5 days, 1-5 weeks, 1-5 months, or 1-5 years.

11. The method of claim 5, wherein the agent and the additional anti-SCLC therapy or the anti-neuroblastoma therapy are administered sequentially or simultaneously.

12. The method of claim 3, wherein the agent is Compound CSRM617 or Compound CSRM843:

COMPOUND CSRM617

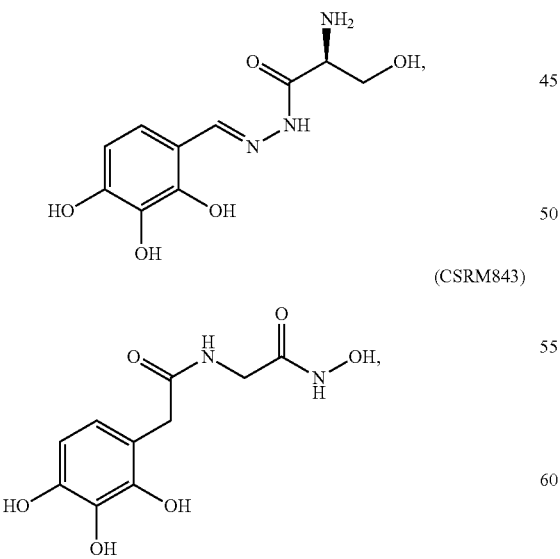

(CSRM843)

or a pharmaceutically acceptable salt thereof.

13. The method of claim 3, wherein the agent is a compound selected from the group consisting of:

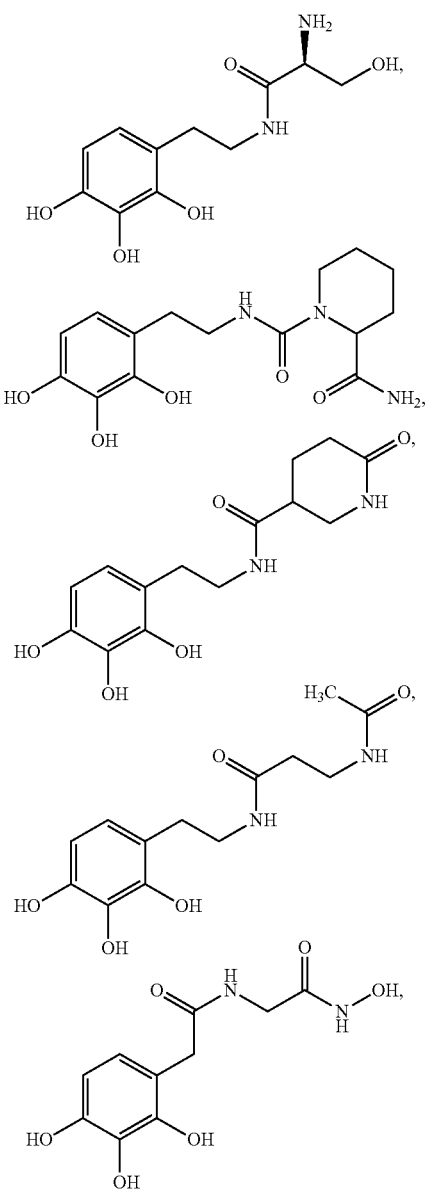

and a prodrug, enantiomer, and pharmaceutically acceptable salt thereof.

14. The method of claim 4, wherein the agent is a compound selected from the group consisting of:

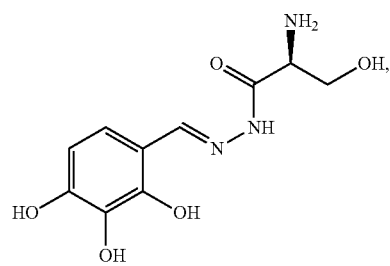

-continued
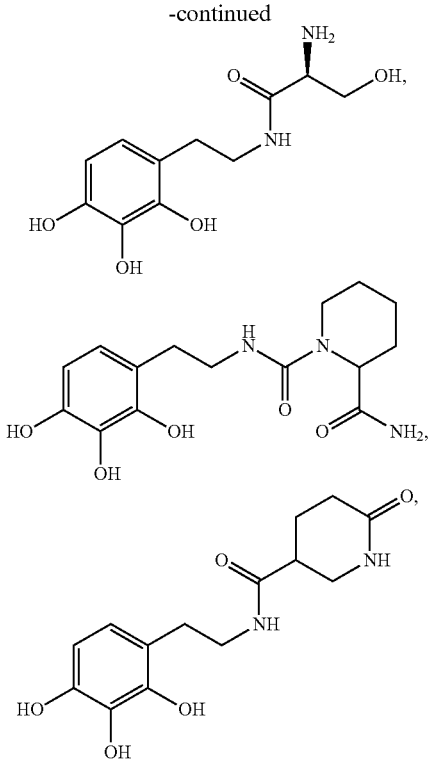
-continued
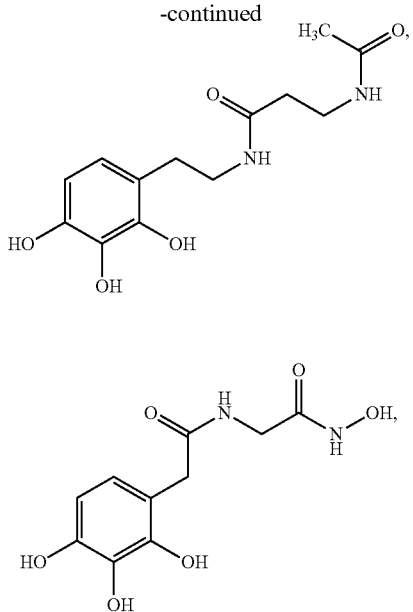
and
a prodrug, enantiomer, and pharmaceutically acceptable salt thereof.
* * * * *